(12) United States Patent
Bartel et al.

(10) Patent No.: US 7,998,988 B2
(45) Date of Patent: Aug. 16, 2011

(54) BIPHENYL COMPOUNDS USEFUL IN THE TREATMENT OR PREVENTION OF CARDIOVASCULAR DISORDERS

(75) Inventors: Stephan Bartel, Kürten (DE); Michael Hahn, Langenfeld (DE); Wahed Ahmed Moradi, Monheim (DE); Klaus Münter, Wülfrath (DE); Thomas Rölle, Leverkusen (DE); Johannes-Peter Stasch, Solingen (DE); Karl-Heinz Schlemmer, Wuppertal (DE); Frank Wunder, Wuppertal (DE)

(73) Assignee: Bayer Schering Pharma Aktiengellschaft, Berlin (DE)

( * ) Notice: Subject to any disclaimer, the term of this patent is extended or adjusted under 35 U.S.C. 154(b) by 259 days.

(21) Appl. No.: 12/083,760

(22) PCT Filed: Oct. 9, 2006

(86) PCT No.: PCT/EP2006/009722
§ 371 (c)(1),
(2), (4) Date: Apr. 29, 2009

(87) PCT Pub. No.: WO2007/045366
PCT Pub. Date: Apr. 26, 2007

(65) Prior Publication Data
US 2009/0227640 A1    Sep. 10, 2009

(30) Foreign Application Priority Data
Oct. 21, 2005 (DE) .......................... 10 2005 050 377

(51) Int. Cl.
*A01N 43/82* (2006.01)
(52) U.S. Cl. ...... 514/364; 514/384; 548/132; 548/263.2
(58) Field of Classification Search .................. 514/364, 514/384; 548/132, 26.2
See application file for complete search history.

(56) References Cited

U.S. PATENT DOCUMENTS

| | | | |
|---|---|---|---|
| 5,041,638 A | 8/1991 | Rosentreter et al. | |
| 5,159,097 A | 10/1992 | Rosentreter et al. | |
| 5,221,760 A | 6/1993 | Rosentreter et al. | |
| 6,166,027 A | 12/2000 | Straub et al. | |
| 6,180,656 B1 | 1/2001 | Furstner et al. | |
| 6,387,940 B1 | 5/2002 | Straub et al. | |
| 6,410,740 B1 | 6/2002 | Straub et al. | |
| 6,414,009 B1 | 7/2002 | Straub et al. | |
| 6,451,805 B1 | 9/2002 | Straub et al. | |
| 6,462,068 B1 | 10/2002 | Straub et al. | |
| 6,864,287 B1 | 3/2005 | Alonso-Alija et al. | |
| 7,087,644 B1 | 8/2006 | Alonso-Alija et al. | |
| 7,517,896 B2 | 4/2009 | Alonso-Alija et al. | |
| 2004/0082798 A1 | 4/2004 | Alonso-Alija et al. | |
| 2004/0176446 A1 | 9/2004 | Alonso-Alija et al. | |
| 2006/0094769 A1 | 5/2006 | Alonso-Alija et al. | |
| 2007/0179139 A1 | 8/2007 | Alonso-Alija et al. | |
| 2008/0058314 A1 | 3/2008 | Alonso-Alija et al. | |

FOREIGN PATENT DOCUMENTS

| | | |
|---|---|---|
| DE | 19943635 A1 | 3/2001 |
| DE | 19943636 A1 | 3/2001 |
| DE | 19943639 A1 | 3/2001 |
| DE | 19943634 A1 | 4/2001 |
| EP | 0341551 A1 | 11/1989 |
| WO | WO-98/16223 A1 | 4/1998 |
| WO | WO-98/16507 A2 | 4/1998 |
| WO | WO-98/23619 A1 | 6/1998 |
| WO | WO-01/19355 A2 | 3/2001 |
| WO | WO-01/19776 A2 | 3/2001 |
| WO | WO-01/19778 A1 | 3/2001 |
| WO | WO-01/19780 A2 | 3/2001 |
| WO | WO-02/070462 A1 | 9/2002 |
| WO | WO-02/070510 A2 | 9/2002 |

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Sausville et al.(Cancer Res. 2006; 66 (7): 3351-3354).*
Wermuth et al., "Molecular Variations Based on Isosteric Replacements", Practice of Medicinal Chemistry, 1996; pp. 203-237.
FN Ko et al.: "YC-1, A Novel Activator of Platelet Guanylate Cyclase," Blood, 84, 1994, pp. 4226-4233.
A. Mulsch et al.: "Effect of YC-1, an NO-independent, Superoxide-Sensitive Stimulator of Soluble Guanylyl Cyclase, on Smooth Muscle Responsiveness to Nitrovasodilators," British Journal of Pharmacology, 120, 1997, pp. 681-689.
D. B. Glass et al.: "Stimulation of Human Platelet Guanylate Cyclase by Fatty Acids," The Journal of Biological Chemistry, vol. 252, No. 4, Feb. 25, 1977, pp. 1279-1285.

(Continued)

Primary Examiner — Yong Chu
Assistant Examiner — Valerie Rodriguez-Garcia
(74) Attorney, Agent, or Firm — Karen B. King

(57) ABSTRACT

The invention relates to biphenyl compounds of formula (I):

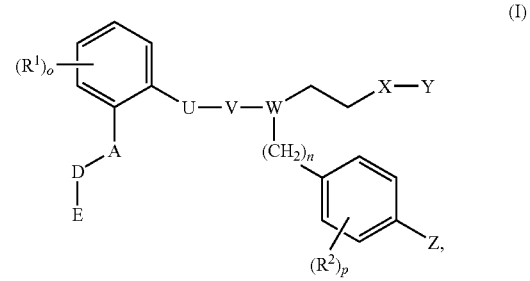

(I)

wherein U, V and W together form a group of the formula *—CH=CH—CH<, *—CH$_2$—CH$_2$—CH< or *—CH$_2$—CH$_2$—N<, in which * means the point of linkage to the phenyl ring; A is O or CH$_2$; and D, E, X, Y, Z, R$^1$, R$^2$, o, n, and p are as defined in the specification. The invention also relates to pharmaceutical compositions of the compound of the compounds. The compounds and pharmaceutical compositions of the invention can be used in the treatment or prevention of cardiovascular disorders.

8 Claims, No Drawings

OTHER PUBLICATIONS

D. J. Pettibone et al.: "A Structurally Novel Stimulator of Guanylate Cyclase with Long-Lasting Hypotensive Activity in the Dog," European Journal of Pharmacology, 116, 1985, pp. 307-312.

S-M Yu et al.: "Vasorelaxant Effect of Isoliquiritigenin, a Novel Soluble Guanylate Cyclase Activator, in Rat Aorta," British Journal of Pharmacology, 114, 1995, pp. 1587-1594.

R. Gerzer et al.: "Soluble Guanylate Cyclase Purified from Bovine Lung Contains Heme and Copper," FEBS Letters, vol. 132, No. 1, Sep. 1981, pp. 71-74.

M. Hoenicka et al.: "Purified Soluble Guanylyl Cyclase Expressed in a Baculovirus/Sf9 System: Stimulation by YC-1, Nitric Oxide, and Carbon Monoxide," J. Mol. Med, 77, 1999, pp. 14-23.

L. J. Ignarro: "Regulation of Cytosolic Guanylyl Cyclase by Porphyrins and Metalloporphyrins," Advances in Pharmacology, vol. 26, 1994, pp. 35-65.

C. G. Wermuth: "Designing Prodrugs and Bioprecursors II: Bioprecursor Prodrugs," The Practice of Medicinal Chemistry, No. 32, 1996, pp. 697-715.

* cited by examiner

BIPHENYL COMPOUNDS USEFUL IN THE TREATMENT OR PREVENTION OF CARDIOVASCULAR DISORDERS

RELATED APPLICATIONS/PATENTS AND INCORPORATION BY REFERENCE

This application is a National Stage Application filed under 35 U.S.C. §371 based on International Application No. PCT/EP2006/009722, filed Oct. 9, 2006, which claims priority to German Patent Application Number 102005050377.2, filed Oct. 21, 2005, the entire contents of which is incorporated herein by reference. The foregoing application, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel heterocyclic compounds, processes for their preparation, their use for the treatment and/or prophylaxis of diseases, and their use for producing medicaments for the treatment and/or prophylaxis of diseases, especially for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. Carbon monoxide (CO) is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole [YC-1, Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223, WO 98/16507 and WO 98/23619).

The above-described stimulators of soluble guanylate cyclase stimulate the enzyme either directly via the heme group (carbon monoxide, nitric oxide or diphenyliodonium hexafluorophosphate) by interacting with the iron center of the heme group and a change in conformation which results therefrom and leads to an increase in the enzymic activity [Gerzer et al., FEBS Lett. 132 (1981), 71] or via a heme-dependent mechanism which is independent of NO but leads to a potentiation of the stimulating effect of NO or CO [e.g. YC-1, Hoenicka et al., J. Mol. Med. 77 (1999) 14; or the pyrazole derivatives described in WO 98/16223, WO 98/16507 and WO 98/23619].

It has not been possible to confirm the stimulating effect, asserted in the literature, of isoliquiritigenin and of fatty acids such as, for example, of arachidonic acid, prostaglandin endoperoxides and fatty acid hydroperoxides on soluble guanylate cyclase [cf., for example, Hoenicka et al., J. Mol. Med. 77 (1999), 14].

If the heme group is removed from soluble guanylate cyclase, the enzyme still shows a detectable basal catalytic activity, i.e. cGMP is still produced. The remaining basal catalytic activity of the heme-free enzyme cannot be stimulated by any of the aforementioned known stimulators.

Stimulation of heme-free soluble guanylate cyclase by protoporphyrin IX has been described [Ignarro et al., Adv. Pharmacol. 26 (1994), 35]. However, protoporphyrin IX can be regarded as a mimic of the NO-heme adduct, which is why addition of protoporphyrin IX to soluble guanylate cyclase ought to lead to production of a structure of the enzyme corresponding to the heme-containing soluble guanylate cyclase which is stimulated by NO. This is also verified by the fact that the stimulating effect of protoporphyrin IX is increased by the NO-independent but heme-dependent stimulator YC-1 described above [Mülsch et al., Naunyn Schmiedebergs Arch. Pharmacol. 355, R47].

In contrast to the above-described stimulators of soluble guanylate cyclase, the compounds of the present invention are able to activate both the heme-containing and the heme-free form of soluble guanylate cyclase. Thus, with these novel activators, the enzyme is stimulated via a heme-independent pathway, which is also verified by the facts that the novel activators firstly show no synergistic effect with NO on the heme-containing enzyme, and secondly the effect of these novel activators cannot be blocked by the heme-dependent inhibitor of soluble guanylate cyclase 1H-1,2,4-oxadiazole-(4,3-a)-quinoxaalin-1-one (ODQ).

EP 0 341 551-A1 discloses alkenoic acid derivatives as leukotriene antagonists for the treatment of disorders of the circulatory and respiratory systems. WO 01/19355, WO 01/19776, WO 01/19778, WO 01/19780, WO 02/070462 and WO 02/070510 describe dicarboxylic acid and amino dicarboxylic acid derivatives as stimulators of soluble guanylate cyclase for the treatment of cardiovascular disorders. However, it has emerged that these compounds have disadvantages in relation to their pharmacokinetic properties, such as, in particular, a low bioavailability and/or an only short duration of action after oral administration.

It was therefore an object of the present invention to provide novel compounds which act as activators of soluble guanylate cyclase but do not have the aforementioned disadvantages of the prior art compounds.

The present invention relates to compounds of the general formula (I)

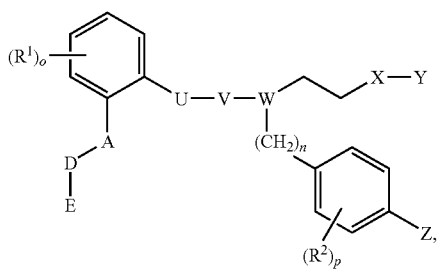

in which
U, V and W together form a group of the formula
*—CH=CH—CH<, *—CH$_2$—CH$_2$—CH< or *—CH$_2$—CH$_2$—N<, in which * means the point of linkage to the phenyl ring,
A is O or CH$_2$,
D is a bond or is (C$_1$-C$_7$)-alkanediyl, (C$_2$-C$_7$)-alkenediyl or (C$_2$-C$_7$)-alkanediyl, each of which may be substituted one or more times by fluorine,
E is hydrogen, trifluoromethyl or a group of the formula

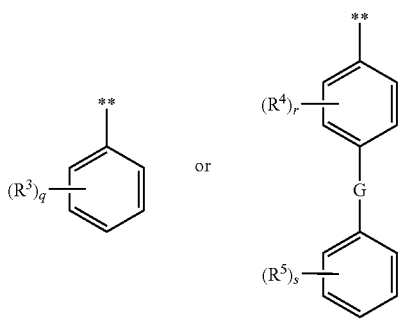

in which ** means the point of linkage to the group D and
G is a bond, CH$_2$, —CH$_2$—CH$_2$— or —CH=CH—,
X is —CH$_2$—CH$_2$— or a group of the formula

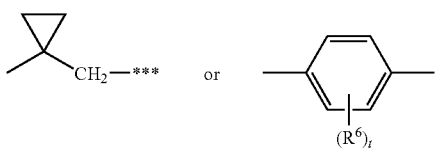

in which *** means the point of linkage to the group Y,
Y is carboxyl
and
Z is a group of the formula

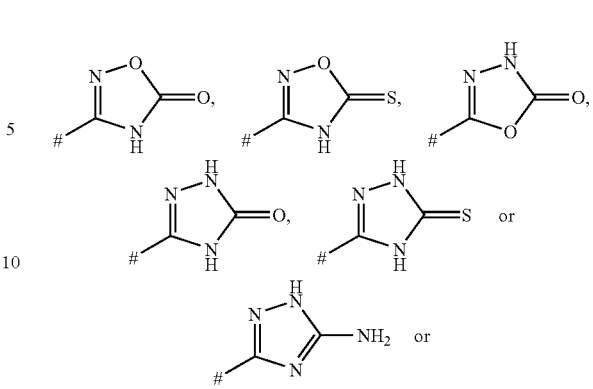

Y is a group of the formula

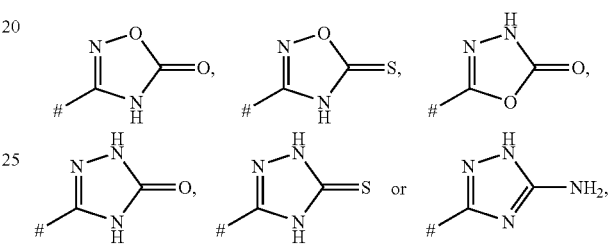

in which # means the respective point of linkage,
and
Z is carboxyl,
n is the number 1 or 2,
R$^1$, R$^2$, R$^3$, R$^4$, R$^5$ and R$^6$ are independently of one another substituents selected from the series halogen, (C$_1$-C$_6$)-alkyl, trifluoromethyl, (C$_1$-C$_6$)-alkoxy, trifluoromethoxy, cyano and nitro,
and
o, p, q, r, s and t are independently of one another each the number 0, 1, 2, 3 or 4,
where in the case where R$^1$, R$^2$, R$^3$, R$^4$, R$^5$ or R$^6$ occur more than once, their meanings may in each case be identical or different,
and the salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

In the context of the present invention, the substituents have the following meaning unless otherwise specified:

$(C_1-C_6)$-Alkyl and $(C_1-C_4)$-alkyl are in the context of the invention a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, iso-butyl, sec-butyl, tert-butyl, 1-ethylpropyl, n-pentyl and n-hexyl.

$(C_1-C_7)$-Alkanediyl is in the context of the invention a straight-chain or branched divalent alkyl radical having 1 to 7 carbon atoms. A straight-chain alkanediyl radical having 1 to 6 carbon atoms is preferred. Examples which may be preferably mentioned are: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl, butane-2,3-diyl, pentane-1,5-diyl, pentane-2,4-diyl, 3-methylpentane-2,4-diyl and hexane-1,6-diyl.

$(C_1-C_7)$-Alkenediyl is in the context of the invention a straight-chain or branched divalent alkenyl radical having 2 to 7 carbon atoms with up to 3 double bonds. A straight-chain alkenediyl radical having 2 to 6 carbon atoms and up to 2 double bonds is preferred. Examples which may be preferably mentioned are: ethene-1,1-diyl, ethene-1,2-diyl, propene-1,1-diyl, propene-1,2-diyl, propene-1,3-diyl, but-1-ene-1,1-diyl, but-1-ene-1,3-diyl, but-2-ene-1,4-diyl, buta-1,3-diene-1,4-diyl, pent-2-ene-1,5-diyl, hex-3-ene-1,6-diyl and hexa-2,4-diene-1,6-diyl.

$(C_1-C_2)$-Alkynediyl is in the context of the invention a straight-chain or branched divalent alkynyl radical having 2 to 7 carbon atoms and up to 3 triple bonds. A straight-chain alkanediyl radical having 2 to 6 carbon atoms and up to 2 triple bonds is preferred. Examples which may be preferably mentioned are: ethyne-1,2-diyl, propyne-1,3-diyl, but-1-yne-1,4-diyl, but-1-yne-1,3-diyl, but-2-yne-1,4-diyl, pent-2-yne-1,5-diyl, pent-2-yne-1,4-diyl and hex-3-yne-1,6-diyl.

$(C_1-C_6)$-Alkoxy and $(C_1-C_4)$-alkoxy are in the context of the invention a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy, n-butoxy, tert-butoxy, n-pentoxy and n-henoxy.

Halogen in the context of the invention includes fluorine, chlorine, bromine and iodine. Chlorine or fluorine are preferred.

If radicals in the compounds according to the invention are substituted, the radicals may, unless otherwise specified, be substituted one or more times. In the context of the present invention, all radicals which occur more than once have a mutually independent meaning. Substitution by one, two or three identical or different substituents is preferred. Substitution by one substituent is very particularly preferred.

Preference is given in the context of the present invention to compounds of the formula (I) in which U, V and W together form a group of the formula
*—CH═CH—CH< or *—CH$_2$—CH$_2$—N< in which * means the point of linkage to the phenyl ring, A is O, D is $(C_1-C_7)$-alkanediyl which may be substituted one or more times by fluorine, E is hydrogen, trifluoromethyl or is a group of the formula

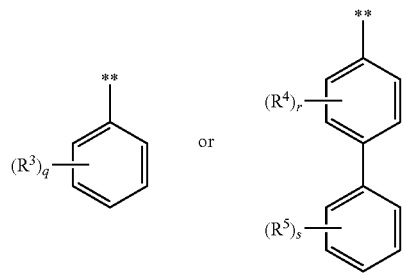

in which ** means the point of linkage to the group D,

X is —CH$_2$—CH$_2$— or a group of the formula

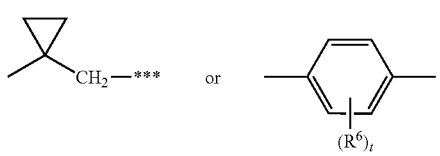

in which *** means the point of linkage to the group Y,

Y is carboxyl and

Z is a group of the formula

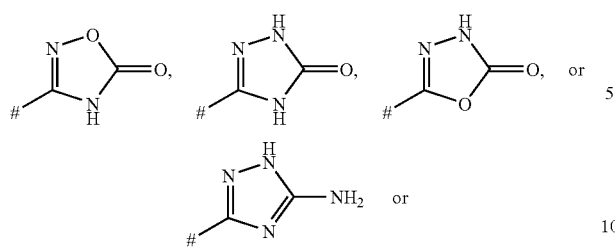

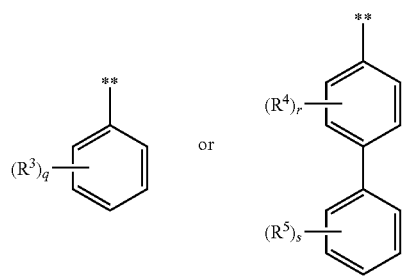

Y is a group of the formula

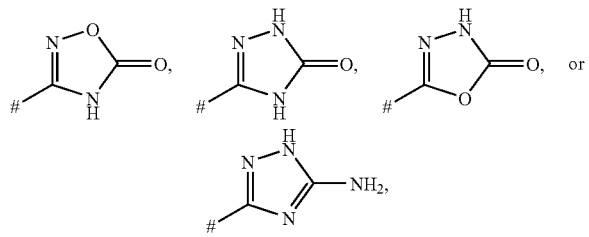

in which # means the respective point of linkage,
and
Z is carboxyl,
n is the number 1 or 2,
$R^1$, $R^3$, $R^4$ and $R^5$ are independently of one another a substituent selected from the series fluorine, chlorine, bromine, $(C_1-C_4)$-alkyl, trifluoromethyl, $(C_1-C_4)$-alkoxy and trifluoromethoxy,
o, q, r and s are independently of one another each the number 0, 1 or 2,
where in the case where $R^1$, $R^3$, $R^4$ or $R^5$ occur more than once, their meanings may in each case be identical or different,
$R^2$ and $R^6$ are each fluorine,
and
p and t are independently of one another each the number 0 or 1,
and the salts, solvates and solvates of the salts thereof.

Particular preference is given in the context of the present invention to compounds of the formula (I-A)

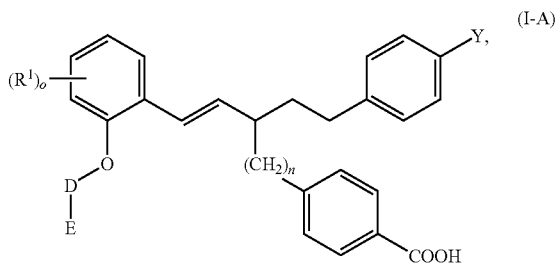

in which
D is $(C_1-C_7)$-alkanediyl which may be substituted one or more times by fluorine, E is hydrogen, trifluoromethyl or is a group of the formula

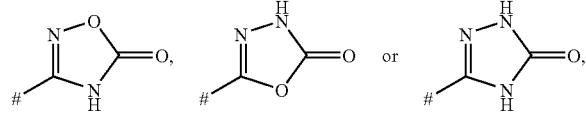

in which ** means the point of linkage to the group D,
Y is a group of the formula

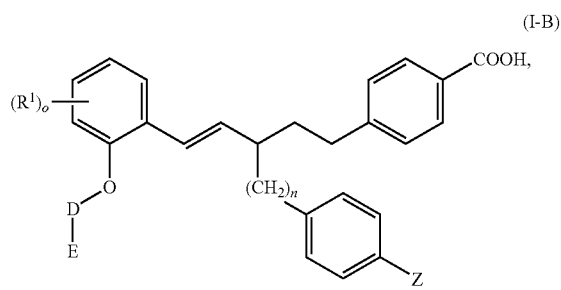

in which # means the point of linkage to the phenyl ring,
n is the number 1 or 2,
$R^1$, $R^3$, $R^4$ and $R^5$ are independently of one another a substituent selected from the series fluorine, chlorine, bromine, methyl, tert-butyl, trifluoromethyl, methoxy and trifluoromethoxy,
and
o, q, r and s are independently of one another each the number 0, 1 or 2,
where in the case that $R^1$, $R^3$, $R^4$ or $R^5$ occur more than once, their meanings may in each case be identical or different,
and the salts, solvates and solvates of the salts thereof.

Particular preference is given in the context of the present invention also to compounds of the formula (I-B)

in which
D is $(C_1-C_7)$-alkanediyl which may be substituted one or more times by fluorine, E is hydrogen, trifluoromethyl or is a group of the formula

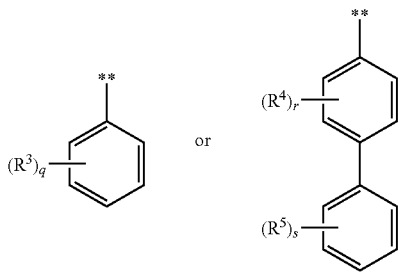

in which ** means the point of linkage to the group D,
Z is a group of the formula

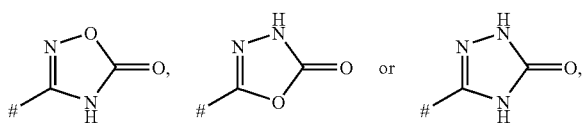

in which # means the point of linkage to the phenyl ring,
n is the number 1 or 2,
$R^1$, $R^3$, $R^4$ and $R^5$ are independently of one another a substituent selected from the series fluorine, chlorine, bromine, methyl, tert-butyl, trifluoromethyl, methoxy and trifluoromethoxy,
and
o, q, r and s are independently of one another each the number 0, 1 or 2,
where in the case that $R^1$, $R^3$, $R^4$ or $R^5$ occur more than once, their meanings may in each case be identical or different,
and the salts, solvates and solvates of the salts thereof.

Particular preference is given in the context of the present invention also to compounds of the formula (I-C)

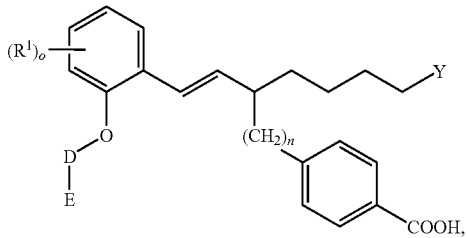

in which
D is ($C_1$-$C_7$)-alkanediyl which may be substituted one or more times by fluorine, E is hydrogen, trifluoromethyl or is a group of the formula

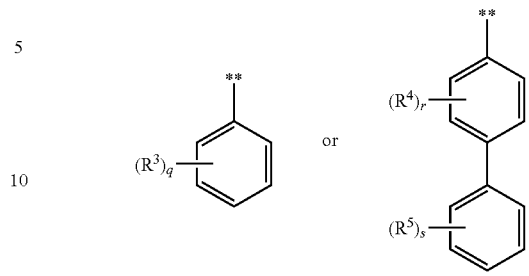

in which ** means the point of linkage to the group D,
Y is a group of the formula

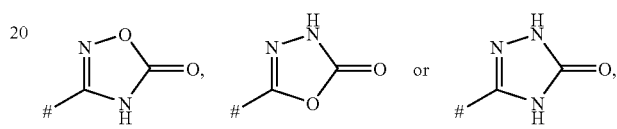

in which # means the respective point of linkage,
n is the number 1 or 2,
$R^1$, $R^3$, $R^4$ and $R^5$ are independently of one another a substituent selected from the series fluorine, chlorine, bromine, methyl, tert-butyl, trifluoromethyl, methoxy and trifluoromethoxy,
and
o, q, r and s are independently of one another each the number 0, 1 or 2,
where in the case that $R^1$, $R^3$, $R^4$ or $R^5$ occur more than once, their meanings may in each case be identical or different,
and the salts, solvates and solvates of the salts thereof.

Particular preference is given in the context of the present invention to compounds of the formulae (I-A) and (I-B) in which
D and F together are n-butyl, n-pentyl, n-hexyl, 5,5,5-trifluoropentan-1-yl, 6,6,6-trifluorohexan-1-yl or are a group of the formula

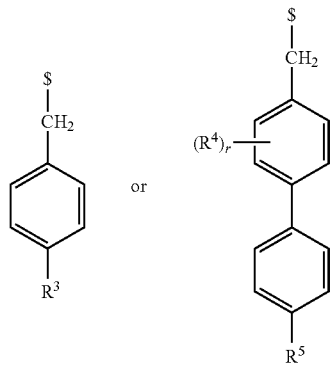

in which $ means the point of linkage to the O atom and
$R^3$ and $R^5$ are each tert-butyl, trifluoromethyl, methoxy or trifluoromethoxy,
n is the number 1,
$R^1$ is fluorine, $R^4$ is fluorine or chlorine,
and
o and r are independently of one another each the number 0 or 1,
and the salts, solvates and solvates of the salts thereof.

Particular preference is given in the context of the present invention also to compounds of the formula (I-C) in which
D and E together are n-butyl, n-pentyl, n-hexyl, 5,5,5-trifluoropentan-1-yl, 6,6,6-trifluorohexan-1-yl or are a group of the formula

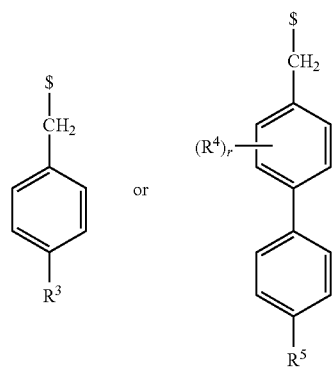

in which $ means the point of linkage to the O atom and
$R^3$ and $R^5$ are each tert-butyl, trifluoromethyl, methoxy or trifluoromethoxy,
n is the number 1 or 2,
$R^1$ is fluorine,
$R^4$ is fluorine or chlorine,
and
o and r are independently of one another each the number 0 or 1,
and the salts, solvates and the solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to processes for preparing the compounds of the invention of the formula (I) characterized in that either
[A-1] Compounds of the Formula (II-1)

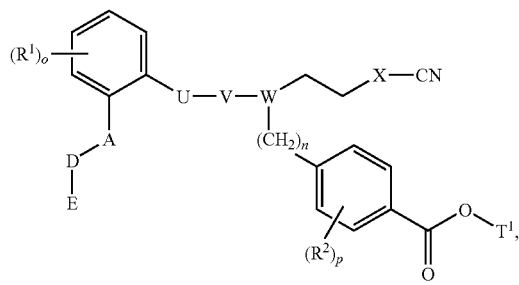

in which $R^1$, $R^2$, A, D, E, U, V, W, X, n, o and p each have the meanings indicated above, and $T^1$ is $(C_1-C_4)$-alkyl,
are initially converted with hydroxylamine in an inert solvent into compounds of the formula (III-1)

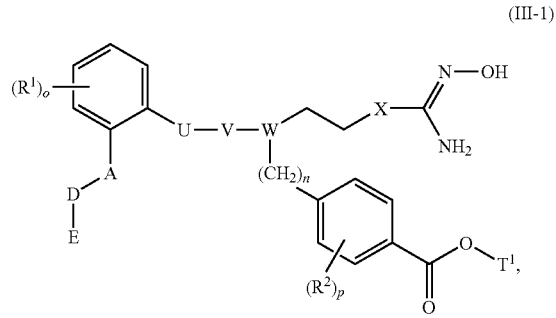

in which $R^1$, $R^2$, A, D, E, U, V, W, X, n, o, p and $T^1$ each have the meanings indicated above,
and then reacted in an inert solvent in the presence of a base with a chloroformic ester of the formula (IV)

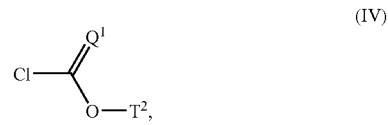

in which
$Q^1$ is O or S
and
$T^2$ is $(C_1-C_{10})$-alkyl,
and where appropriate after subsequent heating in an inert solvent to give compounds of the formula (V-1)

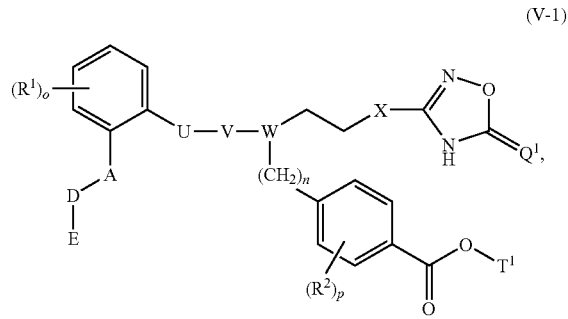

in which $R^1$, $R^2$, A, D, E, U, V, W, X, n, o, p, $Q^1$ and $T^1$ each have the meanings indicated above,
or
[A-2] Compounds of the Formula (II-2)

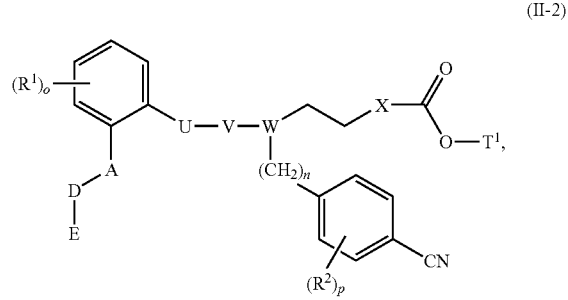

in which $R^1$, $R^2$, A, D, E, U, V, W, X, n, o, p and $T^1$ each have the meanings indicated above, are converted in a manner analogous to process [A-1] into compounds of the formula (V-2)

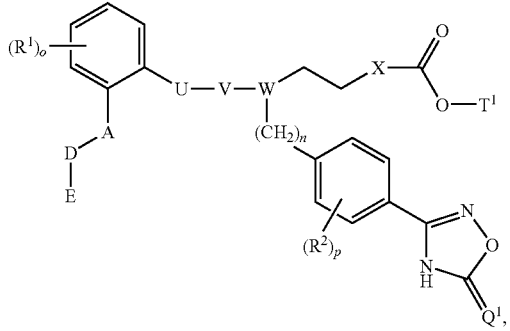

(V-2)

in which $R^1$, $R^2$, A, D, E, U, V, W, X, n, o, p, $Q^1$ and $T^1$ each have the meanings indicated above, or

[B-1] Compounds of the Formula (VI-1)

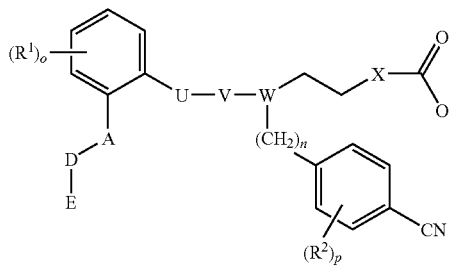

(VI-1)

in which $R^1$, $R^2$, A, D, E, U, V, W, X, n, o and p each have the meanings indicated above, are initially converted with hydrazine in an inert solvent into compounds of the formula (VII-1)

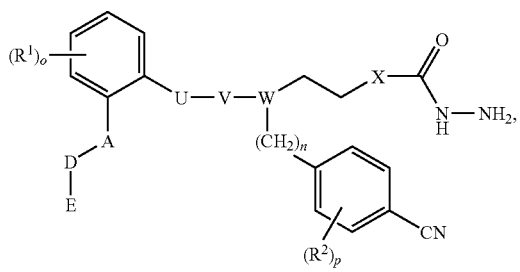

(VII-1)

in which $R^1$, $R^2$, A, D, E, U, V, W, X, n, o and p each have the meanings indicated above, and then reacted in an inert solvent with phosgene or a phosgene derivative such as, for example, di- or triphosgene to give compounds of the formula (VIII-1)

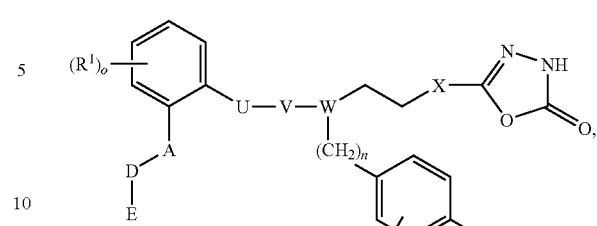

(VIII-1)

in which $R^1$, $R^2$, A, D, E, U, V, W, X, n, o and p each have the meanings indicated above, or Compounds of the Formula (VI-2)

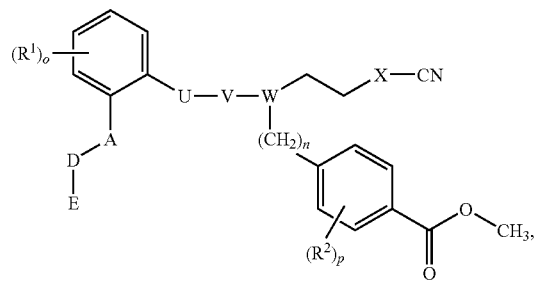

(VI-2)

in which $R^1$, $R^2$, A, D, E, U, V, W, X, n, o and p each have the meanings indicated above, are converted in a manner analogous to process [B-1] into compounds of the formula (VIII-2)

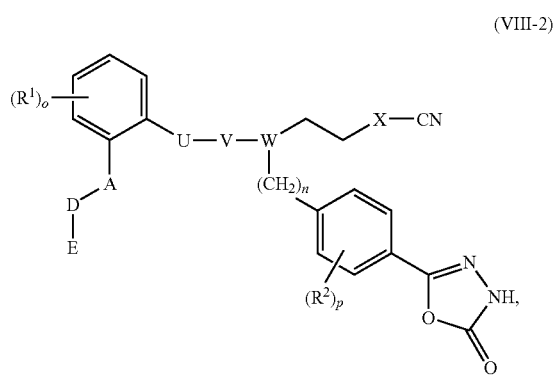

(VIII-2)

in which $R^1$, $R^2$, A, D, E, U, V, W, X, n, o and p each have the meanings indicated above, or

[C-1] Compounds of the Formula (IX-1)

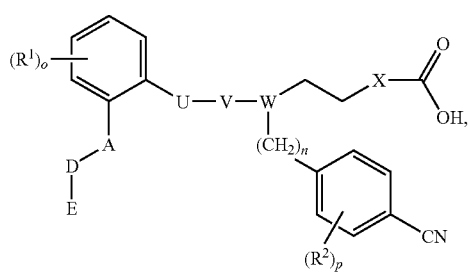
(IX-1)

in which $R^1$, $R^2$, A, D, E, U, V, W, X, n, o and p each have the meanings indicated above,
are initially converted in an inert solvent with oxalyl chloride, thionyl chloride or phosphoryl chloride into the corresponding carbonyl chlorides of the formula (X-1)

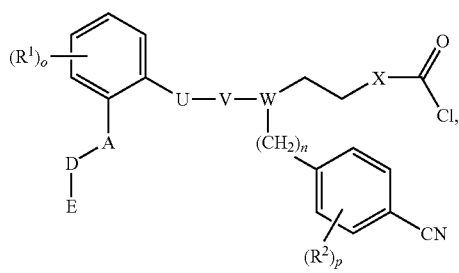
(X-1)

in which $R^1$, $R^2$, A, D, E, U, V, W, X, n, o and p each have the meanings indicated above, these are then reacted in an inert solvent with a semicarbazide of the formula (XI)

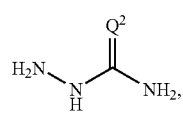
(XI)

in which
$Q^2$ is O, S or NH,
to give compounds of the formula (XII-1)

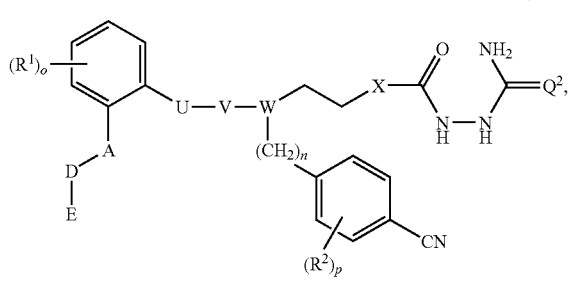
(XII-1)

in which $R^1$, $R^2$, A, D, E, U, V, W, X, n, o, p and $Q^2$ each have the meanings indicated above, and subsequently cyclized in the presence of a base with simultaneous hydrolysis of the nitrile group to give compounds of the formula (XII-1)

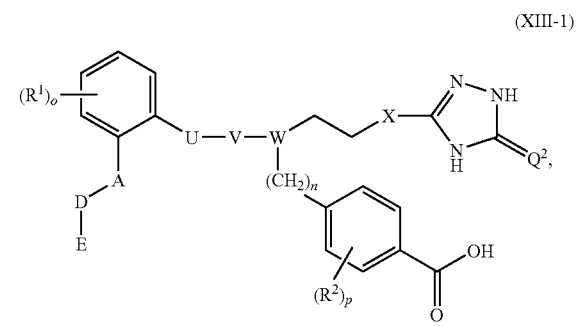
(XIII-1)

in which $R^1$, $R^2$, A, D, E, U, V, W, X, n, o, p and $Q^2$ each have the meanings indicated above,
or
Compounds of the Formula (IX-2)

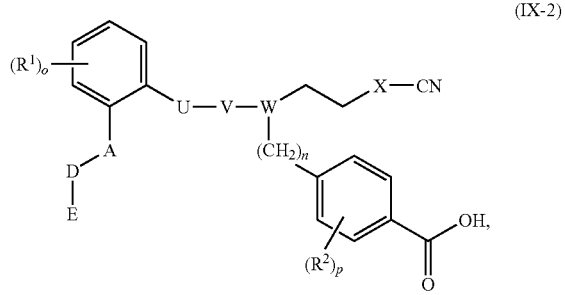
(IX-2)

in which $R^1$, $R^2$, A, D, E, U, V, W, X, n, o and p each have the meanings indicated above,
are converted in a manner analogous to process [C-1] into compounds of the formula (XIII-2)

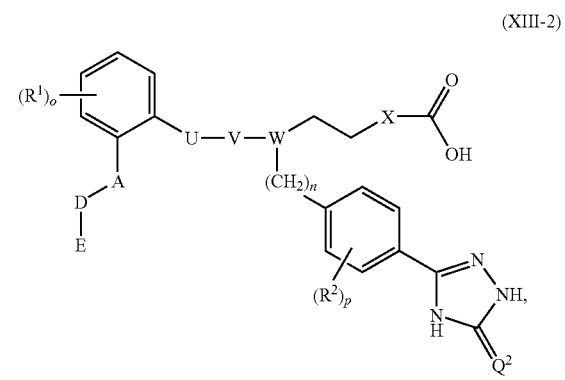
(XIII-2)

in which $R^1$, $R^2$, A, D, E, U, V, W, X, n, o, p and $Q^2$ each have the meanings indicated above,
and the compounds of the formula (V-1), (V-2), (VIII-1) or (VIII-2) resulting in each case are converted by hydrolysis of the ester group —C(O)OT¹ or hydrolysis of the nitrile group into the corresponding carboxylic acids of the formula (I),
and the compounds of the formula (I), including the compounds of the formulae (XIII-1) and (XIII-2), are separated where appropriate by methods known to the skilled person into their enantiomers and/or diastereomers, and/or where appropriate reacted with the appropriate (i) solvents and/or (ii) bases or acids to give the solvates, salts and/or solvates of the salts thereof.

Inert solvents suitable for process step (II-1)→(III-1) are in particular dimethyl sulfoxide or dimethylformamide. The reaction is generally carried out in a temperature range from +50° C. to +100° C.

Process step (III-1)+(IV)→(V-1) is carried out in its first stage (acylation step) preferably in dimethylformamide as solvent in the presence of an organic amine base such as, for example, triethylamine, N,N-diisopropylethylamine, N-methylmorpholine, N-methylpiperidine or pyridine. Pyridine is particularly preferably used as base.

The reagent (IV) [in which $Q^1=O$] preferably employed is 2-ethylhexyl chloroformate. The reaction takes place in this case generally in a temperature range from −20° C. to +40° C., preferably at 0° C. to +20° C.

A heating which is necessary where appropriate in process step (III-1)+(IV)→(V-1) to complete the ring closure to give the 5-oxo-[1,2,4]oxadiazole is preferably carried out as separate reaction stage in an inert solvent such as toluene or xylene in a temperature range from +100° C. to +150° C.

Examples of inert solvents for process step (VI-1)→(VII-1) are alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, or other solvents such as dimethylformamide, dimethyl sulfoxide, N,N'-dimethylpropyleneurea (DMPU) or N-methylpyrrolidone (NMP). It is likewise possible to employ mixtures of the solvents mentioned. Methanol, ethanol, tetrahydrofuran or mixtures thereof are preferred.

The reaction (VI-1)→(VII-1) is generally carried out in a temperature range from +20° C. to +80° C.

Examples of inert solvents for process step (VII-1)→(VIII-1) are halohydrocarbons such as dichloromethane, trichloromethane, tetrachloromethane, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, or hydrocarbons such as benzene, xylene, toluene, hexane, cyclohexane or petroleum fractions. It is likewise possible to employ mixtures of the solvents mentioned. Dioxane is preferably used.

The reaction (VII-1)→(VIII-1) is generally carried out in a temperature range from +50° C. to +150° C., preferably at +80° C. to +120° C.

Process step (IX-1)→(X-1) is carried out with usual chlorinating agents such as, for example, oxalyl chloride, thionyl chloride or phosphoryl chloride. Oxalyl chloride is preferably employed in the presence of small amounts of dimethylformamide. The reaction generally takes place in inert solvents such as tetrahydrofuran or toluene in a temperature range from 0° C. to +120° C.

Examples of inert solvents for process step (X-1)+(XI)→(XII-1) are halohydrocarbons such as dichloromethane, trichloromethane, tetrachloromethane, trichloroethane, tetrachloroethane or 1,2-dichloroethane, ethers such as diethyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as dimethylformamide, dimethyl sulfoxide, N,N'-dimethylpropyleneurea (DMPU), N-methylpyrrolidone (NMP), acetonitrile or else water. It is likewise possible to employ mixtures of the solvents mentioned. Tetrahydrofuran or tetrahydrofuran/water mixtures are preferred.

The reaction (X-1)+(XI)→(XII-1) is generally carried out in a temperature range from −20° C. to +30° C.

The cyclization in process step (XII-1)→(XIII-1) is advantageously carried out with simultaneous hydrolysis of the nitrile group. Bases such as sodium hydroxide or potassium hydroxide are particularly suitable for this purpose. The reaction preferably takes place in water or alcoholic solvents such as methanol, ethanol, n-propanol, isopropanol, n-butanol or tert-butanol or in mixtures of these alcohols with water. Water or n-propanol are particularly preferred. The reaction is generally carried out in a temperature range from +50° C. to +150° C., preferably at +90° C. to +110° C.

Hydrolysis of the carboxylic esters in process step (V-1)/(V-2)→(I) and of the nitriles in process step (VIII-1)/(VIII-2)→(I) takes place by conventional methods, by treating the esters and nitrites respectively in inert solvents with acids or bases, and with the latter converting the initially produced salts into the free carboxylic acids by treatment with acid. The ester cleavage in the case of tert-butyl esters preferably takes place with acids.

Inert solvents suitable for this purpose are water or the organic solvents usual for ester cleavage. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichlormethane, dimethylformamide or dimethyl sulfoxide. It is likewise possible to employ mixtures of the solvents mentioned. In the case of a basic ester hydrolysis, preferably mixtures of water with dioxane, tetrahydrofuran, methanol and/or ethanol are employed, and in the case of nitrile hydrolysis preferably water or n-propanol is employed. In the case of reaction with trifluoroacetic acid, preferably dichloromethane is used, and in the case of reaction with hydrogen chloride, preferably tetrahydrofuran, diethyl ether, dioxane or water is used.

Suitable bases are the usual inorganic bases. These preferably include alkali metal or alkaline earth metal hydroxides such as, for example, sodium, lithium, potassium or barium hydroxide, or alkali metal or alkaline earth metal carbonates such as sodium, potassium or calcium carbonate. Sodium, potassium or lithium hydroxide are particularly preferred.

Suitable acids for the ester cleavage are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, where appropriate with addition of water. Hydrogen chloride or trifluoroacetic acid are preferred in the case of the tert-butyl esters, and hydrochloric acid in the case of the methyl esters.

The ester cleavage generally takes place in a temperature range from 0° C. to +100° C., preferably at +20° C. to +60° C. The nitrile hydrolysis is generally carried out in a temperature range from +50° C. to +150° C., preferably at +90° C. to +110° C.

The reactions mentioned can be carried out under atmospheric, elevated or reduced pressure (e.g. from 0.5 to 5 bar). They are generally carried out in each case under atmospheric pressure.

The compounds of the formulae (II-1), (II-2), (VI-1), (VI-2), (IX-1) and (IX-2) can be prepared by the processes described in EP 0 341 551-A1, WO 01/19355, WO 01/19776, WO 01/19778, WO 01/19780, WO 02/070462 and WO 02/070510 (compare also reaction schemes 1-18 hereinafter);

the content relating thereto in these publications is hereby expressly included as part of the disclosure.

The compounds of the formulae (IV) and (XI) are commercially available, disclosed in the literature or can be prepared in a simple manner by processes disclosed in the literature.

Separation of the compounds of the invention into the corresponding enantiomers and/or diastereomers can take place where appropriate, depending on expediency, even at the stage of the compounds (II-1), (II-2), (V-1), (V-2), (VI-1), (VI-2), (VIII-1), (VIII-2), (IX-1), (IX-2) or of the phenolic precursors thereof depicted in schemes 11-18, which are then reacted further in separated form in accordance with the described process sequences. Such a fractionation of the stereoisomers can be carried out by conventional methods known to the skilled person; chromatographic methods or separation via diastereomeric salts are preferably used.

The preparation of the compounds of the invention can be illustrated by the following synthesis schemes:

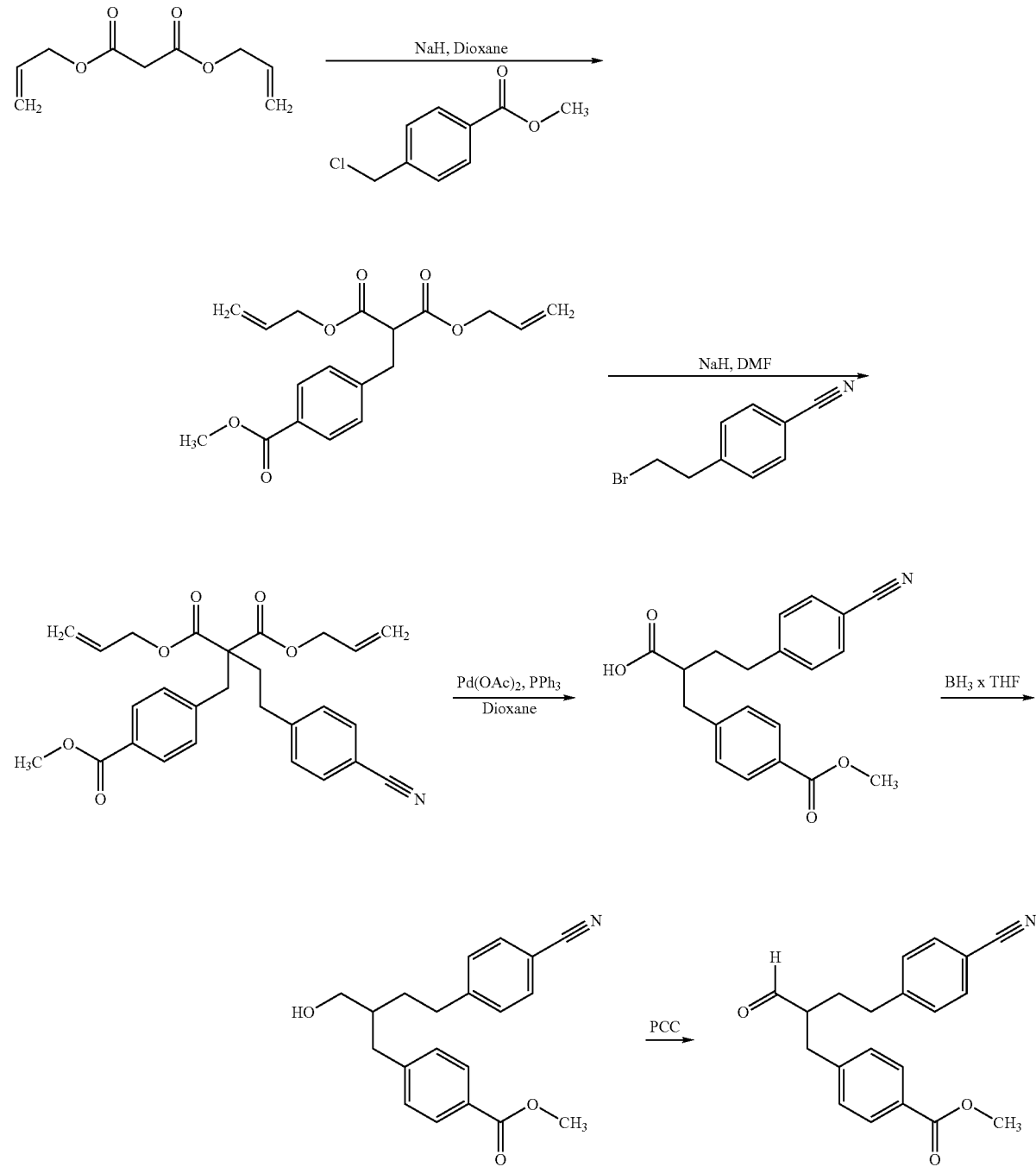

Scheme 2
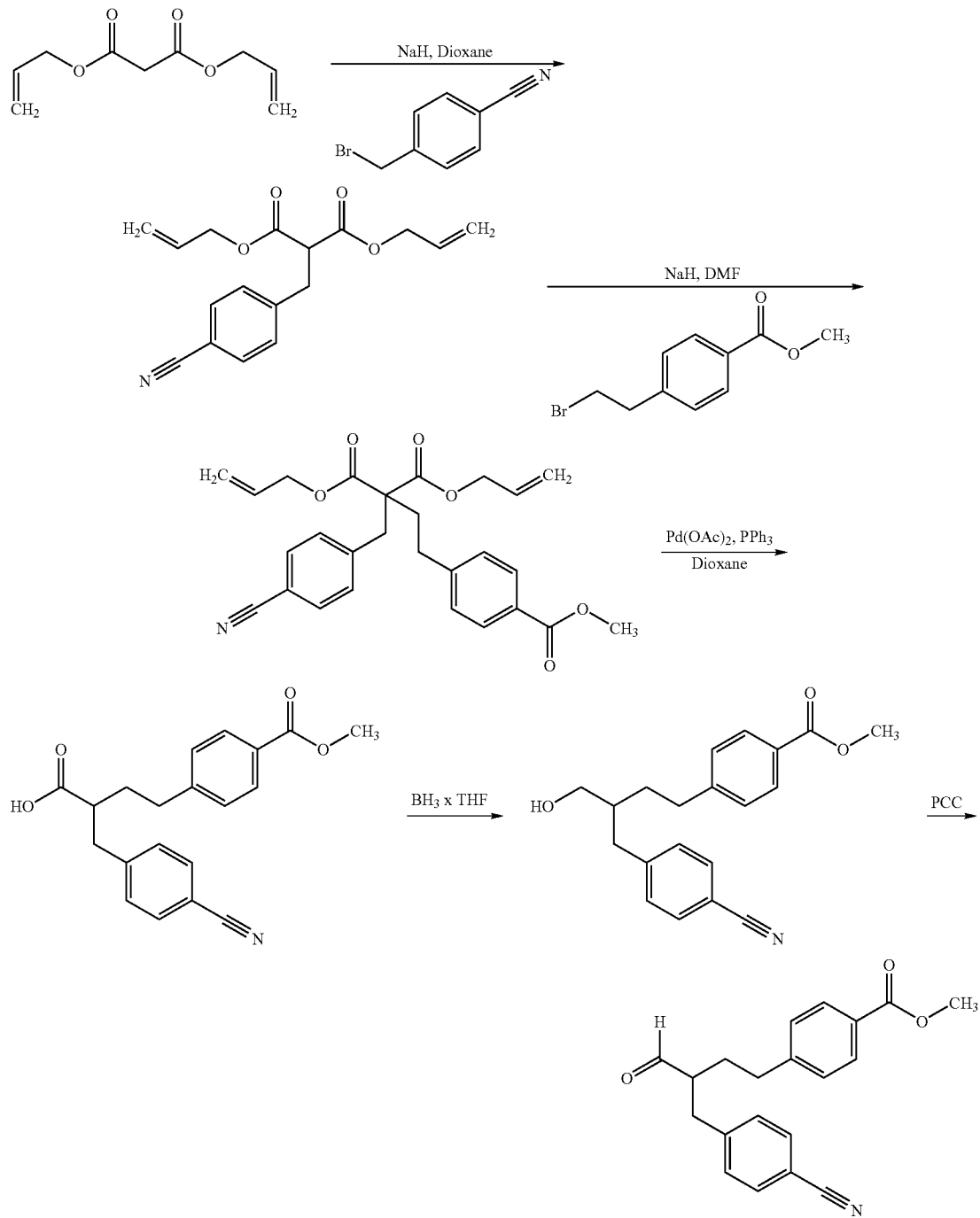
Scheme 3
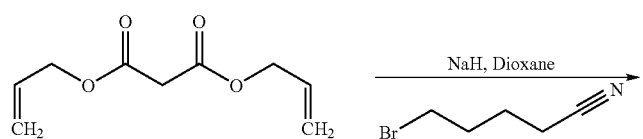

-continued
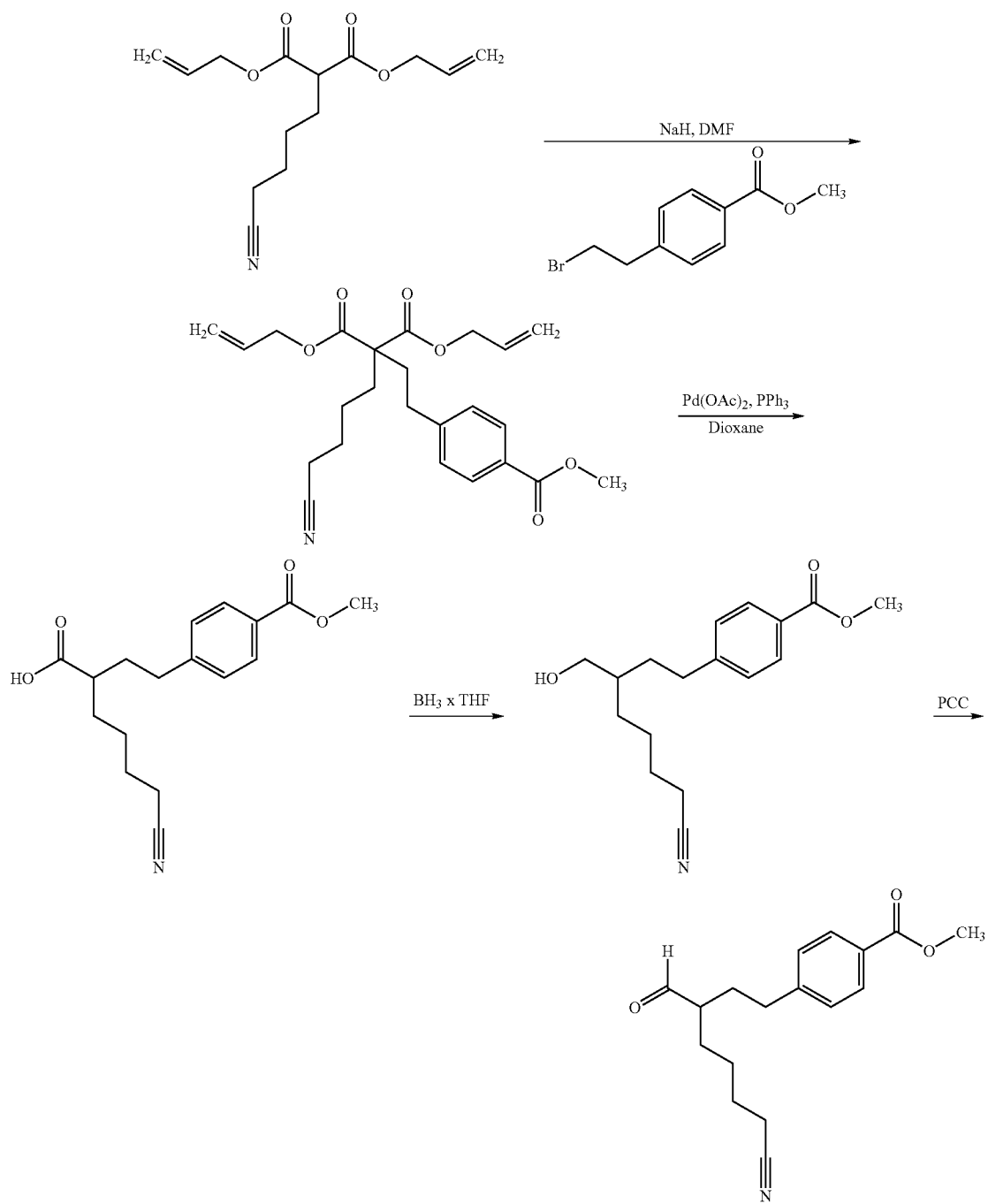
Scheme 4
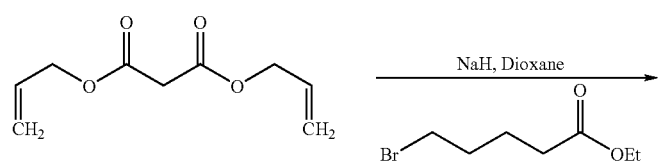

-continued
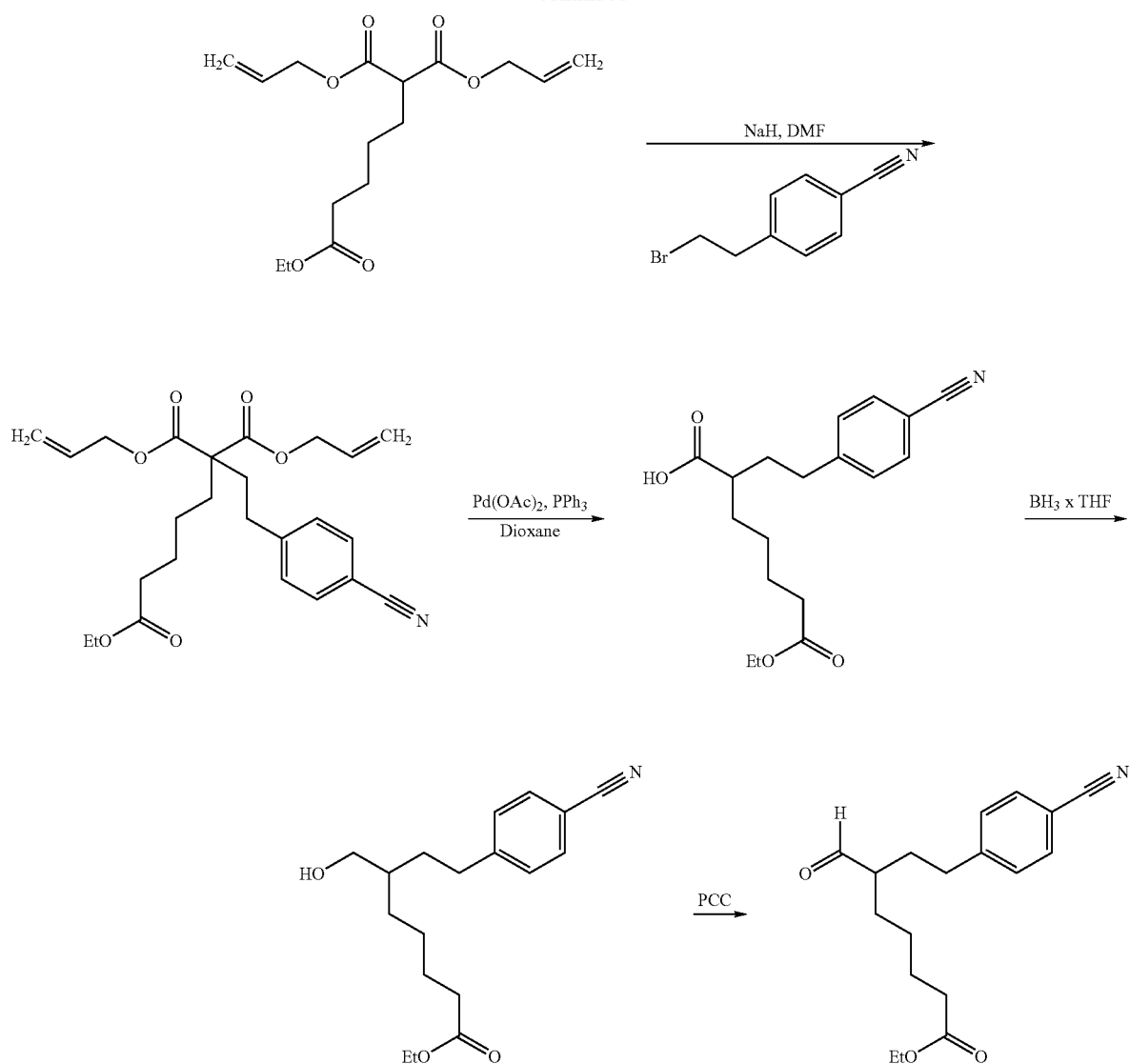
Scheme 5
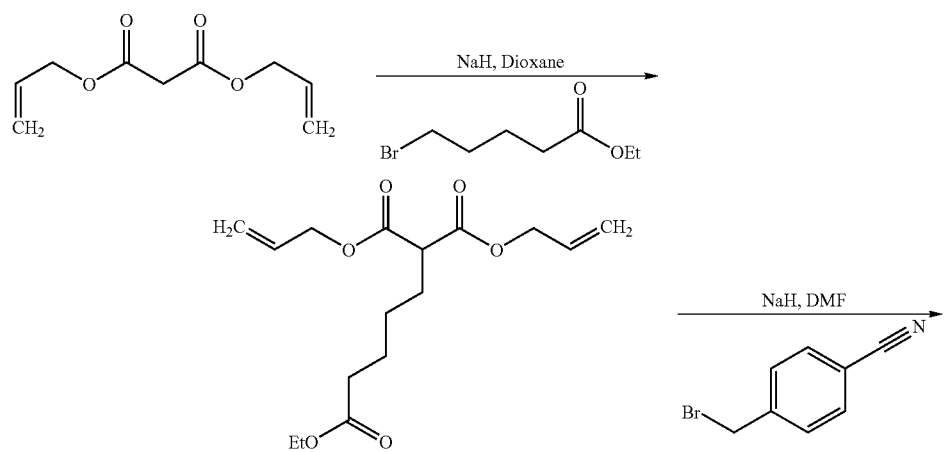

27 28
-continued
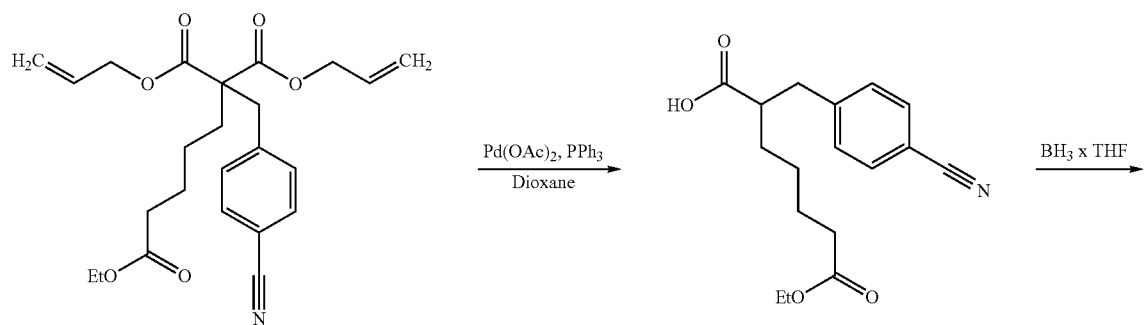
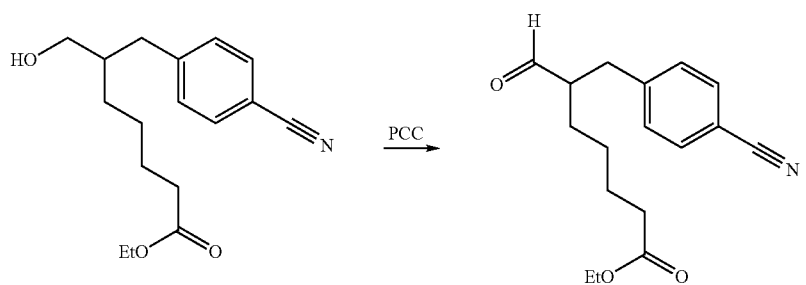
Scheme 6
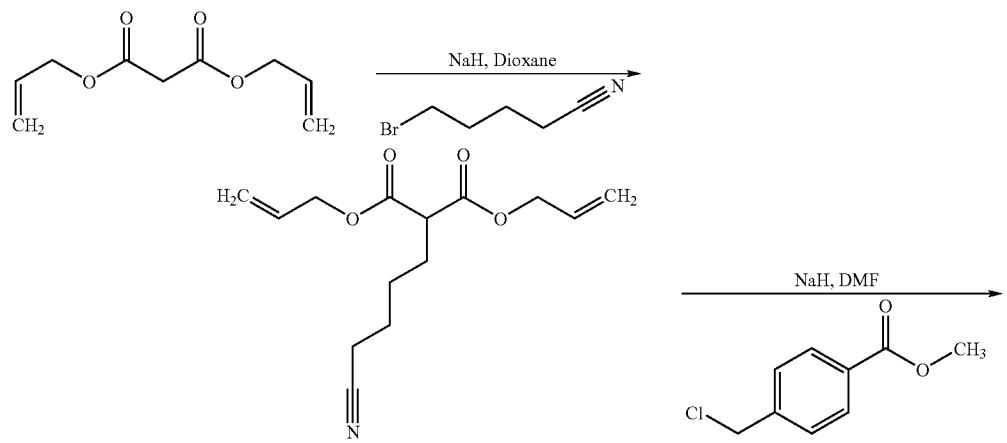
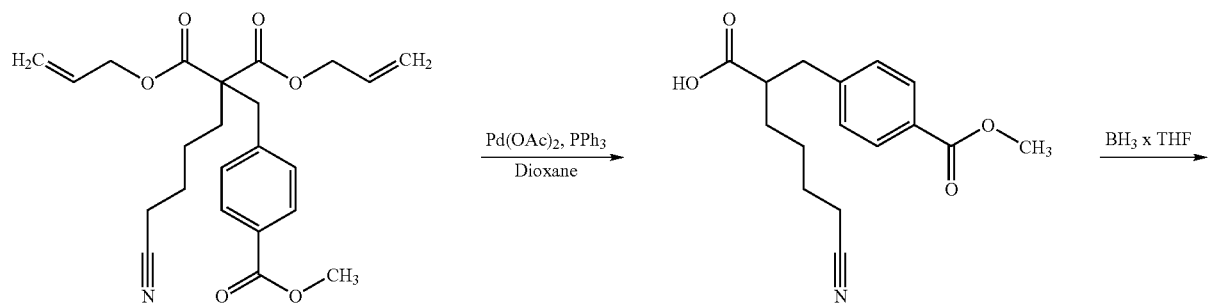

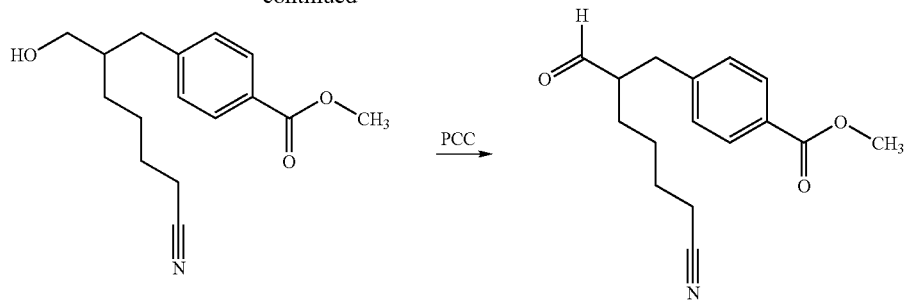
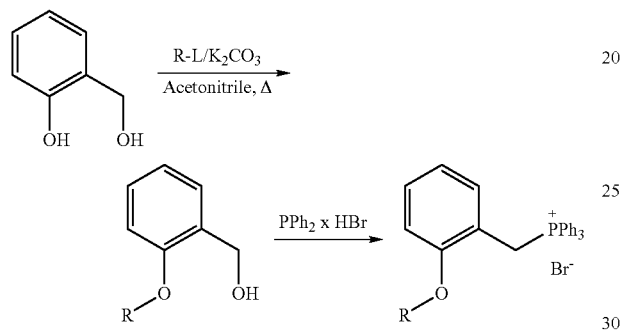
Scheme 7
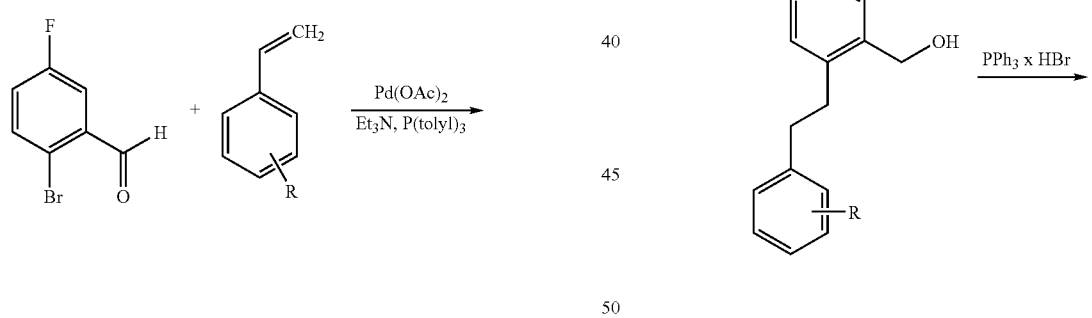
Scheme 8
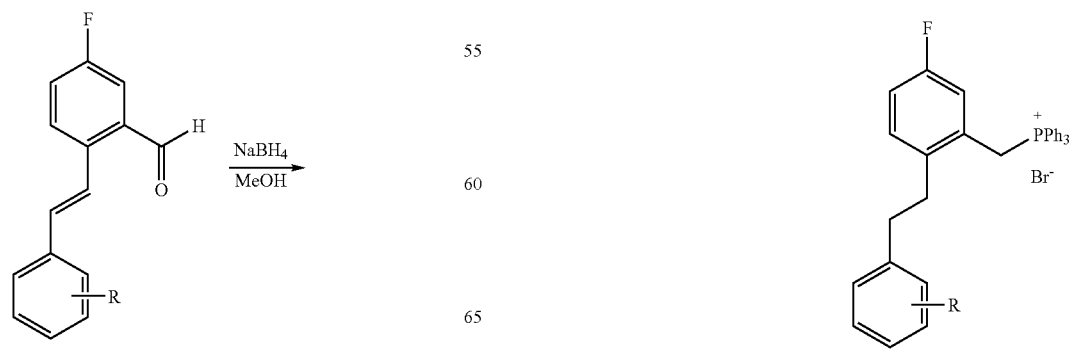

Scheme 9
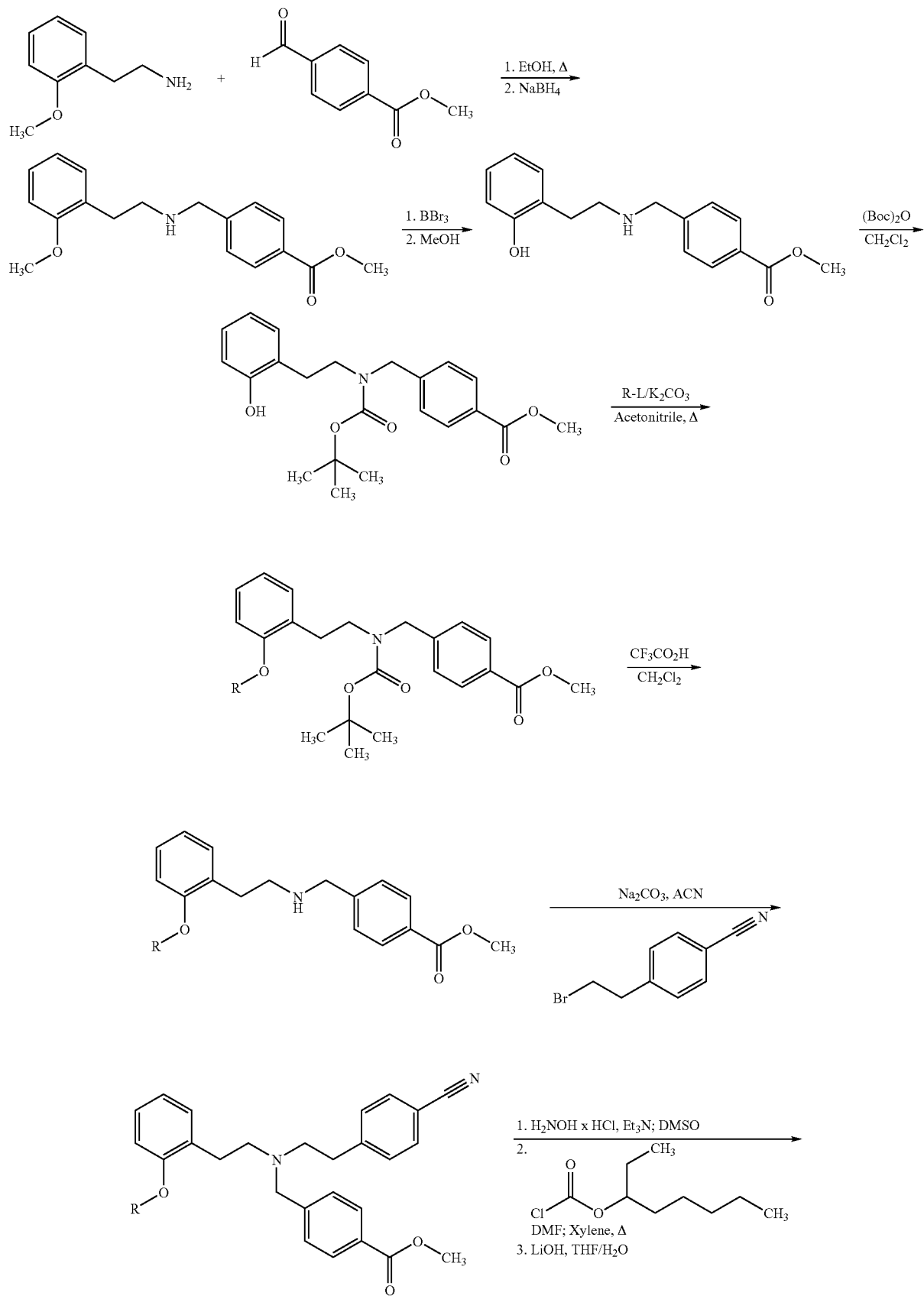

-continued
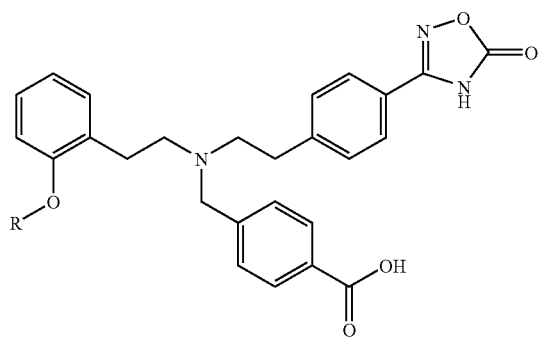
Scheme 10
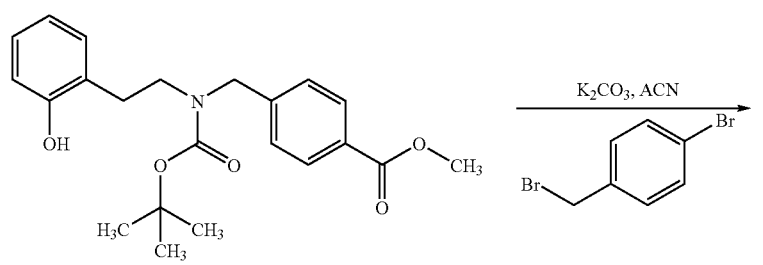
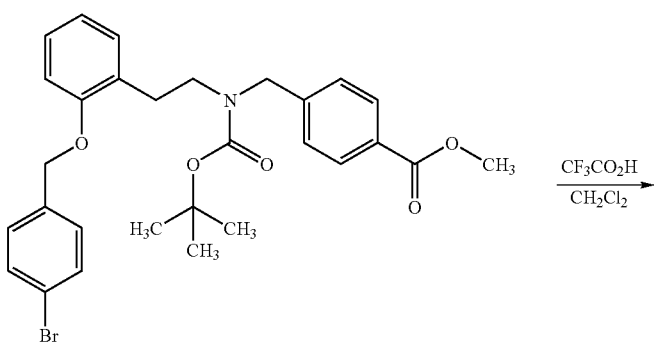
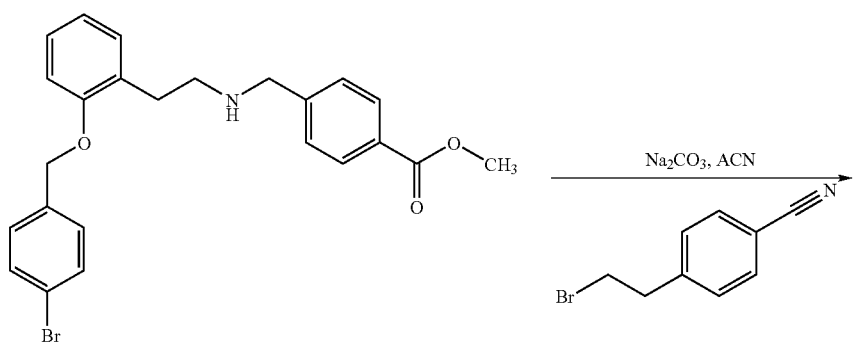

-continued
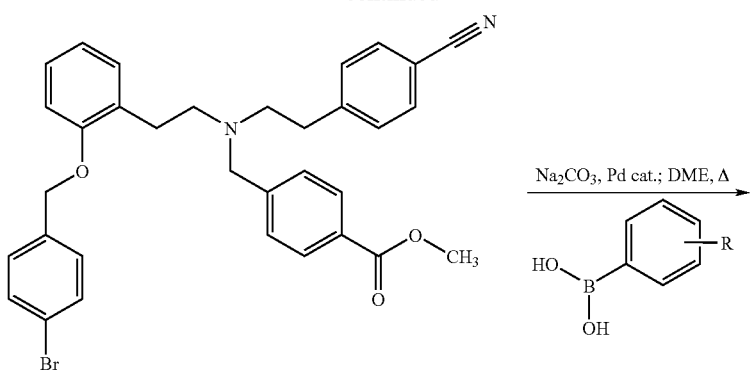
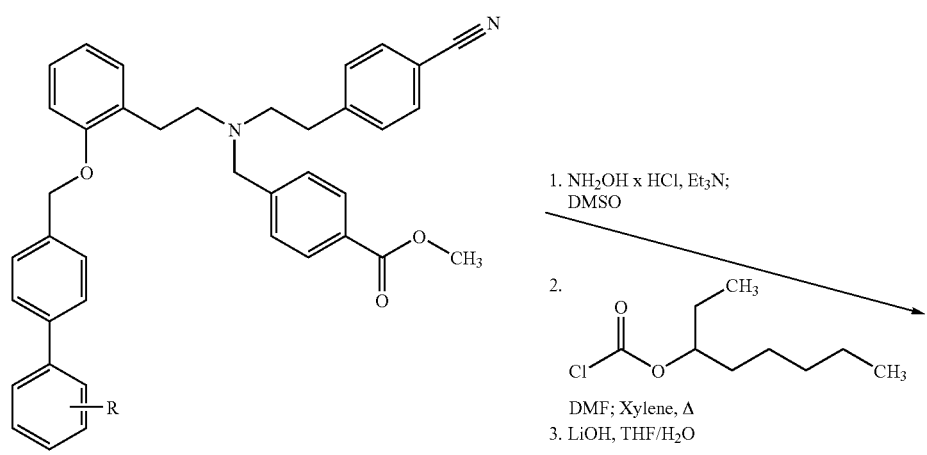
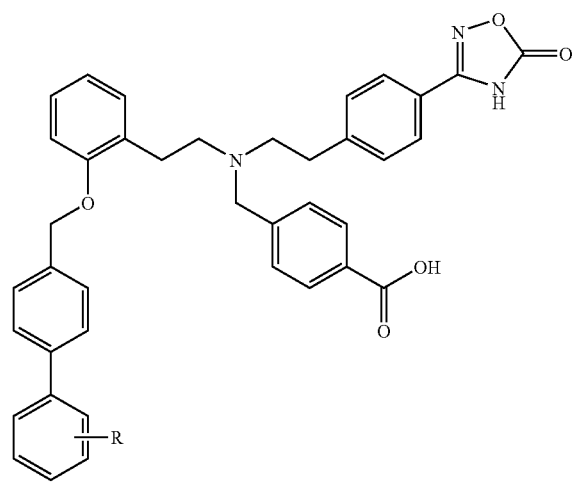

Scheme 11
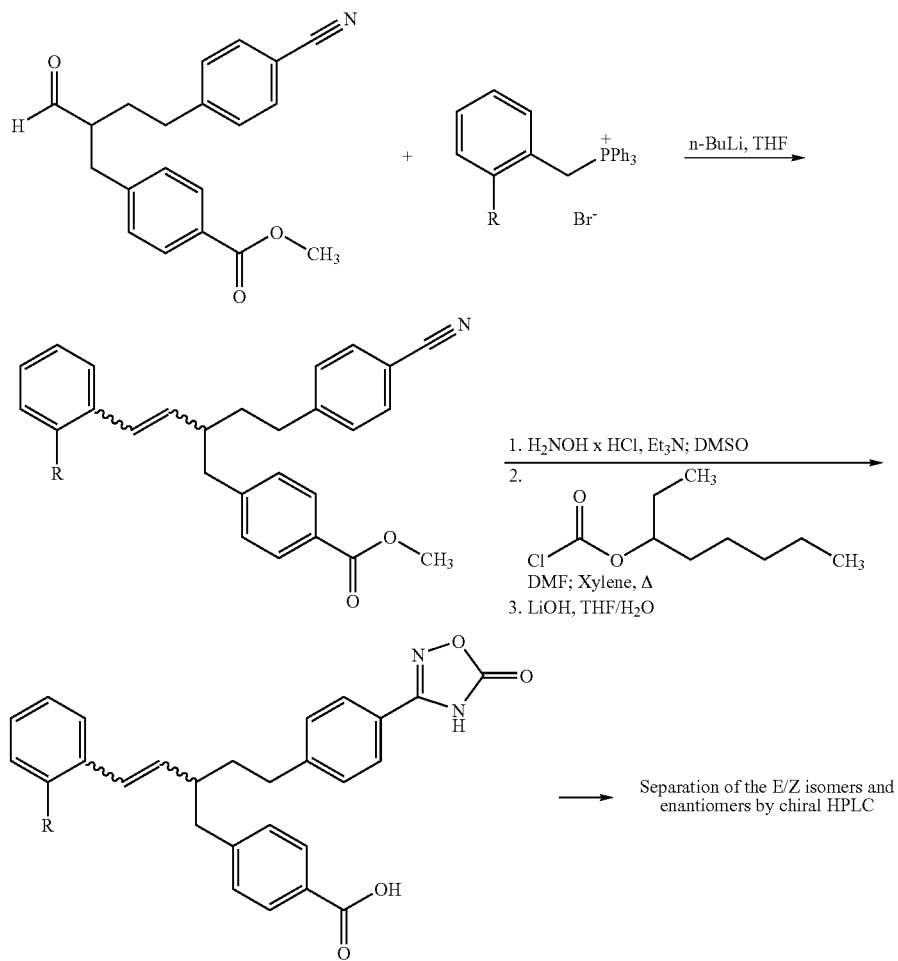
Scheme 12
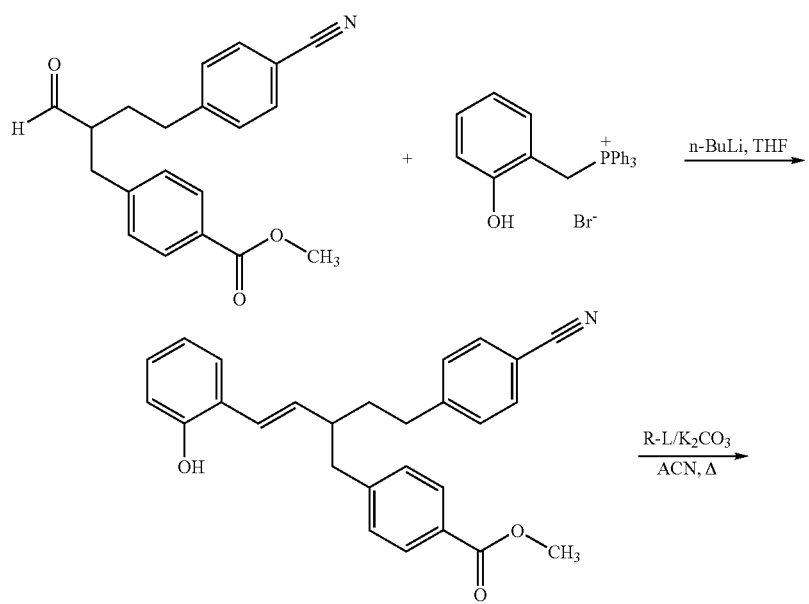

-continued
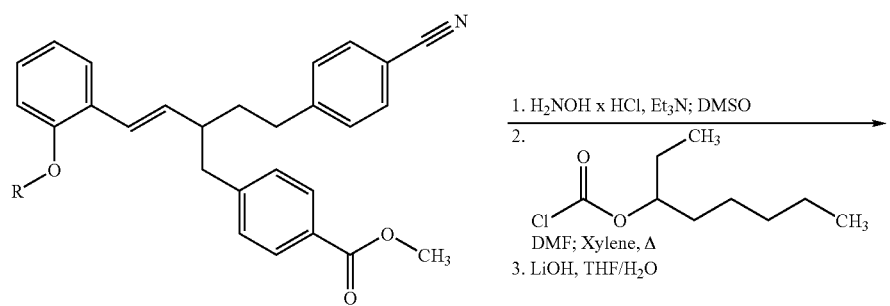
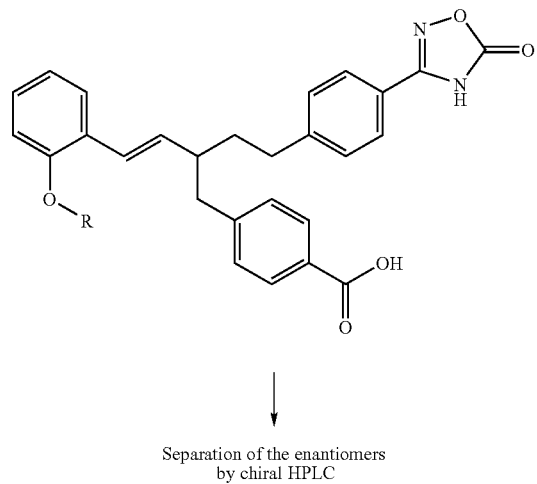
Separation of the enantiomers
by chiral HPLC
Scheme 13
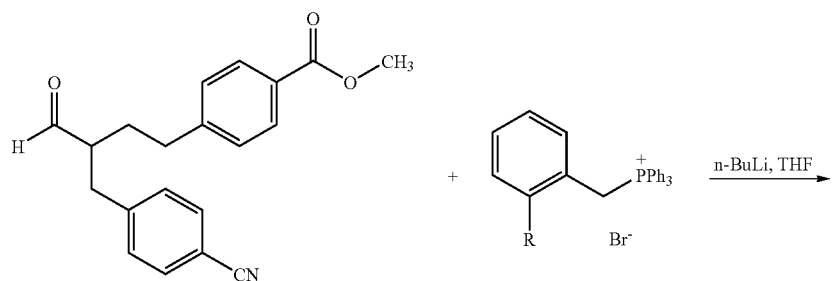
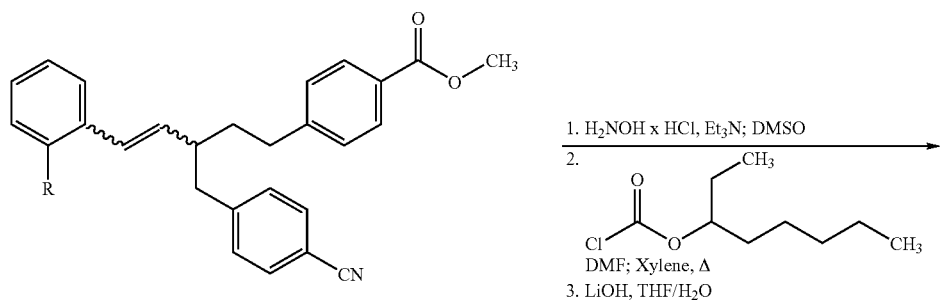

-continued
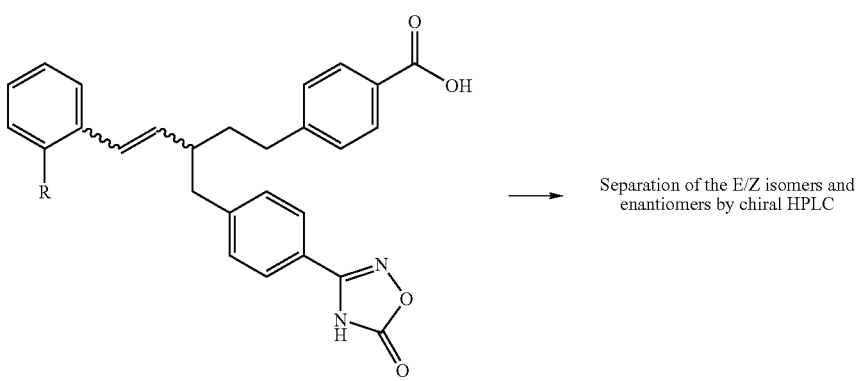
Separation of the E/Z isomers and enantiomers by chiral HPLC
Scheme 14
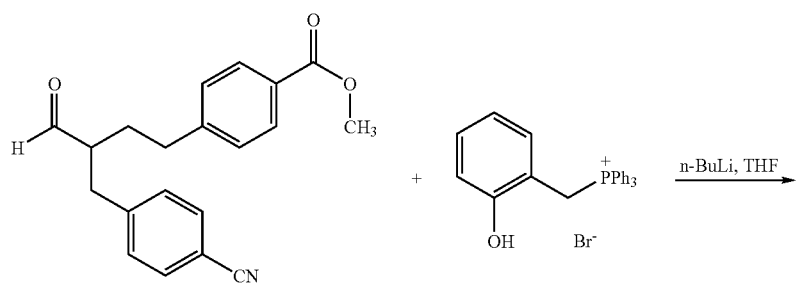
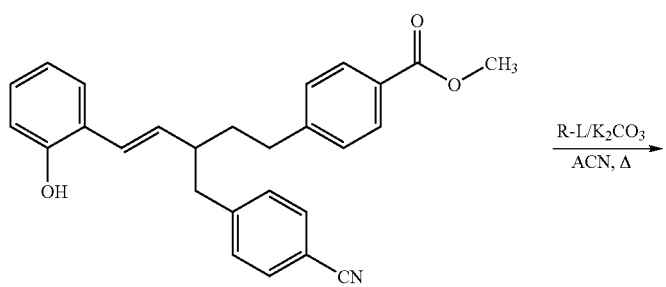
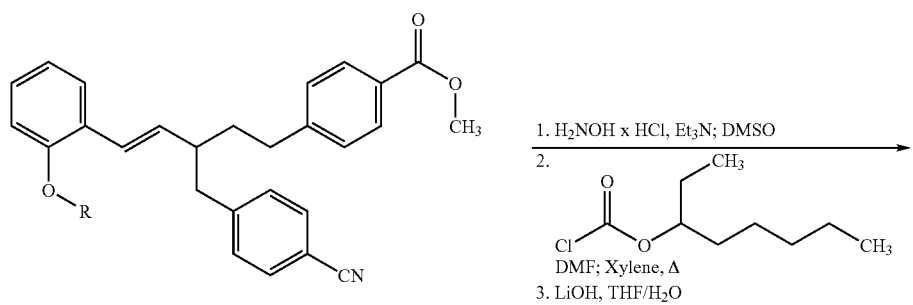

-continued
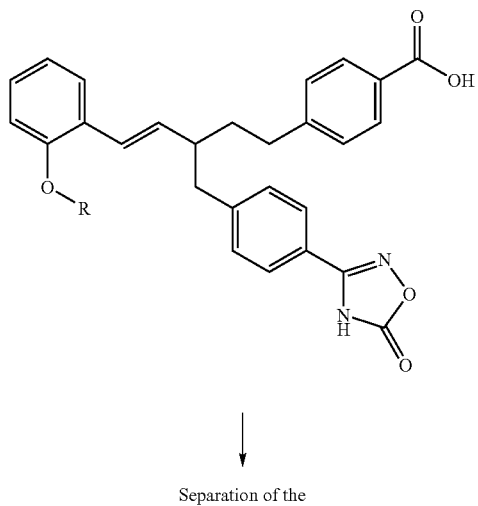
Separation of the
enantiomers by chiral HPLC
Scheme 15
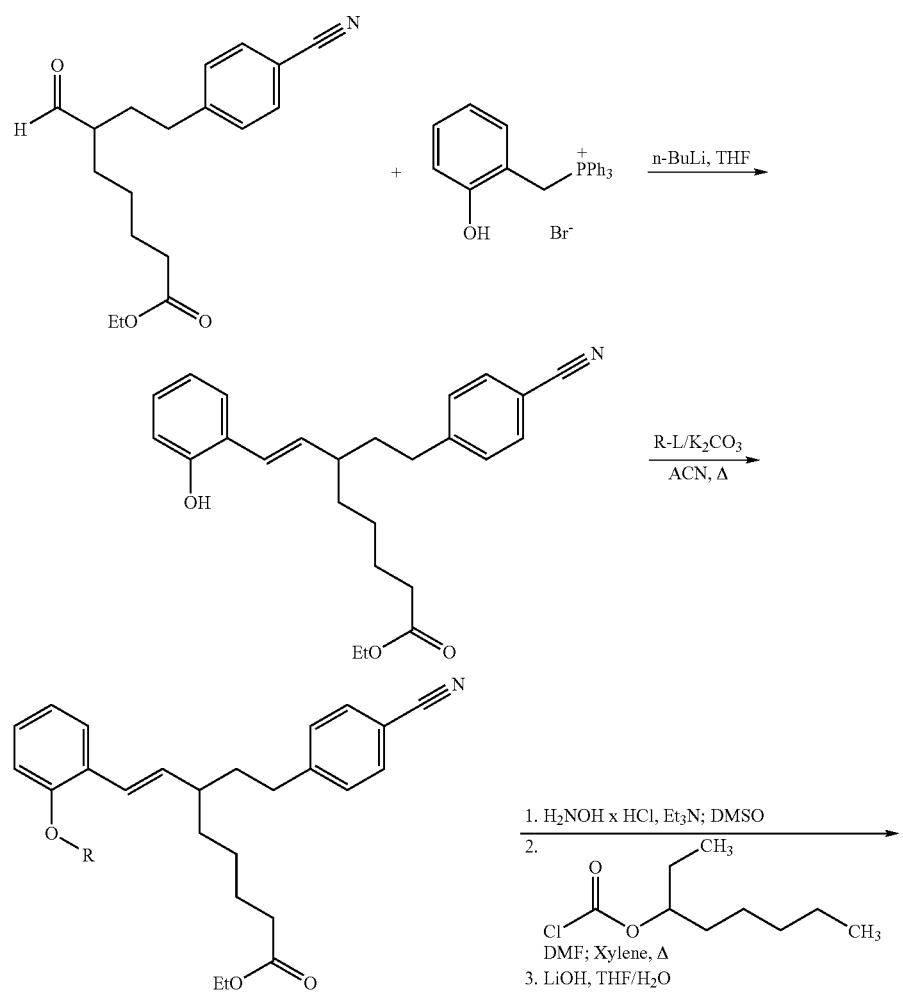

-continued
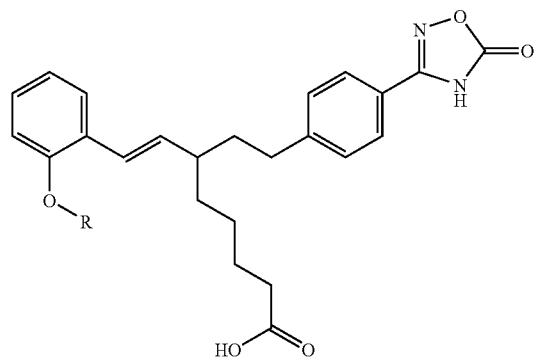
Separation of the enantiomers by chiral HPLC
Scheme 16
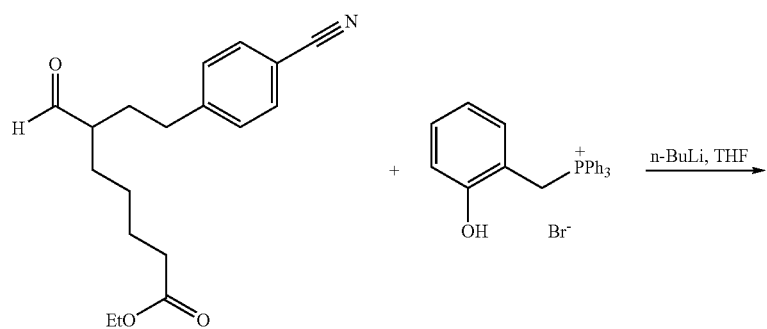
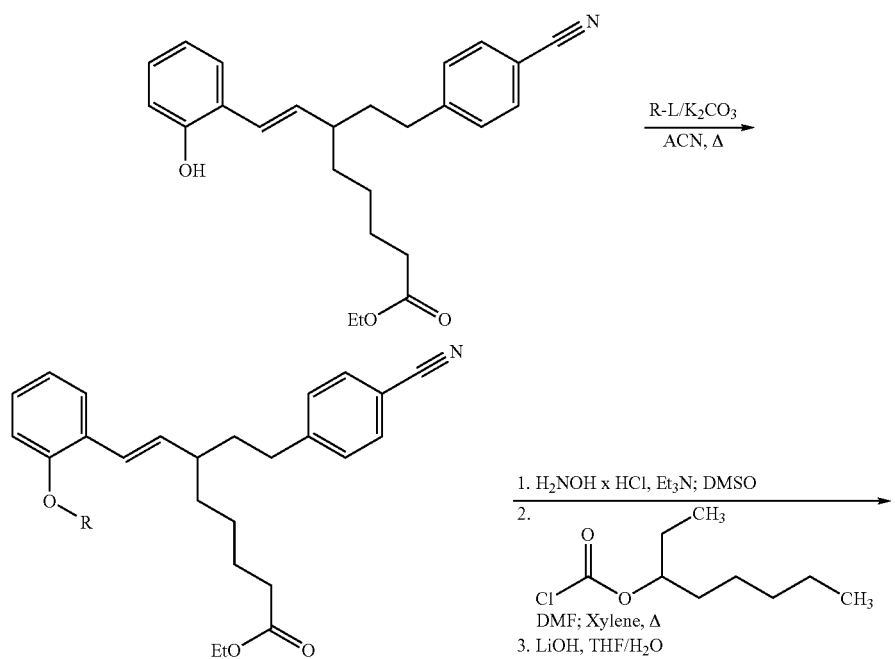
1. H$_2$NOH x HCl, Et$_3$N; DMSO
2. [chloroformate reagent shown] DMF; Xylene, Δ
3. LiOH, THF/H$_2$O

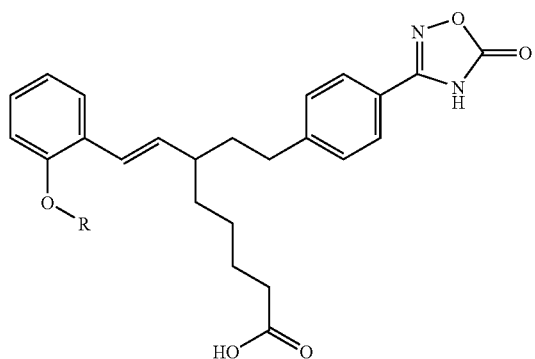
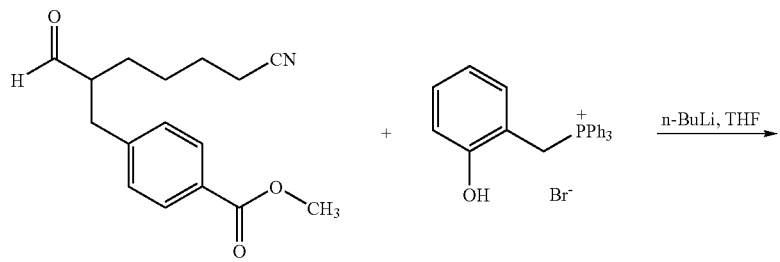
Scheme 17
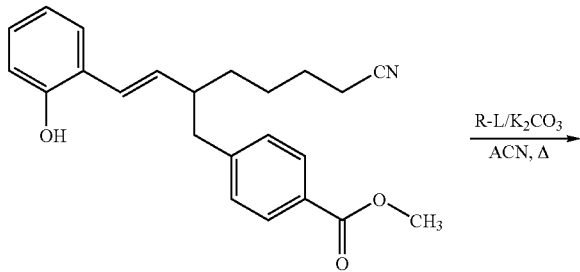
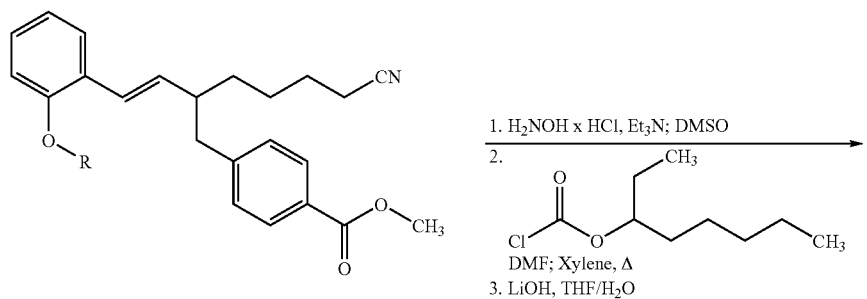

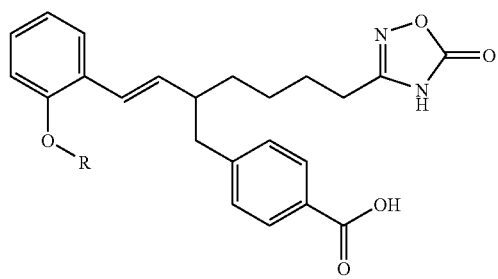
Separation of the enantiomers by chiral HPLC
Scheme 18
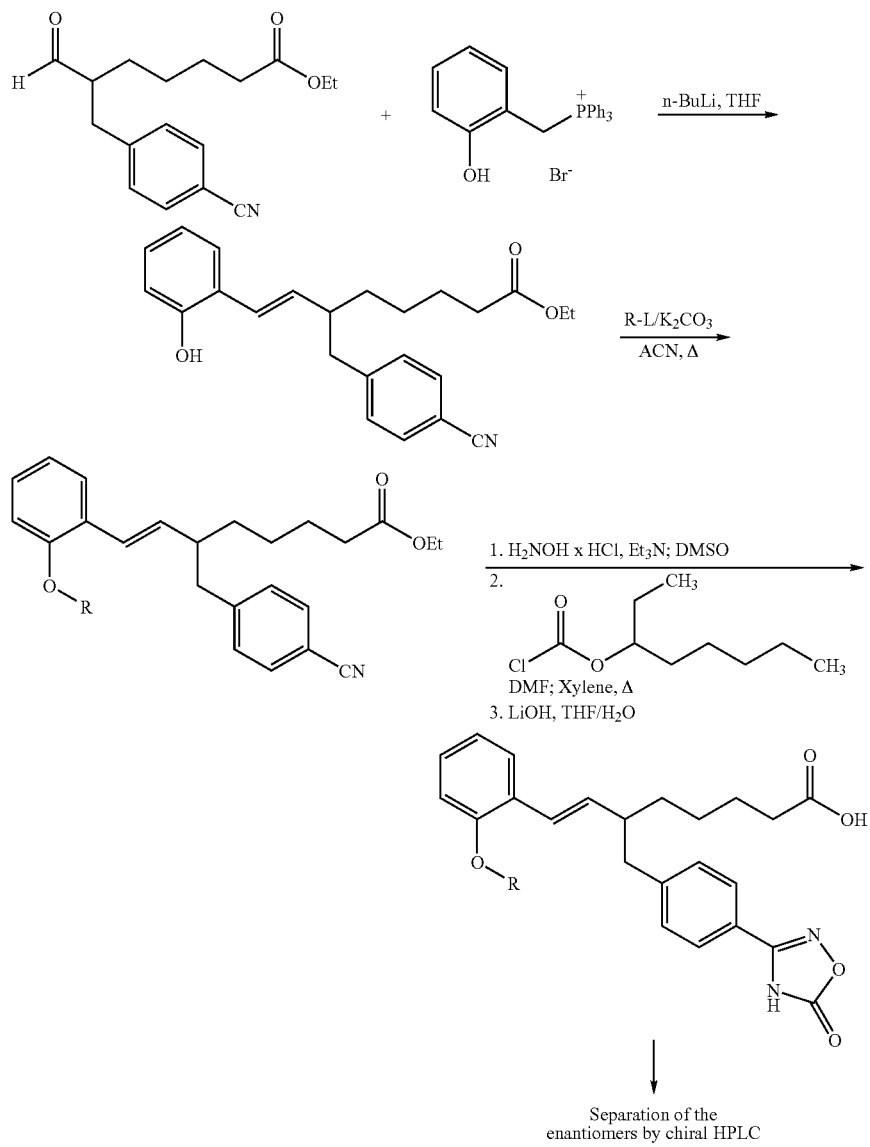
Separation of the enantiomers by chiral HPLC

[Abbreviations: Ac=acetyl; ACN=acetonitrile; (Boc)$_2$O=di-tert-butyl pyrocarbonate; Bu=butyl; DME=1,2-dimethoxyethane; DMF=dimethylformamide; DMSO=dimethyl sulfoxide; Et=ethyl; cat.=catalyst; L=leaving group, e.g. halogen; Me=methyl; PCC=pyridinium chlorochromate; Ph=phenyl; THF=tetrahydrofuran].

The compounds according to the invention have valuable pharmacological properties and can be used for the prevention and treatment of disorders in humans and animals.

The compounds of the present invention exhibit, as particular and surprising feature, advantageous pharmacokinetic properties such as, for example, an increased bioavailability and/or a prolonged duration of action after oral administration.

The compounds according to the invention lead to vasorelaxation, to an inhibition of platelet aggregation and to a reduction in blood pressure, and to an increase in coronary blood flow. These effects are mediated by direct activation of soluble guanylate cyclase and an intracellular increase in cGMP.

The compounds according to the invention can therefore be employed in medicaments for the treatment of cardiovascular disorders such as, for example, for the treatment of high blood pressure and heart failure, stable and unstable angina pectoris, pulmonary hypertension, peripheral and cardiac vascular disorders, arrhythmias, for the treatment of thromboembolic disorders and ischemias such as myocardial infarction, stroke, transistoric and ischemic attacks, disturbances of peripheral blood flow, prevention of restenosis as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, and incontinence, osteoporosis, glaucoma, and gastroparesis.

The compounds according to the invention can additionally be used for the treatment of primary and secondary Raynaud's phenomenon, of microcirculation impairments, claudication, peripheral and autonomic neuropathies, diabetic microangiopathies, diabetic retinopathy, diabetic ulcers on the extremities, CREST syndrome, erythematosis, onychomycosis and rheumatic disorders.

The compounds according to the invention are furthermore suitable for the treatment of respiratory distress syndromes and chronic obstructive airway disorders (COPD), of acute and chronic renal failure and for promoting wound healing.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequalae of cerebral infarctions such as stroke, cerebral ischemias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Examples of suitable combination active ingredients which may be preferably mentioned are:

organic nitrates and NO donors such as, for example, sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;

NO-independent but heme-dependent stimulators of guanylate cyclase, such as, in particular, the compounds described in WO 00/06568, WO 00/06569, WO 02/42301 and WO 03/095451;

agents having antithrombotic activity, for example and preferably from the group of platelet aggregation inhibitors, of anticoagulants or of profibrinolytic substances;

active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidine or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, BAY 59-7939, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinapril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein(a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, Cholesta-Gel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations

| | |
|---|---|
| abs. | Absolute |
| aq. | Aqueous |
| CI | Chemical ionization (in MS) |
| DCI | Direct chemical ionization (in MS) |
| DMF | Dimethylformamide |
| DMSO | Dimethyl sulfoxide |
| ee | Enantiomeric excess |
| EI | Electron impact ionization (in MS) |
| eq. | Equivalent(s) |
| ESI | Electrospray ionization (in MS) |
| Ex. | Example |
| GC | Gas chromatography |
| h | Hour(s) |
| HPLC | High pressure, high performance liquid chromatography |
| LC/MS | Coupled liquid chromatography-mass spectroscopy |
| Min | Minute(s) |
| MS | Mass spectroscopy |
| NMR | Nuclear magnetic resonance spectroscopy |
| $R_f$ | Retention index (in TLC) |
| RT | Room temperature |
| $R_t$ | Retention time (in HPLC) |
| THF | Tetrahydrofuran |
| TLC | Thin-layer chromatography |
| UV | Ultraviolet spectroscopy |
| v/v | Volume to volume ratio (of a solution) |

LC/MS Methods:
Method 1 (LC-MS)

MS instrument type: Micromass ZQ; HPLC instrument type: HP 1100 series; UV DAD; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 2 (LC-MS)

MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; TV detection: 210 nm.
Method 3 (LC-MS)

Instrument: Micromass Platform LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 4 (LC-MS)

Instrument: Micromass Quattro LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 mil/min→2.5 min/3.0 min/4.5 min 2 ml/min; oven: 50° C.; UV detection: 208-400 nm.
Method 5 (LC-MS)

Instrument: Micromass Platform LCZ with HPLC Agilent Series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.
Method 6 (LC-MS)

MS instrument type: Micromass ZQ; HPLC instrument type: HP 1100 series; UV DAD; column: Phenomenex, Gemini 3μ 30 mm×3000 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min→1 ml/min→2.5 min/3.0 min/4.5 min 2 ml/min; oven: 50° C.; UV detection: 210 nm.
GC/MS Methods:
Method 1 (GC-MS)

Instrument: Micromass GCT, GC6890; column: Restek RTX-35MS, 30 m×250 μm×0.25 μm; constant helium flow: 0.88 ml/min; oven: 60° C.; inlet: 250° C.; gradient: 60° C. (hold for 0.30 min), 50° C./min→120° C., 16° C./min→250° C., 30° C./min→300° C. (hold for 1.7 min).
Method 2 (GC-MS)

Instrument: Micromass GCT, GC6890; column: Restek RTX-35 MS, 30 m×250 μm×0.25 μm; constant helium flow: 0.88 ml/min; oven: 60° C.; inlet: 250° C.; gradient: 60° C. (hold for 0.30 min), 50° C./min→120° C., 16° C./min→250° C., 30° C./min→300° C. (hold for 8.7 min).
HPLC Methods:
Method 1 (HPLC)

Instrument: HP 1100 with DAD detection; column: Kromasil 100 RP-18, 60 mm×2.1 mm, 3.5 μm; eluent A: 5 ml of HClO$_4$ (70%)/l of water, eluent B: acetonitrile; gradient: 0 min 2% B→0.5 min 2% B 4.5 min 90% B 9 min 90% B 9.2 min 2% B 10 min 2% B; flow rate: 0.75 ml/min; column temperature: 30° C.; UV detection: 210 nm.
Method 2 (HPLC)

Instrument: HP 1100 with DAD detection; column: Kromasil 100 RP-18, 60 mm×2.1 mm, 3.5 μm; eluent A: 5 ml of HClO$_4$ (70%)/l of water, eluent B: acetonitrile; gradient: 0 min 2% B→0.5 min 2% B→4.5 min 90% B→15 min 90% B→15.2 min 2% B→16 min 2% B; flow rate: 0.75 ml/min; column temperature: 30° C.; UV detection: 210 nm.
Starting Compounds and Intermediates:

Example 1A

Methyl 4-({[2-(2-methoxyphenyl)ethyl] amino}methyl)benzoate

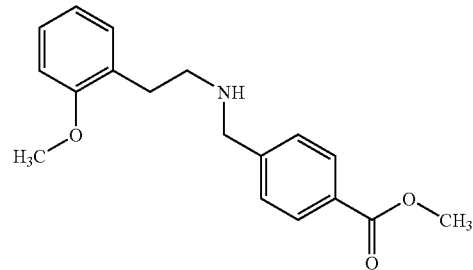

A solution of 92.08 g (0.597 mol) of 2-methoxyphenethylamine and 98 g (0.597 mol) of methyl 4-formylbenzoate in 2 l of ethanol is heated to reflux for 2 hours. The solvent is then stripped off in vacuo, and the resulting residue is dissolved in 1 l of methanol. A total of 46.14 g (1.220 mol) of solid sodium borohydride is added in portions. After stirring at room temperature for two hours, the mixture is poured into water and extracted with ethyl acetate. The organic extract is washed with saturated sodium chloride solution and dried over sodium sulfate. After filtration, the solvent is removed in vacuo. 167.7 g (0.559 mol, 77% yield) of a colorless oil are obtained and are employed in the next stage without further purification.

$^1$H-NMR (200 MHz, DMSO-d$_6$, δ/ppm): 7.90 (2H, d), 7.45 (2H, d), 7.17 (1H, t), 7.12 (1H, d), 6.92 (1H, d), 6.83 (1H, t), 3.83 (3H, s), 3.78 (2H, s), 3.73 (3H, s), 2.75-2.63 (4H, m).

MS (DCI, NH$_3$): 300 (M+H$^+$).

Example 2A

Methyl 4-({[2-(2-hydroxyphenyl)ethyl] amino}methyl)benzoate hydrobromide

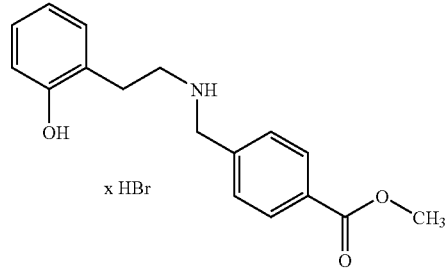

661.4 ml (0.66 mol) of a 1 M solution of boron tribromide in dichloromethane are added to a solution of 60 g (0.2 mol) of methyl 4-({[2-(2-methoxyphenyl)ethyl]amino}methyl)benzoate from Example 1A in 200 ml of dichloromethane at 0° C. Stirring is continued at 0° C. for one hour. Then 300 ml of methanol are added, and the mixture is heated to reflux for 18 hours. The product precipitates on cooling and is filtered off. Further product is obtained after concentrating the mother liquor. The collected product fractions are washed with diethyl ether. 45.04 g (0.16 mol, 56% yield) of a white crystalline solid are obtained.

$R_f$ (dichloromethane/methanol 10:1): 0.54.

$^1$H-NMR (300 MHz, DMSO-$d_6$, δ/ppm): 9.58 (1H, broad), 9.02 (2H, broad), 8.03 (2H, d), 7.68 (2H, d), 7.09 (1H, d), 7.07 (1H, t), 6.82 (1H, d), 6.77 (1H, t), 4.29 (2H, s), 3.89 (3H, s), 3.18-3.10 (2H, m), 2.94-2.88 (2H, m).

MS (ESI): 286 (M+H$^+$).

Example 3A

Methyl 4-({tert-butoxycarbonyl-[2-(2-hydroxyphenyl)ethyl]amino}methyl)benzoate

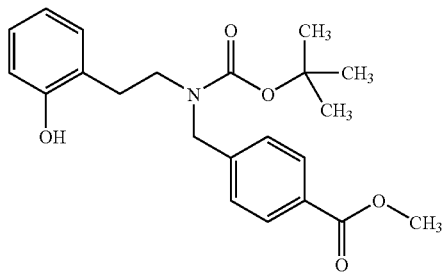

8.95 g (41.03 mmol) of di-tert-butyl dicarbonate, dissolved in 200 ml of THF, are added to a solution of 11.15 g (39.08 mmol) of methyl 4-({[2-(2-hydroxyphenyl)ethyl]amino}methyl)benzoate hydrobromide from Example 2A and 10.89 ml (78.15 mmol) of triethylamine in 300 ml of THF at 0° C. After stirring at room temperature for 12 hours, the solvent is stripped off in vacuo, and the resulting residue is taken up in dichloromethane and washed with half-saturated ammonium chloride solution. Drying over sodium sulfate is followed by filtration and concentration. 12.21 g (31.7 mmol, 82% yield) of a colorless oil are obtained and are employed in the next stage without further purification.

$^1$H-NMR (300 MHz, DMSO-$d_6$, δ/ppm): 9.28 (1H, s), 7.95 (2H, d), 7.34 (2H, d), 7.01 (2H, t), 6.78 (2H, d), 6.69 (2H, t), 4.41 (2H, s), 3.86 (3H, s), 3.33 (2H, s, broad), 2.71 (2H, t), 1.48 (9H, s).

MS (ESI): 386 (M+H$^+$).

Example 4A

Methyl 4-[({2-[2-(4-bromobenzyloxy)phenyl]ethyl}-tert-butoxycarbonylamino)methyl]benzoate

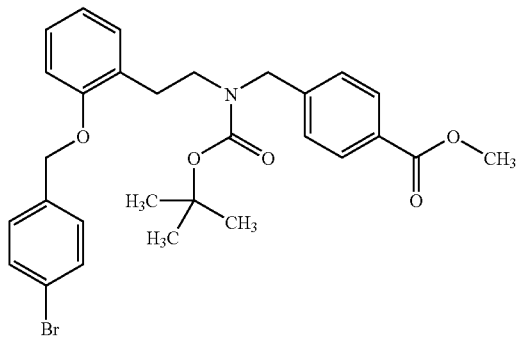

A solution of 5 g (12.87 mmol) of methyl 4-({tert-butoxycarbonyl-[2-(2-hydroxyphenyl)ethyl]amino}methyl)benzoate from Example 3A in 100 ml of dry acetonitrile is mixed with 3.89 g (15.57 mmol) of 4-bromobenzyl bromide and 2.69 g (19.46 mmol) of anhydrous potassium carbonate and heated to reflux for 12 hours. The mixture is then concentrated to dryness. The residue is taken up in ethyl acetate, washed with water and saturated sodium chloride solution and dried over sodium sulfate. The resulting organic phase is concentrated. The crude product is purified by flash chromatography on silica gel (mobile phase: cyclohexane/ethyl acetate 20:1→10:1). 6.88 g (12.4 mmol, 89% yield) of a solid are obtained.

$^1$H-NMR (300 MHz, DMSO-$d_6$, δ/ppm): 7.90 (2H, d), 7.57 (2H, d), 7.38 (2H, d), 7.27-7.06 (4H, m), 7.00 (1H, d), 6.88 (1H, t), 5.06 (2H, s), 4.38 (2H, m), 3.84 (3H, s), 3.36 (2H, m), 2.79 (2H, t), 1.30 (9H, s).

MS (ESI): 576 (M+Na$^+$), 578 (M+Na$^+$), 553 (M$^+$), 555 (M$^+$).

Example 5A

Methyl 4-({2-[2-(4-bromobenzyloxy)phenyl]ethylamino}methyl)benzoate

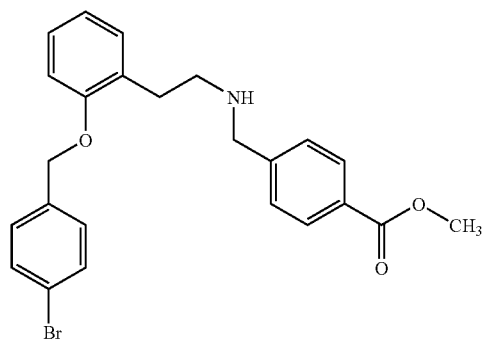

A solution of 4.2 g (7.57 mmol) of methyl 4-[({2-[2-(4-bromobenzyloxy)phenyl]ethyl}-tert-butoxycarbonylamino)methyl]benzoate from Example 4A in 15 ml of dichloromethane is stirred with 15 ml of trifluoroacetic acid at room temperature for 4 hours. The reaction solution is then neutralized with aqueous sodium bicarbonate solution, and the organic phase is separated off and dried over sodium sulfate. Filtration is followed by removal of the solvent in vacuo. 3.2 g (7.04 mmol, 92% yield) of a colorless oil are obtained which are employed in the next stage without further purification.

$^1$H-NMR (300 MHz, DMSO-d$_6$, δ/ppm): 7.86 (2H, d), 7.57 (2H, d), 7.42 (2H, d), 7.37 (2H, d), 7.14 (2H, t), 6.97 (1H, d), 6.86 (1H, t), 5.13 (2H, s), 3.85 (3H, s), 3.79 (2H, s), 2.81-2.67 (4H, m).

MS (CI): 454 (M$^+$).

Example 6A

[4-(2-Bromoethyl)phenyl]methanol

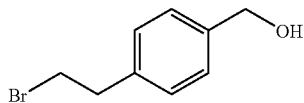

13.10 ml (13.10 mmol) of borane-THF complex are slowly added dropwise to a solution of 2 g (8.73 mmol) of 4-(2-bromoethyl)benzoic acid in 50 ml of dry THF at −10° C. After warming to room temperature, the mixture is stirred for one hour. After the reaction is complete, the mixture is mixed with saturated ammonium chloride solution and taken up in ethyl acetate, and the organic phase is separated off and dried over sodium sulfate. After filtration, the solvent is removed in vacuo. 1.67 g (7.76 mmol, 79% yield) of a colorless oil are obtained and are employed in the next stage without further purification.

$^1$H-NMR (300 MHz, DMSO-d$_6$, δ/ppm): 7.33-7.28 (4H, m), 5.14 (1H, t), 4.48 (2H, d), 3.77 (2H, t), 3.11 (2H, t).

MS (DCI, NH$_3$): 232 (M+NH$_4^+$).

Example 7A 4-(2-Bromoethyl)benzaldehyde

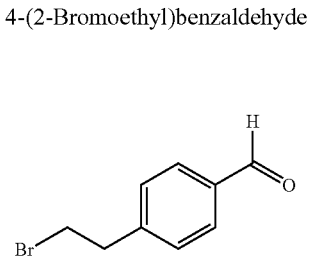

Process 1:

A solution of 200 mg (0.93 mmol) of [4-(2-bromoethyl)phenyl]methanol from Example 6A in 20 ml of dichloromethane is mixed with 240.5 mg (1.12 mmol) of pyridinium chlorochromate (PCC) and stirred at room temperature for 3 hours. The reaction solution is then mixed with about 2 g of silica gel and concentrated to dryness. The resulting residue is purified by flash chromatography on silica gel (mobile phase: cyclohexane/ethyl acetate 4:1). 183 mg (0.85 mmol, 82% yield) of a colorless solid are obtained.

Process 2:

42.26 ml (0.385 mol) of titanium tetrachloride are added over the course of 10 min to a solution of 44.4 g (0.38 mol) of dichloromethyl methyl ether in 230 ml of dichloromethane while cooling (4-5° C.), and the mixture is stirred for 1 hour. Then 64.89 g (0.34 mol) of 2-bromoethylbenzene, dissolved in 24 ml of dichloromethane, are metered into the reaction solution over the course of 50 min at 5-7° C. The reaction solution is then warmed slowly to room temperature and the mixture is stirred overnight. After reaction is complete, 140 ml of water are very cautiously added dropwise over the course of 1 hour (caution: initially endothermic reaction through evolution of gas, then exothermic reaction up to 30° C., cooling necessary). The reaction solution is extracted three times with dichloromethane, and the combined organic phases are washed with 170 ml of water and neutralized with 115 ml of sodium bicarbonate solution and dried over sodium sulfate. After filtration, the solvent is removed in vacuo. The resulting residue is purified by flash chromatography on silica gel (mobile phase: dichloromethane/petroleum ether 1:2→1:1). 29.3 g (0.14 mol, 37% yield) of a colorless solid are obtained.

$^1$H-NMR (300 MHz, DMSO-d$_6$, δ/ppm): 9.99 (1H, s), 7.88 (2H, d), 7.52 (2H, d), 3.80 (2H, t), 3.24 (2H, t).

MS (EI): 212 (M$^+$).

Example 8A 4-(2-Bromoethyl)benzonitrile

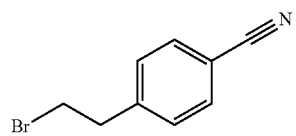

A solution of 29.3 g (0.14 mol) of 4-(2-bromoethyl)benzaldehyde from Example 7A in 112.4 ml of formic acid is mixed with 12.42 g (0.18 mol) of hydroxylamine hydrochloride and heated to reflux for 2 hours. After slow cooling to room temperature, 670 ml of water are added, and the reaction mixture is slowly neutralized with 6 N sodium hydroxide solution while cooling. The mixture is then extracted three times with methyl tert-butyl ether. The combined organic phases are dried over magnesium sulfate and concentrated to dryness. The resulting residue is purified by flash chromatography on silica gel (mobile phase: dichloromethane). 21.3 g (0.10 mol, 74% yield) of a yellowish solid are obtained.

$^1$H-NMR (400 MHz, DMSO-d$_6$, δ/ppm): 7.80 (2H, d), 7.51 (2H, d), 3.77 (2H, t), 3.22 (2H, t).

MS (DCI, NH$_3$): 227 (M+NH$_4^+$).

Example 9A

Methyl 4-({{2-[2-(4-bromobenzyloxy)phenyl]ethyl}-[2-(4-cyanophenyl)ethyl]amino}methyl)benzoate

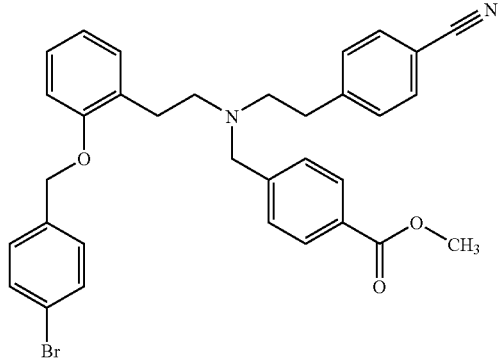

200 mg (0.44 mmol) of methyl 4-({2-[2-(4-bromobenzyloxy)phenyl]ethylamino}methyl)benzoate from Example 5A, 101 mg (0.48 mmol) of 4-(2-bromoethyl)benzonitrile and 51.4 mg (0.48 mmol) of sodium carbonate are heated in 5 ml of acetonitrile to reflux for 5 hours. A further 101 mg (0.48 mmol) of 4-(2-bromoethyl)benzonitrile are then added, and the reaction solution is stirred further under reflux overnight. After the reaction solution has cooled, the mixture is concentrated to dryness, and the residue is taken up in ethyl acetate and washed with water and saturated sodium chloride solution. Drying over sodium sulfate is followed by filtration and concentration. The crude product is purified by preparative HPLC. 183 mg (0.31 mmol, 69% yield) of a pale yellow oil are obtained.

$^1$H-NMR (300 MHz, DMSO-d$_6$, δ/ppm): 7.79 (2H, d), 7.63 (2H, d), 7.49 (2H, d), 7.30 (2H, d), 7.24 (4H, d), 7.18 (1H, t), 7.09 (1H, d), 6.99 (1H, d), 6.86 (1H, t), 5.00 (2H, s), 3.85 (3H, s), 3.70 (2H, s), 2.79-2.59 (8H, m).

MS (ESI): 583 (M+H$^+$).

Example 10A

Methyl 4-[([2-(4-cyanophenyl)ethyl]-{2-[2-(4'-trifluoromethylbiphenyl-4-ylmethoxy)phenyl]-ethyl}amino)methyl]benzoate

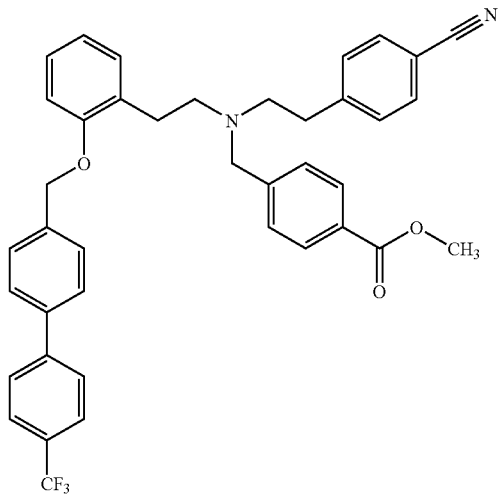

200 mg (0.34 mmol) of methyl 4-({{2-[2-(4-bromobenzyloxy)phenyl]ethyl}-[2-(4-cyanophenyl)ethyl]amino}methyl)benzoate from Example 9A are dissolved in 2 ml of 1,2-dimethoxyethane and, under argon, 78 mg (0.41 mmol) of 4-trifluoromethylphenylboronic acid, 2.5 mg of bis(triphenylphosphine)palladium(II) chloride and 0.38 ml of a 2 M aqueous sodium carbonate solution are added. The reaction mixture is then stirred under reflux for 12 hours. The mixture is subsequently cooled, filtered through 1 g of Extrelut, washed with dichloromethane and concentrated. The resulting crude product is purified by preparative HPLC. 158 mg (0.24 mmol, 71% yield) of a colorless oil are obtained.

$^1$H-NMR (300 MHz, CDCl$_3$, δ/ppm): 7.85 (2H, d), 7.69 (2H, d), 7.62 (2H, d), 7.54 (2H, d), 7.43 (4H, dd), 7.19 (3H, t), 7.10-7.01 (3H, m), 6.92 (2H, d), 5.06 (2H, s), 3.89 (3H, s), 3.69 (2H, s), 2.90-2.76 (4H, m), 2.70 (4H, s).

MS (ESI): 649 (M+H$^+$).

Example 11A

Methyl 4-[({2-[4-(5-oxo-4,5-dihydro-[1,2,4]oxadiazol-3-yl)phenyl]ethyl}-{2-[2-(4'-trifluoromethylbiphenyl-4-ylmethoxy)phenyl]ethyl}amino)methyl]benzoate

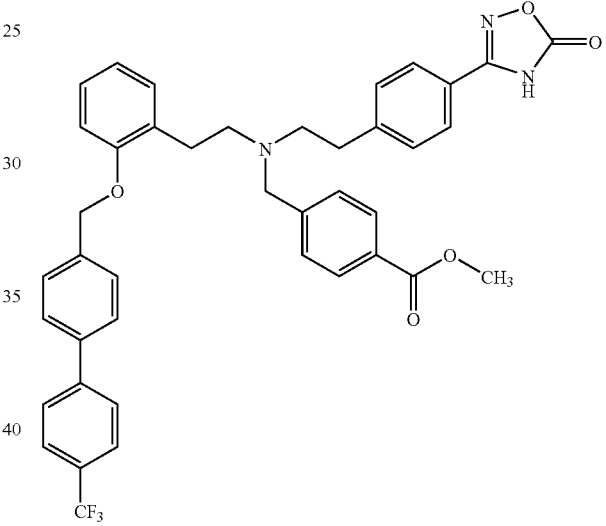

A solution of 80.34 mg (1.16 mmol) of hydroxylamine hydrochloride in 5 ml of DMSO is mixed with 0.16 ml (1.16 mmol) of triethylamine and stirred at room temperature for 10 min. The resulting precipitate is filtered off. Subsequently, 150 mg (0.23 mmol) of methyl 4-[([2-(4-cyanophenyl)ethyl]-{2-[2-(4'-trifluoromethylbiphenyl-4-ylmethoxy)phenyl]ethyl}amino)methyl]-benzoate from Example 10A are metered into the filtrate. The reaction solution is stirred at 75° C. for 12 hours. After complete conversion and cooling, 10 ml of water are added to the reaction solution and, after extraction three times with ethyl acetate, the combined organic phases are washed with saturated sodium chloride solution. The organic phase is then dried over sodium sulfate and concentrated to dryness. 162 mg of a colorless oil are obtained and are reacted further immediately without further purification.

The oil obtained above is dissolved in 10 ml of DMF, and 0.02 ml (0.26 mmol) of pyridine is added. The solution is then cooled to 0° C. and 46 mg (0.24 mmol) of 2-ethylhexyl chloroformate are slowly added. The mixture is stirred at 0° C. for about 30 min and then taken up in water and extracted with ethyl acetate. The organic phase is dried over sodium sulfate and concentrated to dryness. The resulting residue is taken up 20 ml of xylene and heated to reflux for 2 hours.

After reaction is complete, the reaction solution is cooled and concentrated to dryness. The crude product is purified by preparative HPLC. 32.7 mg (0.05 mmol, 19% yield) of a colorless oil are obtained.

LC-MS (method 2): $R_t$ 2.49 min; m/z 708 (M+H$^+$).

Example 12A

Diallyl 2-(4-methoxycarbonylbenzyl)malonate

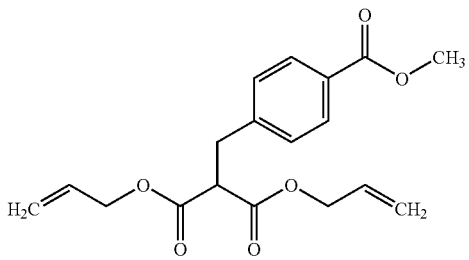

14.42 g (0.36 mol) of sodium hydride are added in portions to a solution of 56.7 g (0.3 mol) of diallyl malonate in 375 ml of dioxane and 75 ml of THF at 0° C. After warming to room temperature, the mixture is stirred at 40° C. for 1 hour. Subsequently, 111.88 g (0.6 mol) of methyl 4-chloromethylbenzoate, dissolved in 375 ml of dioxane, are slowly added dropwise at 40° C., and the reaction solution is stirred at 110° C. overnight. After cooling to room temperature, the reaction mixture is added to 1200 ml of water. Care must be taken during this that the pH is <7 (where appropriate, a few ml of 1 M hydrochloric acid are metered in to about pH 2). The mixture is then extracted three times with ethyl acetate, and the combined organic phases are washed with saturated sodium chloride solution and dried over sodium sulfate. After filtration, the solvent is concentrated to dryness in vacuo. The resulting crude product is purified by flash chromatography (mobile phase: petroleum ether/ethyl acetate 10:1; 3 kg of silica gel). 85.4 g (0.26 mol, 85% yield) of a colorless solid are obtained.

$^1$H-NMR (300 MHz, CDCl$_3$, δ/ppm): 7.96 (2H, d), 7.29 (2H, d), 5.91-5.74 (2H, m), 5.32-5.17 (4H, m), 4.59 (4H, d), 3.93 (3H, s), 3.74 (1H, t), 3.31 (2H, d).

MS (DCI): 349 (M+NH$_4^+$).

Example 13A

Diallyl 2-[2-(4-cyanophenyl)ethyl]-2-(4-methoxycarbonylbenzyl)malonate

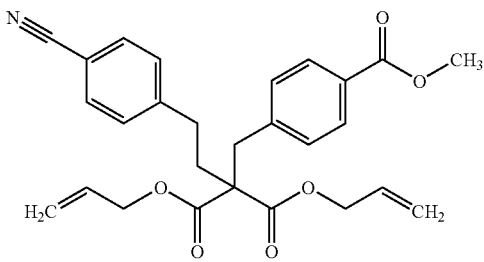

6.70 g (0.17 mol) of sodium hydride are added in portions to a solution of 55.71 g (0.17 mol) of diallyl 2-(4-methoxycarbonylbenzyl)malonate from Example 12A in 34 ml of DMF at 0° C. The reaction solution is then allowed to reach room temperature and is stirred for 1 hour. The reaction solution is then cooled to 0° C., 42.98 g (0.20 mol) of 4-(2-bromoethyl)benzonitrile from Example 8A in 21 ml of DMF are added, and the mixture is stirred at this temperature for 30 min. The mixture is subsequently stirred at room temperature overnight. Water is added dropwise to the reaction mixture, which is then extracted three times with ethyl acetate, and the combined organic phases are washed with saturated sodium chloride solution and dried over sodium sulfate. After filtration, the solvent is concentrated to dryness in vacuo. The resulting crude product is purified by flash chromatography (mobile phase: petroleum ether/ethyl acetate 3:1; 3 kg of silica gel). 36 g (0.078 mol, 46% yield) of a colorless solid are obtained.

$^1$H-NMR (300 MHz, CDCl$_3$, δ/ppm): 7.95 (2H, d), 7.55 (2H, d), 7.21 (4H, t), 5.97-5.69 (2H, m), 5.40-5.23 (4H, m), 4.62 (4H, d), 3.92 (3H, s), 3.40 (2H, s), 2.72-2.61 (2H, m), 2.13-2.01 (2H, m).

MS (DCI): 479 (M+NH$_4^+$).

Example 14A

Methyl 4-[2-carboxy-4-(4-cyanophenyl)butyl]benzoate

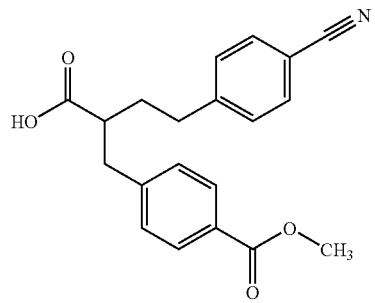

A solution of 41.8 ml (0.3 mol) of triethylamine and 8.6 ml (0.23 mol) of formic acid in 500 ml of dioxane is added to a solution of 43.5 g (0.09 mol) of diallyl 2-[2-(4-cyanophenyl)ethyl]-2-(4-methoxycarbonylbenzyl)malonate from Example 13A, 1.67 g (0.01 mol) of triphenylphosphine and 410 mg of palladium acetate in 505 ml of dioxane at room temperature. The reaction mixture is then stirred at 100° C. for 2 hours. After conversion is complete, the reaction solution is cooled and the solvent is removed in vacuo. The resulting residue is purified by flash chromatography on silica gel (mobile phase: dichloromethane/methanol 50:1). 25 g (0.074 mol, 82% yield) of a colorless solid are obtained.

$^1$H-NMR (400 MHz, DMSO d$_6$, δ/ppm): 12.55-12.24 (1H, broad), 7.86 (2H, d), 7.72 (2H, d), 7.38 (2H, d), 7.32 (2H, d), 3.84 (3H, s), 2.99-2.81 (2H, m), 2.78-2.55 (3H, m), 1.90-1.67 (2H, m).

MS (ESI): 338 (M+H$^+$).

Example 15A

Methyl 4-[4-(4-cyanophenyl)-2-hydroxymethylbutyl]benzoate

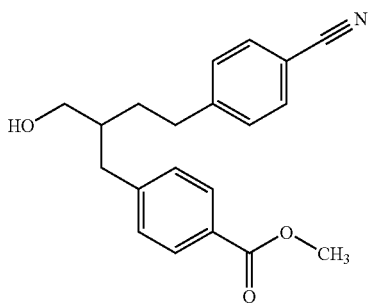

24.28 ml of a 1 M borane-THF complex solution (24.28 mmol) are added dropwise to a solution of 5.32 g (77% purity, 12.14 mmol) of methyl 4-[2-carboxy-4-(4-cyanophenyl)butyl]benzoate from Example 14A in 40 ml of THF at −15° C., and the solution is stirred at this temperature for 4 h. After reaction is complete, saturated sodium bicarbonate solution is added to the reaction mixture, and the solvent is concentrated to dryness. The residue is taken up in dichloromethane, dried over sodium sulfate and, after filtration, again freed of solvent. The resulting crude product is purified by flash chromatography on silica gel (mobile phase: cyclohexane/ethyl acetate 4:1). 2.25 g (55% yield) of a colorless solid are obtained.

$^1$H-NMR (300 MHz, DMSO-$d_6$, δ/ppm): 7.88 (2H, d), 7.71 (2H, d), 7.46 (4H, t), 4.54 (1H, t), 3.83 (3H, s), 3.41 (2H, t), 2.80-2.55 (4H, m), 1.79-1.39 (3H, m).

MS (ESI): 324 (M+H$^+$).

Example 16A

Methyl 4-[4-(4-cyanophenyl)-2-formylbutyl]benzoate

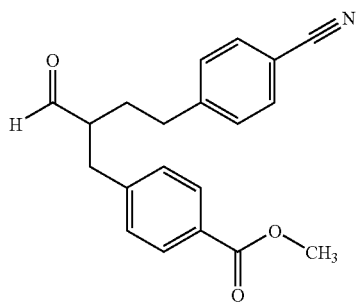

A solution of 5.7 g (17.63 mmol) of methyl 4-[4-(4-cyanophenyl)-2-hydroxymethylbutyl]benzoate from Example 15A in 250 ml of dichloromethane is mixed with 4.56 g (21.15 mmol) of pyridinium chlorochromate (PCC) and stirred at room temperature for 5 hours. After conversion is complete, about 10 g of silica gel are added, and the solvent is removed to dryness in vacuo. The residue is purified by flash chromatography on silica gel (mobile phase: cyclohexane/ethyl acetate 10:1→4:1). 4.16 g (12.94 mmol, 73% yield) of a colorless solid are obtained.

$^1$H-NMR (300 MHz, DMSO-$d_6$, δ/ppm): 9.68 (1H, s), 7.88 (2H, d), 7.73 (2H, d), 7.47 (4H, dd), 3.86 (3H, s), 3.14-3.02 (1H, m), 2.92-2.80 (1H, m), 2.78-2.54 (3H, m), 1.98-1.81 (1H, m), 1.76-1.60 (1H, m).

MS (DCI): 339 (M+NH$_4^+$).

Example 17A

Methyl E-4-[2-[2-(4-cyanophenyl)ethyl]-4-(2-hydroxyphenyl)but-3-enyl]benzoate

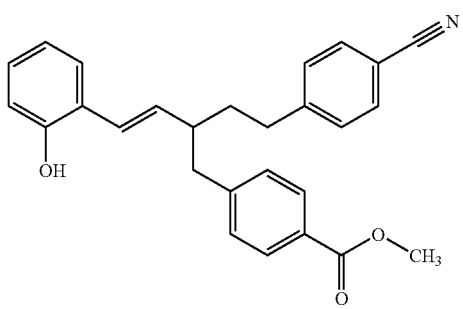

9.39 ml (15.02 mmol) of a 1.6 M solution of n-butyllithium in hexane are slowly added to a solution of 2.459 g (5.36 mmol) of (2-hydroxybenzyl)triphenylphosphonium bromide in 65 ml of anhydrous THF at 0° C. Then, at this temperature, 1.744 g (5.36 mmol) of methyl 4-[4-(4-cyanophenyl)-2-formylbutyl]benzoate from Example 16A, dissolved in 65 ml of THF, are slowly metered in. After warming to room temperature, the reaction solution is stirred for 12 hours and then, after addition of some water, concentrated to dryness. The resulting residue is taken up in ethyl acetate, washed with water and saturated sodium chloride solution and dried over sodium sulfate. After filtration, the solvent is concentrated to dryness. The crude product is purified by flash chromatography on silica gel (mobile phase: cyclohexane/ethyl acetate 4:1). 1.44 g (3.50 mmol, 65% yield) of a colorless solid are obtained.

$^1$H-NMR (300 MHz, DMSO-$d_6$, δ/ppm): 9.39 (1H, s), 7.82 (2H, d), 7.60 (2H, d), 7.41-7.27 (5H, m), 7.01 (1H, t), 6.81-6.68 (2H, m), 6.45 (1H, d), 6.13-5.99 (1H, m), 3.81 (3H, s), 2.92-2.58 (5H, m), 1.86-1.56 (2H, m).

MS (DCI): 429 (M+NH$_4^+$).

Example 18A

Methyl E-4-{4-[2-(4-bromobenzyloxy)phenyl]-2-[2-(4-cyanophenyl)ethyl]but-3-enyl}benzoate

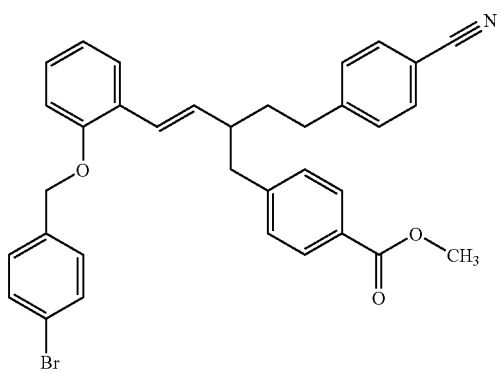

A solution of 230 mg (0.56 mmol) of methyl E-4-[2-[2-(4-cyanophenyl)ethyl]-4-(2-hydroxyphenyl)but-3-enyl]benzoate from Example 17A in 5 ml of dry acetonitrile is mixed with 209 mg (0.84 mmol) of 4-bromobenzyl bromide and 116 mg (0.84 mmol) of anhydrous potassium carbonate and heated to reflux for 12 hours. The mixture is then concentrated to dryness. The residue is taken up in ethyl acetate, washed with water and saturated sodium chloride solution and dried over sodium sulfate. The resulting organic phase is concentrated. The crude product is purified by flash chromatography on silica gel (mobile phase: cyclohexane). 286 mg (0.49 mmol, 88% yield) of a solid are obtained.

$^1$H-NMR (400 MHz, DMSO-$d_6$, δ/ppm): 7.82 (2H, d), 7.68 (2H, d), 7.54 (2H, d), 7.40 (1H, d), 7.38-7.25 (6H, m), 7.18 (1H, t), 7.00 (1H, d), 6.90 (1H, t), 6.44 (1H, d), 6.09 (1H, dd), 5.06 (2H, s), 3.81 (3H, s), 2.91-2.82 (1H, m), 2.79-2.69 (2H, m), 2.68-2.56 (1H, m), 2.54-2.41 (1H, m), 1.85-1.72 (1H, m), 1.71-1.59 (1H, m).

MS (ESI): 602 (M+Na$^+$), 597 (M+NH$_4^+$).

Example 19A

Methyl E-4-{2-[2-(4-cyanophenyl)ethyl]-4-[2-(4'-trifluoromethylbiphenyl-4-ylmethoxy)phenyl]but-3-enyl}benzoate

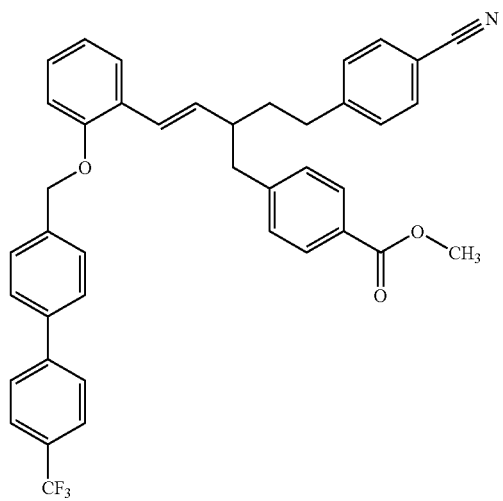

270 mg (0.47 mmol) of methyl E-4-{4-[2-(4-bromobenzyloxy)phenyl]-2-[2-(4-cyanophenyl)ethyl]but-3-enyl}benzoate from Example 18A are dissolved in 3 ml of 1,2-dimethoxyethane and, under argon, 106 mg (0.56 mmol) of 4-trifluoromethylphenylboronic acid, 3.3 mg of bis(triphenylphosphine)palladium(II) chloride and 0.51 ml of a 2 M solution of sodium carbonate in water are added. The reaction mixture is then stirred under reflux for 12 hours. The mixture is subsequently cooled, filtered through 1 g of Extrelut, washed with dichloromethane and concentrated. The resulting crude product is purified by preparative HPLC. 175 mg (0.27 mmol, 58% yield) of a colorless solid are obtained.

$^1$H-NMR (400 MHz, DMSO-$d_6$, δ/ppm): 7.91 (2H, d), 7.71 (4H, s), 7.59 (2H, d), 7.50-7.41 (4H, m), 7.39 (1H, d), 7.22-7.12 (5H, m), 6.99-6.89 (2H, m), 6.66 (1H, d), 6.00 (1H, dd), 5.12 (2H, s), 3.87 (3H, s), 2.79 (2H, d), 2.78-2.70 (1H, m), 2.67-2.54 (1H, m), 2.53-2.42 (1H, m), 1.89-1.74 (1H, m), 1.73-1.58 (1H, m).

MS (ESI): 668 (M+Na$^+$), 663 (M+NH$_4^+$).

Example 20A

Methyl E-4-{2-{2-[4-(5-oxo-4,5-dihydro-[1,2,4]oxadiazol-3-yl)phenyl]ethyl}-4-[2-(4'-trifluoromethylbiphenyl-4-ylmethoxy)phenyl]but-3-enyl}benzoate

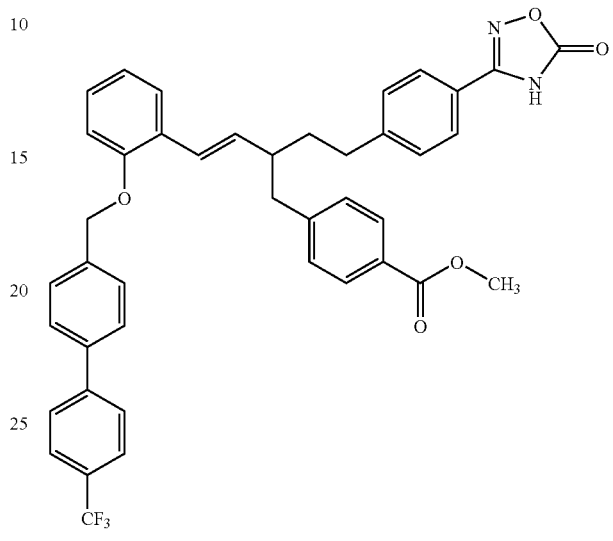

A solution of 96.8 mg (1.39 mmol) of hydroxylamine hydrochloride in 18 ml of DMSO is mixed with 0.19 ml (1.39 mmol) of triethylamine and stirred at room temperature for 10 min. The resulting precipitate is filtered off. Subsequently 180 mg (0.28 mmol) of methyl E-4-{2-[2-(4-cyanophenyl)ethyl]-4-[2-(4'-trifluoromethylbiphenyl-4-ylmethoxy)phenyl]but-3-enyl}benzoate from Example 19A are metered into the filtrate. The reaction solution is then stirred at 75° C. for 12 hours. After complete conversion and cooling, 10 ml of water are added to the reaction solution, which is extracted three times with ethyl acetate, and the combined organic phases are washed with saturated sodium chloride solution. The organic phase is then dried over sodium sulfate and concentrated to dryness. 213 mg of a colorless oil are obtained and are reacted further immediately without further purification.

The oil obtained above is dissolved in 8 ml of DMF, and 0.02 ml (0.29 mmol) of pyridine is added. The solution is then cooled to 0° C. and 47.1 mg (0.26 mmol) of 2-ethylhexyl chloroformate are slowly added. The mixture is stirred at 0° C. for about 30 min, taken up in water and extracted with ethyl acetate. The organic phase is dried over sodium sulfate and concentrated to dryness. The resulting residue is taken up in 8 ml of xylene and heated to reflux for 4 hours. After reaction is complete, the reaction solution is cooled and concentrated to dryness. The crude product is purified by preparative HPLC. 110 mg (0.15 mmol, 57% yield) of a colorless oil are obtained.

$^1$H-NMR (300 MHz, DMSO-$d_6$, δ/ppm): 12.86 (1H, s, broad), 7.90-7.75 (6H, m), 7.74-7.62 (4H, m), 7.50 (2H, d), 7.43 (1H, d), 7.33 (4H, t), 7.19 (1H, t), 7.07 (1H, d), 6.91 (1H, t), 6.50 (1H, d), 6.12 (1H, dd), 5.16 (2H, s), 3.76 (3H, s), 2.94-2.82 (1H, m), 2.81-2.56 (3H, m), 2.55-2.43 (1H, m), 1.90-1.59 (2H, m).

MS (ESI): 727 (M+Na$^+$).

Example 21A

Ethyl 4'-trifluoromethylbiphenyl-4-carboxylate

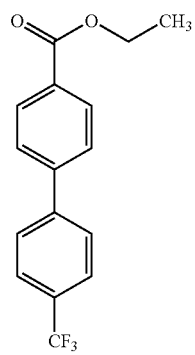

7 g (30.56 mmol) of ethyl 4-bromobenzoate are dissolved in 60 ml of 1,2-dimethoxyethane and, under argon, 6.96 g (36.67 mmol) of 4-trifluoromethylphenylboronic acid, 271 mg of bis(triphenylphosphine)palladium(II) chloride and 40.7 ml of a 2 M solution of sodium carbonate in water are added. The reaction mixture is then heated under reflux for 12 hours. The mixture is subsequently cooled, filtered through 1 g of Extrelut, washed with dichloromethane and concentrated. The crude product is purified by flash chromatography on silica gel (mobile phase: cyclohexane/dichloromethane 2:1). 6.31 g (21.4 mmol, 70% yield) of a colorless solid are obtained.

$^1$H-NMR (300 MHz, CDCl$_3$, δ/ppm): 8.17 (2H, d), 7.72 (4H, s), 7.67 (2H, d), 4.41 (2H, q), 1.43 (3H, t).

MS (EI): 294 (M$^+$).

Example 22A (4'-Trifluoromethylbiphenyl-4-yl)methanol

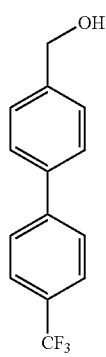

12.73 ml (12.73 mmol) of a 1 M solution of lithium aluminum hydride in THF are added dropwise to a solution of 6.24 g (21.21 mmol) of ethyl 4'-trifluoromethylbiphenyl-4-carboxylate from Example 21A in 60 ml of dry THF at 0° C. After the reaction is complete, the mixture is mixed with saturated ammonium chloride solution and taken up in ethyl acetate, and the organic phase is separated off and dried over sodium sulfate. After filtration, the solvent is removed in vacuo. The resulting crude product is purified by flash chromatography on silica gel (mobile phase: cyclohexane/ethyl acetate 5:1). 5.1 g (20.21 mmol, 95% yield) of a colorless solid are obtained.

$^1$H-NMR (300 MHz, DMSO-d$_6$, δ/ppm): 7.88 (2H, d), 7.82 (2H, d), 7.71 (2H, d), 7.46 (2H, d), 5.23 (1H, t), 4.58 (2H, d).

MS (EI): 252 (M$^+$).

Example 23A

4-Chloromethyl-4'-trifluoromethylbiphenyl

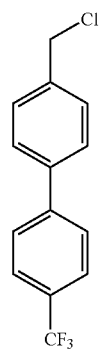

A solution of 5.0 g (19.82 mmol) of (4'-trifluoromethylbiphenyl-4-yl)methanol from Example 22A in 40 ml of chloroform is mixed with 2.89 ml (39.65 mmol) of thionyl chloride dissolved in 10 ml of chloroform, and the mixture is stirred at room temperature for 12 hours. After reaction is complete, the reaction mixture is concentrated to dryness, and the residue is taken up ethyl acetate and washed with saturated sodium carbonate solution. The organic phase is subsequently separated off, dried over sodium sulfate and concentrated after filtration. The crude product is purified by flash chromatography on silica gel (mobile phase: cyclohexane/ethyl acetate 9:1). 5.26 g (19.43 mmol, 98% yield) of a colorless solid are obtained.

$^1$H-NMR (300 MHz, DMSO-d$_6$, δ/ppm): 7.91 (2H, d), 7.82 (2H, d), 7.78 (2H, d), 7.58 (2H, d), 4.83 (2H, s).

MS (EI): 270 (M$^+$).

Example 24A

[2-(4'-Trifluoromethylbiphenyl-4-ylmethoxy)phenyl]methanol

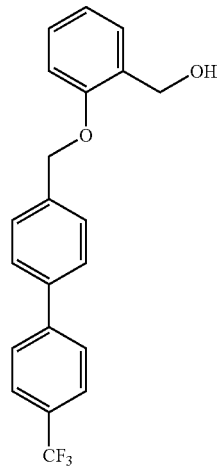

A solution of 4.59 g (36.94 mmol) of 2-hydroxybenzyl alcohol in 200 ml of dry acetonitrile is mixed with 10 g (36.94 mmol) of 4-chloromethyl-4'-trifluoromethylbiphenyl from Example 23A and 6.13 g (44.33 mmol) of anhydrous potassium carbonate and heated to reflux for 12 hours. The mixture is then concentrated to dryness. The residue is taken up in ethyl acetate, washed with water and saturated sodium chloride solution and dried over sodium sulfate. The resulting organic phase is concentrated. The crude product is purified by flash chromatography on silica gel (mobile phase: cyclohexane/ethyl acetate 5:1). 11.8 g (32.92 mmol, 89% yield) of a solid are obtained.

$^1$H-NMR (300 MHz, DMSO-$d_6$, δ/ppm): 7.92 (2H, d), 7.87-7.72 (4H, m), 7.60 (2H, d), 7.41 (1H, d), 7.21 (1H, t), 7.03 (1H, d), 6.96 (1H, t), 5.20 (2H, s), 5.03 (1H, t), 4.58 (2H, d).

MS (DCI): 376 (M+NH$_4^+$).

Example 25A

Triphenyl[2-(4'-trifluoromethylbiphenyl-4-ylmethoxy)benzyl]phosphonium bromide

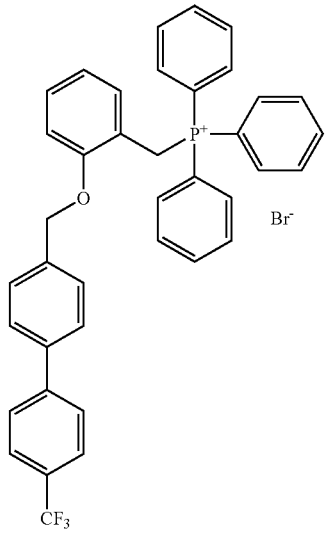

A solution of 11.7 g (32.65 mmol) of [2-(4'-trifluoromethylbiphenyl-4-ylmethoxy)phenyl]-methanol from Example 24A in 100 ml of acetonitrile is mixed with 10.64 g (31.02 mmol) of triphenylphosphonium hydrobromide and heated to reflux for 3 hours. The reaction solution is then concentrated to dryness, and the resulting oil is taken up and triturated in diethyl ether. The product crystallizes as a white solid during this. After filtration, the solid is dried in a oven at 50° C. overnight. 20.5 g (30 mmol, 92% yield) of crystalline product are obtained.

$^1$H-NMR (300 MHz, DMSO-$d_6$, δ/ppm): 7.99-7.79 (8H, m), 7.78-7.50 (12H, m), 7.32 (4H, d), 7.08 (1H, d), 6.97 (1H, d), 6.86 (1H, t), 5.03 (2H, d), 4.70 (2H, s).

Example 26A (5-Bromopentyl)benzene

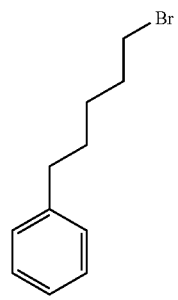

A solution of 416.7 ml (1.83 mol) 48% strength hydrobromic acid is mixed with 50 g (0.304 mol) of 5-phenylpentan-1-ol at 0° C. and stirred at 0° C. for 30 min. The reaction solution is then stirred at 100° C. for 12 hours. After reaction is complete, the mixture is cooled to room temperature and 200 ml of ethyl acetate are added. After extraction, the organic phase is separated off, washed with saturated sodium bicarbonate solution and dried over sodium sulfate. After filtration, the filtrate is is concentrated to dryness. The resulting crude product is purified by flash chromatography on silica gel (mobile phase: cyclohexane). 59.4 g (0.26 mol, 86% yield) of a colorless liquid are obtained.

$^1$H-NMR (300 MHz, CDCl$_3$, δ/ppm): 7.32-7.22 (2H, m), 7.21-7.11 (3H, m), 3.40 (2H, t), 2.61 (2H, t), 1.97-1.81 (2H, m), 1.72-1.58 (2H, m), 1.56-1.39 (2H, m).

MS (CI): 226 (M$^+$).

Example 27A

[2-(5-Phenylpentyloxy)phenyl]methanol

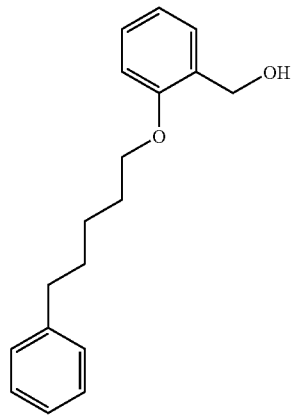

A solution of 10 g (80.56 mmol) of 2-hydroxybenzyl alcohol in 200 ml of dry acetonitrile is mixed with 27.45 g (120.83 mmol) of (5-bromopentyl)benzene from Example 26A and 12.25 g (88.61 mmol) of anhydrous potassium carbonate and heated under reflux for 12 hours. The mixture is then concentrated to dryness. The residue is taken up in ethyl acetate, washed with water and saturated sodium chloride solution and dried over sodium sulfate. The resulting organic phase is concentrated. The crude product is purified by flash chromatography on silica gel (mobile phase: cyclohexane/ethyl acetate 10:1). 18.7 g (81% yield) of a colorless solid are obtained.

$^1$H-NMR (300 MHz, DMSO-$d_6$, δ/ppm): 7.38 (1H, d), 7.31-7.10 (6H, m), 6.91 (2H, t), 4.92 (1H, t), 4.50 (2H, d), 3.95 (2H, t), 2.59 (2H, t), 1.81-1.68 (2H, m), 1.67-1.55 (2H, m), 1.52-1.36 (2H, m).

MS (CI): 288 (M+NH$_4^+$), 270 (M$^+$).

Example 28A

Triphenyl[2-(5-phenylpentyloxy)benzyl]phosphonium bromide

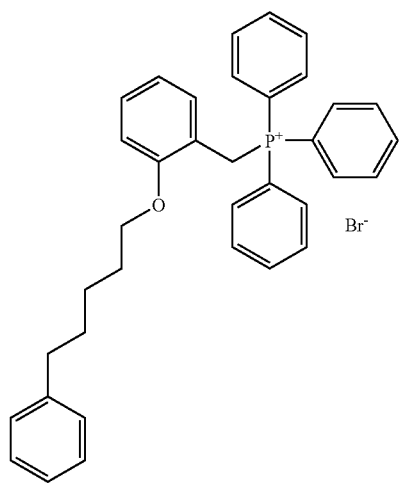

A solution of 18.7 g (69.16 mmol) of [2-(5-phenylpentyloxy)phenyl]methanol from Example 27A in 120 ml of acetonitrile is mixed with 22.55 g (65.71 mmol) of triphenylphosphonium hydrobromide and heated to reflux for three hours. The reaction solution is then concentrated to dryness. 36.6 g (61.45 mmol, 83% yield) of crystalline product are obtained and are reacted without further purification.

$^1$H-NMR (400 MHz, DMSO-$d_6$, δ/ppm): 7.89 (3H, t), 7.78-7.66 (6H, m), 7.64-7.52 (6H, m), 7.32-7.24 (3H, m), 7.21-7.12 (3H, m), 7.01 (1H, d), 6.89-6.77 (2H, m), 4.90 (2H, d), 3.44 (2H, t), 2.56 (2H, t), 1.59-1.46 (2H, m), 1.38-1.25 (2H, m), 1.23-1.12 (2H, m).

MS (ESI): 515 (M$^+$-Br).

Example 29A

E-5-Fluoro-2-[2-(4-methoxyphenyl)vinyl]benzaldehyde

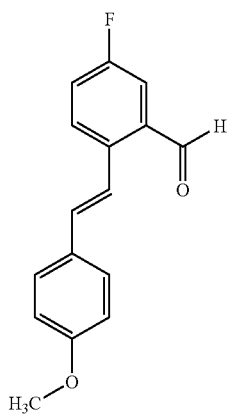

A solution of 10 g (49.26 mmol) of 2-bromo-5-fluorobenzaldehyde in 200 ml of dry DMF is mixed with 7.27 g (54.18 mmol) of 4-methoxystyrene, 1.5 g (4.93 mmol) of tri-2-tolylphosphine, 330 mg (1.48 mmol) of palladium(II) acetate and 10.3 ml (73.89 mmol) of triethylamine under argon and stirred at 100° C. for 12 hours. After reaction is complete, the reaction solution is cooled to room temperature and concentrated to dryness. The resulting residue is taken up in 100 ml of water and extracted three times with 50 ml of diethyl ether each time. The combined organic phases are dried over sodium sulfate. After filtration, the solution is concentrated to dryness, and the residue is purified by flash chromatography on silica gel (mobile phase: cyclohexane/ethyl acetate 10:1). 7.79 g (55% yield) of a colorless solid are obtained.

$^1$H-NMR (400 MHz, DMSO-$d_6$, δ/ppm): 10.40 (1H, s), 8.01-7.89 (2H, m), 7.68-7.49 (4H, m), 7.22 (1H, d), 6.99 (2H, d), 3.80 (3H, s).

MS (DCI): 274 (M+NH$_4^+$).

Example 30A

E-{5-Fluoro-2-[2-(4-methoxyphenyl)vinyl]phenyl}methanol

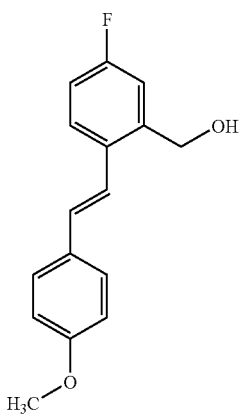

1.73 g (45.60 mmol) of sodium borohydride are added in portions to a solution of 7.79 g (30.40 mmol) of E-5-fluoro-2-[2-(4-methoxyphenyl)vinyl]benzaldehyde from Example 29A in 500 ml of methanol at 0° C., and the mixture is stirred at room temperature for 2 hours. After reaction is complete, the mixture is concentrated to dryness and then taken up in water and dichloromethane. The aqueous phase is then extracted twice more with dichloromethane. The combined organic phases are dried over sodium sulfate, filtered and concentrated to dryness. The resulting residue is purified by flash chromatography on silica gel (mobile phase: cyclohexane/ethyl acetate 4:1→1:1). 6.8 g (85% yield) of a colorless solid are obtained.

$^1$H-NMR (400 MHz, DMSO-$d_6$, δ/ppm): 7.71 (1H, m), 7.54 (2H, d), 7.27-7.12 (2H, m), 7.11-6.99 (2H, m), 6.97 (2H, d), 5.47 (1H, t), 4.67 (2H, d), 3.79 (3H, s).

LC-MS (method 1): R$_t$ 2.49 min; m/z 259 (M+H$^+$).

Example 31A

{5-Fluoro-2-[2-(4-methoxyphenyl)ethyl]phenyl}methanol

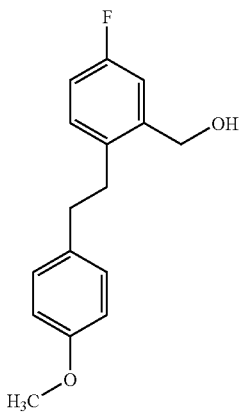

A mixture of 6.8 g (26.33 mmol) of E-{5-fluoro-2-[2-(4-methoxyphenyl)vinyl]phenyl}methanol from Example 30A and 0.5 g of palladium on carbon (10%) in 50 ml of methanol and 250 ml of ethanol is hydrogenated under atmospheric pressure at room temperature for 1 hour. After reaction has stopped, the mixture is filtered through kieselguhr and the filtrate is then concentrated to dryness. The residue is purified by flash chromatography on silica gel (mobile phase: cyclohexane/ethyl acetate 10:1→4:1→1:1). 5.95 g (87% yield) of a colorless solid are obtained.

$^1$H-NMR (400 MHz, DMSO-$d_6$, δ/ppm): 7.21-7.09 (4H, m), 6.97 (1H, t), 6.83 (2H, d), 5.24 (1H, t), 4.51 (2H, d), 3.72 (3H, s), 2.81-2.68 (4H, m).

LC-MS (method 1): R$_t$ 2.49 min; m/z 278 (M+NH$_4^+$).

Example 32A

{5-Fluoro-2-[2-(4-methoxyphenyl)ethyl]benzyl}triphenylphosphonium bromide

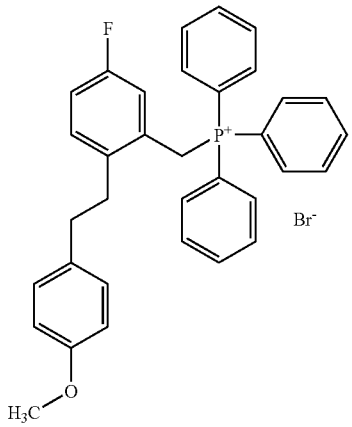

A solution of 5.95 g (22.86 mmol) of {5-fluoro-2-[2-(4-methoxyphenyl)ethyl]phenyl}methanol from Example 31A in 130 ml of acetonitrile is mixed with 7.45 g (21.71 mmol) of triphenylphosphonium hydrobromide and heated to reflux for 3 hours. The reaction solution is then concentrated to dryness, and the resulting oil is taken up and triturated in diethyl ether. The product crystallizes as a white solid during this. After filtration, the solid is dried in a drying oven at 50° C. overnight. 11.5 g (77% yield) of crystalline product are obtained.

$^1$H-NMR (300 MHz, DMSO-$d_6$, δ/ppm): 7.92 (3H, t), 7.81-7.69 (6H, m), 7.68-7.57 (6H, m), 7.30-7.21 (1H, m), 7.19-7.08 (1H, m), 6.94 (2H, d), 6.81 (2H, d), 6.70-6.58 (1H, m), 4.94 (2H, d), 3.71 (3H, s), 2.57-2.46 (2H, t), 2.18 (2H, t).

Example 33A

1-Bromo-4-[bromo(difluoro)methyl]benzene

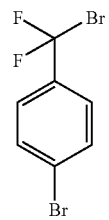

With exclusion of oxygen, a solution of 14.0 g (67.63 mmol) of 1-bromo-4-(difluoromethyl)benzene [CAS 51776-71-7] and 25.3 g (142 mmol) of N-bromosuccinimide (NBS) in 190 ml of tetrachloromethane is irradiated with a sun lamp. During this, the solvent reaches its boiling point. It is irradiated under reflux for 24 hours. The mixture is then allowed to cool to room temperature and precipitated succinimide is filtered off. The filtrate is again mixed with 25 g of NBS and irradiated once more with exclusion of oxygen under reflux for 24 hours. Cooling is followed by filtration again, and the filtrate is concentrated to dryness. 18 g of an orange-colored oil are obtained as crude product, which is purified further by vacuum distillation at 13 mmHg. 12.7 g (44.4 mmol, 66% yield) of a colorless oil are obtained.

Boiling point (13 mmHg): 90-92° C.
$^1$H-NMR (300 MHz, DMSO-$d_6$, δ/ppm): 7.79 (2H, d), 7.63 (2H, d).
MS (ESI): 205/207 (M-Br$^+$).

Example 34A

4-Fluoro-2-(hydroxymethyl)phenol

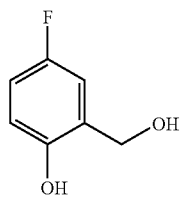

With exclusion of oxygen, 27.1 g (159.28 mmol) of methyl 5-fluoro-2-hydroxybenzoate are introduced into 500 ml of dry THF and cooled to 0° C. Then, while cooling, 238 ml (238 mmol) of a 1 M solution of lithium aluminum hydride in THF are slowly added dropwise, and the mixture is stirred at 0° C. for 1 hour and then at RT overnight. After reaction is complete, the mixture is mixed with saturated ammonium chloride solution and taken up in methylene chloride, and the organic phase is separated off and dried over sodium sulfate. After filtration, the solvent is removed in vacuo. The crude product is purified by chromatography on silica gel (mobile phase: cyclohexane/ethyl acetate 20:1). 18.0 g (126.6 mmol, 79% yield) of a colorless solid are isolated.

$^1$H-NMR (400 MHz, DMSO-$d_6$, δ/ppm): 9.32 (1H, s), 7.06-7.03 (1H, m), 6.86-6.81 (1H, m), 6.74-6.71 (1H, m), 5.09 (1H, t), 4.45 (2H, d).

Example 35A

Methyl 4-bromo-2-fluorobenzoate

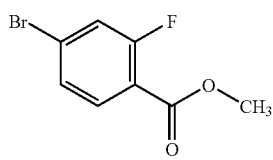

A solution of 8 g (36.53 mmol) of 4-bromo-2-fluorobenzoic acid in 44 ml of methanol is mixed with 0.46 ml (3.65 mmol) of chlorotrimethylsilane and heated to reflux for 12 h. The mixture is then concentrated and the residue is taken up in cyclohexane and filtered through silica gel. 4.49 g (19.25 mmol, 52% yield) of a white solid are obtained.

$R_f$ (cyclohexane/ethyl acetate 2:1): 0.5.
$^1$H-NMR (200 MHz, DMSO-$d_6$, δ/ppm): 7.84 (1H, t), 7.75 (1H, dd), 7.58 (1H, dd), 3.88 (3H, s).
MS (EI): 232 (M$^+$).

Example 36A

Methyl 3-fluoro-4'-methoxy-1,1'-biphenyl-4-carboxylate

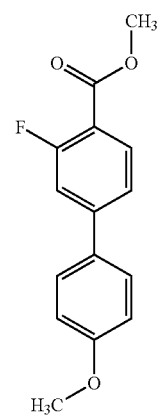

1.45 g (6.22 mmol) of methyl 4-bromo-2-fluorobenzoate from Example 35A are dissolved in 15 ml of 1,2-dimethoxyethane and, under argon, 1.13 g (7.47 mmol) of 4-methoxybenzeneboronic acid, 80 mg (0.11 mmol) of bis(triphenylphosphine)palladium(II) chloride and 7 ml of a 2 M solution of sodium carbonate in water are added. The reaction mixture is then stirred under reflux for 12 h. The mixture is subsequently cooled, filtered through 10 g of Extrelut, washed with dichloromethane and concentrated. The resulting crude product is purified by flash chromatography (silica gel; mobile phase: cyclohexane/ethyl acetate 2:1). 1.36 g (5.23 mmol, 84% yield) of a white solid are obtained.

$R_f$ (cyclohexane/ethyl acetate 2:1): 0.44.
$^1$H-NMR (200 MHz, DMSO-$d_6$, δ/ppm): 7.96 (1H, t), 7.80-7.62 (2H, m), 7.49-7.28 (3H, m), 7.02 (1H, dd), 3.89 (3H, s), 3.82 (3H, s).
MS (EI): 260 (M$^+$).

Example 37A (3-Fluoro-4'-methoxy-1,1'-biphenyl-4-yl)methanol

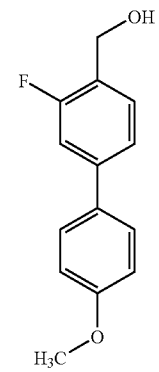

A solution of 1.36 g (5.23 mmol) of methyl 3-fluoro-4'-methoxy-1,1'-biphenyl-4-carboxylate from Example 36A in 10 ml of anhydrous THF is added dropwise to 3.14 ml (3.14 mmol) of a 1 M solution of lithium aluminum hydride in anhydrous THF at 0° C. The mixture is stirred at 0° C. for 2 h. Then 10 ml of saturated ammonium chloride solution are cautiously added and, after dilution with ethyl acetate, the organic phase is separated off. The organic phase is washed successively with water and saturated sodium chloride solution, dried over sodium sulfate and, after filtration, freed of solvent. The resulting crude product is purified by flash chromatography (silica gel; mobile phase: cyclohexane/ethyl acetate 5:1). 914 mg (3.94 mmol, 73% yield) of the title compound are obtained.

$R_f$(cyclohexane/ethyl acetate 2:1): 0.29.

$^1$H-NMR (300 MHz, DMSO-$d_6$, δ/ppm): 7.58-7.45 (3H, m), 7.39 (1H, t), 7.29-7.20 (2H, m), 6.95 (1H, dd), 5.30 (1H, t), 4.58 (2H, d), 3.83 (3H, s).

MS (EI): 232 (M$^+$).

Example 38A 4-(Chloromethyl)-3-fluoro-4'-methoxy-1,1'-biphenyl

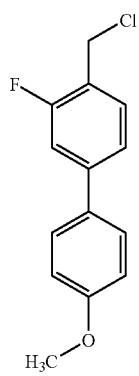

0.54 ml (7.45 mmol) of thionyl chloride, dissolved in 2 ml of chloroform, is slowly added to a solution of 864 mg (3.72 mmol) of (3-fluoro-4'-methoxy-1,1'-biphenyl-4-yl)methanol from Example 37A in 3 ml of chloroform, and the mixture is stirred at room temperature for 12 h. The mixture is then concentrated, taken up in ethyl acetate and washed with water and twice with saturated sodium bicarbonate solution. After drying over magnesium sulfate, filtration and concentration, the product is purified by flash chromatography (silica gel; mobile phase: cyclohexane/ethyl acetate 100:1). 511 mg (2.04 mmol, 55% yield) of a colorless oil are obtained.

$R_f$(cyclohexane/ethyl acetate 2:1): 0.52.

$^1$H-NMR (200 MHz, DMSO-$d_6$, δ/ppm): 7.68-7.52 (3H, m), 7.46-7.21 (3H, m), 6.99 (1H, dd), 4.86 (2H, s), 3.86 (3H, s).

MS (EI): 250 (M$^+$).

Example 39A

{2-[(4-Bromophenyl)(difluoro)methoxy]-5-fluorophenyl}methanol

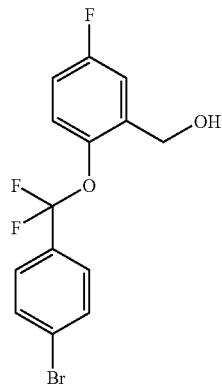

A suspension of 1.17 g (8.23 mmol) of 4-fluoro-2-(hydroxymethyl)phenol from Example 34A, 2.59 g (12.63 mmol) of 1-bromo-4-[bromo(difluoro)methyl]benzene from Example 33A and 1.25 g (9.06 mmol) of potassium carbonate in 10 ml of 2-propanol is heated to reflux for 12 hours. The mixture is then concentrated to dryness. The residue is suspended in methylene chloride, absorbed on silica gel, dried in vacuo and purified by chromatography (mobile phase: cyclohexane/ethyl acetate 10:1, then 100% ethyl acetate). 1.02 g (2.95 mmol, 35% yield) of the title compound are obtained.

$^1$H-NMR (400 MHz, CDCl$_3$, δ/ppm): 7.65-7.58 (4H, m), 7.32-7.24 (2H, m), 7.03-6.96 (1H, m), 4.74 (2H, s), 1.73 (1H, s).

MS (DCI): 364/366 (M+NH$_4^+$).

Example 40A (2-{Difluoro-[4'-(trifluoromethyl)biphenyl-4-yl]methoxy}-5-fluorophenyl)methanol

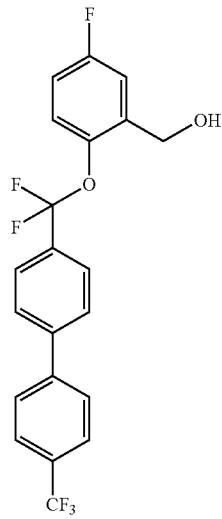

473 mg (1.36 mmol) of {2-[(4-bromophenyl)(difluoro)methoxy]-5-fluorophenyl}methanol from Example 39A are dissolved in 8 ml of 1,2-dimethoxyethane and, under argon, 362.6 mg (1.91 mmol) of 4-trifluoromethylphenylboronic acid, 67 mg of bis(triphenylphosphine)-palladium(II) chloride and 1.5 ml of a 2 M solution of sodium carbonate in water are added. The reaction mixture is then stirred under reflux for 12 hours. The mixture is subsequently cooled, filtered through 5 g of Celite, washed with dichloromethane and concentrated. The resulting crude product is purified by silica gel chromatography (mobile phase: cyclohexane/ethyl acetate 10:1). 532 mg (1.29 mmol, 90% purity, 85% yield) of a colorless oil are obtained.

$^1$H-NMR (300 MHz, CDCl$_3$, δ/ppm): 7.85-7.82 (2H, m), 7.76-7.69 (6H, m), 7.37-7.27 (2H, m), 7.04-6.98 (1H, s), 4.79 (2H, s), 1.76 (1H, s).

MS (DCI): 430 (M+NH$_4^+$).

Example 41A 2-(Bromomethyl)-4-fluorophenyl difluoro[4'-(trifluoromethyl)biphenyl-4-yl]methyl ether

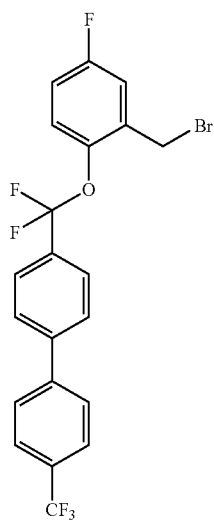

220 mg (0.53 mmol) of (2-{difluoro-[4'-(trifluoromethyl)biphenyl-4-yl]methoxy}-5-fluorophenyl)-methanol from Example 40A, 154 mg (0.59 mmol) of triphenylphosphine and 194.6 mg (0.59 mmol) tetrabromomethane are stirred in 5 ml dichloromethane at RT for 12 hours. 2 g of silica gel are added to the reaction mixture, and the mixture is then dried in vacuo and purified by silica gel chromatography (mobile phase: cyclohexane/ethyl acetate 10:1). 217 mg (0.46 mmol, 95% purity, 81% yield) of a solid are isolated.

MS (ESI): 474 (M$^+$).

Example 42A

{2-[Difluoro-(4'-trifluoromethylbiphenyl-4-yl)methoxy]-5-fluorobenzyl}triphenylphosphonium bromide

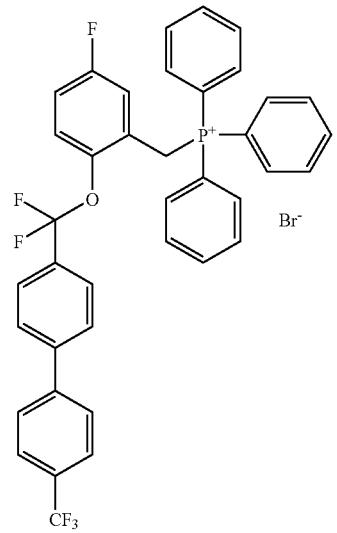

217 mg (0.46 mmol) of 2-(bromomethyl)-4-fluorophenyl difluoro[4'-(trifluoromethyl)biphenyl-4-yl]methyl ether from Example 41A and 148 mg (0.57 mmol) of triphenylphosphine are stirred in 5 ml of THF at RT for 12 hours. The reaction mixture is concentrated and the residue is washed with diethyl ether and n-hexane. The crude product is employed without further purification in the subsequent stage.

MS (ESI): 657 (M+H)$^+$.

Example 43A

Methyl 2-(2-chlorobenzyloxy)-5-fluorobenzoate

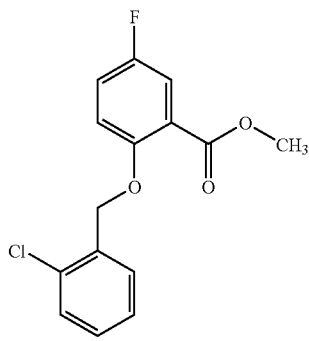

10.0 g (58 mmol) of methyl 5-fluoro-2-hydroxybenzoate [CAS 391-92-4], 13.3 g (64.5 mmol) of 2-chlorobenzyl bromide [CAS 611-17-6], 40.6 g (293 mmol) of potassium carbonate and 14.6 g (88 mmol) of potassium iodide are suspended in 50 ml of acetone, and the mixture is stirred under reflux for 12 h. The solvent is distilled out in vacuo, and the residue is taken up in ethyl acetate and washed twice each with 10% strength sodium hydroxide solution, with 1 N hydrochloric acid and with water. Drying over magnesium sulfate, filtration and washing with ethyl acetate are followed by concentration. The residue is stirred with petroleum ether, and the solid is filtered off with suction and dried on a clay dish. 10.0 g (33.9 mmol, 59% of theory) of the title compound are isolated.

$^1$H-NMR (400 MHz, DMSO-$d_6$, δ/ppm): 7.72 (1H, $m_c$), 7.51 (2H, $m_c$), 7.46-7.36 (3H, m), 7.31 (1H, dd), 5.22 (2H, s), 3.81 (3H, s).

LC-MS (method 2): $R_t$ 2.6 min; m/z 295 (M+H)$^+$.

Example 44A 2-(2-Chlorobenzyloxy)-5-fluorobenzoic acid

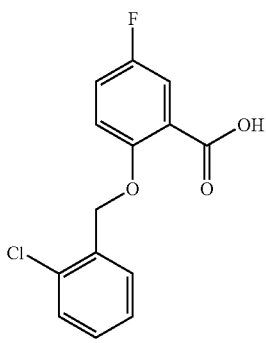

10.0 g (34 mmol) of methyl 2-(2-chlorobenzyloxy)-5-fluorobenzoate are dissolved in 80 ml of methanol and 40 ml of 40% strength sodium hydroxide solution and stirred at RT for 12 h. The solvent is distilled out in vacuo, water is added to the residue until it has all dissolved, and the solution is then extracted with ethyl acetate. The aqueous phase is acidified with hydrochloric acid and extracted three times with ethyl acetate. The combined organic phases are dried over magnesium sulfate, filtered, washed with ethyl acetate and concentrated. The residue is mixed with petroleum ether, and the crystals which have separated out are filtered off with suction and dried on a clay dish. 6.00 g (21.3 mmol, 63% of theory) of the title compound are isolated.

$^1$H-NMR (400 MHz, DMSO-$d_6$, δ/ppm): 7.61 (1H, $m_c$), 7.51 (1H, c), 7.42-7.37 (2H, m), 7.17 (1H, dd), 7.08-6.97 (2H, m), 5.19 (1H, t), 5.16 (2H, s), 4.55 (2H, d).

HPLC (method 1): $R_t$ 4.7 min.

MS (DCI): 284 (M+NH$_4^+$).

Example 45A

[2-(2-Chlorobenzyloxy)-5-fluorophenyl]methanol

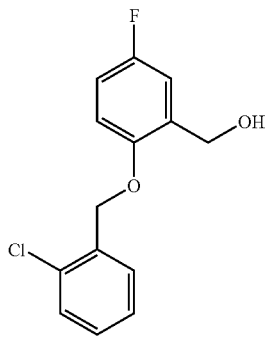

5.50 g (20 mmol) of 2-(2-chlorobenzyloxy)-5-fluorobenzoic acid are dissolved in 25 ml of THF, heated to reflux and then 20 ml of 1 M borane-dimethyl sulfide complex are added dropwise. The reaction solution is then cooled to room temperature and stirred at this temperature for 1 h. The solvent is distilled out in vacuo, and water is added to the residue. Acidification is then carried out cautiously (copious gas evolution) with 1 N hydrochloric acid. 1 N sodium hydroxide solution is then added to make slightly basic, and the aqueous phase is extracted three times with dichloromethane. The organic phases are dried over magnesium sulfate, filtered and washed with dichloromethane, and the filtrate is concentrated. Petroleum ether is added to the residue, and the crystals which have separated out are filtered off with suction and dried on a clay dish. 3.65 g (13.6 mmol, 68% of theory) of the title compound are isolated.

$^1$H-NMR (400 MHz, DMSO-$d_6$, δ/ppm): 7.61 (1H, $m_c$), 7.51 (1H, $m_c$), 7.42-7.37 (2H, m), 7.17 (1H, dd), 7.08-6.97 (2H, m), 5.19 (1H, t), 5.16 (2H, s), 4.55 (2H, d).

HPLC (method 1): $R_t$ 4.7 min.

MS (DCI): 284 (M+NH$_4^+$).

Example 46A

[2-(2-Chlorobenzyloxy)-5-fluorobenzyl]triphenylphosphonium bromide

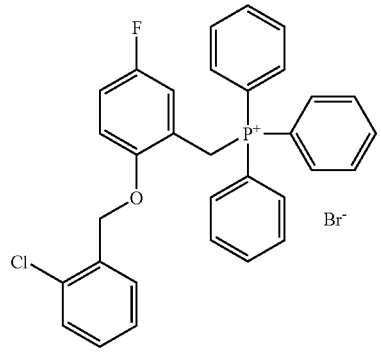

4.60 g (17 mmol) of [2-(2-chlorobenzyloxy)-5-fluorophenyl]methanol are dissolved in 10 ml of acetonitrile, 5.62 g (16 mmol) of triphenylphosphine hydrobromide are added, and the suspension is stirred under reflux for 12 h. A further 2.80 g (8 mmol) of triphenylphosphine hydrobromide are added, and the mixture is stirred under reflux for a further 3 h. The solvent is mostly distilled out in vacuo, and the crystals which have separated out are stirred with petroleum ether, filtered off with suction and dried on a clay dish. 9.82 g (15.7 mmol, 92% of theory) of the title compound are obtained.

$^1$H-NMR (300 MHz, DMSO-$d_6$, δ/ppm): 7.86 (3H, $m_c$), 7.70-7.46 (13H, m), 7.42-7.30 (3H, m), 7.15 (1H, $m_c$), 6.96 (1H, dd), 6.90 (1H, dt), 4.99 (2H, d), 4.66 (2H, d).

HPLC (method 1): $R_t$ 5.0 min.

MS (ESI): 511 (M-Br$^+$).

Example 47A

Methyl 5-fluoro-2-{[2-(trifluoromethyl)benzyl]oxy}benzoate

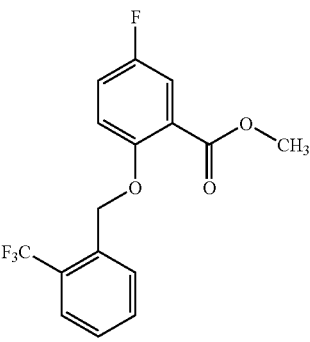

A solution of 7.50 g (44.08 mmol) of methyl 5-fluoro-2-hydroxybenzoate in 40 ml of dry acetonitrile is mixed with 9.44 g (48.49 mmol) of 2-trifluoromethylbenzyl chloride and 18.28 g (132.25 mmol) of anhydrous potassium carbonate and heated under reflux for 12 hours. The mixture is then cooled, filtered, washed with dichloromethane and concentrated, and the residue is purified by chromatography (silica gel; mobile phase: cyclohexane/ethyl acetate 5:1). 9.18 g (28 mmol, 89% purity, 56% yield) of the title compound are obtained.

$^1$H-NMR (400 MHz, DMSO-$d_6$, δ/ppm): 7.93-7.91 (1H, m), 7.80-7.74 (2H, m), 7.60-7.56 (1H, m), 7.53-7.50 (1H, s), 7.46-7.41 (1H, m), 7.29-7.26 (1H, m), 5.32 (2H, s), 3.80 (3H, s).

MS (DCI): 346 (M+NH$_4^+$), 329 (M+H$^+$).

Example 48A (5-Fluoro-2-{[2-(trifluoromethyl)benzyl]oxy}phenyl)methanol

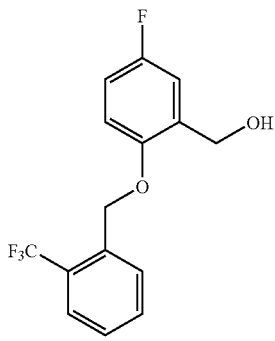

The title compound is prepared in 72% yield from methyl 5-fluoro-2-{[2-(trifluoromethyl)benzyl]-oxy}benzoate (Example 47A) in analogy to [2-(2-chlorobenzyloxy)-5-fluorophenyl]methanol (Example 45A).

$^1$H-NMR (400 MHz, DMSO-4, δ/ppm): 7.81-7.72 (3H, m), 7.61-7.57 (1H, m), 7.20-7.18 (1H, m), 7.06-6.99 (2H, s), 5.23 (2H, s), 5.20 (1H, d), 4.52 (2H, d).

MS (EI): 300 (M$^+$).

Example 49A 2-(Bromomethyl)-4-fluoro-1-{[2-(trifluoromethyl)benzyl]oxy}benzene

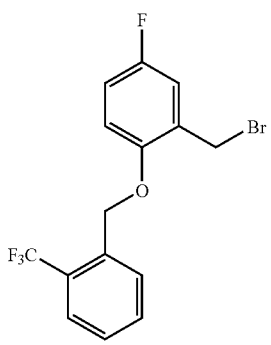

The title compound is prepared in 80% yield from (5-fluoro-2-{[2-(trifluoromethyl)benzyl]oxy}-phenyl)methanol (Example 48A) in analogy to 2-(bromomethyl)-4-fluorophenyl difluoro[4'-(trifluoromethyl)biphenyl-4-yl]methyl ether (Example 41A).

$^1$H-NMR (400 MHz, DMSO-$d_6$, δ/ppm): 7.89-7.74 (3H, m), 7.62-7.58 (1H, m), 7.38-7.35 (1H, m), 7.21-7.16 (1H, m), 5.32 (2H, s), 4.66 (2H, s)

MS (DCI): 380 (M+NH$_4^+$).

Example 50A

[5-Fluoro-2-(2-trifluoromethylbenzyloxy)benzyl]
triphenylphosphonium bromide

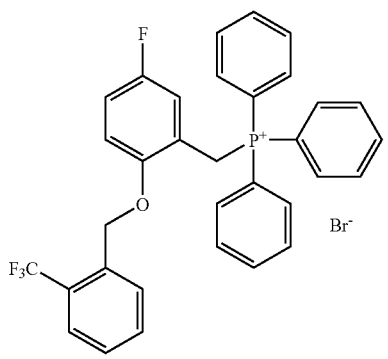

The title compound is prepared from 2-(bromomethyl)-4-fluoro-1-{[2-(trifluoromethyl)benzyl]-oxy}benzene (Example 49A) in analogy to Example 42A.

$^1$H-NMR (400 MHz, DMSO-d$_6$, δ/ppm): 7.87-7.83 (3H, m), 7.79-7.77 (1H, m), 7.69-7.55 (14H, m), 7.47-7.44 (1H, m), 7.20-7.14 (1H, m), 6.94-6.90 (2H, m), 5.02 (2H, d), 4.75 (2H, s).

MS (DCI): 545 (M+H)$^+$.

The compounds listed in the following table are obtained in an analogous manner:

| Example | Structure | Analytical data |
|---|---|---|
| 51A (starting from Ex. 34A and Ex. 38A) | 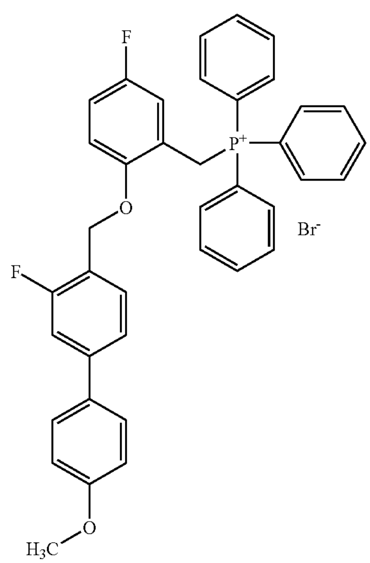 | $^1$H-NMR (300 MHz, DMSO-d$_6$, δ/ppm): 7.94-6.88 (25H, m), 5.00-4.92 (2H, m), 4.72 (2H, s), 3.82 (3H, s). MS (ESI): 601 (M$^+$). |

-continued

| Example | Structure | Analytical data |
|---|---|---|
| 52A (starting from Ex. 34A and 4-chloro-methyl-4'-trifluoromethylbiphenyl [CAS 454464-38-1]) | | $^1$H-NMR (300 MHz, DMSO-$d_6$, δ/ppm): 7.95-7.82 (7H, m), 7.75-7.57 (14H, m), 7.35-7.30 (2H, m), 7.20-7.12 (1H, m), 7.00-6.96 (1H, m), 6.92-6.86 (1H, m), 5.05-4.98 (2H, d), 4.72 (2H, s).<br>MS (ESI): 621 (M$^+$ − Br). |
| 53A (starting from Ex. 34A and 1-chloro-methyl-2-fluorobenzene) | | MS (DCI): 495 (M$^+$ − Br). |
| 54A (starting from Ex. 34A and 1-chloro-methyl-3,5-bis(trifluoromethyl)-benzene) | | MS (DCI): 613 (M$^+$ − Br). |

| Example | Structure | Analytical data |
|---|---|---|
| 55A (starting from Ex. 34A and chloromethyl-benzene) | 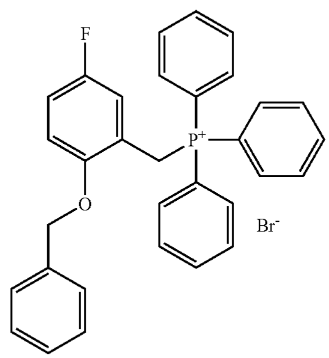 | $^1$H-NMR (400 MHz, DMSO-$d_6$, δ/ppm): 7.88-7.84 (3H, m), 7.68-7.55 (12H, m), 7.39-7.33 (3H, m), 7.21-7.12 (3H, m), 6.96-6.93 (1H, m), 6.89-6.85 (1H, m), 4.98 (2H, d), 4.64 (2H, m). MS (ESI): 557 (M$^+$). |

Example 56A

Methyl 2-(4-tert-butylbenzyloxy)-5-fluorobenzoate

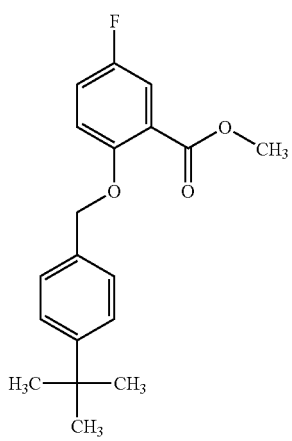

4.44 g (26 mmol) of methyl 5-fluoro-2-hydroxybenzoate [CAS 391-92-4], 5.25 g 28.7 mmol) of 4-tert-butylbenzyl chloride [CAS 19692-45-6], 18.0 g (130 mmol) of potassium carbonate and 6.5 g (39.2 mmol) of potassium iodide are dissolved in 25 ml of acetone and stirred under reflux for 12 h. The solvent is distilled out in vacuo, and the residue is taken up in ethyl acetate and washed once with 10% strength sodium hydroxide solution and three times with 1 N hydrochloric acid. The solution is dried over sodium sulfate, filtered, washed with ethyl acetate and concentrated. 8.36 g (26 mmol, 100% of theory) of the title compound are isolated.

$^1$H-NMR (400 MHz, DMSO-$d_6$, δ/ppm): 7.49-7.35 (6H, m), 7.25 (1H, dd), 5.12 (2H, s), 3.81 (3H, s), 1.28 (9H, s).

LC-MS (method 4): $R_t$ 3.1 min; m/z 334 (M+NH$_4$)$^+$.

Example 57A 2-(4-tert-Butylbenzyloxy)-5-fluorobenzoic acid

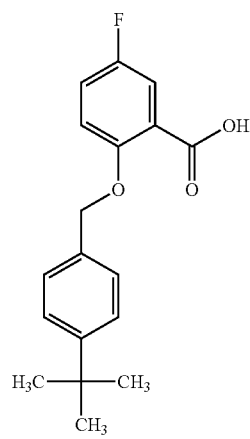

8.0 g (25 mmol) of methyl 2-(4-tert-butylbenzyloxy)-5-fluorobenzoate are dissolved in 64 ml of methanol and 32 ml of 40% strength sodium hydroxide solution and stirred under reflux for 12 h. The crystals which have separated out are filtered off with suction, washed with water, 1 N hydrochloric acid and petroleum ether and dried on a clay dish. 7.10 g (23.5 mmol, 94% of theory) of the title compound are isolated.

$^1$H-NMR (300 MHz, DMSO-$d_6$, δ/ppm): 7.42-7.33 (4H, m), 6.89-6.70 (3H, m), 4.97 (2H, s), 1.28 (9H, s).

LC-MS (method 4): $R_t$ 2.7 min; m/z 302 (M+H)$^+$.

Example 58A

[2-(4-tert-Butylbenzyloxy)-5-fluorophenyl]methanol

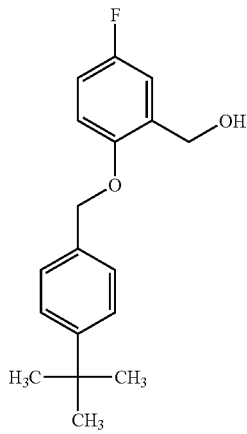

6.65 g (22 mmol) of 2-(4-tert-butylbenzyloxy)-5-fluorobenzoic acid are suspended in 25 ml of THF and cooled to 0° C. 2.4 ml (22 mmol) of N-methylmorpholine and 2.1 ml (22 mmol) of ethyl chloroformate are added, and the solution is stirred at room temperature for 15 min. 2.50 g (66 mmol) of sodium borohydride are added and, after 3 h, methanol is added until gas evolution has subsided. The mixture is acidified with 1 N hydrochloric acid and concentrated in vacuo, and the residue is taken up in ethyl acetate. The organic phase is washed with saturated sodium chloride solution and then dried over sodium sulfate. The solvent is distilled out in vacuo, and the residue is chromatographed on silica gel (mobile phase: cyclohexane/ethyl acetate 10:1). 3.52 g (12.2 mmol, 55% of theory) of the title compound are isolated.

$^1$H-NMR (400 MHz, DMSO-$d_6$, δ/ppm): 7.41-7.35 (4H, m), 7.17-7.15 (1H, m), 7.02-6.99 (2H, m), 5.19 (1H, t), 5.05 (2H, s), 4.52 (2H, d), 1.28 (9H, s).

LC-MS (method 4): $R_t$ 2.8 min; m/z 288 (M+H)$^+$.

Example 59A

[2-(4-tert-Butylbenzyloxy)-5-fluorobenzyl]triphenylphosphonium bromide

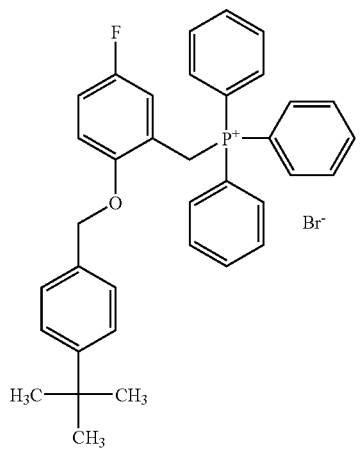

5.80 g (20 mmol) of [2-(4-tert-butylbenzyloxy)-5-fluorophenyl]methanol are dissolved in 70 ml of acetonitrile, 6.56 g (19.5 mmol) of triphenylphosphine hydrobromide are added, and the suspension is stirred under reflux for 24 h. The solvent is mostly distilled out in vacuo, and the crystals which have separated out are stirred with diethyl ether, filtered off with suction, washed with petroleum ether and dried on a clay dish. The resulting crude product is purified by preparative HPLC. 2.64 g (4.3 mmol, 21% of theory) of the title compound are obtained.

$^1$H-NMR (300 MHz, DMSO-$d_6$, δ/ppm): 7.86 (3H, $m_c$), 7.69-7.52 (12H, m), 7.37 (2H, $d_{AB}$), 7.14 (2+1H, $d_{AB}$+m), 6.95 (1H, dd), 6.88 (1H, dd), 4.94 (2H, d), 4.40 (2H, s), 1.28 (9H, s).

LC-MS (method 2): $R_t$ 2.4 min; m/z 533 (M+H—Br)$^+$.

Example 60A 2-(4-Trifluoromethylphenyl)ethanol

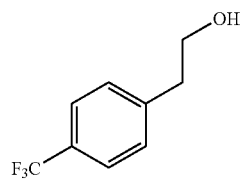

3.0 g (14.7 mmol) of 4-trifluoromethylphenylacetic acid are introduced into 30 ml of abs. THF at 0° C. A 1 M solution of 557.8 mg (14.7 mmol) of lithium aluminum hydride in 14.7 ml of THF is added dropwise, and the solution is stirred at room temperature until reaction is complete. The mixture is added to ice, acidified with hydrochloric acid and extracted with ethyl acetate. The organic phase is concentrated, and the crude product is purified by chromatography on silica gel (mobile phase: cyclohexane/ethyl acetate 6:1). 2 g (92% of theory) of the title compound are obtained.

$^1$H-NMR (400 MHz, CDCl$_3$, δ/ppm): 2.95 (t, 2H), 3.9 (t, 2H), 7.35 (d, 2H), 7.6 (t, 2H).

GC-MS (method 1): $R_t$ 4.61 min; m/z 190 (M$^+$).

Example 61A

Methyl 5-fluoro-2-[2-(4-trifluoromethylphenyl)ethoxy]benzoate 1.79 g (10.5 mmol) of methyl 5-fluorosalicylate, 20 g (10.5 mmol) of 2-(4-trifluoromethylphenyl)ethanol and 2.76 g (10.5 mmol) of triphenylphosphine are introduced into 50 ml of THF and, at 0° C., a solution of 1.83 g (10.5 mmol) of diethyl azodicarboxylate in 10 ml of THF is added dropwise. The mixture is stirred at RT overnight and then the volatile components are removed in vacuo. The resulting crude product is purified by chromatography on silica gel (mobile phase: cyclohexane/ethyl acetate 7:1). 2.09 g (58% yield) of the title compound are obtained.

$^1$H-NMR (300 MHz, CDCl$_3$, δ/ppm): 3.2 (t, 2H), 3.85 (s, 3H), 4.25 (t, 2H), 6.85 (dd, 1H), 7.15 (m, 1H), 7.5 (m, 3H), 7.6 (d, 2H).

GC-MS (method 2): R$_t$ 10.54 min; m/z 342 (M$^+$).

Example 62A

{5-Fluoro-2-[2-(4-trifluoromethylphenyl)ethoxy]phenyl}methanol

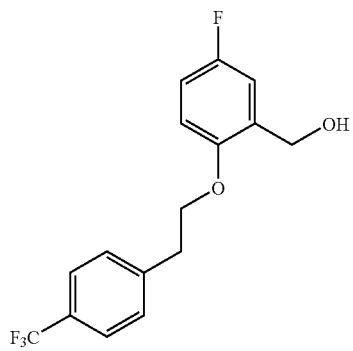

2.0 g (5.84 mmol) of methyl 5-fluoro-2-[2-(4-trifluoromethylphenyl)ethoxy]benzoate are introduced into 25 ml of THF. At 0° C., 4.38 ml (4.38 mmol) of a 1 M lithium aluminum hydride solution in THF are added dropwise, and the mixture is stirred at RT until reaction is complete. The mixture is added to ice-water, acidified with hydrochloric acid and extracted with ethyl acetate. All the volatile components are removed in vacuo, and the crude product is purified by chromatography on silica gel (mobile phase: cyclohexane/ethyl acetate 5:1). 1.7 g (82% yield) of the title compound are obtained.

$^1$H-NMR (400 MHz, CDCl$_3$, δ/ppm): 3.2 (t, 2H); 4.25 (t, 2H); 4.6 (s, 2H); 6.75 (m, 1H); 6.9 (m, 1H); 7.05 (dd, 1H); 7.4 (d, 2H); 7.6 (d, 2H).

GC-MS (method 1): R$_t$ 10.71 min; m/z 314 (M$^+$).

Example 63A

{5-Fluoro-2-[2-(4-trifluoromethylphenyl)ethoxy]benzyl}triphenylphosphonium bromide

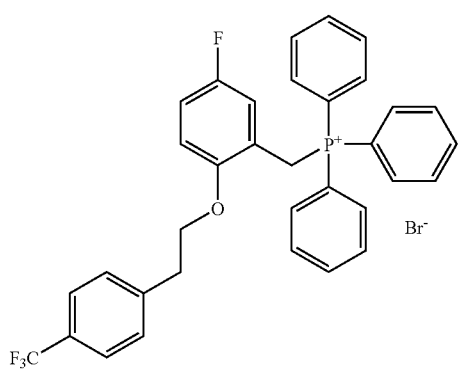

1.7 g (5.41 mmol) of {5-fluoro-2-[2-(4-trifluoromethylphenyl)ethoxy]phenyl}methanol and 1.76 g (5.14 mmol) of triphenylphosphonium hydrobromide are heated under reflux in 20 ml of acetonitrile for three hours. A first product fraction is crystallized at −20° C. The mother liquor is concentrated, the residue is dissolved in dichloromethane, and a second fraction is crystallized with diethyl ether. A total of 2.71 g (76% yield) of the title compound is obtained.

$^1$H-NMR (400 MHz, DMSO-d$_6$, δ/ppm): 2.75 (t, 2H); 3.75 (t, 2H); 4.85 (d, 2H); 6.8 (m, 1H); 6.9 (m, 1H); 7.15 (m, 1H); 7.45 (d, 2H); 7.6 (m, 8H); 7.7 (m, 6H); 7.9 (t, 3H).

LC-MS (method 2): R$_t$ 2.15 min; m/z 559 [M+H]$^+$.

Example 64A

Methyl 5-fluoro-2-[3-(4-trifluoromethylphenyl)prop-2-ynyloxy]benzoate

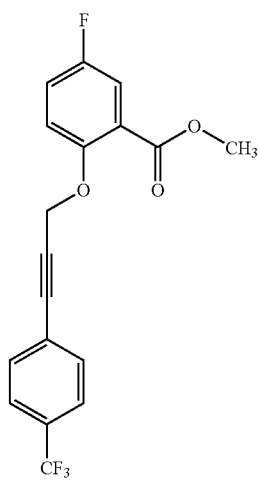

4.12 g (24.2 mmol) of methyl 3-fluorosalicylate [CAS 391-924] are dissolved in 100 ml of acetone, 10.0 g (72.6 mmol) of potassium carbonate, 6.02 g 36.3 mmol) of potassium iodide and 7.00 g (26.6 mmol) of 1-(3-bromoprop-1-ynyl)-4-trifluoromethylbenzene [Beilstein Record No. 7919066] are added, and the mixture is stirred under reflux for 2.5 h. The solvent is distilled out in vacuo, and the residue is taken up in ethyl acetate. The organic phase is washed with water and dried over sodium sulfate. The solvent is distilled out in vacuo, and the residue is chromatographed on silica gel (mobile phase: cyclohexane/ethyl acetate 20:1→5:1). 4.63 g (13.1 mmol, 49% of theory) of the title compound are obtained.

$^1$H-NMR (400 MHz, DMSO-d$_6$, δ/ppm): 7.75 (2H, d$_{AB}$), 7.65 (2H, d$_{AB}$), 7.52-7.45 (2H, m), 7.37 (1H, dd), 5.17 (2H, s), 3.82 (3H, s).

LC-MS (method 4): R$_t$ 2.9 min; m/z 352 (M+H)$^+$.

Example 65A

5-Fluoro-2-[3-(4-trifluoromethylphenyl)prop-2-ynyloxy]benzoic acid

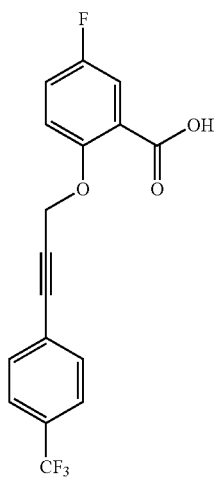

100 mg (0.28 mmol) of methyl 5-fluoro-2-[3-(4-trifluoromethylphenyl)prop-2-ynyloxy]benzoate are dissolved in 2 ml of methanol and 2 ml of water, and 20.3 mg (0.85 mmol) of lithium hydroxide are added. After stirring at room temperature for 12 h, the crystals which have separated out are filtered off with suction, washed with water, 1 N hydrochloric acid and petroleum ether and dried on a clay dish. 74.9 mg (0.20 mmol, 71% of theory) of the title compound are isolated.

$^1$H-NMR (300 MHz, DMSO-$d_6$, δ/ppm): 13.0 (1H, broad s), 7.76 (2H, $d_{AB}$), 7.65 (2H, $d_{AB}$), 7.49-7.39 (2H, m), 7.33 (1H, dd), 5.15 (2H, s).

LC-MS (method 2): $R_t$ 2.4 min; m/z 338 (M+H)$^+$.

Example 66A

{5-Fluoro-2-[3-(4-trifluoromethylphenyl)prop-2-ynyloxy]phenyl}methanol

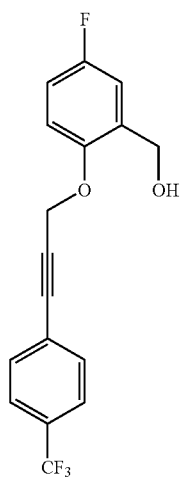

3.50 g (10.3 mmol) of 5-fluoro-2-[3-(4-trifluoromethylphenyl)prop-2-ynyloxy]benzoic acid are suspended in 10 ml of THF, 1.04 g (10.3 mmol) of N-methylmorpholine are added, the mixture cooled to 0° C., and 1.12 g (10.3 mmol) of ethyl chloroformate are added. The mixture is warmed to room temperature and stirred for 30 min. 1.17 g (31.0 mmol) of sodium borohydride are added to this solution, and the mixture is stirred at room temperature for 5 h. Then methanol is added until gas evolution has subsided, and subsequently 1 N hydrochloric acid is used to acidify. The solvent is distilled out in vacuo, and the residue is taken up in ethyl acetate. The organic phase is washed with saturated sodium chloride solution and dried over sodium sulfate, and the solvent is distilled out in vacuo. 4.62 g (8.69 mmol, 85% of theory) of the title compound are isolated.

LC-MS (method 4): $R_t$ 2.7 min; m/z 348 (M+Na)$^+$.

Example 67A

{5-Fluoro-2-[3-(4-trifluoromethylphenyl)prop-2-ynyloxy]benzyl}triphenylphosphonium bromide

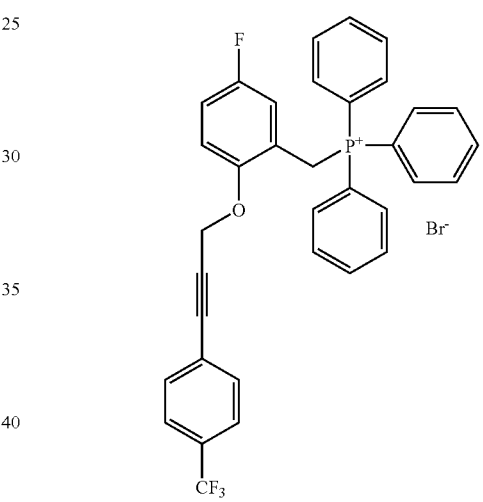

Stage a):

834 mg (3.18 mmol) of triphenylphosphine and 1.05 g (3.18 mmol) of tetrabromomethane are dissolved in 2 ml of THF and stirred at room temperature for 10 min. Then 860 mg (2.63 mmol) of {5-fluoro-2-[3-(4-trifluoromethylphenyl)prop-2-ynyloxy]phenyl}methanol, dissolved in 2 ml of THF, are added dropwise, and the mixture is stirred at room temperature overnight. The solvent is distilled out in vacuo, and the residue is chromatographed on silica gel (mobile phase: cyclohexane/ethyl acetate 10:1). 240 mg (0.62 mmol, 24% of theory) of 5-fluoro-2-[3-(4-trifluoromethylphenyl)prop-2-ynyloxy]benzyl bromide are obtained.

Stage b):

63.7 mg (0.24 mmol) of triphenylphosphine are dissolved in 2 ml of dichloromethane, 94 mg (0.24 mmol) of 5-fluoro-2-[3-(4-trifluoromethylphenyl)prop-2-ynyloxy]benzyl bromide, dissolved in 2 ml of dichloromethane, are added dropwise, and the mixture is stirred at room temperature overnight. The solvent is distilled out in vacuo, and the crystalline residue is stirred with petroleum ether. The resulting colorless crystals are filtered off with suction and dried on a clay dish. 109 mg (0.17 mmol, 69% of theory) of the title compound are obtained.

$^1$H-NMR (300 MHz, DMSO-d$_6$, δ/ppm): 7.89-7.58 (19H, m), 7.21 (1H, tt), 7.06 (1H, dd), 6.86 (1H, dt), 6.88 (1H, dd), 4.98 (2H, d), 4.61 (2H, s).

LC-MS (method 1): R$_t$ 2.4 min; m/z 569 (M+H—Br)$^+$.

Example 68A

Methyl E/Z-4-(2-[2-(4-cyanophenyl)ethyl]-4-{5-fluoro-2-[2-(4-methoxyphenyl)ethyl]phenyl}but-3-enyl)benzoate

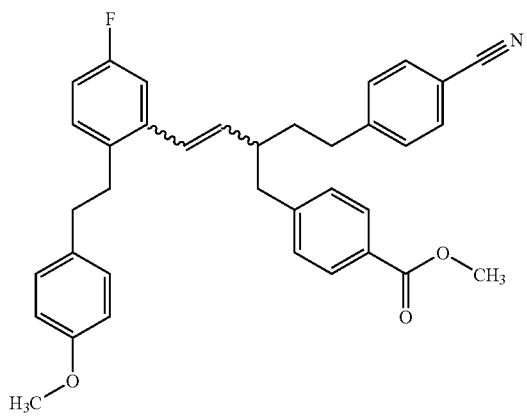

1.46 ml (2.33 mmol) of a 1.6 M solution of n-butyllithium in hexane are slowly added to a solution of 1093 mg (1.87 mmol) of ({5-fluoro-2-[2-(4-methoxyphenyl)ethyl]benzyl}triphenylphosphonium bromide (Example 32A) in 20 ml of THF at 0° C. Then, at this temperature, 500 mg (1.56 mmol) of methyl 4-[4-(4-cyanophenyl)-2-formylbutyl]benzoate from Example 16A are slowly metered in, and the mixture is stirred at 0° C. for 4 hours. After the reaction solution has warmed to room temperature it is stirred for 12 hours and then some water is added, and the mixture is concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 50:1→20:1). 719 mg (1.31 mmol, 84% yield) of a colorless solid are obtained.

$^1$H-NMR (300 MHz, DMSO-d$_6$, δ/ppm): 2:1 E/Z mixture: 7.79 (3H, d), 7.71 (2H, d), 7.64 (1H, d), 7.44-6.72 (9H, m), 6.43 (0.33H, d), 6.32 (0.66H, d), 6.14-5.99 (1H, m), 5.62 (0.33H, t), 3.79 (0.66H, s), 3.74 (2H, s), 3.71 (3H, s), 2.99-2.37 (9H, m), 1.92-1.52 (2H, m).

MS (DCI): 565 (M+NH$_4^+$).

Example 69A

Methyl E/Z-4-(4-{5-fluoro-2-[2-(4-methoxyphenyl)ethyl]phenyl}-2-{2-[4-(5-oxo-4,5-dihydro-[1,2,4]oxadiazol-3-yl)phenyl]ethyl}but-3-enyl)benzoate

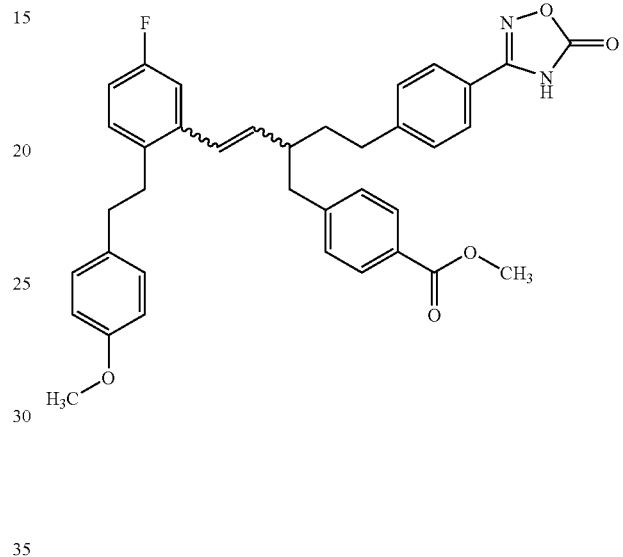

A solution of 444.1 mg (6.39 mmol) of hydroxylamine hydrochloride in 10 ml of DMSO is mixed with 0.89 ml (6.39 mmol) of triethylamine and stirred at room temperature for 10 min. The resulting precipitate is filtered off. Then 180 mg (0.28 mmol) of methyl E/Z-4-(2-[2-(4-cyanophenyl)ethyl]-4-{5-fluoro-2-[2-(4-methoxyphenyl)ethyl]phenyl}but-3-enyl)benzoate from Example 68A are metered into the filtrate. The reaction solution is stirred at 75° C. for 12 hours. After conversion is complete and cooling, 10 ml of water are added to the reaction solution, the mixture is extracted three times with ethyl acetate, and the combined organic phases are washed with saturated sodium chloride solution. The organic phase is then dried over sodium sulfate and concentrated to dryness. 632 mg of a colorless oil are obtained and are reacted further immediately without further purification.

The oil obtained above is dissolved in 10 ml of DMF, and 0.1 ml (1.19 mmol) of pyridine is added. The solution is then cooled to 0° C. and 193.83 mg (1.08 mmol) of 2-ethylhexyl chloroformate are slowly added. The mixture is stirred at 0° C. for about 30 min and then taken up in water and extracted with ethyl acetate. The organic phase is dried over sodium sulfate and concentrated to dryness. The resulting residue is taken up in 10 ml of xylene and heated to reflux for 4 hours. After reaction is complete, the reaction solution is cooled and concentrated to dryness. The crude product is purified by flash chromatography on silica gel (mobile phase: cyclohexane/ethyl acetate 4:1). 447 mg (0.59 mmol, 56% yield; purity 82%) of a colorless oil are obtained.

LC-MS (method 1): R$_t$ 3.05 min; m/z 607 (M+H$^+$).

Example 70A

Diallyl 2-(4-cyanobenzyl)malonate

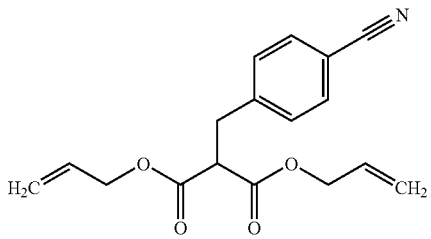

19.79 g (0.494 mol) of sodium hydride are added in portions (caution: evolution of hydrogen) to a solution of 121.5 g (0.659 mol) of diallyl malonate in 1.5 liters of dioxane at 0° C. The mixture is warmed to room temperature and then stirred at 40° C. for 1 hour. Subsequently, at 40° C., 50 g (0.329 mol) of 4-chloromethylbenzonitrile, dissolved in 500 ml of dioxane, are slowly added dropwise, and the reaction solution is stirred at 110° C. overnight. After cooling to room temperature, the reaction mixture is added to 1200 ml of water. Care must be taken during this that the pH remains <7 (where appropriate, a few ml of 1 M hydrochloric acid are metered in to about pH 2). The mixture is then extracted three times with ethyl acetate, and the combined organic phases are washed with saturated sodium chloride solution and dried over sodium sulfate. After filtration, the solvent is concentrated to dryness in vacuo. Excess diallyl malonate is then removed by high vacuum distillation (boiling point: 57° C.; 0.074 mbar). The distillation residue is purified by flash chromatography on silica gel (mobile phase: petroleum ether/ethyl acetate 20:1). 67 g (0.22 mol, 67% yield) of a colorless solid are obtained.

$^1$H-NMR (300 MHz, DMSO-$d_6$, δ/ppm): 7.77 (2H, d), 7.48 (2H, d), 5.90-5.73 (2H, m), 5.29-5.13 (4H, m), 4.64-4.50 (4H, m), 4.09 (1H, t), 3.21 (2H, d).

MS (DCI): 317 (M+NH$_4^+$).

Example 71A

Diallyl 2-(4-cyanobenzyl)-2-[2-(4-methoxycarbonylphenyl)ethyl]malonate

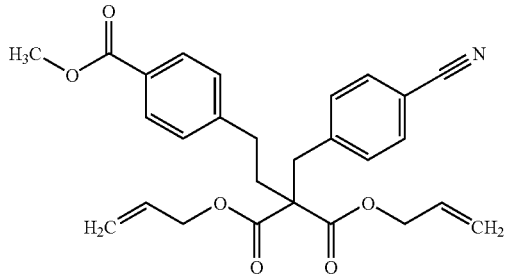

7.13 g (178.36 mmol) of sodium hydride are added in portions to a solution of 48.53 g (162.14 mmol) of diallyl 2-(4-cyanobenzyl)malonate from Example 70A in 180 ml of DMF at 0° C. The reaction solution is then allowed to reach room temperature and is stirred for 30 min. The reaction solution is then cooled to 0° C. again and, after addition of 55 g (194.57 mmol) of methyl 4-(2-bromoethyl)benzoate [CAS 136333-97-6] in 195 ml of DMF, stirred at this temperature for 30 min. The mixture is then stirred at room temperature overnight. Water is added dropwise to the reaction mixture, which is then extracted three times with ethyl acetate, and the combined organic phases are washed with saturated sodium chloride solution and dried over sodium sulfate. After filtration, the solvent is concentrated to dryness in vacuo. The resulting crude product is purified by flash chromatography on silica gel (mobile phase: petroleum ether/ethyl acetate 10:1). 33.4 g (72.37 mol, 44% yield) of a colorless solid are obtained.

$^1$H-NMR (300 MHz, CDCl$_3$, δ/ppm): 7.89 (2H, d), 7.79 (2H, d), 7.38 (2H, d), 7.32 (2H, d), 5.97-5.81 (2H, m), 5.38-5.20 (4H, m), 4.61 (4H, d), 3.82 (3H, s), 3.39 (2H, s), 2.77-2.61 (2H, m), 1.99-1.84 (2H, m).

MS (DCI): 479 (M+NH$_4^+$).

Example 72A

Methyl 4-[3-carboxy-4-(4-cyanophenyl)butyl]benzoate

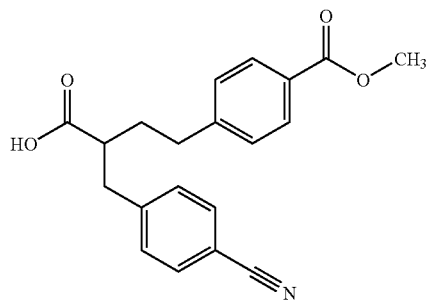

A solution of 7.47 ml (53.63 mmol) of triethylamine and 1.53 ml (40.63 mmol) of formic acid in 170 ml of dioxane is added to a solution of 7.5 g (16.25 mmol) of diallyl 2-(4-cyanobenzyl)-2-[2-(4-methoxycarbonylphenyl)ethyl]malonate from Example 71A, 0.3 g (1.14 mmol) of triphenylphosphine and 70 mg of palladium acetate in 170 ml of dioxane at room temperature. The reaction mixture is then stirred at 100° C. for 2 hours. After conversion is complete, the reaction solution is cooled and the solvent is removed in vacuo. The residue is then taken up in ethyl acetate and water and acidified with 1 N hydrochloric acid, and the organic phase is separated off. The aqueous phase is extracted three times more with ethyl acetate, and the organic phases are then combined, washed with saturated sodium chloride solution and dried over sodium sulfate. After filtration, the solution is concentrated in vacuo. 5.48 g (89% yield, 90% purity) of a colorless solid are obtained.

$^1$H-NMR (400 MHz, DMSO-$d_6$, δ/ppm): 12.46-12.29 (1H, broad), 7.88 (2H, d), 7.74 (2H, d), 7.39 (2H, d), 7.31 (2H, d), 3.83 (3H, s), 2.99-2.83 (2H, m), 2.79-2.56 (3H, m), 1.93-1.67 (2H, m).

MS (DCI): 355 (M+NH$_4^+$).

Example 73A

Methyl 4-[3-(4-cyanobenzyl)-4-hydroxybutyl]benzoate

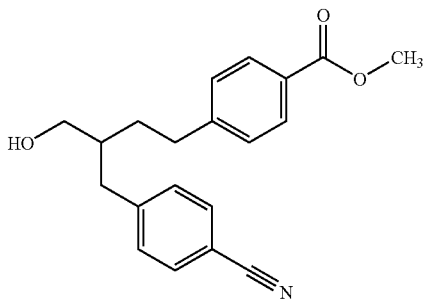

47.43 ml of a 1 M borane-THF complex solution (47.73 mmol) are added dropwise to a solution of 8 g (23.71 mmol) of methyl 4-[3-carboxy-4-(4-cyanophenyl)butyl]benzoate from Example 72A in 200 ml of THF at −10° C. After warming to −5° C., the mixture is stirred at this temperature for 4 hours. After reaction is complete, the reaction mixture is mixed with saturated sodium bicarbonate solution, and the solvent is concentrated to dryness. The residue is taken up in dichloromethane, dried over sodium sulfate and again freed of solvent. The resulting crude product is purified by flash chromatography on silica gel (mobile phase: ethyl acetate/cyclohexane 1:10). 5.8 g (98% purity, 74% yield) of a colorless solid are obtained.

$^1$H-NMR (300 MHz, DMSO-$d_6$, δ/ppm): 7.86 (2H, d), 7.73 (2H, d), 7.38 (2H, d), 7.30 (2H, d), 4.60 (1H, t), 3.83 (3H, s), 3.32 (2H, t), 2.81-2.57 (4H, m), 1.79-1.56 (2H, m), 1.54-1.39 (1H, m).

MS (DCI): 341 (M+NH$_4^+$).

Example 74A

Methyl 4-[3-(4-cyanobenzyl)-4-oxobutyl]benzoate

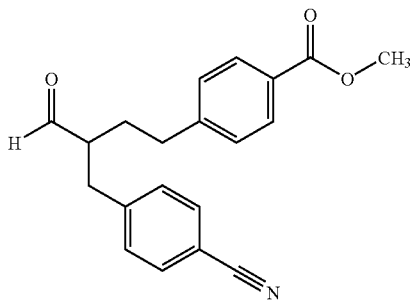

A solution of 400 mg (1.24 mmol) of methyl 4-[3-(4-cyanobenzyl)-4-hydroxybutyl]benzoate from Example 73A in 7 ml of dichloromethane is mixed with 320 mg (1.48 mmol) of pyridinium chlorochromate (PCC) and stirred at room temperature for 5 hours. After conversion is complete, about 1 g of silica gel is added, and the solvent is removed to dryness in vacuo. The residue is purified by flash chromatography on silica gel (mobile phase: cyclohexane/ethyl acetate 10:1→4:1). 302 mg (90% purity, 69% yield) of a colorless solid are obtained.

$^1$H-NMR (300 MHz, DMSO-$d_6$, δ/ppm): 9.68 (1H, s), 7.87 (2H, d), 7.77 (2H, d), 7.43 (2H, d), 7.31 (2H, d), 3.86 (3H, s), 3.16-3.03 (1H, m), 2.94-2.81 (1H, m), 2.80-2.55 (3H, m), 1.99-1.81 (1H, m), 1.78-1.61 (1H, m).

MS (DCI): 339 (M+NH$_4^+$).

Example 75A

Methyl E-4-[3-(4-cyanobenzyl)-5-(2-hydroxyphenyl)pent-4-enyl]benzoate

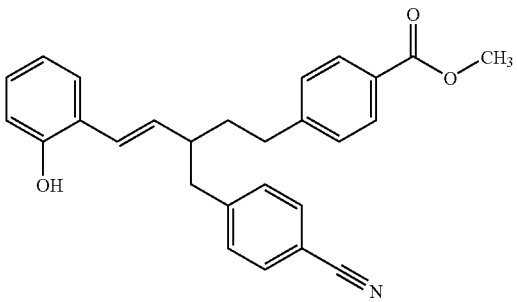

5.91 ml (9.45 mmol) of a 1.6 M solution of n-butyllithium in hexane are slowly added to a solution of 1820 mg (4.05 mmol) of (2-hydroxybenzyl)triphenylphosphonium bromide in 10 ml of anhydrous THF at 0° C. Then, at this temperature, 1085 mg (3.38 mmol) of methyl 4-[3-(4-cyanobenzyl)-4-oxobutyl]benzoate from Example 74A, dissolved in. 10 ml of THF, are slowly metered in. After warming to room temperature, the reaction solution is stirred for 12 hours and then some water is added and the mixture is concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 4:1→2:1). 1150 mg (2.79 mmol, 83% yield) of a colorless solid are obtained.

$^1$H-NMR (300 MHz, DMSO-$d_6$, δ/ppm): 9.47 (1H, s), 7.88 (2H, d), 7.71 (2H, d), 7.42-7.27 (5H, m), 7.01 (1H, t), 6.81-6.68 (2H, m), 6.45 (1H, d), 6.12-6.00 (1H, m), 3.84 (3H, s), 3.42 (2H, m), 2.95-2.56 (3H, m), 1.88-1.56 (2H, m).

MS (DCI): 429 (M+NH$_4^+$).

Example 76A

Methyl E-4-{3-(4-cyanobenzyl)-5-[2-(4'-trifluoromethylbiphenyl-4-ylmethoxy)phenyl]pent-4-enyl}benzoate

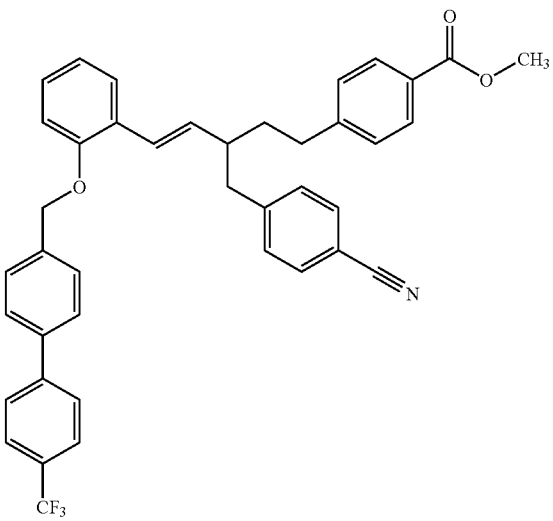

A solution of 1150 mg (2.79 mmol) of methyl E-4-[3-(4-cyanobenzyl)-5-(2-hydroxyphenyl)pent-4-enyl]benzoate from Example 75A in 50 ml of dry acetonitrile is mixed with 908 mg (3.35 mmol) of 4-chloromethyl-4'-trifluoromethylbiphenyl from Example 23A and 579 mg (4.19 mmol) of anhydrous potassium-carbonate and heated to reflux for 12 hours. The mixture is then concentrated to dryness. The residue is taken up in ethyl acetate, washed with water and saturated sodium chloride solution and dried over sodium sulfate. The organic phase is concentrated. The resulting crude product is purified by flash chromatography on silica gel (mobile phase: cyclohexane/ethyl acetate 7:3). 1620 mg (2.51 mmol, 90% yield) of a solid are obtained.

$^1$H-NMR (300 MHz, DMSO-d$_6$, δ/ppm): 7.87 (2H, d), 7.80 (4H, d), 7.77-7.64 (4H, m), 7.51 (2H, d), 7.42 (1H, d), 7.37 (2H, d), 7.28 (2H, d), 7.20 (1H, t), 7.07 (1H, d), 6.92 (1H, t), 6.48 (1H, d), 6.18-6.04 (1H, m), 5.18 (2H, s), 3.78 (3H, s), 2.95-2.82 (1H, m), 2.81-2.41 (4H, m), 1.88-1.55 (2H, m).

LC-MS (method 4): R$_t$ 3.57 min; m/z 646 (M+H$^+$).

Example 77A

Methyl E-4-{3-[4-(5-oxo-4,5-dihydro-[1,2,4]oxadiazol-3-yl)benzyl]-5-[2-(4'-trifluoromethylbiphenyl-4-ylmethoxy)phenyl]pent-4-enyl}benzoate

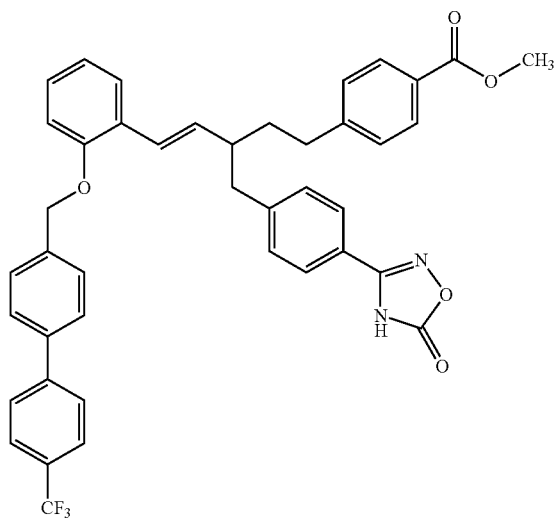

A solution of 872 mg (12.54 mmol) of hydroxylamine hydrochloride in 30 ml of DMSO is mixed with 1.75 ml (12.54 mmol) of triethylamine and stirred at room temperature for 10 min. The resulting precipitate is filtered off. Subsequently 1620 mg (2.51 mmol) of methyl E-4-{3-(4-cyanobenzyl)-5-[2-(4'-trifluoromethylbiphenyl-4-ylmethoxy) phenyl]pent-4-enyl}benzoate from Example 76A are metered into the filtrate. The reaction solution is stirred at 75° C. for 12 hours. After conversion is complete and cooling, 20 ml of water are added to the reaction solution and, after extraction three times with ethyl acetate, the combined organic phases are washed with saturated sodium chloride solution. The organic phase is then dried over sodium sulfate and concentrated to dryness. 1265 mg of a colorless oil are obtained and are immediately reacted further without further purification.

The oil obtained above is dissolved in 50 ml of DMF, and 0.18 ml (2.24 mmol) of pyridine is added. The solution is then cooled to 0° C. and 333 mg (1.86 mmol) of 2-ethylhexyl chloroformate are slowly added. The mixture is stirred at 0° C. for about 30 min and then taken up in water and extracted with ethyl acetate. The organic phase is dried over sodium sulfate and concentrated to dryness. The resulting residue is taken up in 50 ml of xylene and heated to reflux for 4 hours. After reaction is complete, the reaction solution is cooled and concentrated to dryness. The crude product is purified by preparative HPLC. 1000 mg (71% yield) of a colorless oil are obtained.

$^1$H-NMR (400 MHz, DMSO-d$_6$, δ/ppm): 7.90-7.77 (6H, m), 7.74-7.64 (4H, t), 7.49 (2H, d), 7.42 (1H, d), 7.34 (2H, d), 7.29 (2H, d), 7.20 (1H, t), 7.08 (1H, d), 6.92 (1H, t), 6.51 (1H, d), 6.19-6.08 (1H, m), 5.18 (2H, s), 3.79 (3H, s), 2.92-2.81 (1H, m), 2.79-2.44 (4H, m), 1.89-1.76 (1H, m), 1.75-1.62 (1H, m).

MS (EI): 703 (M–H$^-$).

Example 78A

[2-(2-Chlorobenzyloxy)phenyl]methanol

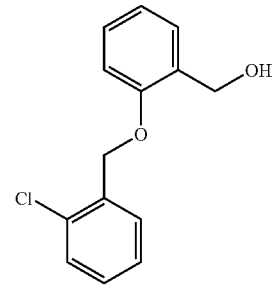

A solution of 2.42 g (19.47 mmol) of 2-hydroxybenzyl alcohol in 100 ml of dry acetonitrile is mixed with 4.12 g (19.47 mmol) of 2-chlorobenzyl bromide and 2.96 g (21.42 mmol) of anhydrous potassium carbonate and heated to reflux for 12 hours. The mixture is then concentrated to dryness. The residue is taken up in ethyl acetate, washed with water and saturated sodium chloride solution and dried over sodium sulfate. The organic phase is concentrated. The resulting crude product is purified by flash chromatography on silica gel (mobile phase: cyclohexane/ethyl acetate 7:3). 3.856 g (15.5 mmol, 79% yield) of a solid are obtained.

$^1$H-NMR (300 MHz, DMSO-d$_6$, δ/ppm): 7.66-7.56 (1H, m), 7.55-7.48 (1H, m), 7.45-7.33 (3H, m), 7.21 (1H, t), 7.08-6.91 (2H, m), 5.18 (2H, s), 5-0.02 (1H, t), 4.56 (2H, d).

LC-MS (method 2): R$_t$ 2.22 min; m/z 231 [M+H—H$_2$O$^+$].

Example 79A

[2-(2-Chlorobenzyloxy)benzyl]triphenylphosphonium bromide

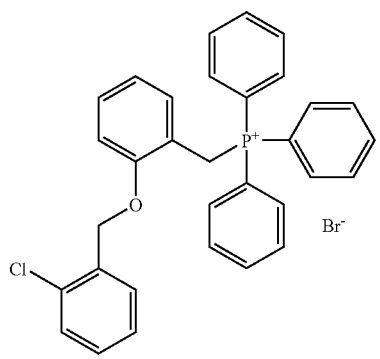

A solution of 3.775 g (15.18 mmol) of [2-(2-chlorobenzyloxy)phenyl]methanol from Example 78A in 60 ml of acetonitrile is mixed with 4.949 g (14.42 mmol) of triphenylphosphonium hydrobromide and heated to reflux for 3 hours. The reaction solution is then concentrated to dryness, and the resulting oil is taken up and triturated in diethyl ether. The product crystallizes as a white solid during this. After filtration, the solid is dried in a drying oven at 50° C. overnight. 8.247 g (91% yield) of crystalline product are obtained.

$^1$H-NMR (300 MHz, DMSO-$d_6$, δ/ppm): 7.87 (3H, t), 7.71-7.46 (13H, m), 7.43-7.28 (4H, m), 7.10 (1H, d), 6.96 (1H, d), 6.89 (1H, t), 5.02 (2H, d), 4.64 (2H, s).

Example 80A

[2-(2-Trifluoromethylbenzyloxy)phenyl]methanol

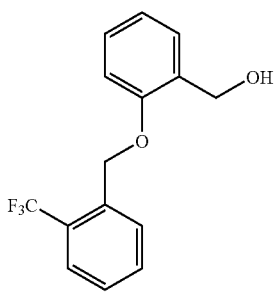

A solution of 2.42 g (19.47 mmol) of 2-hydroxybenzyl alcohol in 100 ml of dry acetonitrile is mixed with 3.91 g (19.47 mmol) of 2-trifluoromethylbenzyl bromide and 2.96 g (21.42 mmol) of anhydrous potassium carbonate and heated to reflux for 12 hours. The mixture is then concentrated to dryness. The residue is taken up in ethyl acetate, washed with water and saturated sodium chloride solution and dried over sodium sulfate. The organic phase is concentrated. The resulting crude product is purified by flash chromatography on silica gel (mobile phase: cyclohexane/ethyl acetate 7:3). 5.08 g (87% yield) of a solid are obtained.

$^1$H-NMR (300 MHz, DMSO-$d_6$, δ/ppm): 7.85-7.67 (3H, m), 7.59 (1H, t), 7.41 (1H, d), 7.21 (1H, t), 7.04-6.89 (2H, m), 5.24 (2H, s), 5.02 (1H, t), 4.53 (2H, d).

MS (DCI): 300 (M+$NH_4^+$).

Example 81A

Triphenyl-[2-(2-trifluoromethylbenzyloxy)benzyl]phosphonium bromide

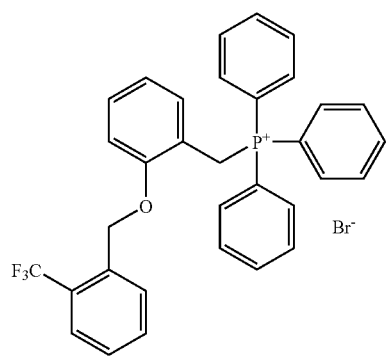

A solution of 4.913 g (17.41 mmol) of [2-(2-trifluoromethylbenzyloxy)phenyl]methanol from Example 80A in 70 ml of acetonitrile is mixed with 5.675 g (16.54 mmol) of triphenylphosphonium hydrobromide and heated to reflux for 3 hours. The reaction solution is then concentrated to dryness, and the resulting oil is taken up and triturated in diethyl ether. The product crystallizes as a white solid during this. After filtration, the solid is dried in a drying oven at 50° C. overnight. 9.621 g (88% yield) of crystalline product are obtained.

$^1$H-NMR (300 MHz, DMSO-$d_6$, δ/ppm): 7.84 (3H, t), 7.79 (1H, d), 7.70-7.49 (1H, m), 7.46 (1H, d), 7.32 (1H, t), 7.10 (1H, d), 6.89 (1H, t), 5.02 (2H, d), 4.72 (2H, s).

Example 82A

1-Allyl 7-ethyl 2-allyloxycarbonylheptanedioate

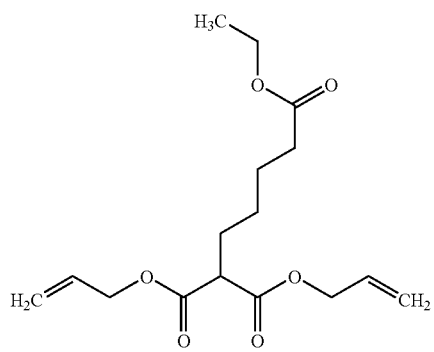

16.29 g (407.19 mmol) of sodium hydride are added in portions to a solution of 100 g (542.92 mmol) of diallyl malonate in 900 ml of dry dioxane at 5° C. After gas evolution ceases, the reaction mixture is warmed to 40° C. and stirred for 30 min. Then 56.76 g (271.46 mmol) of ethyl 5-bromovalerate in 100 ml of dry dioxane are added dropwise, and the mixture is stirred at 110° C. for 12 hours. After the reaction is complete, the mixture is cooled to room temperature and added to about 400 ml of ice-water. After neutralization of the reaction mixture with 1 N hydrochloric acid, the organic phase is separated off, and the aqueous phase is extracted three times with 250 ml of ethyl acetate each time. After the organic phases have been combined they are washed with saturated sodium chloride solution and dried over sodium sulfate. After filtration, the reaction solution is concentrated in vacuo. Subsequently excess diallyl malonate is removed by high vacuum distillation (boiling point: 57° C., 0.074 mbar). The distillation residue is purified by flash chromatography on silica gel (mobile phase: cyclohexane/ethyl acetate 2:1). 73.92 g (236.65 mmol, 44% of theory) of a colorless liquid are obtained.

$^1$H-NMR (400 MHz, DMSO-$d_4$, δ/ppm): 5.99-5.81 (2H, m), 5.38-5.16 (4H, m), 4.68-4.51 (4H, m), 4.04 (2H, q), 3.59 (1H, t), 2.28 (2H, t), 1.86-1.71 (2H, m), 1.61-1.45 (2H, m), 1.35-1.20 (2H, m), 1.17 (3H, t).

MS (DCI): 330 (M+NH$_4^+$).

Example 83A

1-Allyl 7-ethyl 2-allyloxycarbonyl-2-[2-(4-cyanophenyl)ethyl]heptandioate

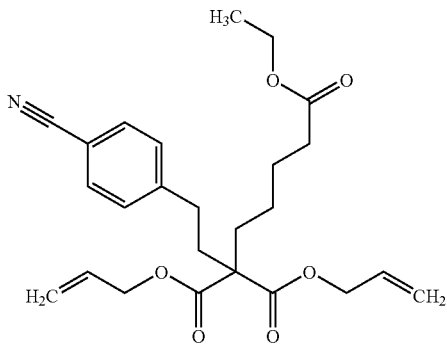

6.37 g (159.27 mmol; content 60%) of sodium hydride are added in portions to a solution of 45.23 g (144.79 mmol) of 1-allyl 7-ethyl 2-allyloxycarbonylheptanedioate from Example 82A in 250 ml of DMF at 0° C. The reaction solution is then allowed to reach room temperature and is stirred for 30 min. The reaction solution is then cooled to 0° C. and, after addition of 36.50 g (173.75 mmol) of 4-(2-bromoethyl)benzonitrile from Example 8A in 250 ml DMF, stirred at this temperature for 30 min. The mixture is then stirred at room temperature overnight. Water is added dropwise to the reaction mixture and, after extraction three times with ethyl acetate, the combined organic phases are washed with saturated sodium chloride solution and dried over sodium sulfate. After filtration, the solvent is concentrated to dryness in vacuo. The resulting crude product is purified by flash chromatography on silica gel (mobile phase: cyclohexane/ethyl acetate 10:1-4:1→1:1). 17.85 g (40.43 mol, 28% yield) of a colorless solid are obtained.

$^1$H-NMR (400 MHz, DMSO-$d_6$, δ/ppm): 7.77 (2H, d), 7.42 (2H, d), 5.97-5.82 (2H, m), 5.37-5.18 (4H, m), 4.60 (4H, d), 4.04 (2H, q), 2.59-2.45 (2H, m), 2.30 (2H, t), 2.14-2.02 (2H, m), 1.96-1.83 (2H, m), 1.60-1.47 (2H, m), 1.24-1.07 (5H, m).

MS (DCI): 459 (M+NH$_4^+$).

Example 84A

2-[2-(4-Cyanophenyl)ethyl]heptandioc acid 7-ethyl ester

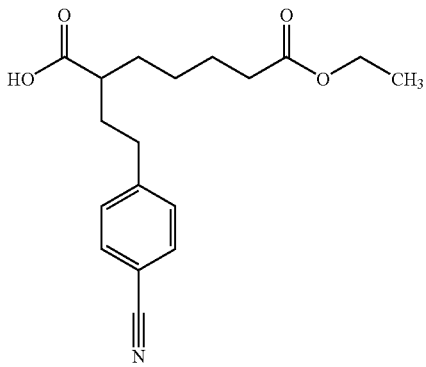

A solution of 18.6 ml (133.4 mmol) of triethylamine and 3.81 ml (101.1 mmol) of formic acid in 175 ml of dioxane is added to a solution of 21 g (40.43 mmol) of 1-allyl 7-ethyl 2-allyloxycarbonyl-2-[2-(4-cyanophenyl)ethyl]heptanedioate from Example 83A, 742 mg (2.83 mmol) of triphenylphosphine and 181 mg (0.81 mmol) of palladium acetate in 175 ml of dioxane at room temperature. The reaction mixture is then stirred at 10° C. for 12 hours. After conversion is complete, the reaction solution is cooled and the solvent is removed in vacuo. The residue is then taken up in ethyl acetate and water and acidified with 1 N hydrochloric acid, and the organic phase is separated off. The aqueous phase is extracted three times with ethyl acetate, and the organic phases are combined, washed with saturated sodium chloride solution and dried over sodium sulfate. After filtration, the reaction solution is concentrated in vacuo. The resulting crude product is purified by flash chromatography on silica gel (mobile phase: cyclohexane/ethyl acetate 4:1→1:1). 8.6 g (64% yield, 95% purity) of a colorless solid are obtained.

$^1$H-NMR (400 MHz, DMSO-$d_6$, δ/ppm): 12.25-12.09 (1H, broad), 7.76 (2H, d), 7.40 (2H, d), 4.04 (2H, q), 2.71-2.57 (2H, m), 2.30-2.14 (4H, m), 1.87-1.74 (1H, m), 1.73 (1H, m), 1.58-1.38 (3H, m), 1.31-1.19 (2H, m), 1.18 (3H, t).

MS (EI): 316 (M−H$^−$).

Example 85A

Ethyl 8-(4-cyanophenyl)-6-hydroxymethyloctanoate

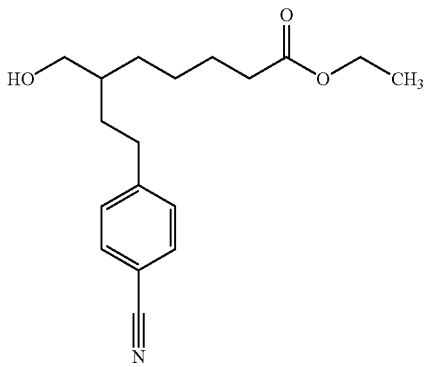

54.19 ml of a 1 M borane-THF complex solution (54.19 mmol) are added dropwise to a solution of 8.6 g (27.1 mmol) of 2-[2-(4-cyanophenyl)ethyl]heptanedioic acid 7-ethyl ester from Example 84A in 200 ml of THF at −10° C. After warming to 0° C., the mixture is stirred at this temperature for 2 hours. After reaction is complete, saturated sodium bicarbonate solution is added to the reaction mixture, and the solvent is concentrated to dryness. The residue is taken up in dichloromethane, dried over sodium sulfate and again freed of solvent. The resulting crude product is purified by flash chromatography on silica gel (mobile phase: ethyl acetate/cyclohexane 1:10→1:4). 5.1 g (97% purity, 60% yield) of a colorless solid are obtained.

$^1$H-NMR (300 MHz, DMSO-$d_6$, δ/ppm): 7.74 (2H, d), 7.41 (2H, d), 4.41 (1H, t), 4.03 (2H, q), 3.41-3.29 (2H, m), 2.67 (2H, t), 2.28 (2H, t), 1.69-1.11 (9H, m), 1.18 (3H, t).

MS (DCI): 321 (M+NH$_4^+$).

Example 86A

Ethyl 8-(4-cyanophenyl)-6-formyloctanoate

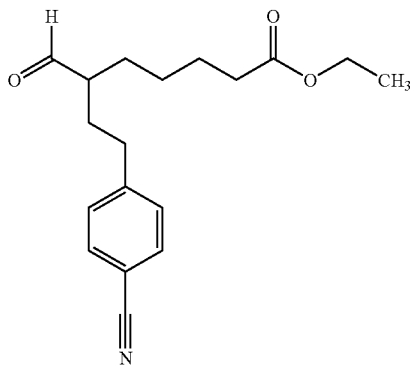

A solution of 4 g (13.18 mmol) of ethyl 8-(4-cyanophenyl)-6-hydroxymethyloctanoate from Example 85A in 100 ml of dichloromethane is mixed with 3.41 g (15.82 mmol) of pyridinium chlorochromate (PCC) and stirred at room temperature for 12 hours. After conversion is complete, the solvent is concentrated to dryness in vacuo. The resulting residue is purified by flash chromatography on silica gel (mobile phase: cyclohexane/ethyl acetate 10:1→4:1). 2.74 g (9.09 mmol, 69% yield) of a colorless solid are obtained.

LC-MS (method 2): R$_t$ 2.38 min; m/z 302 (M+H$^+$).

Example 87A

Ethyl E-6-[2-(4-cyanophenyl)ethyl]-8-(2-hydroxyphenyl)oct-7-enoate

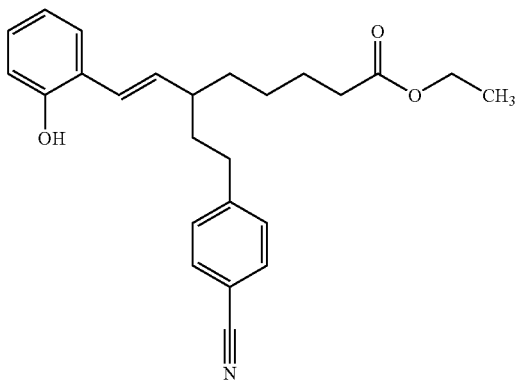

15.91 ml (25.45 mmol) of a 1.6 M solution of n-butyllithium in hexane are slowly added to a solution of 5.066 g (10.91 mmol) of (2-hydroxybenzyl)triphenylphosphonium bromide in 38 ml of anhydrous THF at 0° C. Then, at this temperature, 2.740 g (9.09 mmol) of ethyl 8-(4-cyanophenyl)-6-formyloctanoate from Example 86A, dissolved in 38 ml of THF, are slowly metered in. After the reaction solution has been warmed to room temperature it is stirred for 12 hours and, after addition of some water, concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 10:1→4:1). 2.30 g (5.88 mmol, 63% yield) of a colorless solid are obtained.

$^1$H-NMR (400 MHz, DMSO-$d_6$, δ/ppm): 9.48 (1H, s), 7.73 (2H, d), 7.42 (2H, d), 7.38 (1H, d), 7.03 (1H, t), 6.80 (1H, d), 6.74 (1H, t), 6.57 (1H, d), 6.06-5.93 (1H, m), 4.03 (2H, q), 2.76-2.57 (2H, m), 2.26 (2H, t), 2.17-2.02 (1H, m), 1.80-1.68 (1H, m), 1.67-1.56 (1H, m), 1.56-1.39 (3H, m), 1.38-1.19 (3H, m), 1.13 (3H, t).

MS (DCI): 409 (M+NH$_4^+$).

Example 88A

Ethyl E-8-[2-(4-tert-butylbenzyloxy)phenyl]-6-[2-(4-cyanophenyl)ethyl]oct-7-enoate

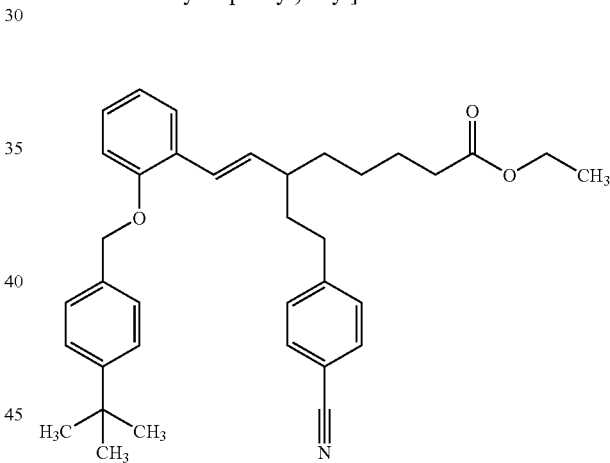

A solution of 2300 mg (5.87 mmol) of ethyl E-6-[2-(4-cyanophenyl)ethyl]-8-(2-hydroxyphenyl)oct-7-enoate from Example 87A in 160 ml of dry acetonitrile is mixed with 1600 mg (7.05 mmol) of 4-(tert-butyl)benzyl bromide and 1220 mg (8.81 mmol) of anhydrous potassium carbonate and heated to reflux for 12 hours. The mixture is then concentrated to dryness. The residue is taken up in ethyl acetate, washed with water and saturated sodium chloride solution and dried over sodium sulfate. The organic phase is concentrated. The resulting crude product is purified by flash chromatography an silica gel (mobile phase: cyclohexane/ethyl acetate 10:1). 2800 mg (5.21 mmol, 88% yield) of a solid are obtained.

$^1$H-NMR (300 MHz, DMSO-$d_6$, δ/ppm): 7.68 (2H, d), 7.45 (1H, d), 7.41-7.32 (6H, m), 7.20 (1H, t), 7.09 (1H, d), 6.91 (1H, t), 6.61 (1H, d), 6.08-5.95 (1H, m), 5.10 (2H, s), 4.00 (2H, q), 2.77-2.45 (3H, m), 2.23 (2H, t), 2.12-1.98 (1H, m), 1.78-1.37 (5H, m), 1.32-1.19 (2H, m), 1.28 (9H, s), 1.13 (3H, t).

MS (DCI): 555 (M+NH$_4^+$).

115

Example 89A

Ethyl E-8-[2-(4-tert-butylbenzyloxy)phenyl]-6-{2-[4-(5-oxo-4,5-dihydro-[1,2,4]oxadiazol-3-yl)phenyl]ethyl}oct-7-enoate

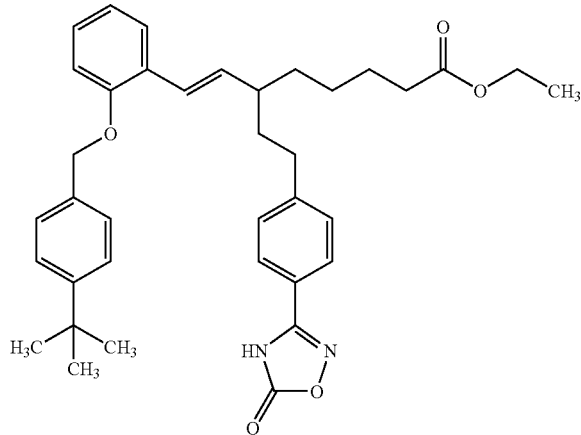

A solution of 1.16 g (16.74 mmol) of hydroxylamine hydrochloride in 20 ml of DMSO is mixed with 2.33 ml (16.74 mmol) of triethylamine and stirred at room temperature for 10 min. The resulting precipitate is filtered off. 1.8 g (3.35 mmol) of ethyl E-8-[2-(4-tert-butylbenzyloxy)phenyl]-6-[2-(4-cyanophenyl)ethyl]oct-7-enoate from Example 88A are then metered into the filtrate. The reaction solution is stirred at 75° C. for 12 hours. After conversion is complete and cooling, 20 ml of water are added to the reaction solution and, after extraction three times with ethyl acetate, the combined organic phases are washed with saturated sodium chloride solution. The organic phase is then dried over sodium sulfate and concentrated to dryness. 1.6 g of a colorless oil are obtained and are immediately reacted further without further purification.

The oil obtained above is dissolved in 20 ml of DMF, and 0.27 ml (3.36 mmol) of pyridine is added. The solution is then cooled to 0° C. and 500 mg (2.80 mmol) of 2-ethylhexyl chloroformate are slowly added. The mixture is stirred at 0° C. for about 30 min and then taken up in water and extracted with ethyl acetate. The organic phase is dried over sodium sulfate and concentrated to dryness. The resulting residue is taken up in 20 ml of xylene and heated to reflux for 2 hours. After the reaction is complete, the reaction solution is cooled and concentrated to dryness. The resulting crude product is purified by flash chromatography on silica gel (mobile phase: cyclohexane/ethyl acetate 4:1→1:1). 1.19 g (70% yield) of a solid are obtained.

$^1$H-NMR (400 MHz, DMSO-$d_6$, δ/ppm): 13.01-12.78 (1H, broad), 7.70 (2H, d), 7.48 (1H, d), 7.42-7.31 (6H, m), 7.20 (1H, t), 7.09 (1H, d), 6.91 (1H, t), 6.63 (1H, d), 6.11-5.98 (1H, m), 5.11 (2H, s), 3.99 (2H, q), 2.76-2.46 (2H, m), 2.24 (2H, t), 2.17-2.02 (1H, m), 1.82-1.69 (1H, m), 1.68-1.55 (1H, m), 1.54-1.38 (3H, m), 1.37-1.17 (3H, m), 1.28 (9H, s), 1.13 (3H, t).

MS (DCI): 614 (M+NH$_4^+$).

116

Example 90A

Diallyl 2-(4-cyanobutyl)malonate

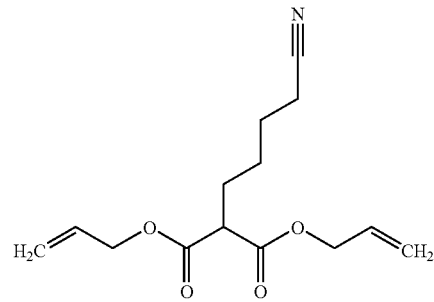

21.71 g (542.9 mmol; 60% pure) of sodium hydride are added in portions to a solution of 100 g (542.9 mmol) of diallyl malonate in 700 ml of dry dioxane at 0° C. After gas evolution ceases, the reaction mixture is warmed to 40° C. and stirred for 1 hour. Then 43.98 g (271.5 mmol) of 5-bromovaleronitrile in 350 ml of dry dioxane are added dropwise, and the mixture is stirred at 110° C. for 12 hours. After the reaction is complete, the mixture is cooled to room temperature, mixed with 400 ml of saturated ammonium chloride solution and extracted with ethyl acetate. After phase separation, the aqueous phase is back-extracted three times with 250 ml of ethyl acetate each time. After the organic phases have been combined they are washed with saturated sodium chloride solution and dried over sodium sulfate, and then the solvent is stripped off in vacuo. Excess diallyl malonate is subsequently removed by high vacuum distillation (boiling point: 57° C.; 0.074 mbar). The distillation residue is purified by flash chromatography on silica gel (mobile phase: cyclohexane/ethyl acetate 2:1). 105 g (233 mmol, approx. 60% purity, 43% yield) of a liquid are obtained. This product is reacted without further purification in the subsequent stage. A small amount is purified by preparative HPLC for analytical characterization.

$^1$H-NMR (300 MHz, DMSO-$d_6$, δ/ppm): 5.96-5.83 (2H, m), 5.35-5.19 (4H, m), 4.64-4.59 (4H, m), 3.66-3.61 (1H, t), 2.54-2.47 (2H, t), 1.86-1.75 (2H, m), 1.62-1.50 (2H, m), 1.42-1.29 (2H, m).

LC-MS (method 1): $R_t$ 2.44 min, m/z 266 (M+H)$^+$.

Example 91A

Diallyl 2-(4-cyanobutyl)-2-[2-(4-methoxycarbonylphenyl)ethyl]malonate

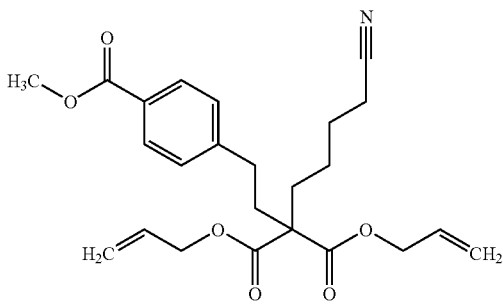

5.62 g (140 mmol; 60% content) of sodium hydride are added in portions to a solution of 48.64 g (127.73 mmol) of diallyl 2-(4-cyanobutyl)malonate from Example 90A in 160 ml of dry DMF at 0° C. The reaction solution is then allowed to reach room temperature and is stirred for 90 min. The reaction solution is then cooled to 0° C. again and, after addition of 45.72 g (153.3 mmol) of methyl 4-(2-bromoethyl)benzoate in 80 ml of dry DMF, stirred at this temperature for 45 min. The mixture is then stirred at room temperature overnight. The reaction mixture is mixed with water and extracted with ethyl acetate. After phase separation, the aqueous phase is extracted three times with 200 ml of ethyl acetate each time. The combined organic phases is washed with saturated sodium chloride solution and dried over sodium sulfate, and then the solvent is stripped off in vacuo. The resulting crude product is purified by silica gel chromatography (mobile phase: cyclohexane/ethyl acetate 10:1→100% ethyl acetate). 18.53 g (43.3 mmol, 34% yield) of a colorless liquid are obtained.

$^1$H-NMR (300 MHz, DMSO-$d_6$, δ/ppm): 7.90-7.88 (2H, d), 7.36-7.34 (2H, d), 5.97-5.83 (2H, m), 5.35-5.21 (4H, m), 4.64-4.59 (4H, m), 3.84 (3H, s), 2.57-2.48 (4H, t), 2.15-2.09 (2H, m), 1.98-1.89 (2H, m), 1.63-1.52 (2H, m), 1.34-1.21 (2H, m).

LC-MS (method 2): $R_t$ 2.59 min; m/z 428 (M+H)$^+$.

Example 92A

Methyl 4-(3-carboxy-7-cyanoheptyl)benzoate

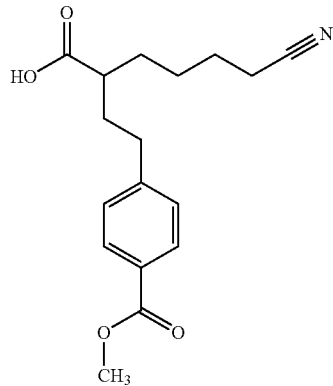

A solution of 7.45 ml (53.42 mmol) of triethylamine and 1.53 ml (40.47 mmol) of formic acid in 67 ml of dioxane is added to a solution of 6.92 g (16.19 mmol) of diallyl 2-(4-cyanobutyl)-2-[2-(4-methoxycarbonylphenyl)ethyl]malonate from Example 91A, 594 mg (2.26 mmol) of triphenylphosphine and 145 mg (0.64 mmol) of palladium acetate in 67 ml of dioxane at room temperature. The reaction mixture is then stirred at 10° C. for 12 hours. After conversion is complete, the reaction solution is cooled and the solvent is removed in vacuo. The residue is taken-up in ethyl acetate and water and acidified with 1 N hydrochloric acid, and the organic phase is separated off. The aqueous phase is extracted three times with ethyl acetate, and the organic phases are then combined, washed with saturated sodium chloride solution and dried over sodium sulfate. After filtration, the organic phase is concentrated in vacuo. The resulting crude product is purified by flash chromatography on silica gel (mobile phase: cyclohexane/ethyl acetate 2:1→1:3, with 1% formic acid). 2.1 g (43% yield, 100% purity) of a colorless solid are obtained.

LC-MS (method 2): $R_t$ 1.88 min; m/z 303 (M$^+$).

Example 93A

Methyl 4-(7-cyano-3-hydroxymethylheptyl)benzoate

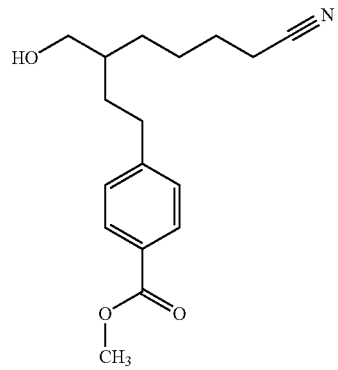

33 ml of a 1 M borane-THF complex solution (33 mmol) are added dropwise to a solution of 5 g (16.48 mmol) of methyl 4-(3-carboxy-7-cyanoheptyl)benzoate from Example 92A in 62 ml of THF at −15° C., and the solution is stirred at this temperature for 2 hours. Then a further 16 ml of 1 M borane-THF complex solution are added dropwise, and stirring is continued for 45 minutes. The reaction mixture is then warmed to 0° C. and stirred at this temperature for 1 hour. After reaction is complete, 100 ml of saturated bicarbonate solution are added to the reaction mixture, and the solvent is concentrated to dryness. The residue is taken up in ethyl acetate and water, and the aqueous phase is extracted with ethyl acetate. The combined organic phases are dried over sodium sulfate and again freed of solvent. The resulting crude product is purified by flash chromatography on silica gel (mobile phase: cyclohexane/ethyl acetate 2:1→1:3→100% ethyl acetate). 2.4 g (93% purity, 47% yield) of a colorless solid are obtained.

$^1$H-NMR (400 MHz, DMSO-$d_6$, δ/ppm): 7.88-7.86 (2H, d), 7.36-7.34 (2H, d), 4.43-4.40 (1H, t), 3.83 (3H, s), 3.37-3.34 (2H, t), 2.68-2.64 (2H, t), 2.49-2.46 (2H, t), 1.67-1.57 (1H, m), 1.56-1.45 (3H, m), 1.42-1.25 (5H, m).

LC-MS (method 2): $R_t$ 1.93 min; m/z 290 (M+H)$^+$.

Example 94A

Methyl 4-(7-cyano-3-formylheptyl)benzoate

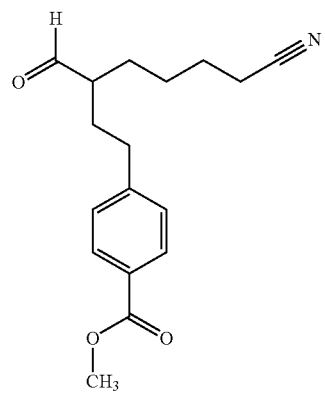

A solution of 2.23 g (7.71 mmol) of methyl 4-(7-cyano-3-hydroxymethylheptyl)benzoate from Example 93A in 100 ml of dichloromethane is mixed with 1.99 g (9.26 mmol) of pyridinium chlorochromate (PCC) and stirred at room temperature for 6 hours. After conversion is complete, the solvent is concentrated to dryness in vacuo. The resulting residue is purified by flash chromatography on silica gel (mobile phase: cyclohexane/ethyl acetate 10:1→4:1). 1.50 g (9.09 mmol, 68% yield) of an oil are obtained.

$^1$H-NMR (400 MHz, CDCl$_3$, δ/ppm): 9.62 (1H, d), 7.98-7.96 (2H, d), 7.25-7.23 (2H, d), 3.91 (3H, s), 2.77-2.62 (2H, m), 2.35 (2H, t), 2.38-2.29 (1H, m), 2.07-1.98 (1H, m), 1.82-1.63 (4H, m), 1.55-1.47 (3H, m).

MS (ESI): 310 (M+Na)$^+$.

Example 95A

Methyl E-4-{7-cyano-3-[2-(2-hydroxyphenyl)vinyl]heptyl}benzoate

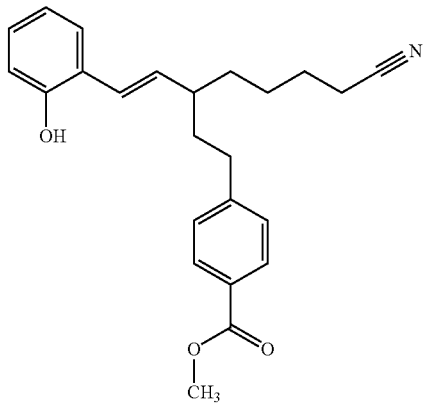

9.07 ml (14.52 mmol) of a 1.6 M solution of n-butyllithium in hexane are slowly added dropwise to a suspension of 3.26 g (7.26 mmol) of 2-hydroxyphenyltriphenylphosphonium bromide in 40 ml of dry THF at 0° C., and the mixture is stirred for 5 minutes. Then, at this temperature, 1.49 g (5.19 mmol) of methyl 4-(7-cyano-3-formylheptyl)benzoate from Example 94A in 10 ml of dry THF are slowly added dropwise. The reaction mixture is stirred at 0° C. for 10 minutes. The cooling is then removed, and the reaction solution is stirred at room temperature for 10 minutes and then mixed with silica gel and concentrated to dryness. The resulting residue is purified directly by flash chromatography on silica gel (mobile phase: cyclohexane/ethyl acetate 1:2→1:5). 1.71 g (75% purity, 3.40 mmol, 65% yield) of an oil are obtained.

$^1$H-NMR (300 MHz, DMSO-d$_6$, δ/ppm): 9.50 (1H, s), 7.88-7.86 (2H, d), 7.40-7.34 (3H, m), 7.05-7.00 (1H, m), 6.84-6.68 (2H, m), 6.62-6.56 (1H, m), 6.05-5.97 (1H, dd), 3.83 (3H, s), 2.75-2.56 (2H, m), 2.52-2.44 (3H, m), 2.18-2.06 (1H, m), 1.81-1.28 (7H, m).

LC-MS (method 2): R$_t$ 2.60 min; m/z 377 (M$^+$).

Example 96A

Methyl E-4-(3-{2-[2-(4-tert-butylbenzyloxy)phenyl]vinyl}-7-cyanoheptyl)benzoate

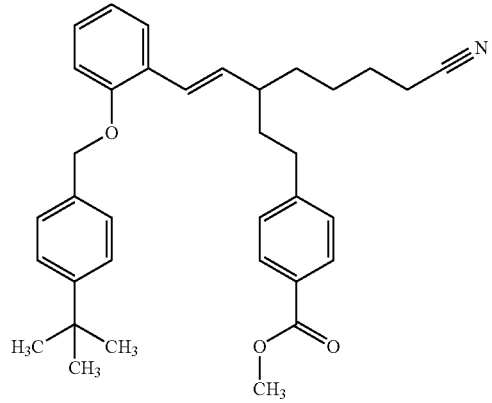

A solution of 1.70 g (3.38 mmol, 75% pure) of methyl 4-{7-cyano-3-[2-(2-hydroxyphenyl)vinyl]heptyl}benzoate from Example 95A in 20 ml of dry acetonitrile is mixed with 1.53 g (7.76 mmol) of 4-(tert-butyl)benzyl bromide and 1.4 g (10.13 mmol) of anhydrous potassium carbonate and heated to reflux for 12 hours. The mixture is then filtered and the filtrate is concentrated to dryness. The resulting crude product is taken up on silica gel and purified by flash chromatography (mobile phase: cyclohexane/ethyl acetate 10:1). 1700 mg (3.12 mmol, 96% purity, 92% yield) of an oil are obtained.

$^1$H-NMR (400 MHz, CDCl$_3$, δ/ppm): 7.93-7.71 (2H, d), 7.46-7.35 (5H, m), 7.24-7.18 (3H, m), 6.97-6.93 (2H, m), 6.77-6.73 (1H, d), 5.98-5.92 (1H, dd), 5.11-5.05 (2H, m), 3.90 (3H, s), 2.79-2.70 (1H, m), 2.66-2.57 (1H, m), 3.36 (2H, t), 2.20-2.11 (1H, m), 1.82-1.73 (1H, m), 1.70-1.56 (3H, m), 1.56-1.35 (9H, s).

LC-MS (method 4): R$_t$ 3.36 min; m/z 523 (M$^+$).

Example 97A

4-[3-((E)-2-{2-[(4-tert-Butylbenzyl)oxy]phenyl}vinyl)-7-cyanoheptyl]benzohydrazide

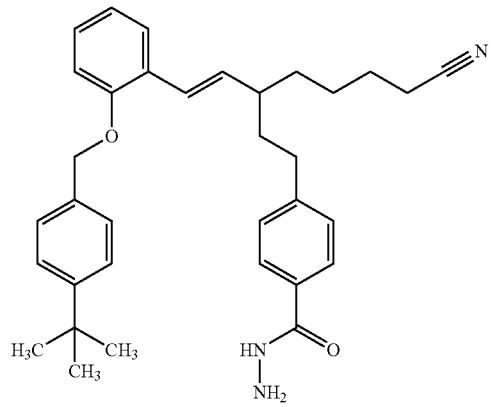

A solution of 1 g (1.83 mmol, 96% pure) of methyl 4-(3-{2-[2-(4-tert-butylbenzyloxy)phenyl]vinyl}-7-cyanoheptyl)benzoate from Example 96A in 1.90 ml of methanol and 3.80 ml of THF is mixed with 3.82 g (76.38 mmol) of hydrazine monohydrate and stirred at 60° C. for 12 hours. The reaction mixture is concentrated to dryness, and the residue is coevaporated again with dichloromethane. The resulting crude product (1.1 g) is immediately reacted in the next stage.

LC-MS (method 2): R$_t$ 2.88 min; m/z 524 (M+H)$^+$.

Example 98A

E-8-[2-(4-tert-Butylbenzyloxy)phenyl]-6-{2-[4-(5-oxo-4,5-dihydro[1,3,4]oxadiazol-2-yl)phenyl]-ethyl}oct-7-enenitrile

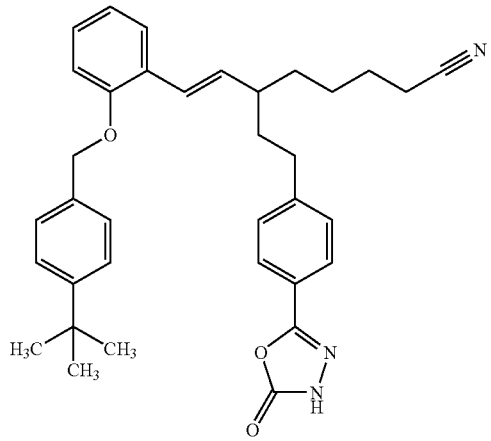

A solution of 566.6 mg (2.86 mmol) of trichloromethyl chloroformate in 2.5 ml of dry dioxane is mixed with 1.0 g of 4-[3-((E)-2-{2-[(4-tert-butylbenzyl)oxy]phenyl}vinyl)-7-cyanoheptyl]-benzohydrazide from Example 97A (crude product) in 7.5 ml of dioxane and heated to reflux for 3 hours. The mixture is then directly taken up on silica gel, concentrated to dryness and purified by flash chromatography (mobile phase: dichloromethane/methanol 5:1). 236 mg (0.429 mmol, 23% yield based on two stages) of a solid are obtained.

$^1$H-NMR (300 MHz, DMSO-d$_6$, δ/ppm): 12.52 (1H, s), 7.68-7.62 (2H, d), 7.50-7.45 (1H, m), 7.40-7.32 (6H, m), 7.24-7.11 (1H, m), 7.11-7.06 (1H, m), 6.95-6.88 (1H, t), 6.68-6.61 (1H, d), 6.01-6.02 (1H, dd), 5.12-5.08 (2H, m), 2.75-2.55 (3H, m), 2.17-2.05 (1H, m), 1.81-1.28 (9H, m), 1.25 (9H, s).

LC-MS (method 4): R$_t$ 3.15 min; m/z 549 (M)$^+$.

Example 99A

Methyl 4-[(4E)-5-{2-[(4-tert-butylbenzyl)oxy]phenyl}-3-(4-cyanobenzyl)pent-4-en-1-yl]benzoate

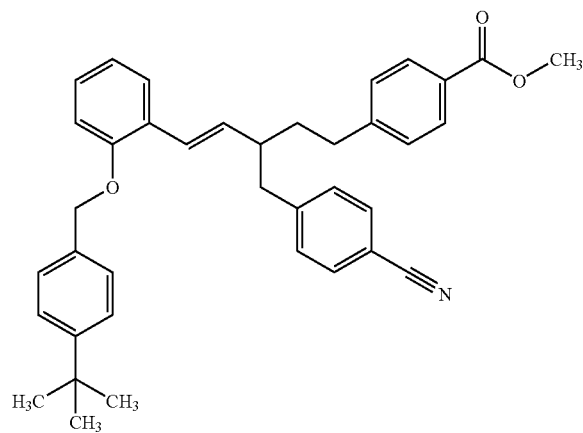

A solution of 1.4 g (3.13 mmol, 92% pure) of methyl E-4-[3-(4-cyanobenzyl)-5-(2-hydroxyphenyl)pent-4-enyl] benzoate (Example 75A) in 7 ml of dry acetonitrile is mixed with 1.42 g (6.26 mmol) 4-(tert-butyl)benzyl bromide and 1.30 g (9.39 mmol) of anhydrous potassium carbonate and heated to reflux for 12 hours. The mixture is then filtered and the filtrate is concentrated to dryness. The residue is directly purified by chromatography on silica gel (mobile phase: cyclohexane/ethyl acetate 10:1, then 1:5). 1.85 g (3.32 mmol, 93% purity, 98% yield) of an oil are isolated.

$^1$H-NMR (300 MHz, CDCl$_3$, δ/ppm): 7.94-7.88 (2H, m), 7.52-7.14 (12H, m), 6.97-6.89 (2H, m), 6.67-6.57 (1H, m), 6.02-5.92 (1H, m), 5.05-5.02 (2H, m), 3.90 (3H, s), 2.85-2.67 (3H, m), 2.67-2.55 (1H, m), 2.54-2.42 (1H, m), 1.88-1.61 (2H, m), 1.33 (9H, s).

LC-MS (method 4): R$_t$ 3.53 min; m/z 557 (M$^+$).

Example 100A

4-[(4E)-5-{2-[(4-tert-Butylbenzyl)oxy]phenyl}-3-(4-cyanobenzyl)penten-1-yl]benzoic acid

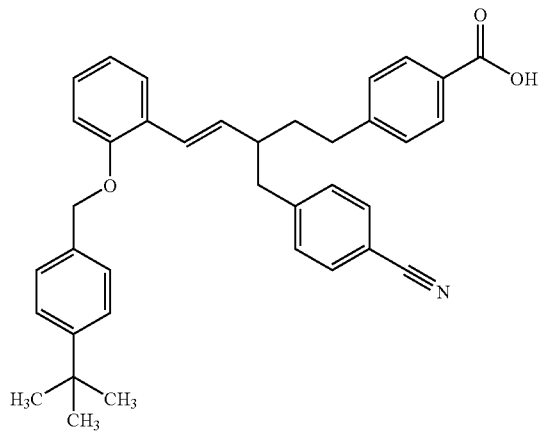

A solution of 350 mg (0.63 mmol) of methyl 4-[(4E)-5-{2-[(4-tert-butylbenzyl)oxy]phenyl}-3-(4-cyanobenzyl)pent-4-en-1-yl]benzoate from Example 99A in 2 ml of THF and 1 ml of water is mixed with 60 mg (2.51 mmol) of lithium hydroxide and stirred at 60° C. for 12 h. The reaction mixture is adjusted to pH 34 with 1 M hydrochloric acid and concentrated. The residue is directly taken up on silica gel and purified by chromatography (mobile phase: cyclohexane/ ethyl acetate 1:2, then 100% ethyl acetate). 350 mg (0.61 mmol, 95% purity, 97% yield) of a solid are isolated.

$^1$H-NMR (400 MHz, DMSO-d$_6$, δ/ppm): 12.92-12.66 (1H, broad), 7.85-7.79 (2H, d), 7.69-7.64 (2H, d), 7.43-7.23 (9H, m), 7.21-7.14 (1H, m), 7.06-7.02 (1H, d), 6.93-6.86 (1H, t), 6.60-6.42 (1H, d), 6.13-6.03 (1H, dd), 5.09-5.00 (2H, m), 2.93-2.84 (1H, m), 2.79-2.67 (2H, m), 2.67-2.55 (1H, m), 1.85-1.59 (2H, m), 1.26 (9H, s).

LC-MS (method 2): R$_t$ 3.39 min; m/z 543 (M)$^+$.

Example 101A

2-{4-[(4E)-5-{2-[(4-tert-Butylbenzyl)oxy]phenyl}-3-(4-cyanobenzyl)pent-4-en-1-yl]benzoyl}-hydrazinecarbothioamide

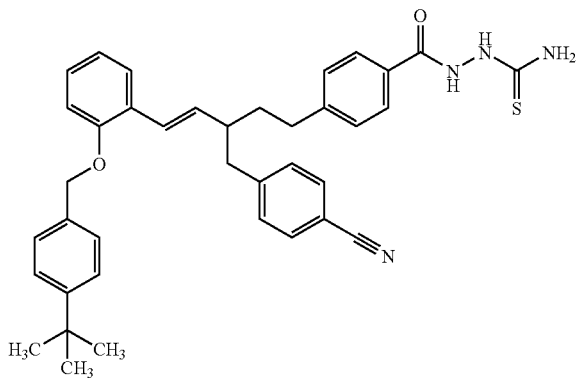

5.9 mg (0.05 mmol) of oxalyl chloride are slowly added dropwise to a solution of 12.7 mg (0.02 mmol) of 4-[(4E)-5-{2-[(4-tert-butylbenzyl)oxy]phenyl}-3-(4-cyanobenzyl)pent-4-en-1-yl]-benzoic acid from Example 100A in 0.2 ml of dry THF with 1 drop of DMF while cooling in ice. The reaction mixture is stirred at RT for 30 minutes and then concentrated in vacuo, and the residue is coevaporated twice with dichloromethane and then taken up in 0.2 ml of THF. This solution is added dropwise to a solution of 4.2 mg (0.05 mmol) of thiosemicarbazide in 0.25 ml of THF at 0° C. The mixture is stirred at RT for 1 hour and then concentrated, and the residue is reacted without further purification in the next stage.

LC-MS (method 4): $R_t$ 3.09 min; m/z 616 (M)$^+$.

Example 102A

Methyl 4-{(3E)-4-{2-[(4-tert-butylbenzyl)oxy]phenyl}-2-[2-(4-cyanophenyl)ethyl]but-3-en-1-yl}-benzoate

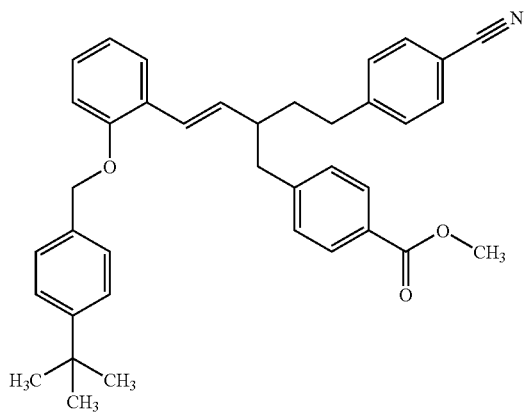

A solution of 2 g (3.6 mmol) of methyl E-4-[2-[2-(4-cyanophenyl)ethyl]-4-(2-hydroxyphenyl)but-3-enyl]benzoate (Example 17A) in 8 ml of dry acetonitrile is mixed with 2.20 g (9.71 mmol) of 4-(tert-butyl)benzyl bromide and 2.02 g (14.59 mmol) of anhydrous potassium carbonate and heated to reflux for 12 hours. The mixture is then filtered and the filtrate is concentrated to dryness. The residue is purified by chromatography on silica gel (mobile phase: cyclohexane/ethyl acetate 10:1). 1.9 g (3.30 mmol, 97% purity, 92% yield) of an oil are isolated.

$^1$H-NMR (400 MHz, CDCl$_3$, δ/ppm): 7.94-7.89 (2H, m), 7.49-7.30 (7H, m), 7.21-7.12 (5H, m), 6.97-6.90 (2H, m), 6.68-7.62 (1H, m), 5.06-5.02 (2H, m), 3.89 (3H, s), 2.83-2.69 (3H, m), 2.65-2.39 (2H, m), 1.86-1.59 (2H, m), 1.33 (9H, s).

LC-MS (method 2): $R_t$ 3.37 min; m/z 575 (M+NH$_4^+$), 557 (M$^+$).

Example 103A

4-{(3E)-4-{2-[(4-tert-Butylbenzyl)oxy]phenyl}-2-[2-(4-cyanophenyl)ethyl]but-3-en-1-yl}benzohydrazide

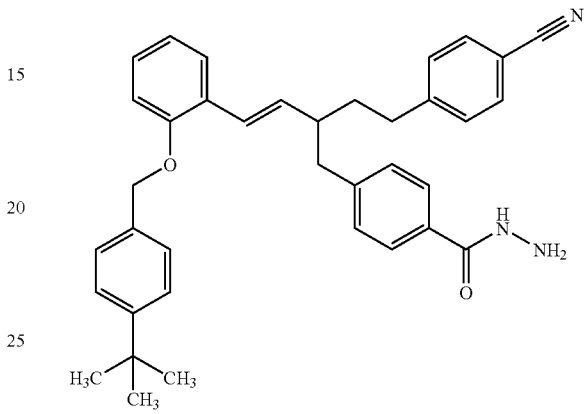

800 mg (1.43 mmol) of methyl 4-{(3E)-4-{2-[(4-tert-butylbenzyl)oxy]phenyl}-2-[2-(4-cyanophenyl)ethyl]but-3-en-1-yl}benzoate (Example 102A) are introduced into 3 ml of methanol and 1.5 ml of THF, and 2.88 g (57.4 mmol) of hydrazine monohydrate are added dropwise. The reaction mixture is stirred at 65° C. for 3 hours and then at RT for a further 12 hours. After removal of the solvent in vacuo, the residue is purified by flash chromatography on silica gel (mobile phase: dichloromethane/methanol/aq. ammonia 20:1:0.1). 185 mg (89% purity) of the title compound are obtained.

LC-MS (method 4): $R_t$ 3.25 min; m/z 557 (M$^+$).

Example 104A

4-{(4E)-5-{2-[(4-tert-Butylbenzyl)oxy]phenyl}-3-[4-(5-oxo-4,5-dihydro-1,3,4-oxadiazol-2-yl)benzyl]pent-4-en-1-yl}benzonitrile

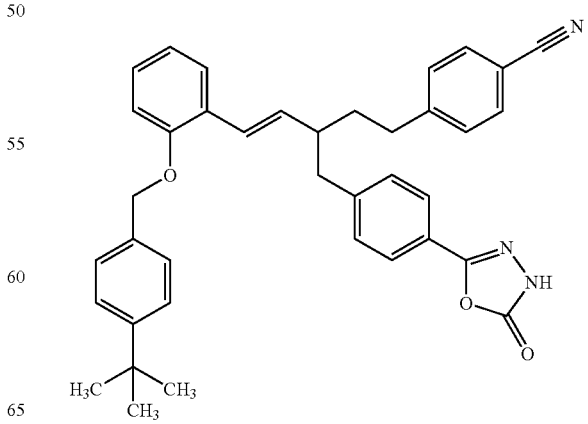

A solution of 185 mg (0.29 mmol, 89% purity) of 4-{(3E)-4-{2-[(4-tert-butylbenzyl)oxy]phenyl}-2-[2-(4-cyanophenyl)ethyl]but-3-en-1-yl}benzohydrazide from Example 103A in 1 ml of dioxane is slowly added dropwise to a solution of 87.3 mg (0.44 mmol) of trichloromethyl chloroformate in 0.5 ml of dioxane. The reaction mixture is stirred under reflux for two hours. After cooling, the mixture is concentrated in vacuo, directly taken up on silica gel and purified by flash chromatography (mobile phase: dichloromethane/methanol/aq. ammonia 10:1:0.1). 166 mg (0.28 mmol, 96% yield) of an oil are isolated.

$^1$H-NMR (400 MHz, CDCl$_3$, δ/ppm): 8.37 (1H, s), 7.77-7.65 (2H, d), 7.49-7.44 (2H, d), 7.42-7.11 (10H, m), 6.98-6.88 (2H, m), 6.69-6.60 (1H, d), 6.04-5.92 (1H, dd), 5.09-4.96 (2H, m), 2.81-2.71 (3H, m), 2.66-2.55 (1H, m), 2.52-2.41 (1H, m), 1.86-1.75 (1H, m), 1.72-1.60 (1H, m), 1.32 (9H, s).

LC-MS (method 4): R$_t$ 3.39 min; m/z 583 (M$^+$).

Example 105A

4-{(3E)-4-{2-[(4-tert-Butylbenzyl)oxy]phenyl}-2-[2-(4-cyanophenyl)ethyl]but-3-en-1-yl}benzoic acid

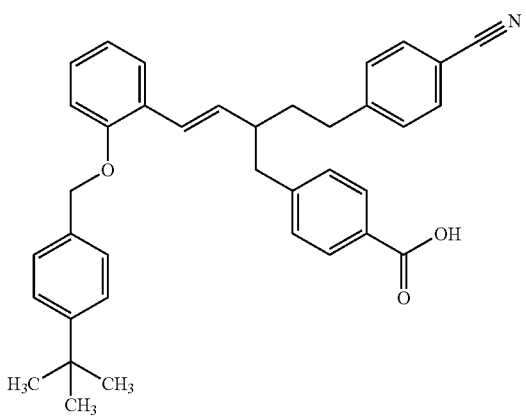

A solution of 1.1 g (1.97 mmol) of methyl-4-{(3E)-4-{2-[(4-tert-butylbenzyl)oxy]phenyl}-2-[2-(4-cyanophenyl)ethyl]but-3-en-1-yl}benzoate from Example 102A in 7.20 ml of THF and 3.60 ml of water is mixed with 189 mg (7.89 mmol) of lithium hydroxide and stirred at 60° C. for 12 h. The reaction mixture is adjusted to pH 34 with 1 M hydrochloric acid and concentrated. The residue is taken up on silica gel and purified by chromatography (mobile phase: cyclohexane/ethyl acetate 1:1, with 0.1% formic acid). 990 mg (1.77 mmol, 97% purity, 90% yield) of a solid are isolated.

$^1$H-NMR (400 MHz, DMSO-d$_6$, δ/ppm): 12.88-12.64 (1H, broad), 7.82-7.80 (2H, d), 7.66-7.63 (2H, d), 7.42-7.23 (9H, m), 7.21-7.13 (1H, m), 7.07-7.01 (1H, d), 6.93-6.86 (1H, t), 6.49-6.44 (1H, d), 6.12-6.04 (1H, dd), 5.08-4.99 (2H, m), 2.90-2.57 (4H, m), 2.57-2.41 (1H, m), 1.86-1.58 (2H, m), 1.26 (9H, s).

LC-MS (method 1): R$_t$ 3.39 min; m/z 543 (M$^+$).

Example 106A 2-(4-{(3E)-4-{2-[(4-tert-Butylbenzyl)oxy]phenyl}-2-[2-(4-cyanophenyl)ethyl]but-3-en-1-yl}-benzoyl)hydrazinecarboxamide

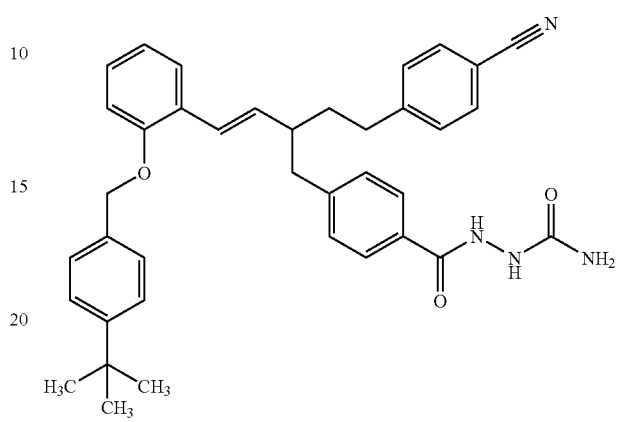

836 mg (6.62 mmol) of oxalyl chloride are slowly added dropwise to a solution of 600 mg (1.10 mmol) of 4-{(3E)-4-{2-[(4-tert-butylbenzyl)oxy]phenyl}-2-[2-(4-cyanophenyl)ethyl]but-3-en-1-yl}benzoic acid from Example 105A in 6 ml of dry toluene with 4 drops of DMF while cooling in ice. The reaction mixture is stirred at RT for 10 minutes and then heated to reflux for 1 hour. After cooling, the mixture is concentrated in vacuo, and the residue is coevaporated twice with toluene and then taken up in 6 ml of THF. This solution is added dropwise to a previously prepared solution of 135.4 mg (1.21 mmol) of semicarbazide hydrochloride and 88.3 mg (2.21 mmol) of sodium hydroxide in 1 ml of THF and 0.25 ml of water at 0° C. The mixture is stirred at 0° C. for 2 hours and then at RT for 30 minutes, and the residue after concentration is reacted without further purification in the next stage.

LC-MS (method 1): R$_t$ 3.17 min, m/z 600 (M)$^+$.

Example 107A 2-(4-{(3E)-4-{2-[(4-tert-Butylbenzyl)oxy]phenyl}-2-[2-(4-cyanophenyl)ethyl]but-3-en-1-yl}-benzoyl)hydrazinecarboximidamide

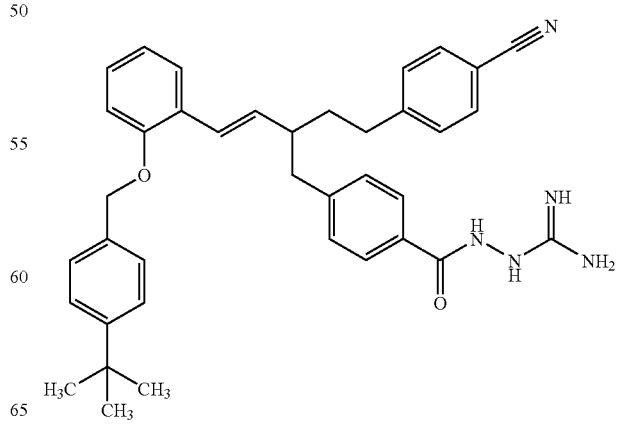

210 mg (1.66 mmol) of oxalyl chloride are slowly added dropwise to a solution of 150 mg (0.28 mmol) of 4-{(3E)-4-{2-[(4-tert-butylbenzyl)oxy]phenyl}-2-[2-(4-cyanophenyl)ethyl]but-3-en-1-yl}benzoic acid from Example 105A in 1.5 ml of dry toluene with 2 drops of DMF while cooling in ice. The reaction mixture is stirred at RT for 5 minutes and then heated to reflux for 1 hour. After cooling, the mixture is concentrated in vacuo, and the residue is coevaporated twice with toluene and then taken up in 3 ml of THF. This solution is added to a previously prepared solution of 33.5 mg (0.30 mmol) of aminoguanidine hydrochloride and 22 mg (0.55 mmol) of sodium hydroxide in 1 ml of THF and 0.25 ml of water at 0° C. The mixture is stirred at 0° C. for 2 hours and then concentrated, and the residue is reacted without further purification in the next stage.

LC-MS (method 5): $R_t$ 3.91 min; m/z 599 (M⁺).

Example 108A

1-Allyl 7-ethyl 2-allyloxycarbonyl-2-(4-cyanobenzyl)heptanedioate

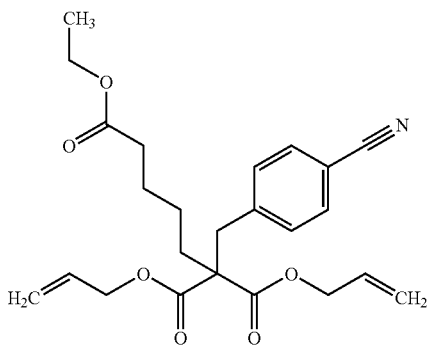

1.69 g (70.43 mmol) of sodium hydride are added in portions to a solution of 20 g (64.03 mmol) of 1-allyl 7-ethyl 2-allyloxycarbonylheptanedioate from Example 82A in 140 ml of dimethylformamide at 0° C. The reaction mixture is then allowed to reach room temperature and is stirred for 30 min. The reaction solution is cooled to 0° C. again and, after addition of 16.32 g (83.24 mmol) of 4-bromomethylbenzonitrile in 140 ml of DMF, stirred at this temperature for 30 min. The mixture is then stirred at room temperature overnight. Water is added dropwise to the reaction mixture and, after extraction three times with ethyl acetate, the combined organic phases are washed with saturated sodium chloride solution and dried over sodium sulfate. After filtration, the solvent is concentrated to dryness in vacuo. The resulting crude product is purified by flash chromatography an silica gel (mobile phase: cyclohexane/ethyl acetate 10:1→4:1→1:1). 20.08 g (46.97 mmol, 73% yield) of a colorless solid are obtained.

¹H-NMR (400 MHz, CDCl₃, δ/ppm): 7.56 (2H, d), 7.22 (2H, d), 5.91-5.78 (2H, m), 5.37-5.18 (4H, m), 4.66-4.54 (4H, m), 4.13 (2H, q), 3.29 (2H, s), 2.31 (2H, t), 1.87-1.77 (2H, m), 1.69-1.57 (2H, m), 1.39-1.28 (2H, m), 1.26 (3H, t).

MS (DCI): 445 (M+NH₄⁺).

Example 109A 2-(4-Cyanobenzyl)-heptanedioic acid 7-ethyl ester

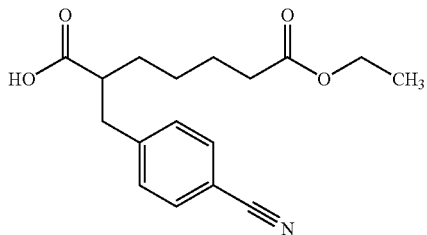

A solution of 24.21 ml (173.69 mmol) of triethylamine and 4.96 ml (131.58 mmol) of formic acid in 500 ml of dioxane is added to a solution of 22.5 g (52.63 mmol) of 1-allyl 7-ethyl 2-allyloxycarbonyl-2-(4-cyanobenzyl)-heptanedioate from Example 108A, 970 mg (3.68 mmol) of triphenylphosphine and 240 mg (1.05 mmol) of palladium acetate in 500 ml of dioxane at room temperature. The reaction mixture is then stirred at 10° C. for 2 hours. After conversion is complete, the reaction solution is cooled, and the solvent is removed in vacuo. The residue is then taken up in ethyl acetate and water and acidified with 1 N hydrochloric acid, and the organic phase is separated off. The aqueous phase is extracted three times more with ethyl acetate, and the organic phases are then combined, washed with saturated sodium chloride solution and dried over sodium sulfate. After filtration, the solution is concentrated in vacuo. 17.5 g (87% yield, 80% purity) of a colorless solid are obtained.

LC-MS (method 2): $R_t$ 1.97 min; m/z 304 (M+H⁺).

Example 110A

Ethyl 6-(4-cyanobenzyl)-7-hydroxyheptanoate

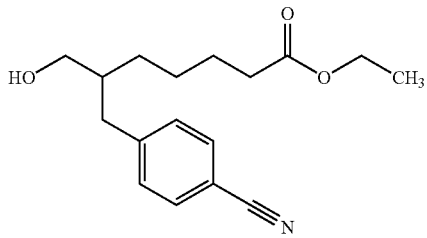

34.42 ml of a 1 M borane-THF complex solution (34.42 mmol) are added dropwise to a solution of 6.64 g (22.94 mmol) of 2-(4-cyanobenzyl)heptanedioic acid 7-ethyl ester from Example 109A in 260 ml of THF at −10° C. After warming to 0° C., the mixture is stirred at this temperature for 2 hours. After the reaction is complete, saturated sodium bicarbonate solution is added to the reaction mixture, and the solvent is concentrated to dryness. The residue is taken up in dichloromethane, dried over sodium sulfate and again freed of solvent. The resulting crude product is purified by flash chromatography on silica gel (mobile phase: ethyl acetate/cyclohexane 1:8→1:2). 5.84 g (88% yield, 20.19 mmol) of a colorless solid are obtained.

¹H-NMR (400 MHz, DMSO-4, δ/ppm): 8.14 (2H, d), 7.80 (2H, d), 4.91 (1H, t), 4.44 (2H, q), 3.69-3.58 (2H, m), 3.16-3.06 (1H, m), 3.01-2.92 (1H, m), 2.62 (2H, t), 2.14-2.01 (1H, m), 1.92-1.78 (2H, m), 1.77-1.60 (3H, m), 1.59-1.48 (1H, m), 1.57 (3H, t).

MS (DCI): 307 (M+N$_4^+$).

Example 111A

Ethyl 6-(4-cyanobenzyl)-7-oxoheptanoate

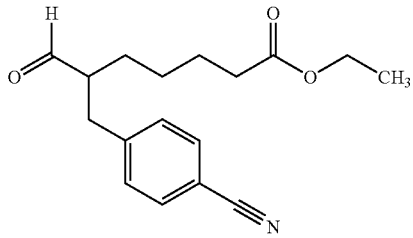

A solution of 4.6 g (15.90 mmol) of ethyl 6-(4-cyanobenzyl)-7-hydroxyheptanoate from Example 110A in 250 ml of dichloromethane is mixed with 4.11 g (19.08 mmol) of pyridinium chlorochromate (PCC) and stirred at room temperature for 12 hours. After conversion is complete, 10 g of silica gel are added, and the solvent is cautiously concentrated to dryness in vacuo. The resulting residue is purified by flash chromatography on silica gel (mobile phase: cyclohexane/ethyl acetate 1:1). 4.09 g (14.23 mmol, 89% yield) of a colorless solid are obtained.

¹H-NMR (400 MHz, DMSO-d$_6$, δ/ppm): 9.60 (1H, s), 7.75 (2H, d), 7.41 (2H, d), 4.03 (2H, q), 3.08-2.97 (1H, m), 2.82-2.64 (2H, m), 2.24 (2H, t), 1.63-1.19 (6H, m), 1.17 (3H, t).

MS (DCI): 305 (M+NH$_4^+$).

Example 112A

Ethyl E-6-(4-cyanobenzyl)-8-(2-hydroxyphenyl)oct-7-enoate

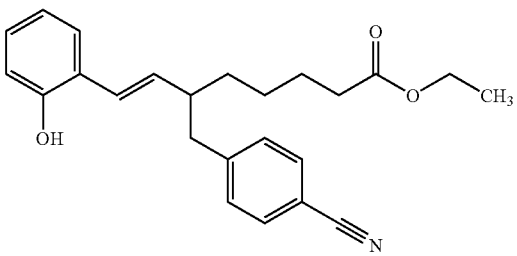

15.98 ml (39.95 mmol) of a 2.5 M solution of n-butyllithium in hexane are slowly added to a solution of 6.411 g (14.27 mmol) of (2-hydroxybenzyl)triphenylphosphonium bromide in 300 ml of anhydrous THF at 0° C. Then, at this temperature, 4.1 g (14.27 mmol) of ethyl 6-(4-cyanobenzyl)-7-oxoheptanoate from Example 111A are slowly metered in. After warming to room temperature, the reaction solution is stirred for 12 hours and then mixed with saturated ammonium chloride solution and concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 4:1). 1.75 g (4.64 mmol, 32% yield) of a colorless solid are obtained.

¹H-NMR (400 MHz, DMSO-d$_6$, δ/ppm): 9.42 (1H, s), 7.72 (2H, d), 7.40 (2H, d), 7.29 (1H, d), 7.00 (1H, t), 6.79-6.67 (2H, m), 6.39 (1H, d), 6.04-5.94 (1H, m), 4.01 (2H, q), 2.87-2.77 (1H, m), 2.76-2.66 (1H, m), 2.48-2.38 (1H, m), 2.25 (2H, t), 1.57-1.39 (3H, m), 1.38-1.19 (3H, m), 1.13 (3H, t).

MS (DCI): 395 (M+NH$_4^+$).

Example 113A

Ethyl E-8-[2-(4-tert-butylbenzyloxy)phenyl]-6-(4-cyanobenzyl)oct-7-enoate

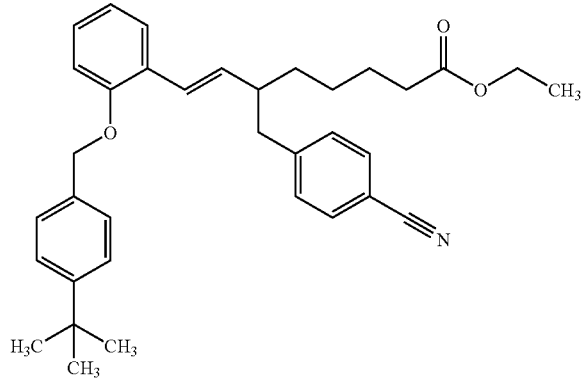

A solution of 1.75 g (4.64 mmol) of ethyl E-6-(4-cyanobenzyl)-8-(2-hydroxyphenyl)oct-7-enoate from Example 112A in 50 ml of dry acetonitrile is mixed with 1579 mg (6.95 mmol) of 4-(tert-butyl)benzyl bromide and 961 mg (6.95 mmol) of anhydrous potassium carbonate and heated to reflux for 12 hours. The mixture is then concentrated to dryness. The residue is taken up in ethyl acetate, washed with water and saturated sodium chloride solution and dried over sodium sulfate. The organic phase is concentrated. The resulting crude product is purified by flash chromatography on silica gel (mobile phase: cyclohexane/ethyl acetate 8:1→4:1). 2.24 g (4.28 mmol, 92% yield) of a solid are obtained.

¹H-NMR (300 MHz, DMSO-d$_6$, δ/ppm): 7.68 (2H, d), 7.44-7.32 (5H, m), 7.28 (2H, d), 7.14 (1H, t), 7.01 (1H, d), 6.88 (1H, t), 6.42 (1H, d), 6.08-5.95 (1H, m), 5.04 (2H, s), 4.00 (2H, q), 2.89-2.78 (1H, m), 2.75-2.60 (2H, m), 2.54-2.40 (1H, m), 2.23 (2H, t), 1.60-1.21 (5H, m), 1.28 (9H, s), 1.13 (3H, t).

MS (DCI): 541 (M+NH$_4^+$).

Example 114A

Ethyl E-8-[2-(4-tert-butylbenzyloxy)phenyl]-6-[4-(5-oxo-4,5-dihydro[1,2,4]oxadiazol-3-yl)benzyl]oct-7-enoate

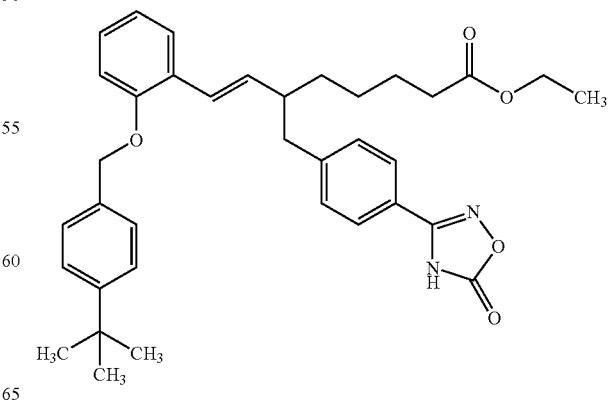

A solution of 823 mg (11.84 mmol) of hydroxylamine hydrochloride in 10 ml of DMSO is mixed with 1.65 ml (11.84 mmol) of triethylamine and stirred at room temperature for 10 min. The resulting precipitate is filtered off. Then 1.24 g (2.37 mmol) of ethyl E-8-[2-(4-tert-butylbenzyloxy)phenyl]-6-(4-cyanobenzyl)oct-7-enoate from Example 113A are metered into the filtrate. The reaction solution is stirred at 75° C. for 12 hours. After conversion is complete and cooling, 10 ml of water are added to the reaction solution and, after extraction three times with ethyl acetate, the combined organic phases are washed with saturated sodium chloride solution. The organic phase is then dried over sodium sulfate and concentrated to dryness. 1380 mg of a colorless oil are obtained and are reacted further immediately without further purification.

The oil obtained above is dissolved in 15 ml of DMF, and 0.22 ml (2.77 mmol) of pyridine is added. The solution is then cooled to 0° C. and 412 mg (2.31 mmol) of 2-ethylhexyl chloroformate are slowly added. The mixture is stirred at 0° C. for about 30 min and then taken up in water and extracted with ethyl acetate. The organic phase is dried over sodium sulfate and concentrated to dryness. The resulting residue is taken up in 15 ml of xylene and heated to reflux for 4 hours. After reaction is complete, the reaction solution is cooled and concentrated to dryness. 1.38 g (90% purity, 92% yield) of a solid are obtained.

LC-MS (method 2): $R_t$ 3.18 min; m/z 583 (M+H$^+$).

Example 115A

Diallyl 2-(4-cyanobutyl)-2-(4-methoxycarbonylbenzyl)malonate

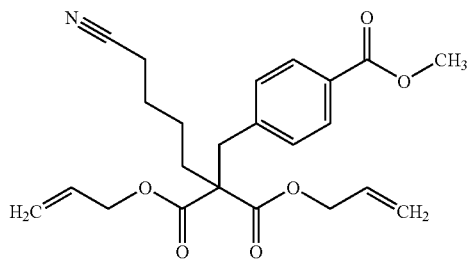

1.88 g (78.23 mmol) of sodium hydride are added in portions to a solution of 20 g (60.18 mmol) of diallyl 2-(4-methoxycarbonylbenzyl)malonate from Example 12A in 140 ml of DMF at 0° C. The reaction solution is then warmed to 40° C. and is stirred at this temperature for 30 min. The reaction solution is then cooled to 0° C. again and, after addition of 10.73 g (66.20 mmol) of bromovaleronitrile in 140 ml of DMF, stirred at this temperature for 30 min. The mixture is then stirred at room temperature overnight. Water is added dropwise to the reaction mixture and, after extraction three times with ethyl acetate, the combined organic phases are washed with saturated sodium chloride solution and dried over sodium sulfate. After filtration, the solvent is concentrated to dryness in vacuo. The resulting crude product is purified by flash chromatography on silica gel (mobile phase: cyclohexane/ethyl acetate 9:1→4:1). 15.5 g (37.49 mmol, 62% yield) of a colorless solid are obtained.

$^1$H-NMR (400 MHz, CDCl$_3$, δ/ppm): 7.94 (2H, d), 7.17 (2H, d), 5.95-5.80 (2H, m), 5.38-5.20 (4H, m), 4.69-4.56 (4H, m), 3.91 (3H, s), 3.32 (2H, s), 2.34 (2H, t), 1.85-1.74 (2H, m), 1.71-1.59 (2H, m), 1.53-1.40 (2H, m).

MS (DCI): 431 (M+NH$_4^+$).

Example 116A

Methyl 4-(2-carboxy-6-cyanohexyl)benzoate

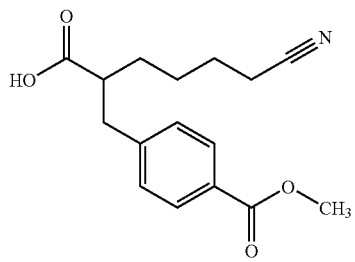

17.24 ml (123.71 mmol) of triethylamine and 4.24 ml (112.46 mmol) of formic acid in 500 ml of dioxane is added to a solution of 15.5 g (37.49 mmol) of diallyl 2-(4-cyanobutyl)-2-(4 methoxycarbonylbenzyl)malonate from Example 115A, 690 mg (2.62 mmol) of triphenylphosphine and 170 mg (0.75 mmol) of palladium acetate in 500 ml of dioxane at room temperature. The reaction mixture is then stirred at 10° C. for 12 hours. After conversion is complete, the reaction solution is cooled and the solvent is removed in vacuo. The residue is then taken up in ethyl acetate and water and acidified with 1 N hydrochloric acid and the organic phase is separated off. The aqueous phase is extracted three times more with ethyl acetate, and then the organic phases are combined, washed with saturated sodium chloride solution and dried over sodium sulfate. After filtration, the solution is concentrated in vacuo. 8.1 g (74% yield) of a colorless solid are obtained.

LC-MS (method 2): $R_t$ 1.76 min; m/z 290 (M+H$^+$).

Example 117A

Methyl 4-(6-cyano-2-hydroxymethylhexyl)benzoate

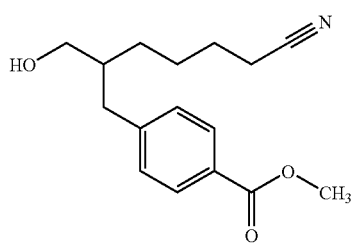

27.65 ml of a 1 M borane-THF complex solution are added dropwise to a solution of 3.835 g (13.83 mmol) of methyl 4-(2-carboxy-6-cyanohexyl)benzoate from Example 116A in 200 ml of THF at −10° C. After warming to 0° C., the mixture is stirred at this temperature for 2 hours. After reaction is complete, saturated sodium bicarbonate solution is added to the reaction mixture, and the solvent is concentrated to dryness. The residue is taken up in dichloromethane, dried over sodium sulfate and again freed of solvent. The resulting crude product is purified by flash chromatography on silica gel (mobile phase: ethyl acetate/cyclohexane 1:8→1:2). 2.95 g (77% yield) of a colorless solid are obtained.

¹H-NMR (400 MHz, DMSO-d₆, δ/ppm): 7.88 (2H, d), 7.33 (2H, d), 4.50 (1H, t), 3.84 (3H, s), 3.28 (2H, t), 2.75-2.64 (1H, m), 2.59-2.52 (1H, m), 2.45 (2H, t), 1.76-1.62 (1H, m), 1.54-1.43 (2H, m), 1.43-1.26 (3H, m), 1.24-1.10 (1H, m).

MS (DCI): 293 (M+NH₄⁺).

Example 118A

Methyl 4-(6-cyano-2-formylhexyl)benzoate

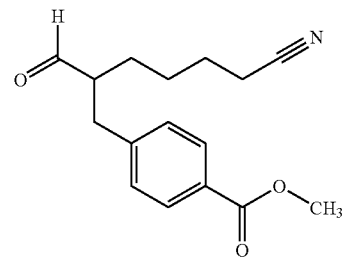

A solution of 3.8 g (13.80 mmol) of methyl 4-(6-cyano-2-hydroxymethylhexyl)benzoate from Example 117A in 250 ml of dichloromethane is mixed with 3.57 g (16.56 mmol) of pyridinium chlorochromate (PCC) and stirred at room temperature for 12 hours. After conversion is complete, 10 g of silica gel are added and the solvent is cautiously concentrated to dryness in vacuo. The resulting residue is purified by flash chromatography on silica gel (mobile phase: cyclohexane/ethyl acetate 1:1). 3.49 g (92% yield) are obtained as a colorless solid.

¹H-NMR (400 MHz, DMSO-d₆, δ/ppm): 9.64 (1H, s), 7.87 (2H, d), 7.36 (2H, d), 3.84 (3H, s), 3.09-2.99 (1H, m), 2.84-2.66 (2H, m), 2.47 (2H, t), 1.68-1.22 (6H, m).

MS (DCI): 291 (M+NH₄⁺).

Example 119A

Methyl E-4-{6-cyano-2-[2-(2-hydroxyphenyl)vinyl]hexyl}benzoate

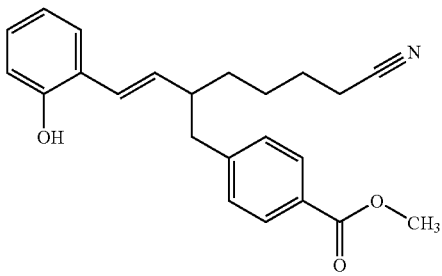

14.34 ml (35.85 mmol) of a 2.5 M solution of n-butyllithium in hexane are slowly added to a solution of 5.753 g (12.81 mmol) of (2-hydroxybenzyl)triphenylphosphonium bromide in 300 ml of anhydrous THF at 0° C. Then, at this temperature, 3.5 g (12:81 mmol) of methyl 4-(6-cyano-2-formylhexyl)benzoate from Example 118A are slowly metered in. After warming to room temperature, the reaction solution is stirred for 4 hours, then mixed with saturated ammonium chloride solution and concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 4:1). 2976 mg (64% yield) of a colorless solid are obtained.

¹H-NMR (400 MHz, DMSO-d₆, δ/ppm): 9.42 (1H, s), 7.86 (2H, d), 7.35 (2H, d), 7.30 (1H, d), 6.99 (1H, t), 6.80-6.67 (2H, m), 6.44 (1H, d), 6.06-5.95 (1H, m), 3.82 (3H, s), 2.87-2.77 (1H, m), 2.76-2.65 (1H, m), 2.54-2.40 (1H, m), 2.46 (2H, t), 1.61-1.29 (6H, m).

MS (DCI): 381 (M+NH₄⁺).

Example 120A

Methyl E-4-(2-{2-[2-(4-tert-butylbenzyloxy)phenyl]vinyl}-6-cyanohexyl)benzoate

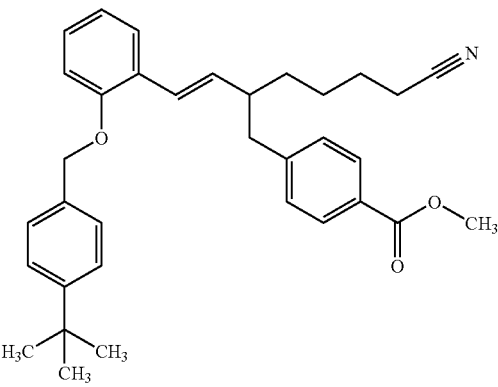

A solution of 2.976 g (8.19 mmol) of methyl E-4-{6-cyano-2-[2-(2-hydroxyphenyl)vinyl]hexyl}-benzoate from Example 119A in 100 ml of dry acetonitrile is mixed with 2.789 g (12.28 mmol) of 4-(tert-butyl)benzyl bromide and 1.697 g (12.28 mmol) of anhydrous potassium carbonate and heated to reflux for 12 hours. The mixture is then filtered and the filtrate is concentrated to dryness. The residue is taken up in ethyl acetate, washed with water and saturated sodium chloride solution and dried over sodium sulfate. The organic phase is concentrated. The resulting crude product is purified by flash chromatography on silica gel (mobile phase: cyclohexane/ethyl acetate 8:1→4:1). 3.85 g (92% yield) of a solid are obtained.

¹H-NMR (300 MHz, DMSO-d₆, δ/ppm): 7.83 (2H, d), 7.43-7.35 (3H, m), 7.34-7.23 (4H, m), 7.16 (1H, t), 7.00 (1H, d), 6.88 (1H, t), 6.45 (1H, d), 6.09-5.98 (1H, m), 5.02 (2H, s), 3.80 (3H, s), 2.89-2.76 (1H, m), 2.75-2.61 (1H, m), 2.55-2.47 (1H, m), 2.44 (2H, t), 1.60-1.31 (6H, m), 1.28 (9H, s).

MS (DCI): 527 (M+NH₄⁺).

Example 121A

E-8-[2-(4-tert-Butylbenzyloxy)phenyl]-6-[4-(5-oxo-4,5-dihydro[1,3,4]oxadiazol-2-yl)benzyl]oct-7-enenitrile

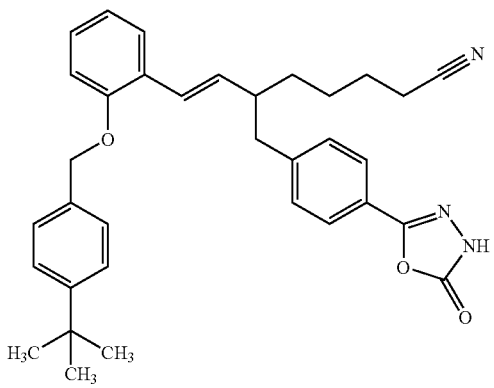

A solution of 200 mg (0.39 mmol) of methyl E-4-(2-{2-[2-(4-tert-butylbenzyloxy)phenyl]vinyl}-6-cyanohexyl)benzoate from Example 120A in 2 ml of methanol and 1 ml of THF is mixed with 785 mg (15.70 mmol) of hydrazine monohydrate and stirred at 70° C. for 12 hours. The reaction mixture is concentrated to dryness, and the residue is coevaporated again with dichloromethane. The resulting crude product (166 mg) is reacted directly in the next reaction.

A solution of 96.65 mg (0.49 mmol) of trichloromethyl chloroformate in 0.5 ml of dry dioxane is mixed with 166 mg of the intermediate obtained above (crude product) in 1 ml of dioxane and heated to reflux for 1 hour. The mixture is then concentrated to dryness, and the resulting residue is purified by preparative HPLC. 47 mg (22% yield based on the two stages) of a solid are obtained.

LC-MS (method 1): $R_t$ 3.26 min; m/z 534 (M−H)⁻.

Example 122A (7E)-8-{2-[(4-tert-Butylbenzyl)oxy]phenyl}-6-[2-(4-cyanophenyl)ethyl]oct-7-enoic acid

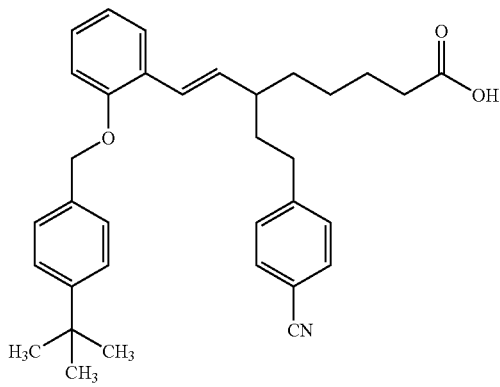

A solution of 798 mg (1.48 mmol) of ethyl 7E-8-[2-(4-tert-butylbenzyloxy)phenyl]-6-[2-(4-cyanophenyl)ethyl]oct-7-enoate in 20 ml of THF and 20 ml of water is mixed with 71 mg (2.97 mmol) of lithium hydroxide and stirred at 50° C. for 12 hours. Cooling is followed by dilution with water and diethyl ether and separation of the phases. The aqueous phase is acidified with 1 M hydrochloric acid and extracted with diethyl ether. The organic phase is washed with saturated sodium chloride solution, dried over sodium sulfate and concentrated. 700 mg (1.4 mmol, 93% of theory) of the title compound are obtained.

HPLC (method 3): $R_t$=5.69 min

MS (ESIneg): m/z=508 (M−H)⁻

¹H-NMR (400 MHz, DMSO-d₆, δ/ppm): 11.96 (s, 1H), 7.65 (d, 2H), 7.47 (d, 1H), 7.4-7.3 (m, 6H), 7.2 (t, 1H), 7.1 (d, 1H), 6.92 (t, 1H), 6.6 (d, 1H), 6.02 (dd, 1H), 5.1 (s, 2H), 2.75-2.57 (m, 2H), 2.18 (t, 2H), 2.11-2.0 (m, 1H), 1.78-1.54 (m, 2H), 1.5-1.38 (m, 3H), 1.38-1.15 (m, 12H).

Example 123A

2-{(7E)-8-{2-[(4-tert-Butylbenzyl)oxy]phenyl}-6-[2-(4-cyanophenyl)ethyl]oct-7-enoyl}hydrazinecarboxamide

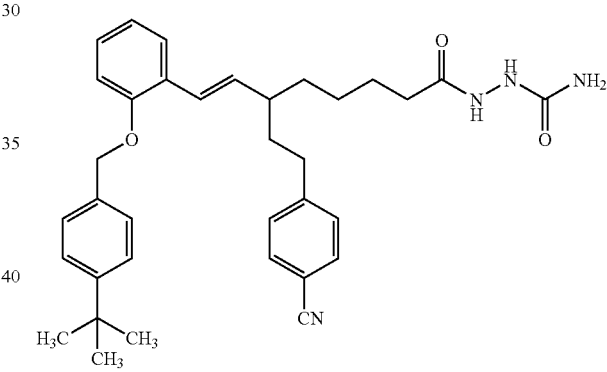

4 drops of DMF are added to a solution of 700 mg (1.37 mmol) of (7E)-8-{2-[(4-tert-butylbenzyl)oxy]phenyl}-6-[2-(4-cyanophenyl)ethyl]oct-7-enoic acid in 8 ml of toluene. Then 0.72 ml (8.24 mmol) of oxalyl chloride is added dropwise, and the mixture is stirred at room temperature for 10 min. The reaction solution is then heated to 80° C. and stirred at this temperature for 1 h. After cooling, the solvent is stripped off and the residue is mixed twice more with toluene and again evaporated to dryness each time (intermediate).

168.5 mg (1.5 mmol) of semicarbazide hydrochloride are dissolved in 5 ml of THF and 2 ml of water, and 110 mg (2.75 mmol) of sodium hydroxide are added. The solution is cooled to 0° C., and the intermediate obtained above, dissolved in 10 ml of THF, is slowly added dropwise. The mixture is stirred at 0° C. for 2 h and then concentrated. 778 mg (1.3 mmol, 100% of theory) of the title compound are obtained and are reacted without further purification and characterization.

Example 124A

Methyl 4-((3E)-2-(2-{4-[(amino(hydroxyimino)methyl]phenyl}ethyl)-4-{2-[(4-tert-butylbenzyl)oxy]phenyl}but-3-en-1-yl)benzoate

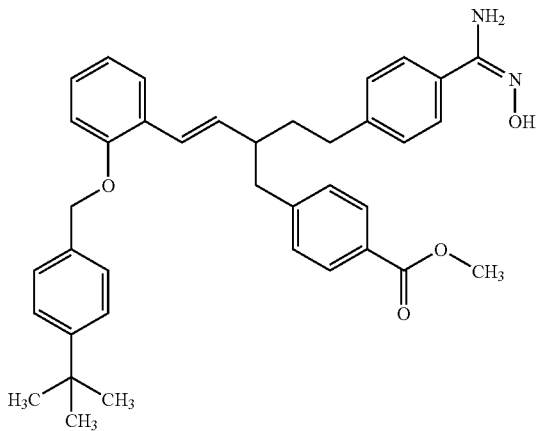

1.25 g (17.9 mmol) of hydroxylammonium chloride are introduced into 20 ml of DMSO, and 2.5 ml of triethylamine are added. The mixture is stirred at room temperature for 10 min and the precipitated solid is filtered off with suction. The mother liquor is added to 2 g (3.59 mmol) of methyl 4-{(3E)-4-{2-[(4-tert-butylbenzyl)oxy]phenyl}-2-[2-(4-cyanophenyl)ethyl]but-3-en-1-yl}benzoate, and the mixture is then stirred at 75° C. for 12 h. After conversion is complete, the reaction solution is added to ice-water. The resulting crystals are filtered off with suction and washed with water, and then taken up in diethyl ether and washed with sodium chloride solution. The organic phase is dried over sodium sulfate and concentrated. 1.9 g (83% purity, 2.67 mmol, 74% of theory) of the title compound are obtained.

LC-MS (method 4): $R_t$=2.77 min
MS (ESIpos): m/z=591 (M+H)$^+$.

Example 125A

Methyl 4-((3E)-4-{2-[(4-tert-butylbenzyl)oxy]phenyl}-2-{2-[4-(5-oxo-4,5-dihydro-1,2,4-oxadiazol-3-yl)phenyl]ethyl}but-3-en-1-yl)benzoate

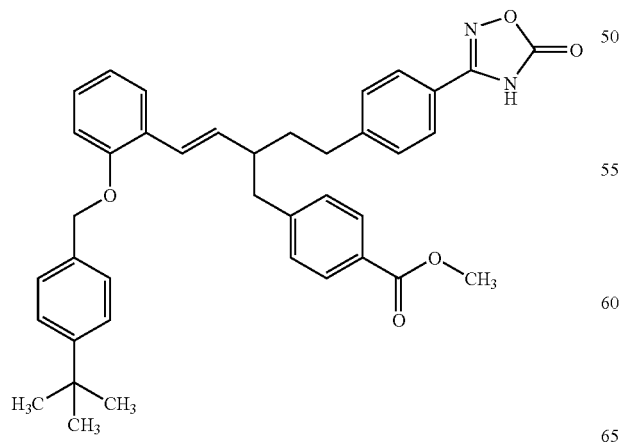

A solution of 1.9 g (83% content, 2.67 mmol) of methyl 4-((3E)-2-(2-{4-[(amino(hydroxyimino)methyl]phenyl}ethyl)-4-{2-[(4-tert-butylbenzyl)oxy]phenyl}but-3-en-1-yl)benzoate in 20 ml of DMF is mixed with 0.31 ml (3.86 mmol) of pyridine and cooled in an ice bath. Then 0.63 ml (3.2 mmol) of 2-ethylhexyl chloroformate is added dropwise, and the mixture is stirred at 0° C. for 30 min. After conversion is complete, water is added, and the mixture is extracted with diethyl ether. The organic phase is dried over sodium sulfate and concentrated. The resulting residue is purified by flash chromatography on silica gel (mobile phase: cyclohexane/ethyl acetate 4:1). The product obtained in this way is taken up in 20 ml of xylene and heated at reflux for 2 h. This is followed by addition of water and extraction with diethyl ether. The organic phase is washed with sodium chloride solution, and dried over sodium sulfate and concentrated. The resulting residue is purified by flash chromatography on silica gel (mobile phase: cyclohexane/ethyl acetate 4:1→1:1). 503 mg (0.82 mmol, 24% of theory) of the title compound are obtained.

HPLC (method 2): $R_t$=3.31 min
MS (ESIpos): m/z=617 (M+H)$^+$.

Example 126A

Triphenyl[2-(trifluoromethoxy)benzyl]phosphonium bromide

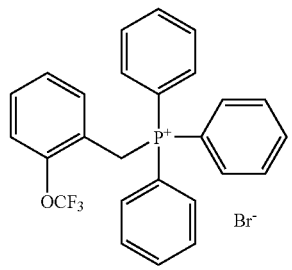

5 g (26 mmol) of 2-trifluoromethoxybenzyl alcohol and 8.5 g (24.7 mmol) of triphenylphosphonium bromide are heated under reflux in 100 ml of acetonitrile for 3 h. After cooling, the resulting precipitate is filtered off with suction and dried. 13.5 g (quant.) of the title compound are obtained.

LC-MS (method 3): $R_t$=1.91 min; MS (ESIpos): m/z=437 (M-Br)$^+$.

Example 127A

Methyl E-4-[3-(4-cyanobenzyl)-5-(2-hydroxyphenyl)pent-4-enyl]benzoate (enantiomer 1)

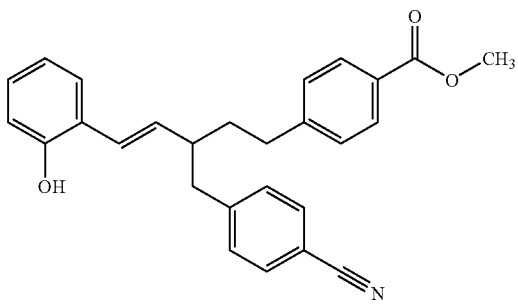

11.3 g (27.5 mmol) of the racemic methyl E-4-[3-(4-cyanobenzyl)-5-(2-hydroxyphenyl)pent-4-enyl]benzoate obtained in Example 75A are fractionated further by preparative HPLC on a chiral phase. Respectively 4.14 g and 3.69 g of the two E isomers are obtained, each enantiopure, as colorless solids (Example 127A and 128A).

Enantiomer Separation Method:

Column: Daicel Chiralpak AD-H 250 mm×4.6 mm, 5 μm; eluent: isohexane/isopropanol 50:50 (v/v); flow rate: 1 ml/min; UV detection: 210 nm; temperature: 25° C.

$R_t$ 6.77 min; purity 96.85%; >99.5% ee

Yield: 4.14 g

LC-MS (method 6): $R_t$=3.03 min; MS (ESIpos): m/z=412 (M+H)$^+$.

Example 128A

Methyl E-4-[3-(4-cyanobenzyl)-5-(2-hydroxyphenyl)pent-4-enyl]benzoate (enantiomer 2)

Enantiomer separation method: see Example 127A.

$R_t$ 7.82 min; purity 96%; >99% ee

Yield: 3.69 g

LC-MS (method 6): $R_t$=3.03 min; MS (ESIpos): m/z=412 (M+H)$^+$.

EXEMPLARY EMBODIMENTS

Example 1

4-[({2-[4-(5-Oxo-4,5-dihydro-[1,2,4]oxadiazol-3-yl)phenyl]ethyl}-{2-[2-(4'-trifluoromethylbiphenyl-4-ylmethoxy)phenyl]ethyl}amino)methyl]benzoic acid A solution of 32.7 mg (0.05 mmol) of methyl 4-[({2-[4-(5-oxo-4,5-dihydro-[1,2,4]oxadiazol-3-yl)phenyl]ethyl}-{2-[2-(4'-trifluoromethylbiphenyl-4-ylmethoxy)phenyl]ethyl}amino)methyl]-benzoate from Example 11A in 2 ml of THF and 2 ml of water is mixed with 2.2 mg (0.09 mmol) of lithium hydroxide and stirred at 50° C. for 12 h. After cooling, the THF is stripped off and the aqueous phase is adjusted to pH 4-5 with 1 M hydrochloric acid. It is then extracted three times with ethyl acetate, and the combined organic phases are dried over sodium sulfate. The residue obtained after filtration and concentration is purified by preparative HPLC. 7.4 mg (0.01 mmol, 23% yield) of a colorless oil are obtained.

$^1$H-NMR (400 MHz, DMSO d$_6$, δ/ppm): 13.0-12.5 (2H, broad), 7.79 (2H, d), 7.62 (1H, d), 7.52 (2H, d), 7.49-7.39 (4H, m), 7.31-7.13 (8H, m), 7.12-7.00 (2H, m), 6.86 (1H, t), 5.08 (2H, s), 3.71 (2H, s), 2.82-2.61 (8H, m).

LC-MS (method 3): $R_t$ 2.51 min; m/z 694 (M+H$^+$).

The examples listed in the following table are obtained in an analogous manner:

| Example | Structure | Analytical data |
|---|---|---|
| 2 (starting from (5-bromo-pentyl)-benzene and Ex. 3A) | 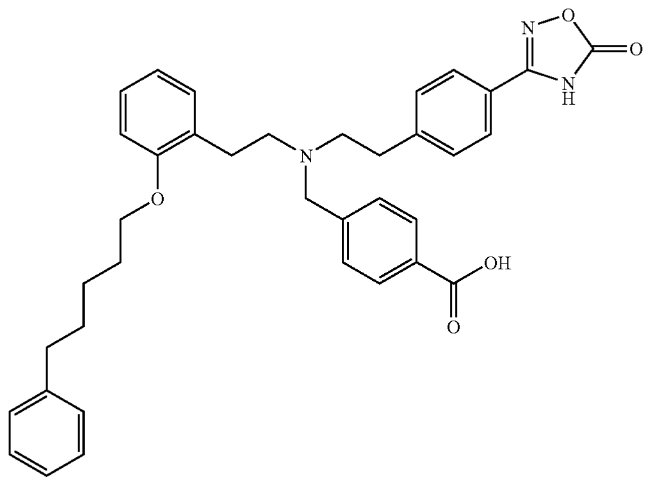 | $^1$H-NMR (300 MHz, DMSO-$d_6$, δ/ppm): 12.97-12.51 (2H, broad), 7.81-7.78 (2H, d), 7.70-7.67 (2H, d), 7.32-7.03 (11H, m), 6.88-6.78 (2H, m), 3.98-3.11 (m), 2.56-2.45 (m), 1.66-1.47 (4H, m), 1.42-1.29 (3H, s). LC-MS (method 2): $R_t$ 2.05 min; m/z 606 (M + H$^+$). |
| 3 (starting from Ex. 9A) | 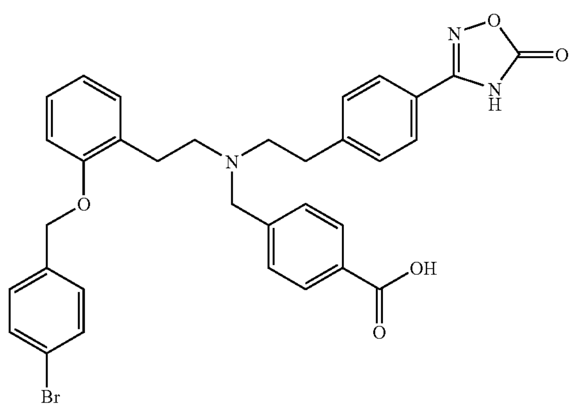 | $^1$H-NMR (300 MHz, DMSO-$d_6$, δ/ppm): 13.0-12.5 (2H, broad), 7.79 (2H, m$_c$), 7.67 (2H, m$_c$), 7.48 (2H, m$_c$), 7.32-7.12 (8H, m), 6.98 (1H, m$_c$), 6.85 (2H, m$_c$), 5.02 (2H, s), 2.42 (2H, m$_c$), 2.23 (2H, m$_c$). HPLC (method 1): 4.5 min. MS: 628 (M + H$^+$ $^{79}$Br), 630 (M + H$^+$ $^{81}$Br). |
| 4 (starting from Ex. 9A and 4-methoxy-benzene-boronic acid) | 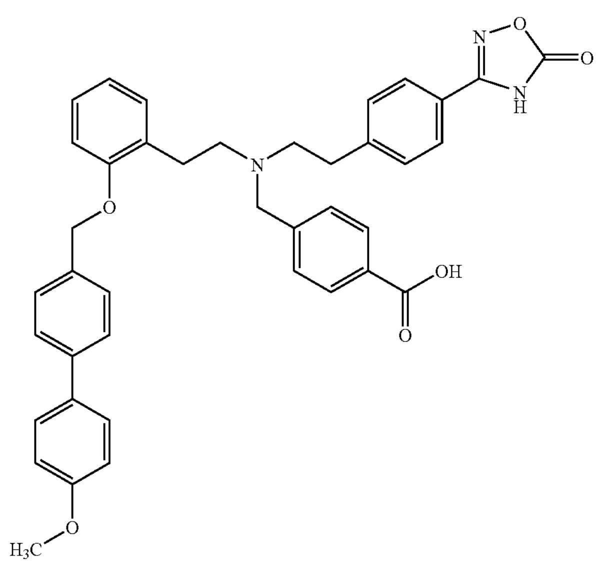 | $^1$H-NMR (300 MHz, DMSO-$d_6$, δ/ppm): 13.0-12.5 (2H, braod), 7.78 (2H, d$_{AB}$), 7.63 (2H, d$_{AB}$), 7.53-7.45 (4H, m), 7.41 (2H, d$_{AB}$), 7.29-7.13 (6H, m), 7.07 (1H, m$_c$), 6.97 (2H, m$_c$), 6.85 (1H, m$_c$), 5.06 (2H, s), 3.28 (3H, s), 2.73 (4H, m$_c$), 2.28 (2H, m$_c$). HPLC (method 1): 4.7 min. MS: 656 (M + H$^+$). |

-continued

| Example | Structure | Analytical data |
| --- | --- | --- |
| 5 (starting from Ex. 9A and 4-fluorobenzene boronic acid) | 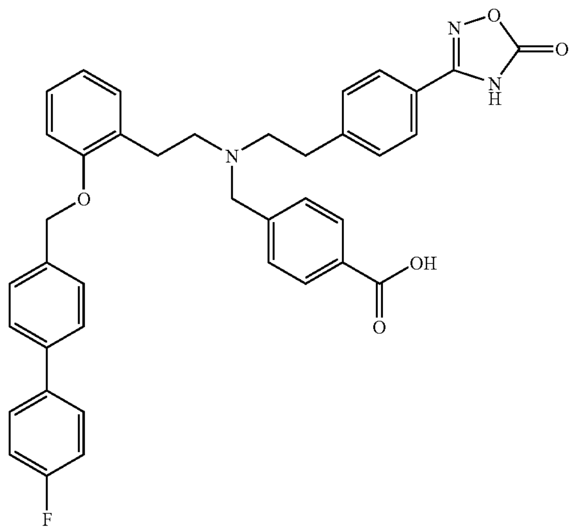 | LC-MS (method 2): $R_t$ 2.03 min; m/z 644 (M + H$^+$). |
| 6 (starting from Ex. 9A and benzene-boronic acid) | 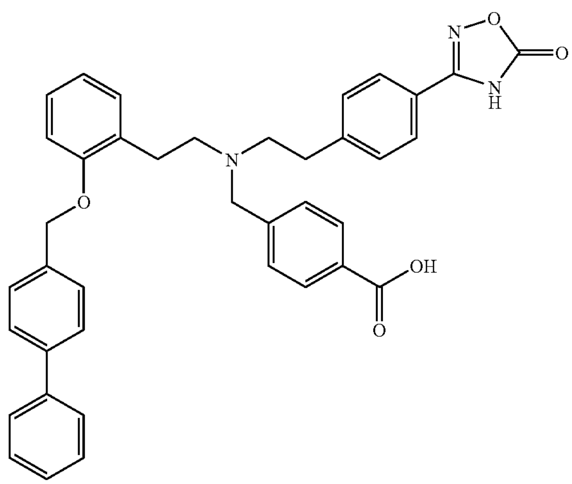 | LC-MS (method 3): $R_t$ 2.00 min; m/z 626 (M + H$^+$). |
| 7 (starting from Ex. 9A and 4-methyl-benzene-boronic acid) | 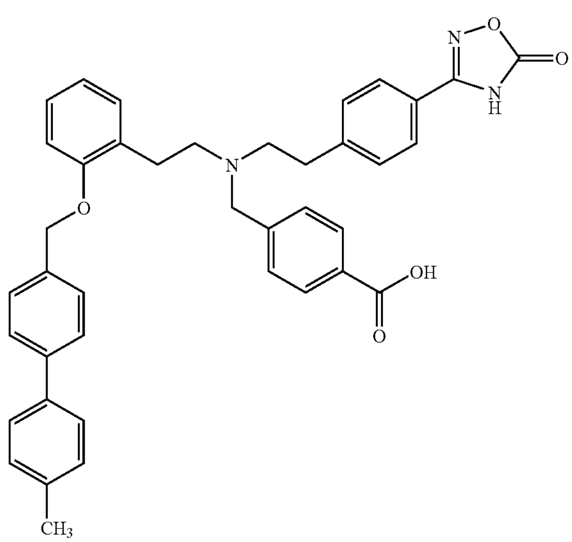 | $^1$H-NMR (400 MHz, DMSO-d$_6$, δ/ppm): 13.00-12.49 (2H, broad), 7.79 (2H, d), 7.63 (1H, d), 7.59-7.38 (6H, m), 7.34-7.13 (8H, m), 7.12-6.98 (2H, m), 6.84 (1H, t), 5.06 (2H, s), 3.73 (2H, s), 2.86-2.62 (8H, m), 2.33 (3H, s). LC-MS (method 3): $R_t$ 2.01 min; m/z 640 (M + H$^+$). |

| Example | Structure | Analytical data |
|---|---|---|
| 8 (starting from Ex. 9A and 4-chloro-benzene-boronic acid) | 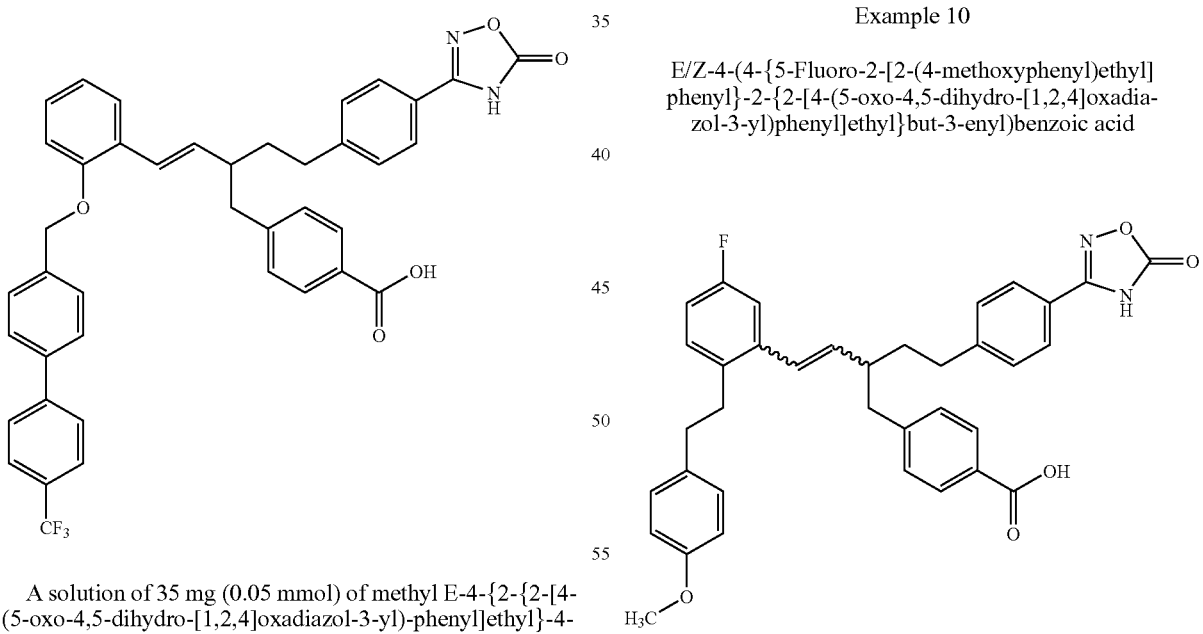 | LC-MS (method 3): $R_t$ 2.01 min: m/z 660 (M+). |

Example 9 rac-EA-{2-{2-[4-(5-Oxo-4,5-dihydro-[1,2,4]oxadiazol-3-yl)phenyl]ethyl}-4-[2-(4'-trifluoromethylbiphenyl-4-yl-methoxy)phenyl]but-3-enyl}benzoic acid A solution of 35 mg (0.05 mmol) of methyl E-4-{2-{2-[4-(5-oxo-4,5-dihydro-[1,2,4]oxadiazol-3-yl)-phenyl]ethyl}-4-[2-(4'-trifluoromethylbiphenyl-4-ylmethoxy)phenyl]but-3-enyl}benzoate from Example 20A in 2 ml of THF and 2 ml of water is mixed with 2.38 mg (0.1 mmol) of lithium hydroxide and stirred at 50° C. for 12 h. After cooling, the THF is stripped off and the aqueous phase is adjusted to pH 4-5 with 1 M hydrochloric acid. It is then extracted three times with ethyl acetate, and the combined organic phases are dried over sodium sulfate. The residue obtained after filtration and concentration is purified by preparative HPLC. 19.8 mg (0.028 mmol, 57% yield) of a colorless solid is obtained.

$^1$H-NMR (400 MHz, DMSO-d$_6$, δ/ppm): 12.92-12.68 (2H, broad), 7.90-7.77 (6H, m), 7.70 (2H, d), 7.68 (2H, d), 7.50 (2H, d), 7.4-3 (1H, d), 7.35 (2H, d), 7.28 (2H, d), 7.19 (1H, t), 7.06 (1H, d), 6.92 (1H, t), 6.51 (1H, d), 6.12 (1H, dd), 5.16 (2H, s), 2.94-2.82 (1H, m), 2.79-2.69 (2H, m), 2.68-2.57 (1H, m), 2.56-2.44 (1H, m), 1.89-1.76 (1H, m), 1.75-1.61 (1H, m).
LC-MS (method 4): $R_t$ 3.23 min; m/z 690 (M+).

Example 10

E/Z-4-(4-{5-Fluoro-2-[2-(4-methoxyphenyl)ethyl]phenyl}-2-{2-[4-(5-oxo-4,5-dihydro-[1,2,4]oxadiazol-3-yl)phenyl]ethyl}but-3-enyl)benzoic acid A solution of 447 mg (0.74 mmol) of methyl E/Z-4-(4-{5-fluoro-2-[2-(4-methoxyphenyl)ethyl]phenyl}-2-{2-[4-(5-oxo-4,5-dihydro-[1,2,4]oxadiazol-3-yl)phenyl]ethyl}but-3-enyl)benzoate from Example 69A in 10 ml of THF and 10 ml of water is mixed with 35.3 mg (1.47 mmol) of lithium hydroxide and stirred at 50° C. for 12 h. After cooling, the THF is stripped off and the aqueous phase is adjusted to pH 4-5 with 1 M hydrochloric acid. It is then extracted three times with ethyl acetate, and the combined organic phases are dried over sodium sulfate. The residue obtained after filtration and concentration is purified by flash chromatography on silica gel (mobile phase: cyclohexane/ethyl acetate 4:1→2:1→1:1). 291 mg (0.49 mmol, 63% yield) of a colorless solid are obtained.

¹H-NMR (300 MHz, DMSO-$d_6$, δ/ppm): 2:1 E/Z mixture: 13.03-12.59 (2H, broad), 7.80 (2H, t), 7.71 (0.66H, d), 7.63 (0.33H, d), 7.42-6.72 (12H, m), 6.45 (0.33H, d), 6.36 (0.66H, d), 6.18-6.02 (1H, m), 5.67 (0.33H, t), 3.69 (3H, s), 2.99-2.42 (9H, m), 1.93-1.57 (2H, m).

MS (DCI): 593 (M+H⁺).

291 mg (0.49 mmol) of the E/Z-4-(4-{5-fluoro-2-[2-(4-methoxyphenyl)ethyl]phenyl}-2-{2-[4-(5-oxo-4,5-dihydro-[1,2,4]oxadiazol-3-yl)phenyl]ethyl}but-3-enyl)benzoic acid obtained in this way are fractionated further by preparative HPLC on a chiral phase. Respectively 53 mg and 64.5 mg of the two E isomers, each enantiopure, and 72.4 mg of the racemic Z isomer are obtained as colorless solids (see Examples 11-13).

Example 11

E-4-(4-{5-Fluoro-2-[2-(4-methoxyphenyl)ethyl]phenyl}-2-{2-[4-(5-oxo-4,5-dihydro-[1,2,4]oxadiazol-3-yl)phenyl]ethyl}but-3-enyl)benzoic acid (enantiomer 1)

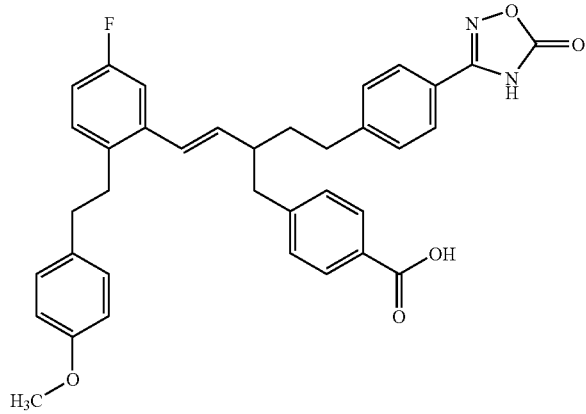

Enantiomer Separation Method:

Column: Daicel Chiralpak AD-H 250 mm×20 mm; eluent: isopropanol (with 1% water and 0.2% trifluoroacetic acid)/isohexane 30:70 (v/v); flow rate: 15 ml/min; UV detection: 220, nm; temperature: 24° C.

$R_t$ 14.87 min; purity 95%; >99% ee

Yield: 53 mg

¹H-NMR (300 MHz, DMSO-$d_6$, δ/ppm): 13.02-12.49 (2H, broad), 7.81 (2H, d), 7.70 (2H, d), 7.39 (2H, d), 7.30 (2H, d), 7.26-7.15 (1H, m), 7.14-7.06 (1H, m), 6.99-6.88 (3H, m), 6.79 (2H, d), 6.37 (1H, d), 6.15-6.00 (1H, m), 3.69 (3H, s), 2.99-2.39 (9H, m), 1.94-1.67 (2H, m).

MS (DCI): 593 (M+H⁺).

Example 12

E-4-(4-{5-Fluoro-2-[2-(4-methoxyphenyl)ethyl]phenyl}-2-{2-[4-(5-oxo-4,5-dihydro-[1,2,4]oxadiazol-3-yl)phenyl]ethyl}but-3-enyl)benzoic acid (enantiomer 2)

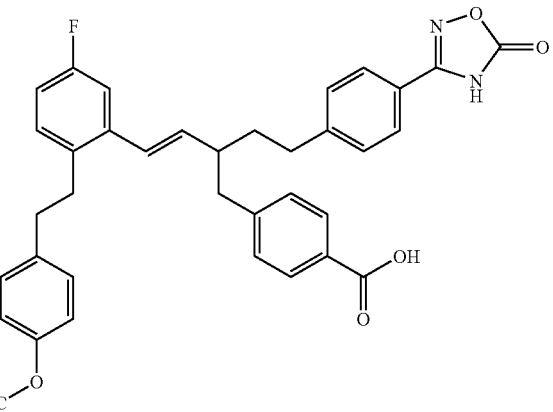

Enantiomer separation method: see Example 11.

$R_t$ 16.66 min; purity 92%; >94% ee

Yield: 64.5 mg

¹H-NMR (300 MHz, DMSO-$d_6$, δ/ppm): 13.02-12.49 (2H, broad), 7.81 (2H, d), 7.70 (2H, d), 7.39 (2H, d), 7.30 (2H, d), 7.26-7.15 (1H, m), 7.14-7.06 (1H, m), 6.99-6.88 (3H, m), 6.79 (2H, d), 6.37 (1H, d), 6.15-6.00 (1H, m), 3.69 (3H, s), 2.99-2.39 (9H, m), 1.94-1.67 (2H, m).

MS (DCI): 593 (M+H⁺).

Example 13 rac-Z-4-(4-{5-Fluoro-2-[2-(4-methoxyphenyl)ethyl]phenyl}-2-{2-[4-(5-oxo-4,5-dihydro-[1,2,4]oxadiazol-3-yl)phenyl]ethyl}but-3-enyl)benzoic acid

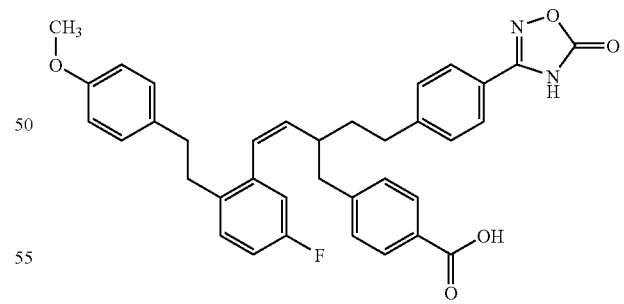

Isomer separation method: see Example 11.

$R_t$ 13.23 min; purity 97%

Yield: 72.4 mg

¹H-NMR (300 MHz, DMSO-$d_4$, δ/ppm): 13.05-12.61 (2H, broad), 7.79 (2H, d), 7.62 (2H, d), 7.24 (2H, d), 7.18 (2H, d), 7.14-7.06 (1H, m), 6.99 (2H, d), 6.98-6.88 (1H, m), 6.79 (2H, d), 6.46 (1H, d), 6.18-6.08 (1H, m), 5.68 (1H, t), 3.69 (3H, s), 2.95-2.80 (1H, m), 2.77-2.41 (8H, m), 1.83-1.54 (2H, m).

MS (DCI): 593 (M+H⁺).

The examples listed in the following table are obtained in an analogous manner:

| Example | Structure | Analytical data |
|---|---|---|
| 14 (starting from Ex. 28A and Ex. 16A) | 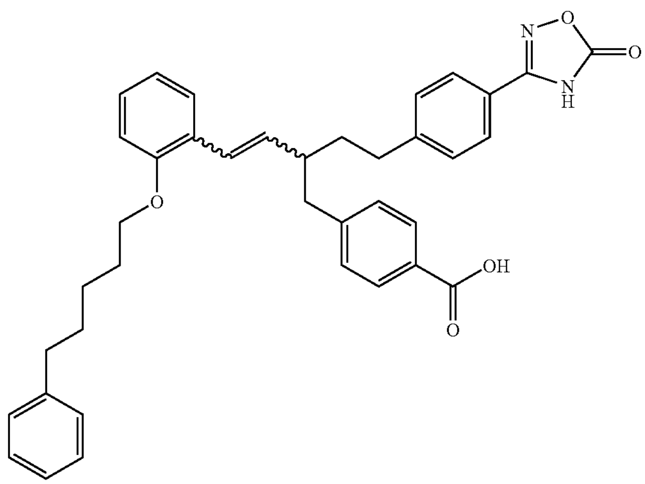 | LC-MS (method 2): R$_t$ 3.01 min; m/z 603 (M + H)$^+$. |
| 15 (E enantiomer 1, starting from Ex. 14 after separation) | 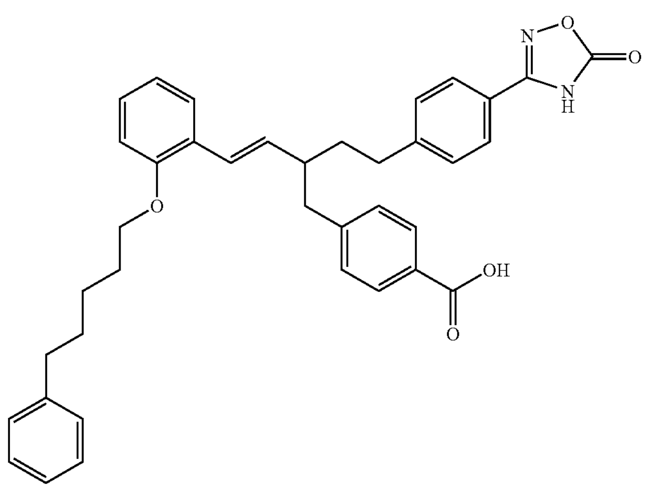 | $^1$H-NMR (300 MHz, DMSO-d$_6$, δ/ppm): 12.95-12.60 (2H, broad), 7.81 (2H, d), 7.70 (2H, d), 7.38 (3H, d), 7.32-7.18 (4H, m), 7.17-7.08 (4H, m), 6.97-6.82 (2H, m), 6.42 (1H, d), 6.16-6.01 (1H, m), 3.96-3.83 (2H, m), 2.94-2.40 (7H, m), 1.90-1.51 (6H, m), 1.48-1.29 (2H, m). LC-MS (method 2): R$_t$ 3.01 min; m/z 603 (M + H$^+$). chiral HPLC: R$_t$ 17.35 min; putiry 98%; >99.5% ee. |
| 16 (E enantiomer 2, starting from Ex. 14 after separation) | 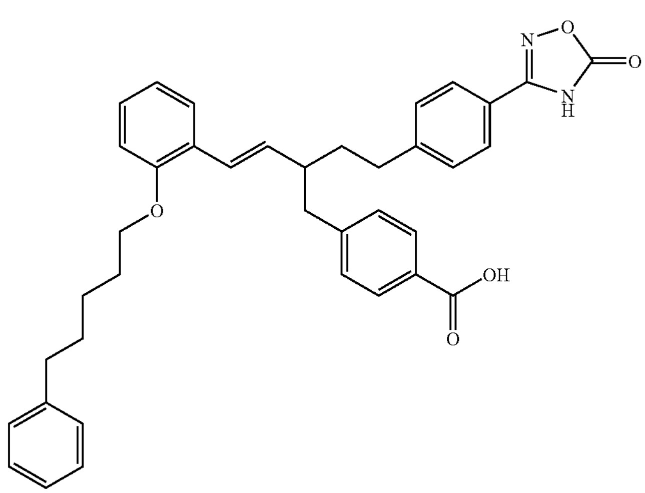 | $^1$H-NMR and LC-MS see Example 15; chiral HPLC: R$_t$ 12.12 min; purity 94%; >99.5% ee. |

-continued

| Example | Structure | Analytical data |
|---|---|---|
| 17 (starting from Ex. 25A and Ex. 16A) | 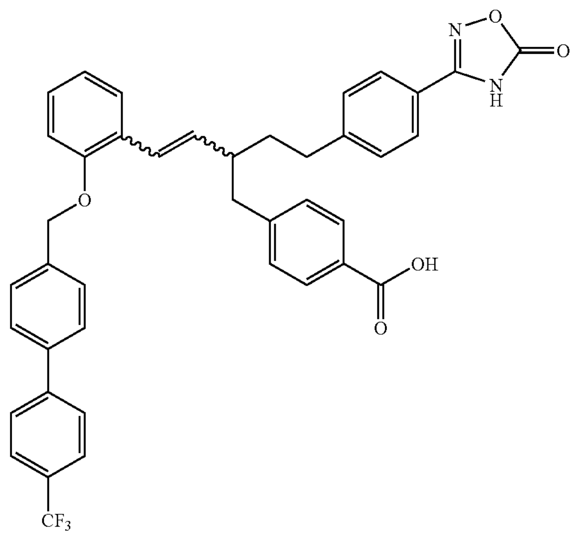 | LC-MS (method 1): R$_t$ 3.24 min; m/z 691 (M + H$^+$). |
| 18 (E enantiomer 1, starting from Ex. 17 after separation) | 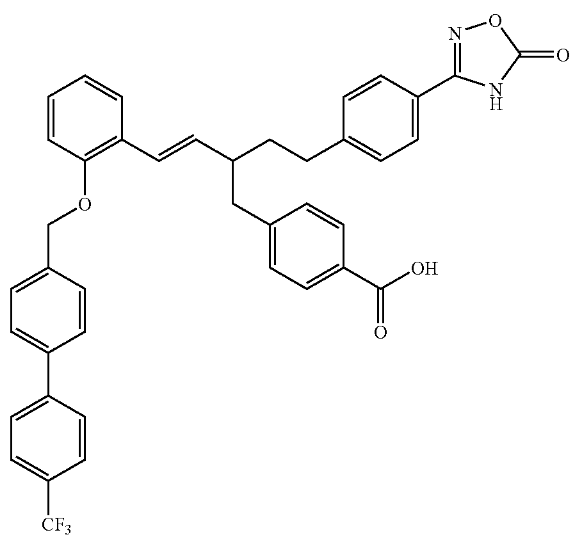 | $^1$H-NMR (400 MHz, DMSO-d$_6$, δ/ppm): 12.92-12.68 (2H, broad), 7.90-7.77 (6H, m), 7.70 (2H, d), 7.68 (2H, d), 7.50 (2H, d), 7.43 (1H, d), 7.35 (2H, d), 7.28 (2H, d), 7.19 (1H, t), 7.06 (1H, d), 6.92 (1H, t), 6.51 (1H, d), 6.12 (1H, dd), 5.16 (2H, s), 2.94-2.82 (1H, m), 2.79-2.69 (2H, m), 2.68-2.57 (1H, m), 2.56-2.44 (1H, m), 1.89-1.76 (1H, m), 1.75-1.61 (1H, m), LC-MS (method 1): R$_t$ 3.24 min; m/z 691 (M + H$^+$). chiral HPLC: R$_t$ 9.79 min; purity >99.5%; >99.5% ee. |
| 19 (E enantiomer 2, starting from Ex. 17 after separation) | 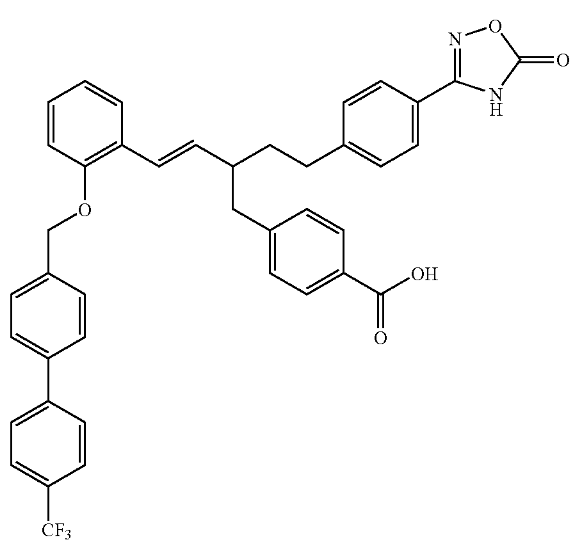 | $^1$H-NMR and LC-MS see Example 18; chiral HPLC: R$_t$ 7.46 min; purity 98.5%; >99.5% ee. |

-continued

| Example | Structure | Analytical data |
|---|---|---|
| 20 (rac-Z, starting from Ex. 17 after separation) | 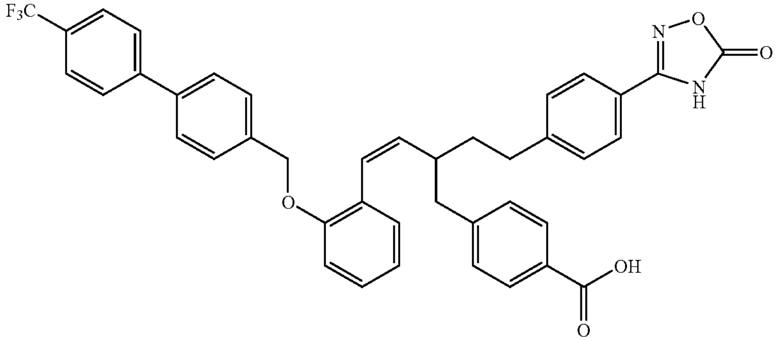 | LC-MS (method 1): $R_t$ 3.24 min; m/z 691 (M + H$^+$). |
| 21 (starting from Ex. 50A and Ex. 16A) | 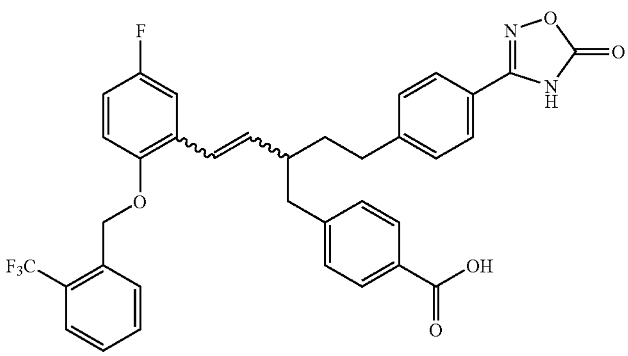 | $^1$H-NMR (400 MHz, DMSO-d$_6$, δ/ppm): 12.87-12.76 (2H, m), 7.79-7.75 (3H, m), 7.70-7.52 (5H, m), 7.32-7.16 (5H, m), 7.04-6.93 (2H, m), 6.46-6.39 (1H, m), 6.23-6.14 (1H, m), 5.61-5.55 (0.5H, m), 5.17-5.07 (2H, m), 2.89-2.81 (1H, m), 2.73-2.53 (3H, m), 2.52-2.40 (1H, m), 1.83-1.52 (2H, m). LC-MS (method 4): $R_t$ 3.01 min; m/z 633 (M + H$^+$). |
| 22 (E enantiomer 1, starting from Ex. 21 after separation) | 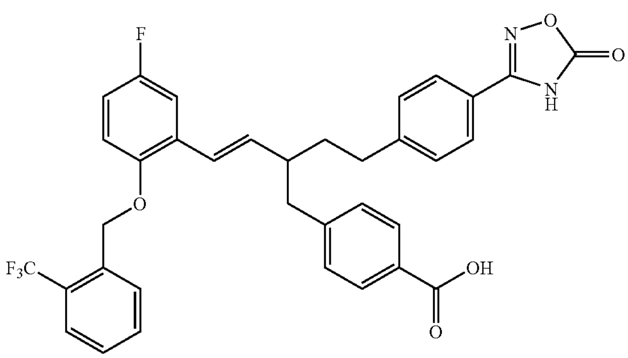 | LC-MS (method 4): $R_t$ 3.01 min; m/z 633 (M + H$^+$). |
| 23 (E enantiomer 2, starting from Ex. 21 after separation) | 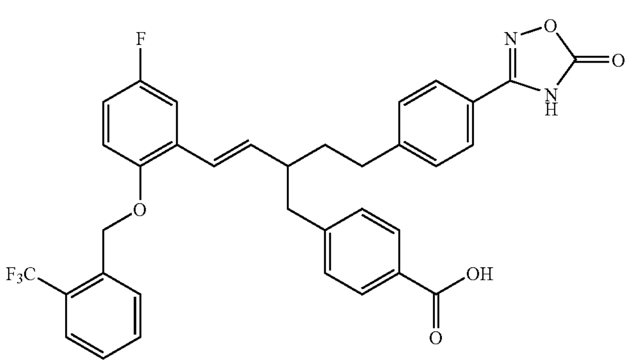 | LC-MS (method 2): $R_t$ 2.82 min; m/z 633 (M + H$^+$). |

| Example | Structure | Analytical data |
|---|---|---|
| 24 (Z enantiomer 1, starting from Ex. 21 after separation) | 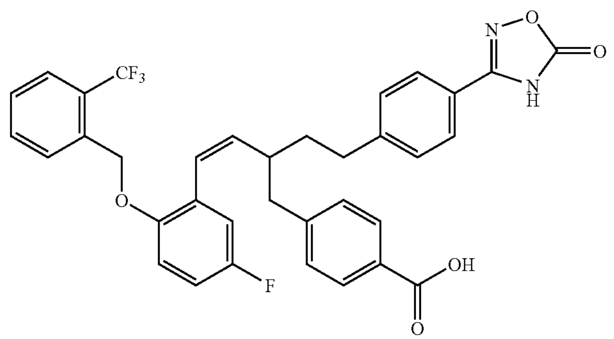 | $^1$H-NMR (400 MHz, CDCl$_3$, δ/ppm): 10.91-10.88 (1H, broad), 7.88-7.86 (2H, m), 7.69-7.67 (2H, m), 7.55-7.51 (1H, m), 7.45-7.39 (3H, m), 7.07-7.05 (2H, m), 6.94-6.87 (3H, m), 6.83-6.79 (1H, m), 6.63-6.60 (2H, m), 5.66-5.61 (1H, m), 5.24-5.16 (2H, m), 2.78-2.62 (4H, m), 2.41-2.33 (1H, m), 1.91-1.47 (2H, m). |
| 25 (Z enantiomer 2, starting from Ex. 21 after separation) | 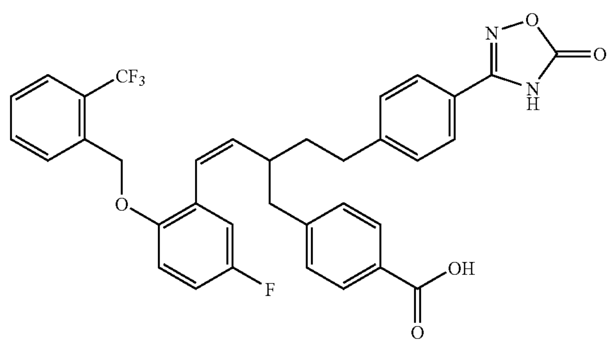 | LC-MS (method 2): R$_t$ 2.81 min; m/z 633 (M + H$^+$). |
| 26 (starting from Ex. 53A and Ex. 16A) | 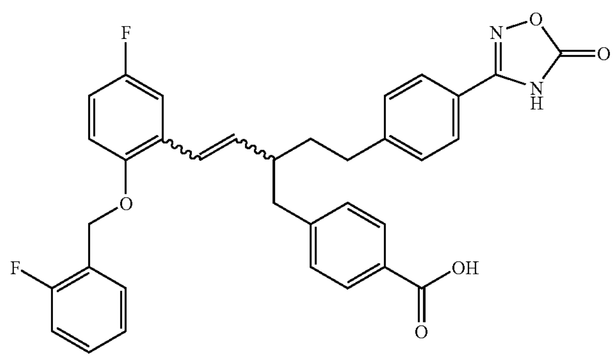 | $^1$H-NMR (400 MHz, DMSO-d$_6$, δ/ppm): 12.86-12.76 (2H, broad), 7.80-7.77 (2H, m), 7.69-7.66 (1H, m), 7.61-7.59 (1H, m), 7.48-7.14 (9H, m), 7.11-6.96 (2H, m), 6.44-6.38 (1H, m), 6.23-6.10 (1H, m), 5.60-5.54 (0.5H, m), 5.09-5.0 (2H, m), 2.86-2.80 (1H, m), 2.73-2.56 (3H, m), 2.52-2.38 (1H, m), 1.82-1.54 (2H, m). LC-MS (method 1): R$_t$ 2.91 min; m/z 583 (M + H$^+$). |
| 27 (E enantiomer 11, starting from Ex. 26 after separation) | 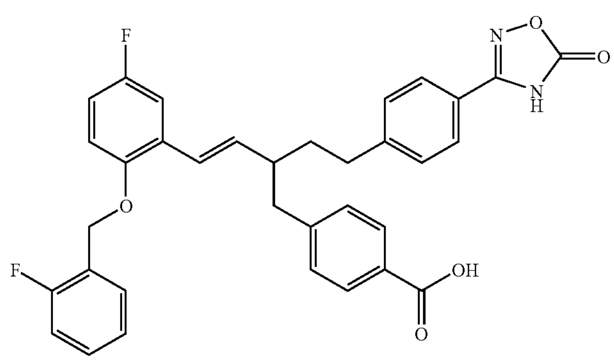 | LC-MS (method 1): R$_t$ 2.91 min; m/z 583 (M + H$^+$). |

-continued

| Example | Structure | Analytical data |
|---|---|---|
| 28 (E enantiomer 2, starting from Ex. 26 after separation) | 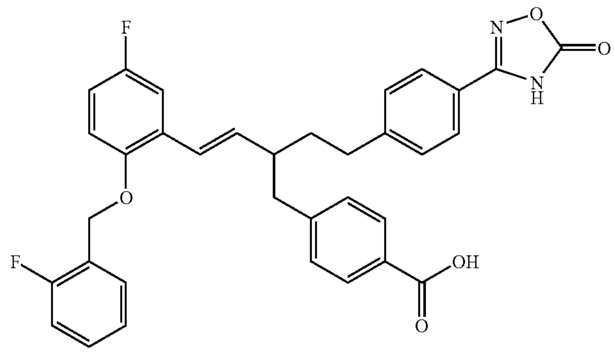 | $^1$H-NMR (400 MHz, DMSO-d$_6$, δ/ppm): 12.92-12.72 (2H, m), 7.81-7.77 (2H, m), 7.70-7.64 (2H, m), 7.47-7.35 (2H, m), 7.33-7.16 (7H, m), 7.12-6.98 (2H, m), 6.43-6.35 (1H, m), 6.24-6.15 (1H, m), 5.10-5.07 (2H, m), 2.88-2.80 (1H, m), 2.75-2.58 (3H, m), 2.54-2.42 (1H, m), 1.82-1.57 (2H, m). LC-MS (method 1): R$_t$ 2.91 min; m/z 583 (M + H$^+$). |
| 29 (Z enantiomer 1, starting from Ex. 26 after separation) | 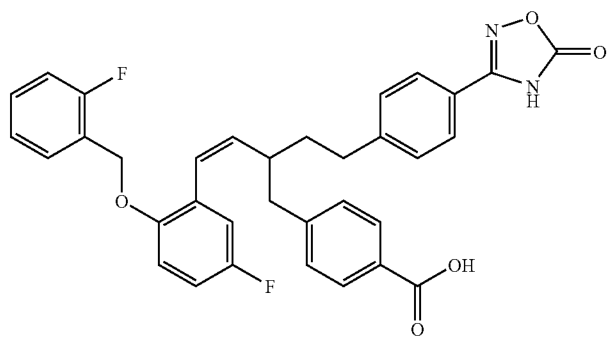 | $^1$H-NMR (400 MHz, DMSO-d$_6$, δ/ppm): 12.93-12.75 (2H, broad), 7.82-7.77 (2H, m), 7.62-7.56 (2H, m), 7.48-7.43 (1H, m), 7.41-7.34 (1H, m), 7.24-7.12 (6H, m), 7.07-6.96 (2H, m), 6.44-6.40 (1H, m), 6.11-6.06 (1H, m), 5.60-5.53 (1H, m), 5.11-4.98 (2H, m), 2.85-2.60 (4H, m), 2.46-2.41 (1H, m), 1.76-1.52 (2H, m). LC-MS (method 1): R$_t$ 2.89 min; m/z 583 (M + H$^+$). |
| 30 (Z enantiomer 2, starting from Ex. 26 after separation) | 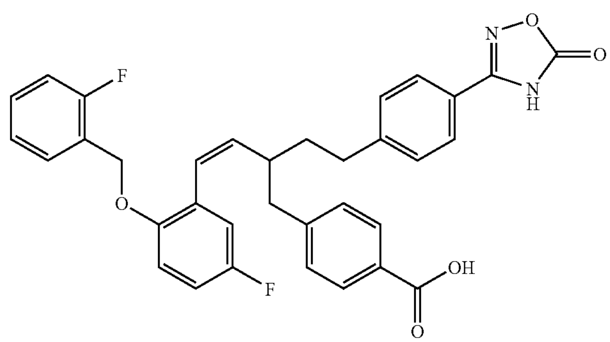 | LC-MS (method 1): R$_t$ 2.89 min; m/z 583 (M + H$^+$). |
| 31 (starting from Ex. 42A and Ex.16A) | 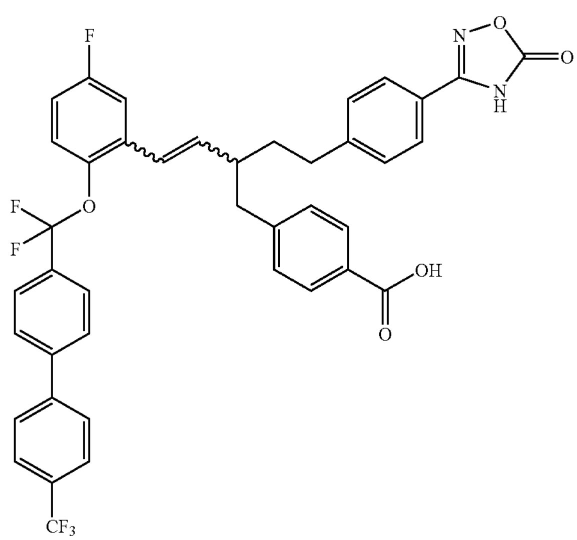 | LC-MS (method 4): R$_t$ 3.27 min; m/z 745 (M + H$^+$). |

-continued

| Example | Structure | Analytical data |
|---|---|---|
| 32 (E enantiomer 1, starting from Ex. 31 after separation) | 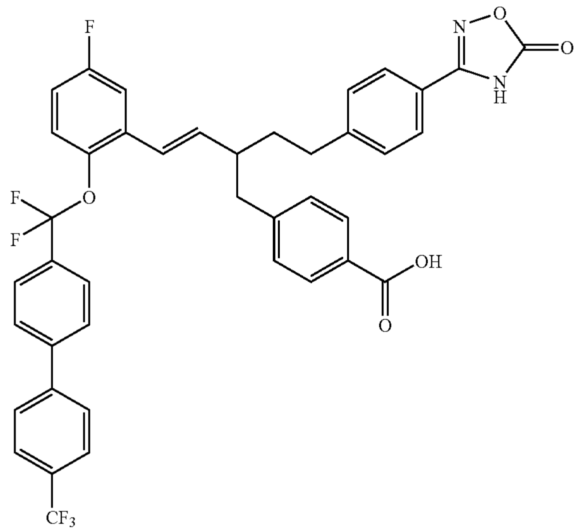 | ¹H-NMR (400 MHz, CDCl₃, δ/ppm): 11.23 (1H, broad), 8.00-7.88 (2H, m), 7.82-7.75 (2H, m), 7.74-7.64 (6H, m), 7.56-7.43 (3H, m), 7.34-7.27 (1H, m), 7.25-7.21 (1H, m), 7.20-7.06 (3H, m), 7.00-6.94 (1H, m), 6.63-6.55 (1H, m), 6.13-6.04 (1H, m), 2.87-2.64 (3H, m), 2.58-2.36 (2H, m), 1.84-1.44 (2H, m). LC-MS (method 4): R$_t$ 3.27 min; m/z 745 (M + H⁺). |
| 33 (E enantiomer 2, starting from Ex. 31 after separation) | 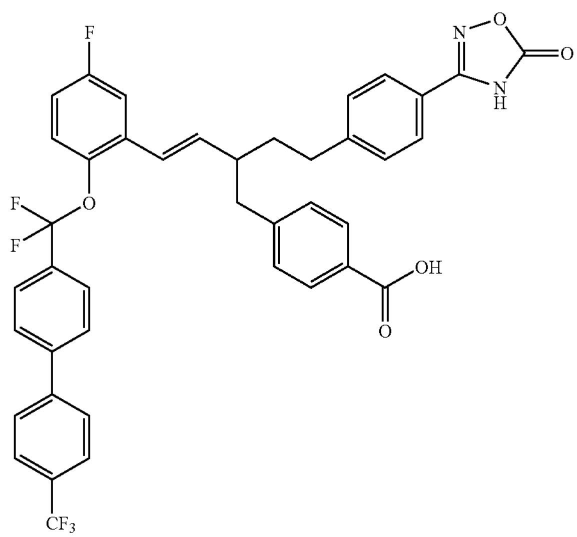 | LC-MS (method 4): R$_t$ 3.27 min; m/z 745 (M + H⁺). |
| 34 (rac-Z, starting from Ex. 31 after separation) | 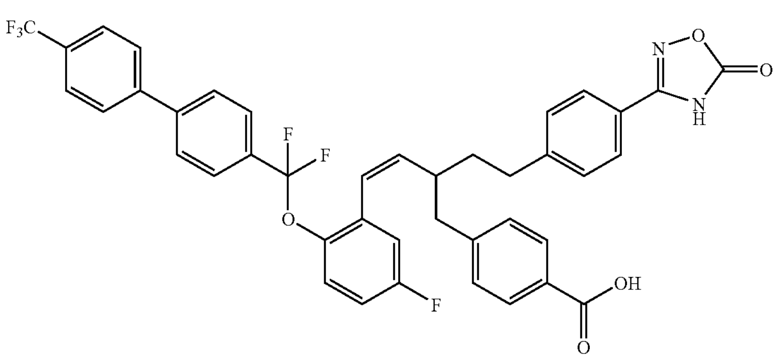 | ¹H-NMR (400 MHz, CDCl₃), δ/ppm): 11.44 (1H, broad), 8.01-7.89 (2H, m), 7.80-7.63 (8H, m), 7.57-7.46 (2H, m), 7.34-7.27 (1H, m), 7.24-7.09 (5H, m), 7.00-6.92 (1H, m), 6.60-6.52 (1H, m), 6.11-6.01 (1H, m), 2.87-2.64 (3H, m), 2.62-2.37 (2H, m), 11.90-1.63 (2H, m). LC-MS (method 4): R$_t$ 3.26 min; m/z 745 (M + H⁺). |

| Example | Structure | Analytical data |
| --- | --- | --- |
| 35 (starting from Ex. 54A and Ex. 16A) | 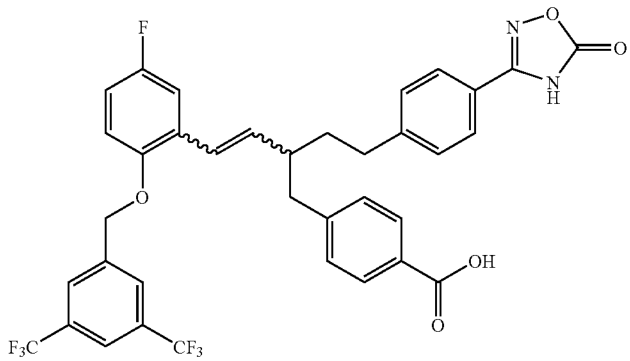 | ¹H-NMR (400 MHz, DMSO-d₆, δ/ppm): 12.91-12.68 (2H, broad), 8.10-8.04 (3H, m), 7.79-7.56 (4H, m), 7.36-6.97 (6H, m), 6.52-6.43 (1H, m), 6.33-6.14 (1H, m), 5.66-5.57 (0.5H, m), 5.29-5.09 (2H, m), 2.91-2.81 (1H, m), 2.78-2.57 (3H, m), 2.54-2.43 (1H, m), 1.84-1.56 (2H, m). LC-MS (method 2): R$_t$ 2.92 and 2.96 min; m/z 701 (M + H⁺). |
| 36 (E enantiomer 1, starting from Ex. 35 after separation) | 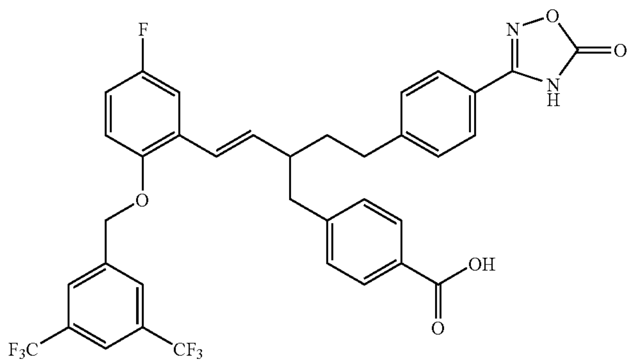 | LC-MS (method 1): R$_t$ 3.09 min; m/z 701 (M + H⁺). |
| 37 (E enantiomer 2, starting from Ex. 35 after separation) | 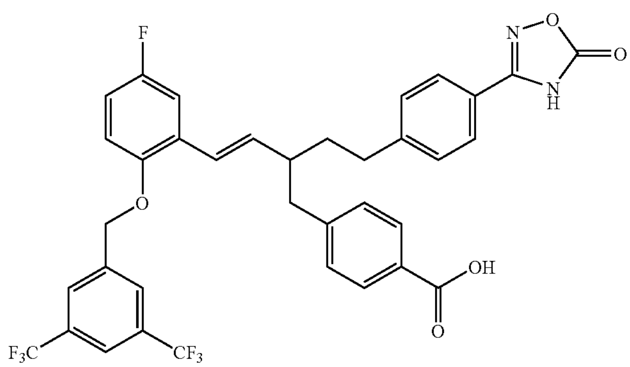 | ¹H-NMR (400 MHz, DMSO-d₆, δ/ppm): 12.76 (2H, broad), 8.12-8.05 (4H, m), 7.87-7.67 (3H, m), 7.36-7.19 (5H, m), 7.09-7.00 (2H, m), 6.53-6.42 (1H, m), 6.32-6.20 (1H, m), 5.32-5.22 (2H, m), 2.91-2.33 (5H, m), 1.97-1.57 (2H, m). LC-MS (method 1): R$_t$ 3.10 min; m/z 701 (M + H⁺). |
| 38 (Z enantiomer 1, starting from Ex. 35 after separation) | 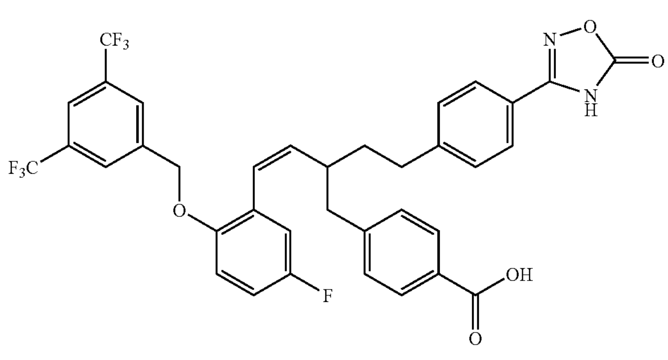 | ¹H-NMR (400 MHz, DMSO-d₆, δ/ppm): 12.72 (2H, broad), 8.11-8.00 (3H, m), 7.87-7.62 (3H, m), 7.26-6.95 (7H, m), 6.51-6.40 (1H, m), 6.25-6.07 (1H, m), 5.67-5.51 (1H, m), 5.30-5.06 (2H, m), 2.89-2.48 (4H, m), 2.46-2.34 (1H, m), 1.81-1.47 (2H, m). LC-MS (method 1): R$_t$ 3.13 min; m/z 701 (M + H⁺). |

| Example | Structure | Analytical data |
|---|---|---|
| 39 (Z enantiomer 2, starting from Ex. 35 after separation) | 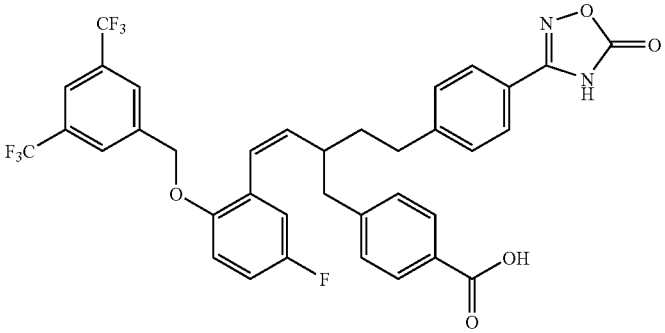 | LC-MS (method 1): $R_t$ 3.13 min; m/z 701 (M + H$^+$). |
| 40 (starting from Ex. 46A and Ex. 16A) | 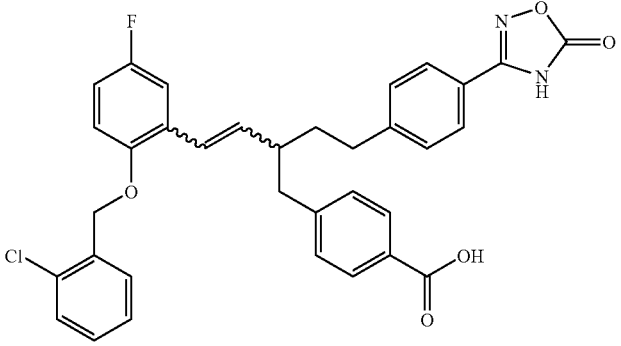 | $^1$H-NMR (300 MHz, CDCl$_3$, δ/ppm): 11.21 (1H, br. s), 11.16 (1H, br. s), 7.93 (4H, dd), 7.56 (2H, d), 7.47 (2H, d), 7.41-7.36 (2H, m), 7.18 (2H, d), 7.09 (2H, d), 6.95-6.19 (4H, m), 6.71 (1H, d), 6.62 (1H, d), 6.57-6.53 (2H, m), 6.06 (1H, dd), 5.60 (2H, m$_c$), 5.14 (2H, s), 5.07 (2H, d), 2.77-2.59 (6H, m). HPLC (method 2): $R_t$ 5.3 min. |
| 41 (E enantiomer 1, starting from Ex. 40 after separation) | 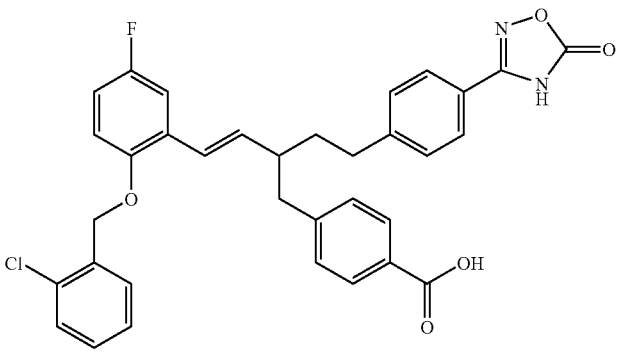 | $^1$H-NMR (300 MHz, DMSO-d$_6$, δ/ppm): 12.88 (1H, br. s), 12.68 (1H, br. s), 7.79 (2H, d), 7.67 (2H, d), 7.51-7.47 (2H, m), 7.38-7.24 (7H, m), 7.10-6.97 (2H, m), 6.43 (1H, d), 6.21 (1H, dd), 5.10 (2H, s), 2.84 (1H, dd), 2.75-2.57 (6H, m), 1.79-1.75 (1H, m), 1.70-1.62 (1H, m). LC-MS (method 2): $R_t$ 2.8 min; m/z 599 (M + H$^+$). spec. rotation: $α_D^{20}$ (acetone): −14.8° |
| 42 (E enantiomer 2, starting from Ex. 40 after separation) | 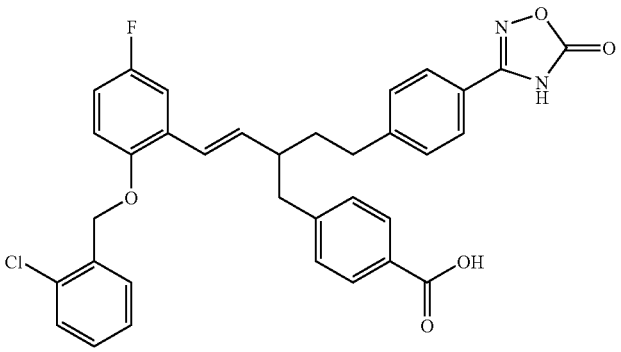 | $^1$H-NMR (300 MHz, DMSO-d$_6$, δ/ppm): 12.88 (1H, br. s), 12.74 (1H, br. s), 7.78 (2H, d), 7.67 (2H, d), 7.51-7.47 (2H, m), 7.38-7.24 (7H, m), 7.10-6.98 (2H, m), 6.43 (1H, d), 6.20 (1H, dd), 5.10 (2H, s), 2.84 (1H, dd), 2.74-2.58 (6H, m), 1.79-1.75 (1H, m), 1.70-1.62 (1H, m). LC-MS (method 2): $R_t$ 2.8 min; m/z 599 (M + H)$^+$. |

-continued

| Example | Structure | Analytical data |
|---|---|---|
| 43 (Z enantiomer 1, starting from Ex. 40 after separation) | 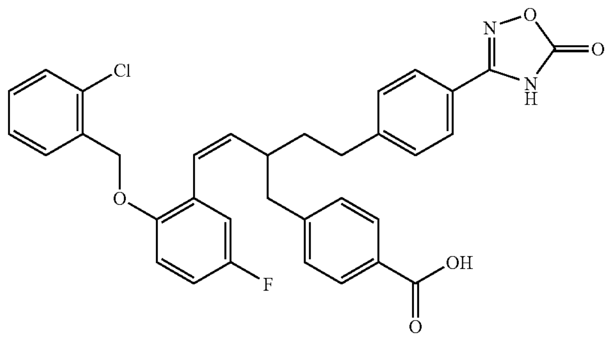 | ¹H-NMR (300 MHz, DMSO-d₆, δ/ppm): 12.86 (1H, br. s), 12.77 (1H, br. s), 7.78 (2H, d), 7.59 (2H, d), 7.52-7.46 (2H, m), 7.38-7.29 (2H, m), 7.20-7.16 (4H, m), 7.01-6.99 (2H, m), 6.46 (1H, d), 6.13 (1H, d), 5.59 (1H, t), 5.04 (2H, d$_{AB}$), 2.84 (1H, d), 2.73-2.60 (3H, m), 1.76-1.71 (1H, m), 1.63-1.55 (1H, m), 1.23 (1H, br. s). LC-MS (method 1): R$_t$ 2.8 min; m/z 599 (M + H)⁺. spec. rotation: α$_D^{20}$ (acetone): +89.0° |
| 44 (Z enantiomer 2, starting from Ex. 40 after separation) | 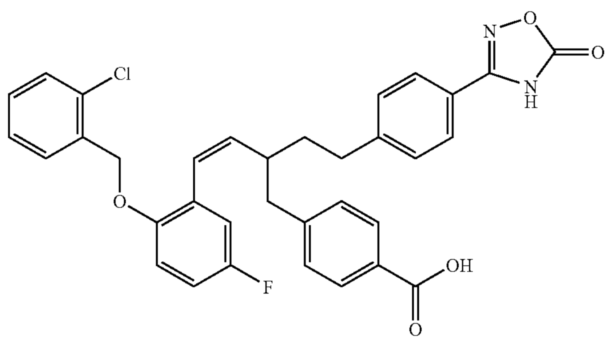 | ¹H-NMR (300 MHz, DMSO-d₆, δ/ppm): 12.86 (2H, br. s), 7.78 (2H, d), 7.59 (2H, d), 7.52-7.46 (2H, m), 7.38-7.29 (2H, m), 7.21-7.15 (4H, m), 7.01-6.99 (2H, m), 6.46 (1H, d), 6.13 (1H, d), 5.58 (1H, t), 5.04 (2H, d$_{AB}$), 2.84 (1H, d), 2.76-2.58 (3H, m), 1.78-1.67 (1H, m), 1.63-1.52 (1H, m), 1.23 (1H, br. s). LC-MS (method 2): R$_t$ 2.8 min; m/z 599 (M + H)⁺. |
| 45 (starting from Ex. 63A and Ex. 16A) | 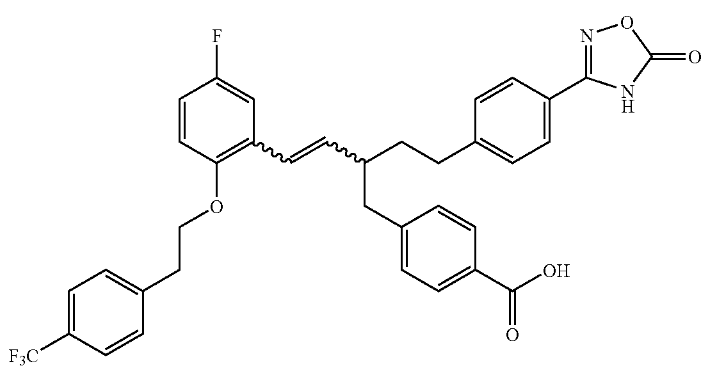 | ¹H-NMR (400 MHz, DMSO-d₆, δ/ppm): (E/Z = 3:1) 12.97-12.67 (2H, broad), 7.90-6.84 (16H, m), 6.32 (0.33H, d), 6.27 (1H, d), 6.19-6.05 (1.33H, m), 5.52 (0.33H, t), 4.22-4.11 (2H, m), 3.16-3.00 (3H, m), 2.90-2.31 (4H, m), 1.84-1.48 (4H, m). LC-MS (method 2): R$_t$ 2.82 and 2.87 min; m/z 647 (M + H⁺). |
| 46 (starting from Ex. 67A and Ex. 16A) | 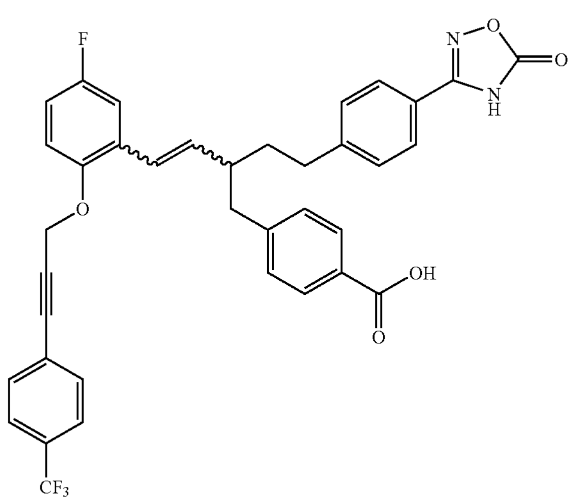 | LC-MS (method 4): R$_t$ 3.09 min; m/z 657 (M + H⁺). |

-continued
| Example | Structure | Analytical data |
|---|---|---|
| 47 (starting from Ex. 51A and Ex. 16A) | 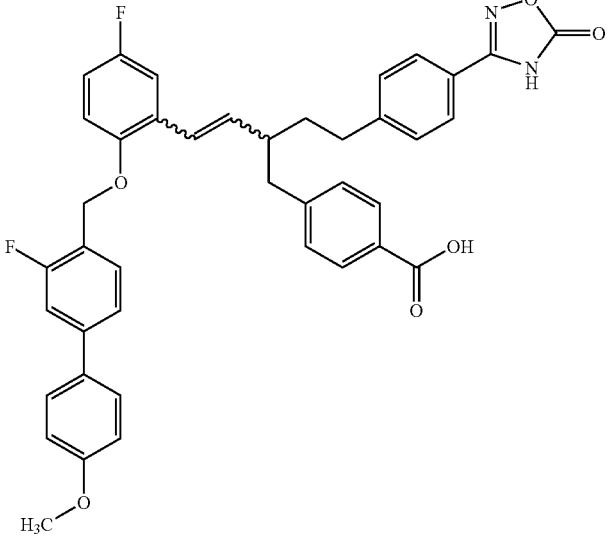 | LC-MS (method 4): $R_t$ 3.13 min; m/z 689 (M + H$^+$). |
| 48 (starting from Ex. 55A and Ex. 16A) | 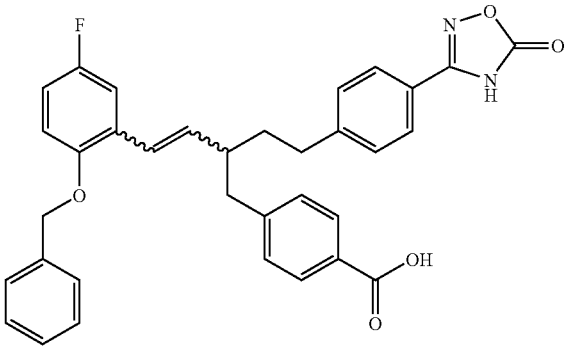 | $^1$H-NMR (300 MHz, DMSO-d$_6$, δ/ppm): 12.82 (2H, broad), 7.83-7.78 (2H, m), 7.70-7.60 (2H, m), 7.35-7.26 (8H, m), 7.21-7.18 (2H, m), 7.06-6.96 (2H, m), 6.49-6.41 (1H, m), 6.26-6.11 (1H, m), 5.05-4.98 (2H, m), 2.92-2.80 (1H, m), 2.76-2.63 (3H, m), 2.56-2.39 (1H, m), 1.86-1.54 (2H, m). LC-MS (method 4): $R_t$ 2.87 min; m/z 565 (M + H$^+$). |
| 49 (starting from Ex. 59A and Ex. 16A) | 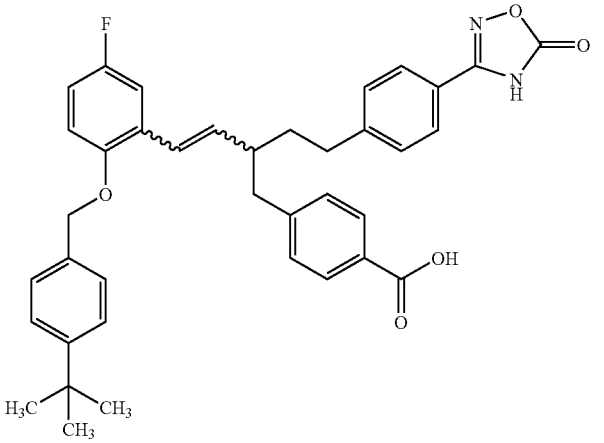 | LC-MS (method 4): $R_t$ 3.17 min; m/z 621 (M + H$^+$). |

| Example | Structure | Analytical data |
|---|---|---|
| 50 (E enantiomer 1, starting from Ex. 49 after separation) | 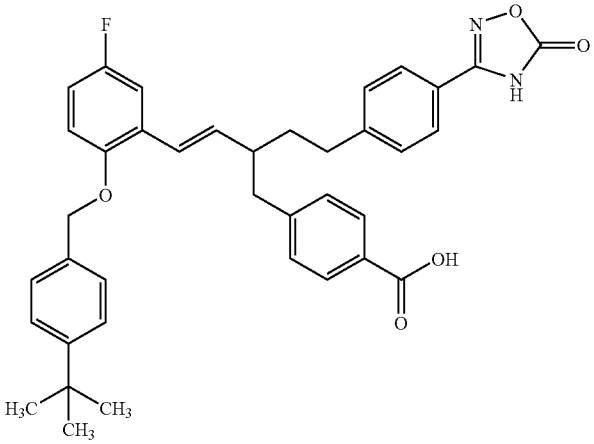 | $^1$H-NMR (300 MHz, DMSO-$d_6$, δ/ppm): 12.99-12.64 (2H, broad), 7.81 (2H, d), 7.69 (2H, d), 7.37 (4H, d), 7.31-7.21 (5H, m), 7.09-6.94 (2H, m), 6.44 (1H, d), 6.28 (1H, m), 5.0 (2H, s), 2.92-2.45 (5H, m), 1.89-1.60 (2H, m), 1.26 (9H, s). LC-MS (method 4): R$_t$ 2.80 min; m/z 621 (M + H$^+$). chiral HPLC: R$_t$ 8.24 min; purity >96.5%; >99.5% ee. |
| 51 (E enantiomer 2, starting from Ex. 49 after separation) | 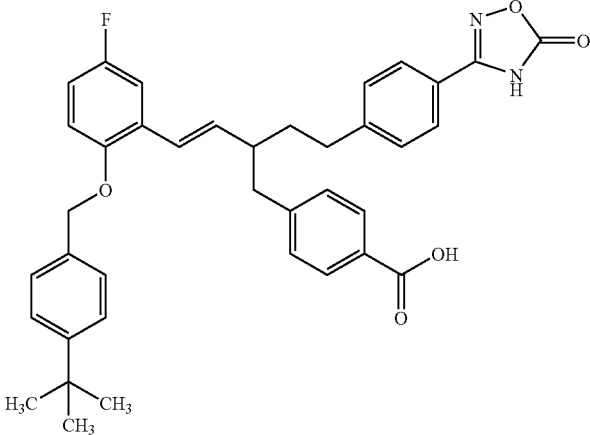 | $^1$H-NMR and LC-MS see Example 50; chiral HPLC: R$_t$ 13.84 min; purity >99.5%; >99.5% ee. |
| 52 (Z enantiomer 1, starting from Ex. 49 after separation) | 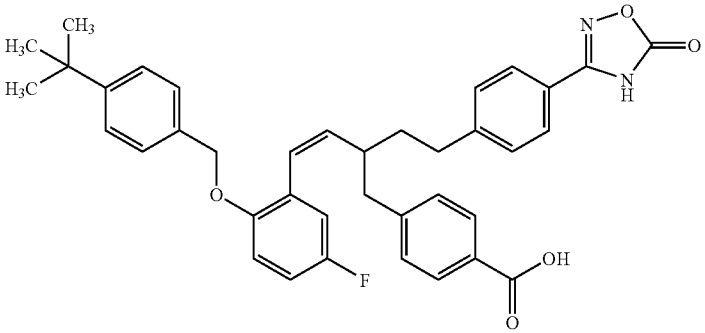 | $^1$H-NMR (300 MHz, DMSO-$d_6$, δ/ppm): 12.96-12.79 (2H, broad), 7.80 (2H, d), 7.61 (2H, d), 7.35-7.25 (5H, m), 7.24-7.14 (4H, m), 6.98 (2H, d), 6.47 (1H, d), 6.10 (1H, d), 5.59 (1H, t), 4.98 (2H, d), 2.91-2.79 (1H, m), 2.77-2.56 (4H, m), 1.82-1.68 (1H, m), 1.67-1.51 (1H, m), 1.23 (9H, s). LC-MS (method 4): R$_t$ 2.85 min; m/z 621 (M + H$^+$). chiral HPLC: R$_t$ 5.13 min; purity >92%; >99.5% ee. |

| Example | Structure | Analytical data |
|---|---|---|
| 53 (Z enantiomer 2, starting from Ex. 49 after separation) | 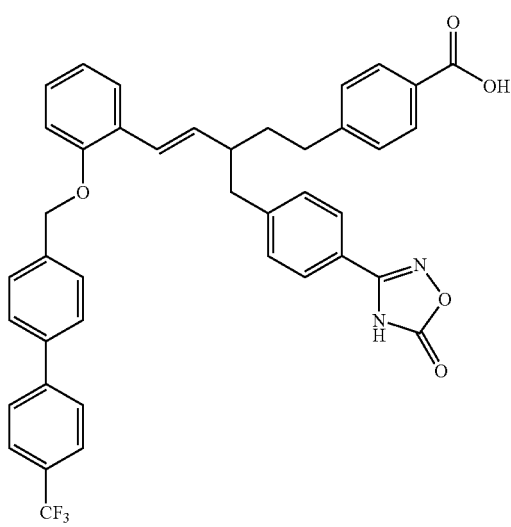 | ¹H-NMR and LC-MS see Example 52; chiral HPLC: $R_t$ 6.52 min; purity >95%; >99.5% ee. |

[E/Z isomer and enantiomer separation method (chiral HPLC): column: Daicel Chiralpak AD-H 250 mm × 20 mm; eluent: isopropanol (with 1% water and 0.2% trifluoroacetic acid)/isohexane 30:70 (v/v); flow rate: 15 ml/min; UV detection: 220 nm; temperature: 24° C.].

Example 54

E-4-{3-[4-(5-Oxo-4,5-dihydro[1,2,4]oxadiazol-3-yl)benzyl]-5-[2-(4'-trifluoromethylbiphenyl-4-yl-methoxy)phenyl]pent-4-enyl}benzoic acid (racemate)

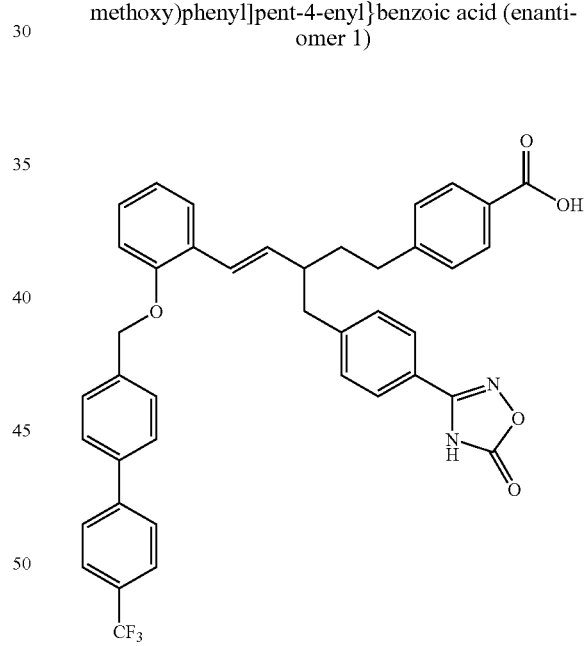

A solution of 1000 mg (1.42 mmol) of methyl E-4-{3-[4-(5-oxo-4,5-dihydro-[1,2,4]oxadiazol-3-yl)benzyl]-5-[2-(4'-trifluoromethylbiphenyl-4-ylmethoxy)phenyl]pent-4-enyl}benzoate from Example 77A in 20 ml of THF and 20 ml of water is mixed with 68 mg (2.84 mmol) of lithium hydroxide and stirred at 50° C. for 12 h. After cooling, the THF is stripped off and the aqueous phase is adjusted to pH 4-5 with 1 M hydrochloric acid. It is then extracted three times with ethyl acetate, and the combined organic phases are dried over sodium sulfate. The residue obtained after filtration and concentration is purified by preparative HPLC. 870 mg (1.26 mmol, 89% yield) of a colorless solid are obtained.

LC-MS (method 1): $R_t$ 3.32 min; m/z 691 (M+H⁺).

500 mg (0.72 mmol) of the racemic E-4-{3-[4-(5-oxo-4,5-dihydro-[1,2,4]oxadiazol-3-yl)benzyl]-5-[2-(4'-trifluoromethylbiphenyl-4-ylmethoxy)phenyl]pent-4-enyl}benzoic acid obtained in this way are further fractionated by preparative HPLC on a chiral phase. Respectively 288 mg and 160 mg of the two E isomers, each enantiopure, are obtained (see Examples 55 and 56).

Example 55

E-4-{3-[4-(5-Oxo-4,5-dihydro-[1,2,4]oxadiazol-3-yl)benzyl]-5-[2-(4'-trifluoromethylbiphenyl-4-yl-methoxy)phenyl]pent-4-enyl}benzoic acid (enantiomer 1)

Enantiomer Separation Method:
Column: Daicel Chiralpak AD-H 250 mm×20 mm; eluent: isopropanol (with 1% water and 0.2% trifluoroacetic acid)/isohexane 30:70 (v/v); flow rate: 15 ml/min; UV detection: 220 mm; temperature: 24° C.

$R_t$ 7.33 min; purity>98%; >99.5% ee
Yield: 160 mg

¹H-NMR (400 MHz, DMSO-d₆, δ/ppm): 12.92-12.62 (2H, broad), 7.91-7.77 (6H, m), 7.68 (4H, t), 7.50 (2H, d), 7.44 (1H, d), 7.34 (2H, d), 7.27 (2H, d), 7.19 (1H, t), 7.06 (1H, d), 6.91 (1H, t), 6.53 (1H, d), 6.19-6.09 (1H, m), 5.18 (2H, s)2.97-2.81 (1H, m), 2.80-2.70 (2H, m), 2.6.9-2.57 (2H, m), 1.88-1.76 (1H, m), 1.75-1.61 (1H, m).

LC-MS (method 1): $R_t$ 3.24 min; m/z 691 (M+H⁺). ,

Example 56

E-4-{3-[4-(5-Oxo-4,5-dihydro-[1,2,4]oxadiazol-3-yl)benzyl]-5-[2-(4'-trifluoromethylbiphenyl-4-yl-methoxy)phenyl]pent-4-enyl}benzoic acid (enantiomer 2)

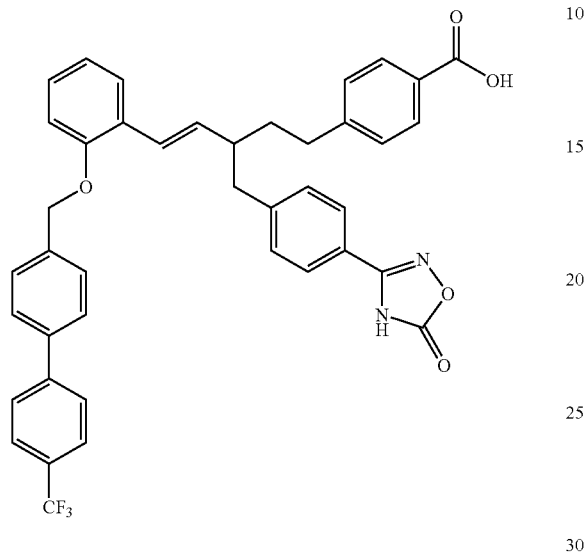

Enantiomer separation method: see Example 55.
$R_t$ 6.13 min; purity 90%; >99.5% ee
Yield: 288 mg
$^1$H-NMR (400 MHz, DMSO-4, δ/ppm): 12.92-12.62 (2H, broad), 7.91-7.77 (6H, m), 7.68 (4H, t), 7.50 (2H, d), 7.44 (1H, d), 7.34 (2H, d), 7.27 (2H, d), 7.19 (1H, t), 7.06 (1H, d), 6.91 (1H, t), 6.53 (1H, d), 6.19-6.09 (1H, m), 5.18 (2H, s), 2.97-2.81 (1H, m), 2.80-2.70 (2H, m), 2.69-2.57 (2H, m), 1.88-1.76 (1H, m), 1.75-1.61 (1H, m).
LC-MS (method 1): $R_t$ 3.24 min; m/z 691 (M+H$^+$).

The examples listed in the following table are obtained in an analogous manner:

| Example | Structure | Analytical data |
|---|---|---|
| 57 (Z enantiomer 1, starting from Ex. 74A and Ex. 25A) | 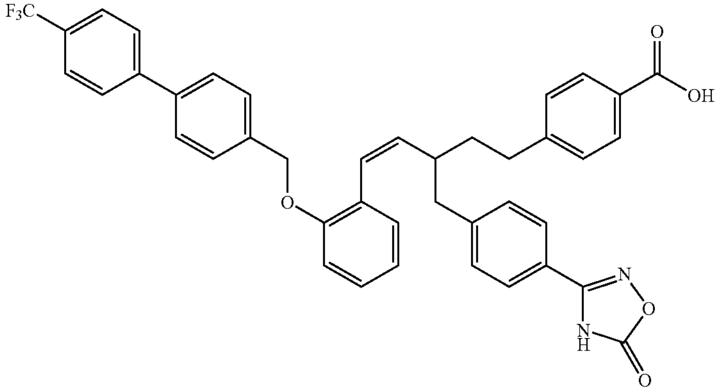 | $^1$H-NMR (300 MHz, DMSO-d$_6$, δ/ppm): 12.93-12.67 (2H, broad), 7.91-7.70 (6H, m), 7.69-7.59 (4H, m), 7.48 (2H, d), 7.26 (2H, d). 7.18 (1H, d), 7.11 (2H, d), 7.01 (1H,d), 6.76 (1H, t), 6.68 (1H, d), 6.53 (1H, d), 5.56 (1H, t), 5.10 (2H, q), 2.95-2.38 (5H, m), 1.81-1.51 (2H,m). MS (EI): 689 (M − H$^-$), 691 (M + H$^+$). chiral HPLC: $R_t$ 5.36 min; >99% ee. |

-continued

| Example | Structure | Analytical data |
|---|---|---|
| 58 (Z enantiomer 2, starting from Ex. 74A and Ex. 25A) | 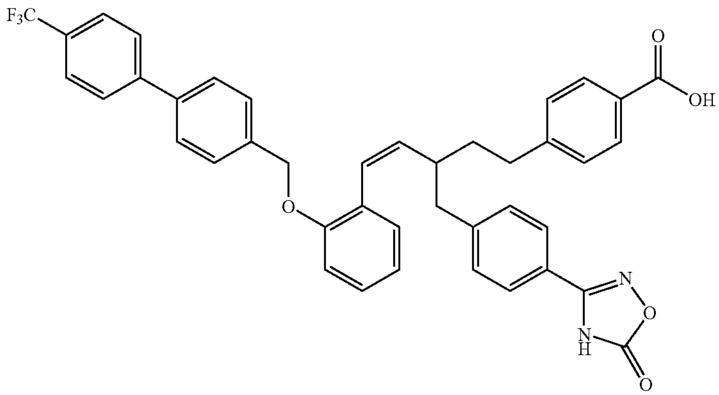 | ¹H-NMR and MS see Example 57; chiral HPLC: R$_t$ 9.96 min; >95% ee. |
| 59 (E enantiomer 1, starting from Ex. 74A and Ex. 79A) | 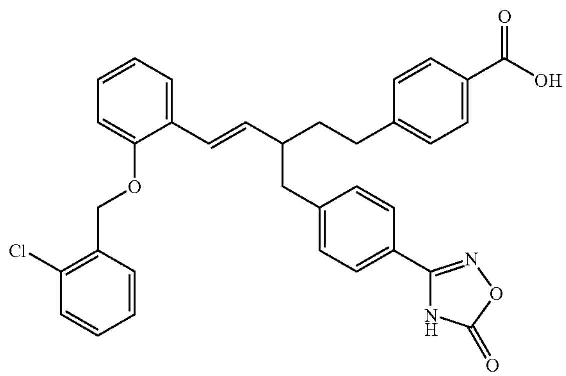 | ¹H-NMR (300 MHz, DMSO-d$_6$, δ/ppm): 12.89-12.65 (2H, broad), 7.79 (2H, d), 7.66 (2H, d), 7.49 (2H, d), 7.42 (1H, d), 7.39-7.28 (4H, m), 7.22 (2H, d), 7.18 (1H, d), 7.06 (1H, d), 6.92 (1H, t), 6.48 (1H, d), 6.17-6.06 (1H, m), 5.12 (2H, s), 2.90-2.80 (1H, m), 2.78-2.65 (2H, m), 2.64-2.54 (1H, m), 2.53-2.40 (1H, m), 1.86-1.72 (1H, m), 1.71-1.57 (1H, m). LC-MS (method 2): R$_t$ 2.79 min; m/z 581 (M + H⁺). chiral HPLC: R$_t$ 16.17 min; >99.5% ee. |
| 60 (E enantiomer 2, starting from Ex. 74A and Ex. 79A) | 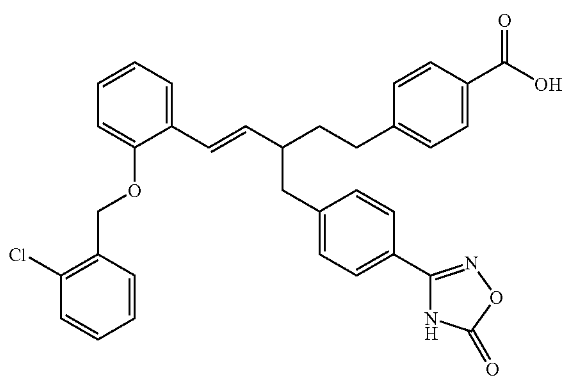 | ¹H-NMR and LC-MS see Example 59; chiral HPLC: R$_t$ 17.91 miin; >97% ee. |
| 61 (E enantiomer 1, starting from Ex. 74A and Ex. 81A) | 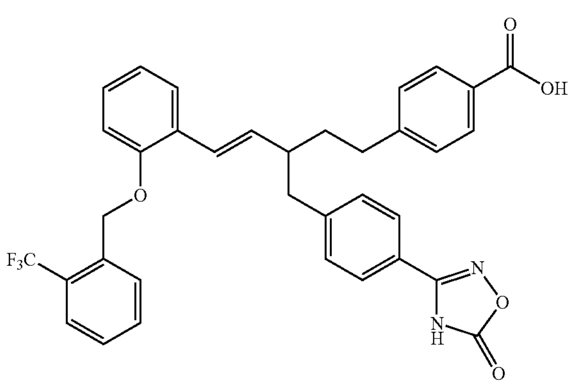 | ¹H-NMR (400 MHz, DMSO-d$_6$, δ/ppm): 13.10-12.50 (2H, broad), 7.80 (3H, d), 7.71-7.61 (4H, m), 7.60-7.52 (1H, m), 7.46 (1H, d), 7.32 (2H, d), 7.27-7.16 (3H, m), 7.02 (1H, d), 6.95 (1H, t), 6.46 (1H, d), 6.14-6.02 (1H, m), 5.20 (2H, s), 2.90-2.80 (1H, m), 2.76-2.64 (2H, m), 2.62-2.38 (2H, m), 1.85-1.71 (1H, m), 1.70-1.58 (1H, m). LC-MS (method 2): R$_t$ 2.81 min; m/z 615 (M + H⁺). chiral HPLC: R$_t$ 13.02 min; 98.9% ee. |

-continued

| Example | Structure | Analytical data |
|---|---|---|
| 62 (E enantiomer 2, starting from Ex. 74A and Ex. 81A) | 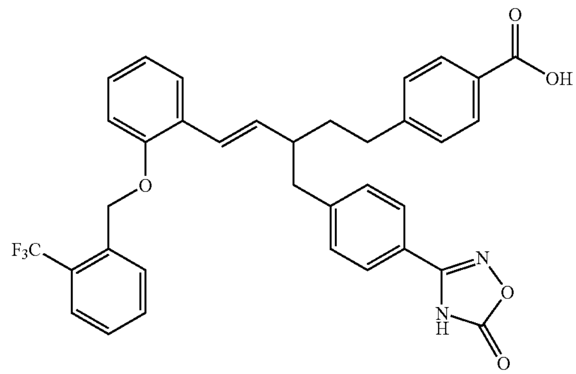 | ¹H-NMR and LC-MS see Example 61; chiral HPLC: R$_t$ 11.08 min; >99.5% ee. |
| 63 (E enantiomer 1, starting from Ex. 74A and Ex. 28A) | 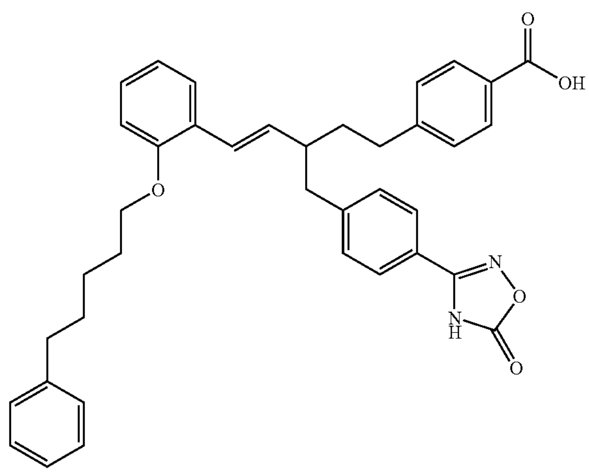 | ¹H-NMR (400 MHz, DMSO-d$_6$, δ/ppm): 12.91-12.81 (1H, broad), 12.80-12.69 (1H, broad), 7.86 (2H, d), 7.68 (2H, d), 7.40-7.32 (3H, m), 7.29 (2H, d), 7.21 (2H, t), 7.19-7.08 (4H, m), 6.97-6.83 (2H, m), 6.42 (1H, d), 6.15-6.03 (1H, m), 3.99-3.85 (2H, m), 2.92-2.81 (1H, m), 2.79-2.69 (2H, m), 2.68-2.41 (3H, m), 1.89-1.76 (1H, m), 1.75-1.64 (3H, m), 1.63-1.52 (2H, m), 1.47-1.28 (3H, m). MS (EI): 603 (M + H⁺). chiral HPLC: R$_t$ 9.95 min; >99% ee. |
| 64 (E enantiomer 2, starting from Ex. 74A and Ex. 28A) | 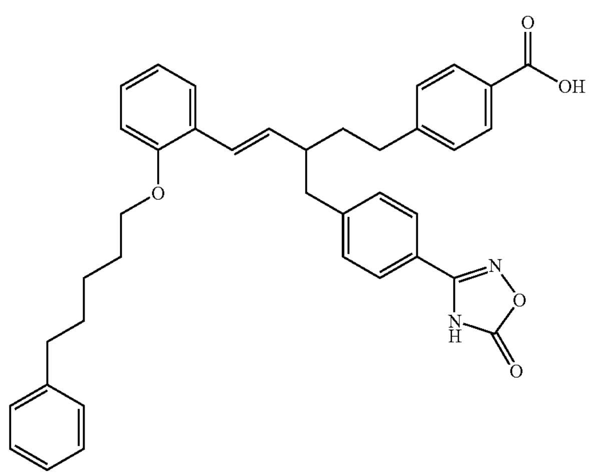 | ¹H-NMR and MS see Example 63; chiral HPLC: R$_t$ 10.88 min; >93% ee. |

| Example | Structure | Analytical data |
|---|---|---|
| 65 (E isomers, starting from Ex. 75A and 4-tert-butyl-benzyl bromide) | 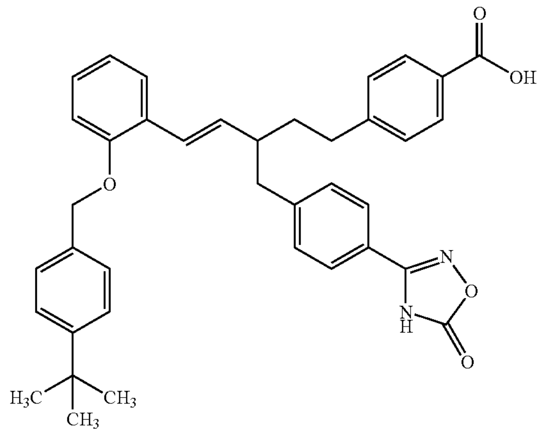 | $^1$H-NMR (300 MHz, DMSO-d$_6$, δ/ppm): 13.11-12.61 (2H, broad), 7.84-7.81 (2H, d), 7.69-7.66 (2H, d), 7.44-7.40 (1H, m), 7.36-7.25 (8H, m), 7.20-7.15 (1H, m), 7.06-7.02 (1H, m), 6.93-6.87 (1H, t), 6.51-6.44 (1H, d), 6.16-6.07 (1H, dd), 5.09-4.99 (2H, m), 2.92-2.58 (5H, m), 1.92-1.60 (2H, m), 1.24 (9H, s). LC-MS (method 4): R$_t$ 3.19 min; m/z 603 (M + H$^+$). |
| 66 (E enantiomer 1, starting from Ex. 65) | 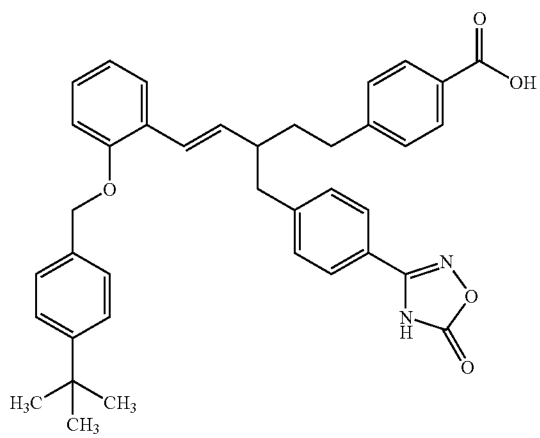 | chiral HPLC: R$_t$ 6.35 min; >99.5% ee. LC-MS (method 1): R$_t$ 3.27 min; m/z 603 (M + H$^+$). |
| 67 (E enantiomer 2, starting from Ex. 65) | 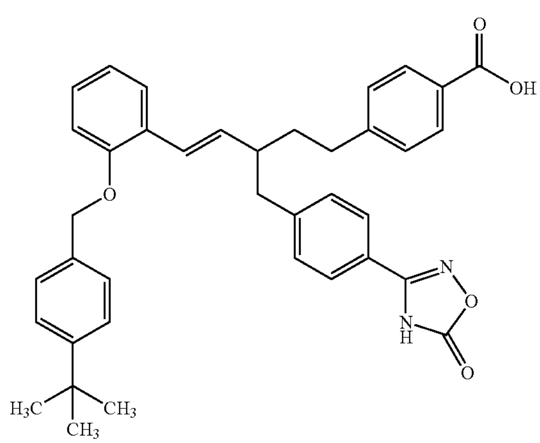 | chiral HPLC: R$_t$ 9.09 min; >99.5% ee. LC-MS (method 2): R$_t$ 3.00 min; m/z 603 (M + H$^+$). |

-continued

| Example | Structure | Analytical data |
|---|---|---|
| 68 (E enantiomer 1, starting from Ex. 74A and Ex. 32A) | 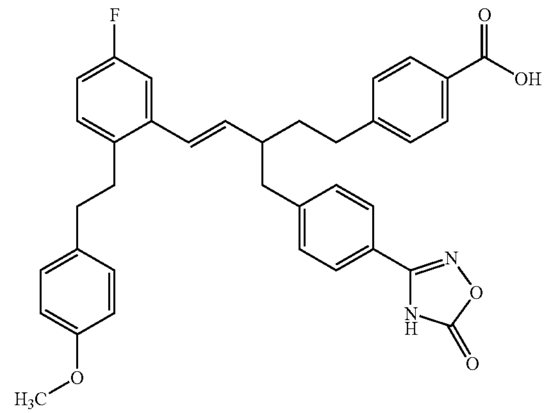 | ¹H-NMR (400 MHz, DMSO-d₆, δ/ppm): 12.87-12.61 (2H, broad), 7.85 (2H, d), 7.64 (2H, d), 7.37 (2H, d), 7.32 (2H, d), 7.21 (1H, d), 7.09 (1H, t), 6.94 (1H, t), 6.90 (2H, d), 6.75 (2H, d), 6.35 (1H, d), 6.13-6.01 (1H, m), 3.69 (3H, s), 3.00-2.87 (1H, m), 2.82-2.47 (6H, m), 2.43 (2H, t), 1.94-1.81 (1H, m), 1.80-1.69 (1H, m). LC-MS (method 2): $R_t$ 2.81 min; m/z 593 (M + H⁺). chiral HPLC: $R_t$ 6.22 min; >99.5% ee. |
| 69 (E enantiomer 2, starting from Ex. 74A and Ex. 32A) | 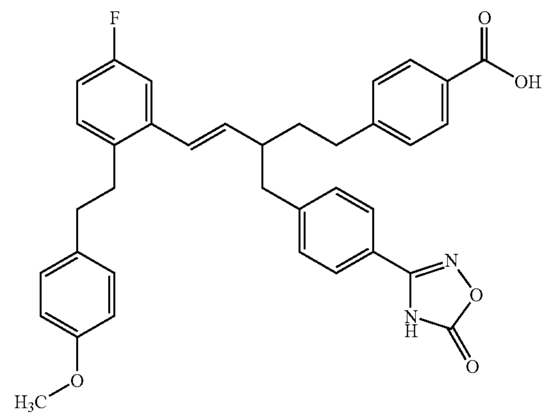 | ¹H-NMR and LC-MS see Example 68; chiral HPLC: $R_t$ 7.28 min; 97.94% ee. |

[E/Z isomer and enantiomer separation method (chiral HPLC): column: Daicel Chiralpak AD-H 250 mm × 20 mm; eluent: isopropanol (with 1% water and 0.2% trifluoroacetic acid)/isohexane 30:70 (v/v); flow rate: 15 ml/min; UV detection: 220 nm; temperature: 24° C.].

Example 70

E-8-[2-(4-tert-Butylbenzyloxy)phenyl]-6-{2-[4-(5-oxo-4,5-dihydro-[1,2,4]oxadiazol-3-yl)phenyl]-ethyl}oct-7-enoic acid (racemate)

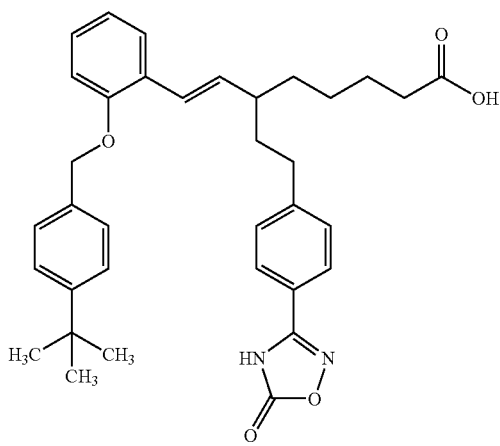

A solution of 1150 mg (1.93 mmol) of ethyl 8-[2-(4-tert-butylbenzyloxy)phenyl]-6-{2-[4-(5-oxo-4,5-dihydro-[1,2,4]oxadiazol-3-yl)phenyl]ethyl}oct-7-enoate from Example 89A in 10 ml of THF and 10 ml of water is mixed with 93.30 mg (3.85 mmol) of lithium hydroxide and stirred at 50° C. for 12 h. After cooling, the THF is stripped off and the aqueous phase is adjusted to pH 4-5 with 1 M hydrochloric acid. It is then extracted three times with ethyl acetate, and the combined organic phases are dried over sodium sulfate. The residue obtained after filtration and concentration is purified by preparative HPLC. 1.04 g (93% yield) of a colorless solid are obtained.

MS (EI): 569 (M+H⁺), 591 (M+Na⁺).

800 mg (1.41 mmol) of the racemic E-8-[2-(4-tert-butylbenzyloxy)phenyl]-6-{2-[4-(5-oxo-4,5-dihydro-[1,2,4]oxadiazol-3-yl)phenyl]ethyl}oct-7-enoic acid obtained in this way are further fractionated by preparative HPLC on a chiral phase. Respectively 381 mg and 412 mg of the two E isomers, each enantiopure, are obtained (see Examples 71 and 72).

Example 71

E-8-[2-(4-tert-Butylbenzyloxy)phenyl]-6-{2-[4-(5-oxo-4,5-dihydro-[1,2,4]oxadiazol-3-yl)phenyl]-ethyl}oct-7-enoic acid (enantiomer 1)

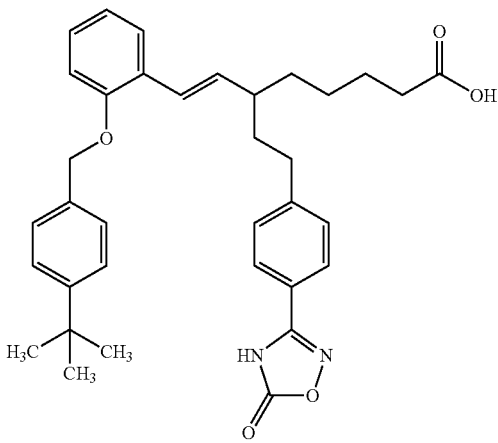

Enantiomer Separation Method:
Column: Daicel Chiralpak AD-H 250 mm×20 mm; eluent: isopropanol (with 1% water and 0.2% trifluoroacetic acid)/isohexane 30:70 (v/v); flow rate: 15 ml/min; UV detection: 220 nm; temperature: 24° C.

$R_t$ 5.48 min; purity>99.5%; >99.5% ee

Yield: 381 mg $^1$H-NMR (300 MHz, DMSO-$d_6$, δ/ppm): 13.40-12.40 (1H, broad), 12.10-11.80 (1H, broad), 7.70 (2H, d), 7.47 (1H, d), 7.41-7.34 (6H, m), 7.19 (1H, t), 7.09 (1H, d), 6.91 (1H, t), 6.64 (1H, d), 6.12-5.98 (1H, m), 5.12 (2H, s), 2.78-2.54 (2H, m), 2.21-2.02 (3H, m), 1.82-1.68 (1H, m), 1.67-1.56 (1H, m), 1.55-1.39 (3H, m), 1.38-1.18 (3H, m), 1.26 (9H, s).

MS (EI): 567 (M−H)⁻.

Example 72

E-8-[2-(4-tert-Butylbenzyloxy)phenyl]-6-{2-[4-(5-oxo-4,5-dihydro-[1,2,4]oxadiazol-3-yl)phenyl]-ethyl}oct-7-enoic acid (enantiomer 2)

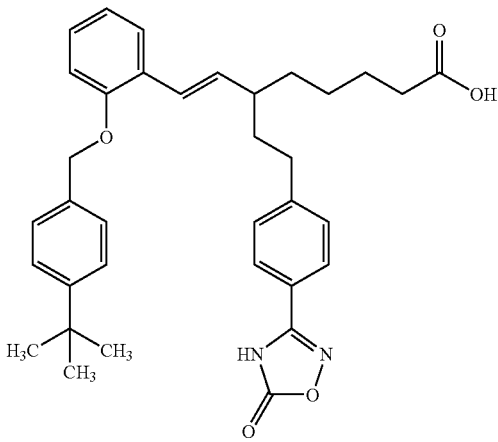

Enantiomer separation method: see Example 71.

$R_t$ 6.25 min; purity>99.5%; >98.5% ee

Yield: 412 mg $^1$H-NMR (300 MHz, DMSO-$d_6$, δ/ppm): 13.40-12.40 (1H, broad), 12.10-11.80 (1H, broad), 7.70 (2H, d), 7.47 (1H, d), 7.41-7.34 (6H, m), 7.19 (1H, t), 7.09 (1H, d), 6.91 (1H, t), 6.64 (1H, d), 6.12-5.98 (1H, m), 5.12 (2H, s), 2.78-2.54 (2H, m), 2.21-2.02 (3H, m), 1.82-1.68 (1H, m), 1.67-1.56 (1H, m), 1.55-1.39 (3H, m), 1.38-1.18 (3H, m), 1.26 (9H, s).

MS (EI): 567 (M−H)⁻.

Example 73

E-8-[2-(4-tert-Butylbenzyloxy)phenyl]-6-{2-[4-(5-oxo-4,5-dihydro-[1,3,4]oxadiazol-3-yl)phenyl]-ethyl}oct-7-enoic acid (racemate)

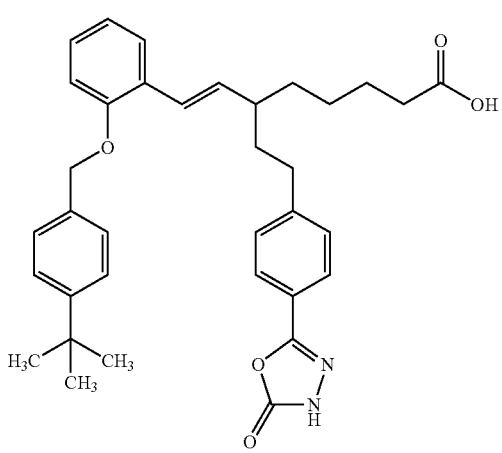

220 mg (0.4 mmol) of (7E)-8-{2-[(4-tert-butylbenzyl)oxy]phenyl}-6-{2-[4-(5-oxo-4,5-dihydro-[1,3,4]oxadiazol-2-yl)phenyl]ethyl}oct-7-enenitrile from Example 98A in 8 ml of n-propanol are mixed with 898 mg (16 mmol) of potassium hydroxide and heated to reflux for 12 hours. The mixture is then adjusted to pH 4 with 1 N hydrochloric acid and concentrated to dryness in vacuo. The residue is taken up in dichloromethane/methanol (10:1), and filtered, the filtrate is again concentrated, and the residue is purified by flash chromatography on silica gel (mobile phase: ethyl acetate/cyclohexane 1:1, with 0.1% formic acid). 95 mg (0.167 mmol, 42% yield) of a solid are obtained.

$^1$H-NMR (400 MHz, DMSO-$d_6$, δ/ppm): 12.80-11.67 (2H, broad), 7.68-7.64 (2H, d), 7.48-7.45 (1H, m), 7.40-7.31 (6H, m), 7.23-7.17 (1H, m), 7.11-7.06 (1H, m), 6.94-6.89 (1H, t), 6.66-6.59 (1H, d), 6.08-6.02 (1H, dd), 5.13-5.07 (2H, m), 2.73-2.53 (2H, m), 2.18-2.14 (2H, t), 2.13-2.05 (1H, m), 1.79-1.69 (1H, m), 1.66-1.53 (1H, m), 1.53-1.39 (3H, m), 1.37-1.19 (3H, m), 1.25 (9H, s).

LC-MS (method 4): $R_t$ 3.01 min; m/z 569 (M+H)⁺.

95 mg (0.17 mmol) of the racemic E-8-[2-(4-tert-butylbenzyloxy)phenyl]-6-{2-[4-(5-oxo-4,5-dihydro-[1,3,4]oxadiazol-3-yl)phenyl]ethyl}oct-7-enoic acid obtained in this way are fractionated further by preparative HPLC on a chiral phase. Respectively 35 mg and 39 mg of the two E isomers, each enantiopure, are obtained (see Examples 74 and 75).

Example 74

E-8-[2-(4-tert-Butylbenzyloxy)phenyl]-6-{2-[4-(5-oxo-4,5-dihydro-[1,3,4]oxadiazol-3-yl)phenyl]-ethyl}oct-7-enoic acid (enantiomer 1)

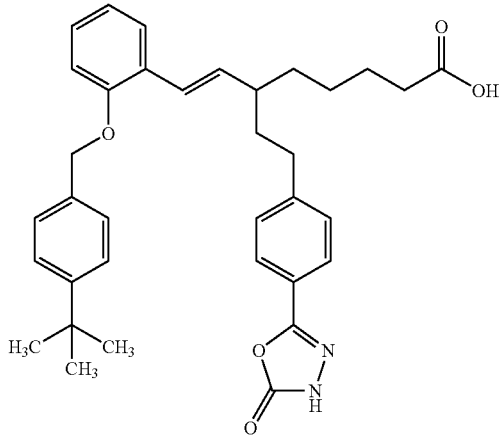

Enantiomer Separation Method:
Column: Daicel Chiralpak AD-H 250 mm×20 mm; eluent: isopropanol (with 1% water and 0.2% trifluoroacetic acid)/isohexane 60:40 (v/v); flow rate: 15 ml/min; UV detection: 220 nm; temperature: 25° C.
$R_t$ 5.53 min; purity>99.5%; >99.5% ee
Yield: 35 mg
LC-MS (method 1): $R_t$ 3.22 min; m/z 568 ($M^+$).

Example 75

E-8-[2-(4-tert-Butylbenzyloxy)phenyl]-6-{2-[4-(5-oxo-4,5-dihydro-[1,3,4]oxadiazol-3-yl)phenyl]-ethyl}oct-7-enoic acid (enantiomer 2)

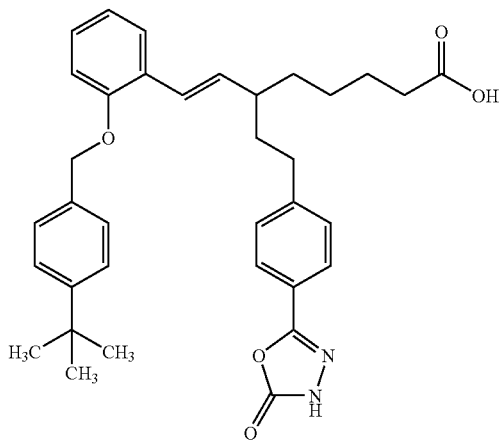

Enantiomer separation method: see Example 74.
$R_t$ 6.02 min; purity>99.0%; >94% ee
Yield: 39 mg
LC-MS (method 1): $R_t$ 3.22 min; m/z 568 ($M^+$).

Example 76

4-((3E)-4-{2-[(4-tert-Butylbenzyl)oxy]phenyl}-2-{2-[4-(5-thioxo-4,5-dihydro-1H-1,2,4-triazol-3-yl)phenyl]ethyl}but-3-en-1-yl)benzoic acid

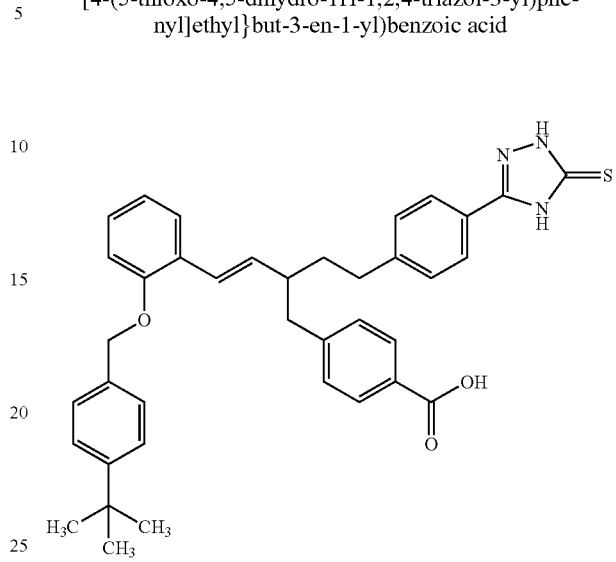

The crude product from Example 101A and 64.52 mg (1.15 mmol) of potassium hydroxide are stirred in 1 ml of n-propanol at 110° C. for 12 hours. After cooling, the reaction mixture is adjusted to pH 2-3 with 1 N hydrochloric acid and concentrated, and the residue is purified by preparative HPLC. 7 mg of the title compound are isolated.
LC-MS (method 2): $R_t$ 2.90 min; m/z 617 ($M^+$).

Example 77

4-{(4E)-5-{2-[(4-tert-Butylbenzyl)oxy]phenyl}-3-[4-(5-oxo-4,5-dihydro-1,3,4-oxadiazol-2-yl)benzyl]pent-4-en-1-yl}benzoic acid (racemate)

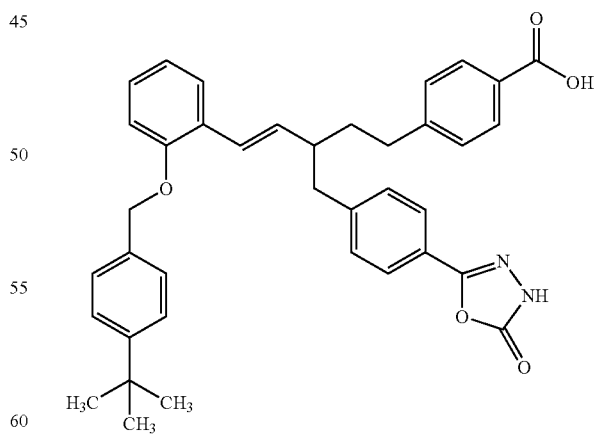

143 mg (0.22 mmol) of 4-{(4E)-5-{2-[(4-tert-butylbenzyl)oxy]phenyl}-3-[4-(5-oxo-4,5-dihydro-1,3,4-oxadiazol-2-yl)benzyl]pent-4-en-1-yl}benzonitrile from Example 104A in 5.7 ml of n-propanol are mixed with 489 mg (8.72 mmol) of potassium hydroxide and stirred at 110° C. for 15 hours. The mixture is then adjusted to pH 3-4 with 1 N hydrochloric acid and concentrated in vacuo. The resulting residue is purified by preparative HPLC. 136 mg (0.21 mmol, 91.5% purity, 94.7% yield) of a solid are obtained.

$^1$H-NMR (400 MHz, DMSO-d$_6$, δ/ppm): 13.0-12.0 (broad), 7.83-7.79 (2H, d), 7.67-7.62 (2H, m), 7.44-7.39 (1H, m), 7.36-7.23 (8H, m), 7.05-7.02 (1H, m), 6.92-6.86 (1H, m), 6.51-6.45 (1H, d), 6.15-6.07 (1H, dd), 5.07-4.99 (2H, m), 2.90-2.57 (5H, m), 1.86-1.62 (2H, m), 1.25 (9H, s).

LC-MS (method 2): R$_t$ 3.06 min; m/z 602 (M$^+$).

135 mg (0.21 mmol) of the racemic 4-{(4E)-5-{2-[(4-tert-butylbenzyl)oxy]phenyl}-3-[4-(5-oxo-4,5-dihydro-1,3,4-oxadiazol-2-yl)benzyl]pent-4-en-1-yl}benzoic acid obtained in this way are fractionated further by preparative HPLC on a chiral phase. Respectively 68 mg and 64 mg of the two E isomers, each enantiopure, are obtained (see Examples 78 and 79).

Example 78

4-{(4E)-5-{2-[(4-tert-Butylbenzyl)oxy]phenyl}-3-[4-(5-oxo-4,5-dihydro-1,3,4-oxadiazol-2-yl)benzyl]pent-4-en-1-yl}benzoic acid (enantiomer 1)

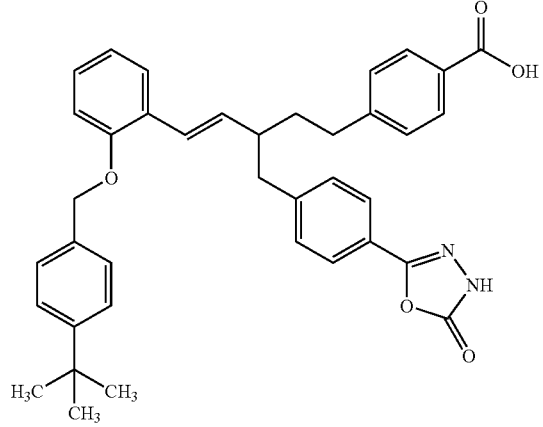

Enantiomer Separation Method:
Column: Daicel Chiralpak AD-H 250 mm×20 mm; eluent: ethanol (with 1% water and 0.2% trifluoroacetic acid)/isohexane 20:80 (v/v); flow rate: 15 ml/min; UV detection: 220 nm; temperature: 30° C.

R$_t$ 16.56 min; purity>99%; >99.5% ee
Yield: 68 mg
LC-MS (method 2): R$_t$ 3.05 min; m/z 602 (M$^+$).

Example 79

4-{(4E)-5-{2-[(4-tert-Butylbenzyl)oxy]phenyl}-3-[4-(5-oxo-4,5-dihydro-1,3,4-oxadiazol-2-yl)benzyl]pent-4-en-1-yl}benzoic acid (enantiomer 2)

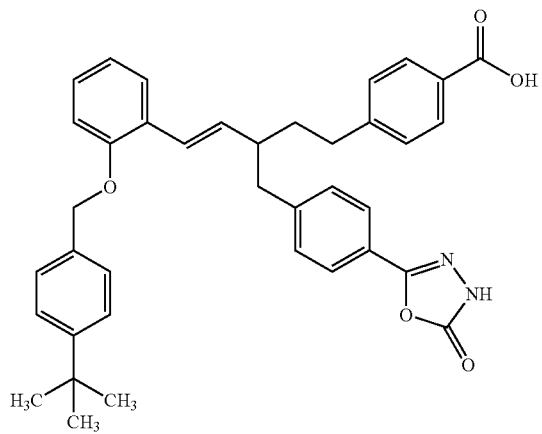

Enantiomer separation method: see Example 78.
R$_t$ 18.25 min; purity>99%; >99% ee
Yield: 64 mg
LC-MS (method 2): R. 3.05 min; m/z 602 (M$^+$).

Example 80

4-{(4E)-5-{2-[(4-tert-Butylbenzyl)oxy]phenyl}-3-[4-(5-oxo-4,5-dihydro-1H-1,2,4-triazol-3-yl)benzyl]pent-4-en-1-yl}benzoic acid

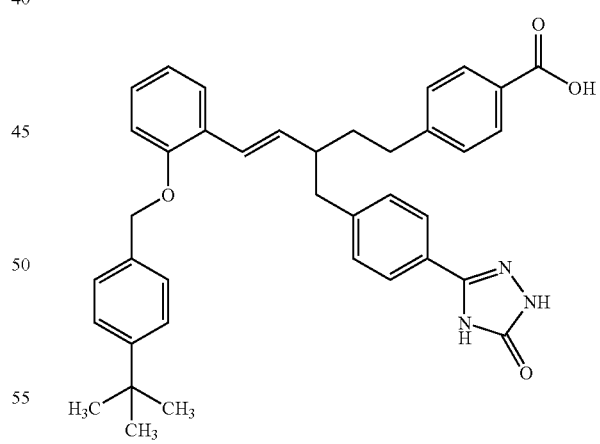

The crude product from Example 106A is suspended in 10 ml of 2 M sodium hydroxide solution and heated to reflux for 12 hours. The mixture is then adjusted to pH 3-4 with 1 N hydrochloric acid and concentrated. The residue is taken up in dichloromethane/methanol (10:1) and filtered, and the filtrate is again concentrated. The resulting crude product is purified by preparative HPLC. 268 mg (64% purity, 34% yield) of a solid are isolated. A small amount thereof is purified by another preparative HPLC for analytical characterization.

¹H-NMR (300 MHz, DMSO-d$_6$, δ/ppm): 11.91 (1H, s), 11.58 (1H, s), 7.82-7.80 (2H, d), 7.66-7.63 (2H, d), 7.45-7.40 (1H, m), 7.36-7.13 (9H, m), 7.07-7.01 (1H, m), 6.93-6.87 (1H, t), 6.52-6.47 (1H, d), 6.16-6.08 (1H, dd), 5.09-5.00 (2H, m), 2.89-2.58 (5H, m), 1.85-1.58 (2H, m), 1.24 (9H, s).

LC-MS (method 2): R$_t$ 2.72 min; m/z 602 (M+H$^+$).

Example 81

4-((4E)-3-[4-(5-Amino-1H-1,2,4-triazol-3-yl)benzyl]-5-{2-[(4-tert.-butylbenzyl)oxy]phenyl}pent-4-en-1-yl)benzoic acid

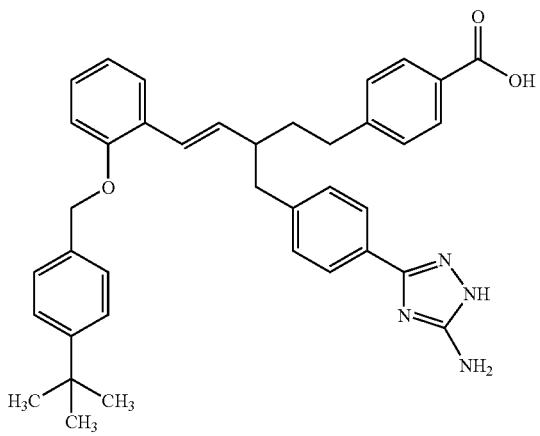

The crude product from Example 107A is suspended in 2 ml of 2 M sodium hydroxide solution and heated to reflux for 12 hours. The mixture is then adjusted to pH 3-4 with 1 N hydrochloric acid and concentrated. The residue is taken up in dichloromethane/methanol (10:1) and filtered, the filtrate is again concentrated and the crude product is purified by preparative HPLC. 17 mg of a solid are isolated.

¹H-NMR (300 MHz, DMSO-d$_6$, δ/ppm): 12.77 (1H, broad), 11.97 (1H, s), 7.82-7.80 (2H, d), 7.76-7.74 (2H, d), 7.44-7.40 (1H, m), 7.37-7.27 (5H, m), 7.26-7.22 (2H, m), 7.20-7.13 (3H, m), 7.07-7.02 (1H, m), 6.93-6.87 (1H, t), 6.16-6.10 (1H, dd), 6.05-5.89 (1H, broad), 5.08-5.02 (2H, m), 2.81-2.54 (5H, m), 1.84-1.58 (2H, m), 1.24 (9H, s).

LC-MS (method 1): R$_t$ 2.89 min; m/z 601 (M+H$^+$).

Example 82

E-8-[2-(4-tert-Butylbenzyloxy)phenyl]-6-[4-(5-oxo-4,5-dihydro-[1,2,4]oxadiazol-3-yl)benzyl]oct-7-enoic acid (racemate)

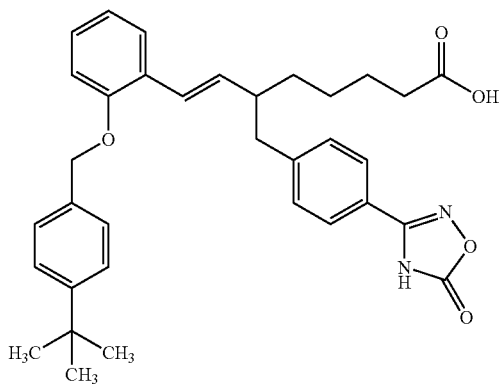

A solution of 1.38 g (2.25 mmol) of ethyl E-8-[2-(4-tert-butylbenzyloxy)phenyl]-6-[4-(5-oxo-4,5-dihydro-[1,2,4] oxadiazol-3-yl)benzyl]oct-7-enoate from Example 114A in 10 ml of THF and 10 ml of water is mixed with 107.7 mg (4.5 mmol) of lithium hydroxide and stirred at 60° C. for 12 h. After cooling, the THF is stripped off and the aqueous phase is adjusted to pH 4-5 with 1 M hydrochloric acid. It is then extracted three times with ethyl acetate, and the combined organic phases are dried over sodium sulfate. The residue obtained after filtration and concentration is purified by preparative HPLC. 867 mg (69% yield) of a colorless solid are obtained.

LC-MS (method 2): R. 2.84 min; m/z 555 (M+H$^+$).

800 mg (1.44 mmol) of the racemic E-8-[2-(4-tert-butyl-benzyloxy)phenyl]-6-[4-(5-oxo-4,5-dihydro-[1,2,4]oxadiazol-3-yl)benzyl]oct-7-enoic acid obtained in this way are further fractionated by preparative HPLC on a chiral phase. Respectively 390 mg and 357 mg of the two E isomers, each enantiopure, are obtained (see Examples 83 and 84).

Example 83

E-8-[2-(4-tert-Butylbenzyloxy)phenyl]-6-[4-(5-oxo-4,5-dihydro-[1,2,4]oxadiazol-3-yl)benzyl]oct-7-enoic acid (enantiomer 1)

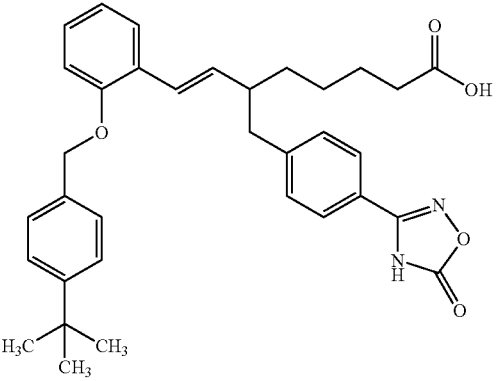

Enantiomer Separation Method:

Column: Daicel Chiralpak AD-H 250 mm×20 mm; eluent: isopropanol (with 1% water and 0.2% trifluoroacetic acid)/isohexane 30:70 (v/v); flow rate: 15 ml/min; UV detection: 220 nm; temperature: 24° C.

R$_t$ 3.87 min; purity>99%; >99.5% ee

Yield: 390 mg

¹H-NMR (400 MHz, DMSO-d$_6$, δ/ppm): 12.91-12.77 (1H, broad), 11.96 (1H, s), 7.69 (2H, d), 7.41-7.32 (5H, m), 7.27 (2H, d), 7.15 (1H, t), 7.01 (1H, d), 6.88 (1H, t), 6.44 (1H, d), 6.10-5.99 (1H, m), 5.03 (2H, s), 2.88-2.76 (1H, m), 2.71-2.61 (1H, m), 2.56-2.41 (1H, m), 2.18 (2H, t), 1.56-1.41 (3H, m), 1.41-1.20 (3H, m), 1.28 (9H, s).

MS (EI): 553 (M−H)⁻.

Example 84

E-8-[2-(4-tert-Butylbenzyloxy)phenyl]-6-[4-(5-oxo-4,5-dihydro-[1,2,4]oxadiazol-3-yl)benzyl]oct-7-enoic acid (enantiomer 2)

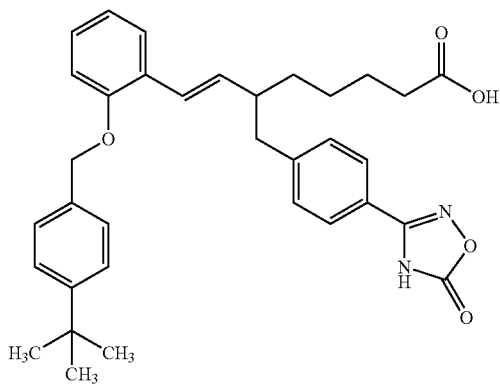

Enantiomer separation method: see Example 83.
$R_t$ 4.55 min; purity>99.5%; >98.8% ee
Yield: 357 mg
$^1$H-NMR and MS see Example 83.

Example 85

E-8-[2-(4-tert-Butylbenzyloxy)phenyl]-6-[4-(5-oxo-4,5-dihydro-[1,3,4]oxadiazol-2-yl)benzyl]oct-7-enoic acid

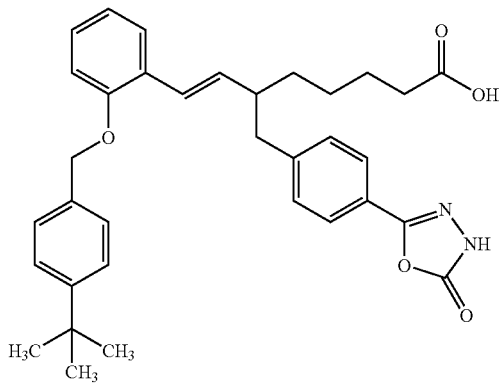

47 mg (0.09 mmol) of E-8-[2-(4-tert-butylbenzyloxy)phenyl]-6-[4-(5-oxo-4,5-dihydro-[1,3,4]oxadiazol-2-yl)benzyl]oct-7-enenitrile from Example 121A in 10 ml of n-propanol are mixed with 196 mg (3.51 mmol) of potassium hydroxide and stirred at 110° C. for 15 hours. The mixture is then adjusted to pH 4 with 1 N hydrochloric acid and extracted three times with diethyl ether. The combined organic phases are dried over sodium sulfate and then concentrated in vacuo. The resulting residue is purified by preparative HPLC. 12 mg (0.02 mmol, 24% yield) of a solid are obtained.

$^1$H-NMR (400 MHz, DMSO-$d_6$, δ/ppm): 12.56-12.43 (1H, broad), 12.03-12.91 (1H, broad), 7.66 (2H, d), 7.41-7.29 (5H, m), 7.27 (2H, d), 7.14 (1H, t), 7.00 (1H, d), 6.88 (1H, t), 6.44 (1H, d), 6.10-5.98 (1H, m), 5.02 (2H, s), 2.88-2.77 (1H, m), 2.76-2.59 (2H, m), 2.18 (2H, t), 1.56-1.20 (8H, m), 1.27 (9H, s).

LC-MS (method 2): $R_t$ 2.88 min; m/z 554 (M−H)$^-$.

Example 86

4-[3-((7E)-2-{2-[(4-tert-Butylbenzyl)oxy]phenyl}vinyl)-7-(5-oxo-4,5-dihydro-1H-1,2,4-triazol-3-yl)heptyl]benzoic acid

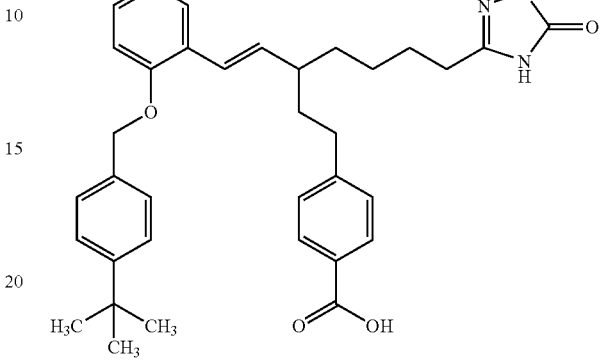

778 mg (1.3 mmol) of 2-{(7E)-8-{2-[(4-tert-butylbenzyl)oxy]phenyl}-6-[2-(4-cyanophenyl)ethyl]-oct-7-enoyl}hydrazinecarboxamide are suspended in 10 ml of 2 M sodium hydroxide solution, and the mixture is stirred at 100° C. for 12 h. After cooling it is acidified with 1 M hydrochloric acid and extracted with ethyl acetate. The organic phase is dried over sodium sulfate and concentrated. The resulting residue is purified by preparative HPLC. 580 mg (85% purity, 0.87 mmol, 56% of theory) of the title compound are obtained.

LC-MS (method 4): $R_t$=2.81 min
MS (ESIpos): m/z=568 (M+H)$^+$.

580 mg (content 85%, 0.87 mmol) of 4-[3-((7E)-2-{2-[(4-tert-butylbenzyl)oxy]phenyl}vinyl)-7-(5-oxo-4,57-dihydro-1H-1,2,4-triazol-3-yl)heptyl]benzoic acid are further fractionated by preparative HPLC on a chiral phase. Respectively 139 mg and 143 mg of the two E isomers, each enantiopure, are obtained (see Examples 87 and 88).

Example 87

4-[3-((7E)-2-{2-[(4-tert-Butylbenzyl)oxy]phenyl}vinyl)-7-(5-oxo-4,5-dihydro-1H-1,2,4-triazol-3-yl)heptyl]benzoic acid (enantiomer 1)

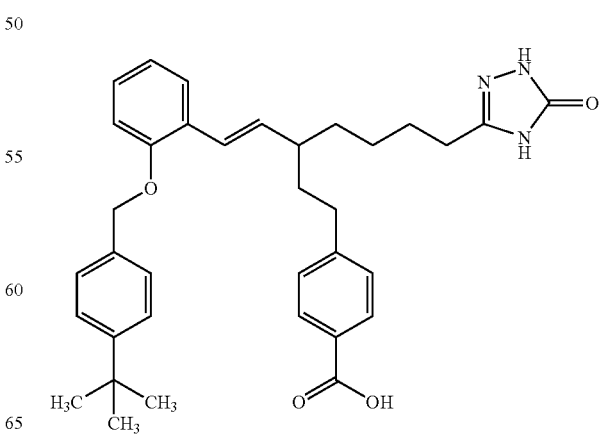

Enantiomer Separation Method:
Column: Daicel Chiralcel OD-H 250 mm×20 mm; eluent: isopropanol (with 1% water and 0.2% trifluoroacetic acid)/isohexane 20:80 (v/v); flow rate: 15 ml/min; UV detection: 220 nm; temperature: 30° C.

$R_t$ 9.17 min; purity>98%; >98.5% ee

Yield: 139 mg

MS (ESIpos): m/z=568 (M−H)⁻

$^1$H-NMR (400 MHz, DMSO-$d_6$, δ/ppm): 12.85-12.68 (1H, broad), 11.13 (1H, s), 11.04 (1H, s), 7.82 (2H, d), 7.47 (1H, dd), 7.38 (4H, s), 7.28 (2H, d), 7.20 (1H, t), 7.09 (1H, d), 6.91 (1H, t), 6.64 (1H, d), 6.10-5.99 (1H, m), 5.10 (2H, s), 2.72-2.61 (1H, m), 2.60-2.51 (1H, m), 2.31 (2H, t), 2.16-2.03 (1H, m), 1.80-1.66 (1H, m), 1.65-1.38 (4H, m), 1.37-1.18 (12H, m, including 9H, s).

Example 88

4-[3-((7E)-2-{2-[(4-tert-Butylbenzyl)oxy]phenyl}vinyl)-7-(5-oxo-4,5-dihydro-1H-1,2,4-triazol-3-yl)heptyl]benzoic acid (enantiomer 2)

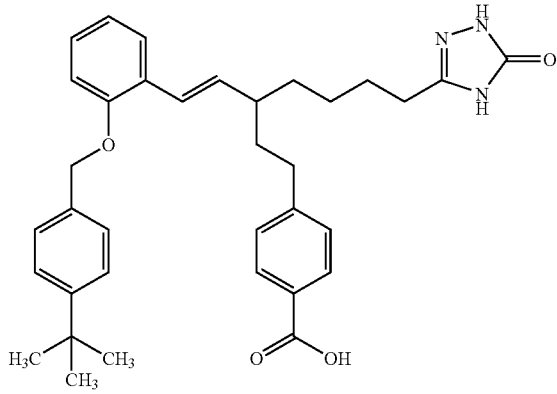

Enantiomer separation method: see Example 87.
$R_t$ 11.13 min; purity>99%; >95% ee
Yield: 143 mg.

Example 89

4-((3E)-4-{2-[(4-tert-Butylbenzyl)oxy]phenyl}-2-{2-[4-(5-oxo-4,5-dihydro-1,2,4-oxadiazol-3-yl)phenyl]ethyl}but-3-en-1-yl)benzoic acid

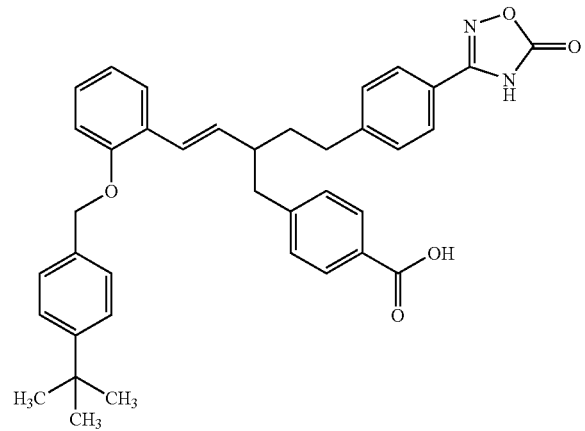

A solution of 500 mg (0.81 mmol) of methyl 4-((3E)-4-{2-[(4-tert-butylbenzyl)oxy]phenyl}-2-{2-[4-(5-oxo-4,5-dihydro-1,2,4-oxadiazol-3-yl)phenyl]ethyl}but-3-en-1-yl)benzoate in 5 ml of THF and 5 ml of water is mixed with 38.8 mg (1.62 mmol) of lithium hydroxide and stirred at 50° C. for 12 h. Cooling is followed by addition of water and extraction with diethyl ether. The aqueous phase is acidified with 1 M hydrochloric acid and extracted with diethyl ether. The resulting organic phase is washed with sodium chloride solution, dried over sodium sulfate and concentrated. 420 mg (0.7 mmol, 79% of theory) of the title compound are obtained.

LC-MS (method 1): $R_t$=3.31 min

MS (ESIpos): m/z=603 (M+H)⁺

$^1$H-NMR (400 MHz, DMSO-$d_6$, δ/ppm): 12.8 (2H, broad), 7.8 (d, 2H), 7.69 (d, 2H), 7.4 (d, 1H), 7.35 (d, 4H), 7.3-7.22 (m, 4H), 7.18 (t, 1H), 7.03 (d, 1H), 6.9 (t, 1H), 6.5 (d, 1H), 6.12 (dd, 1H), 5.05 (s, 2H), 2.9-2.82 (m, 1H), 2.78-2.58 (m, 3H), 1.88-1.5 (m, 3H).

400 mg (0.66 mmol) of 4-((3E)-4-{2-[(4-tert-butylbenzyl)oxy]phenyl}-2-{2-[4-(5-oxo-4,5-dihydro-1,2,4-oxadiazol-3-yl)phenyl]ethyl}but-3-en-1-yl)benzoic acid are further fractionated by preparative HPLC on a chiral phase. 155 mg of each of the two E isomers are obtained enantiopure (see Examples 90 and 91).

Example 90

4-((3E)-4-{2-[(4-tert-Butylbenzyl)oxy]phenyl}-2-{2-[4-(5-oxo-4,5-dihydro-1,2,4-oxadiazol-3-yl)phenyl]ethyl}but-3-en-1-yl)benzoic acid (enantiomer 1)

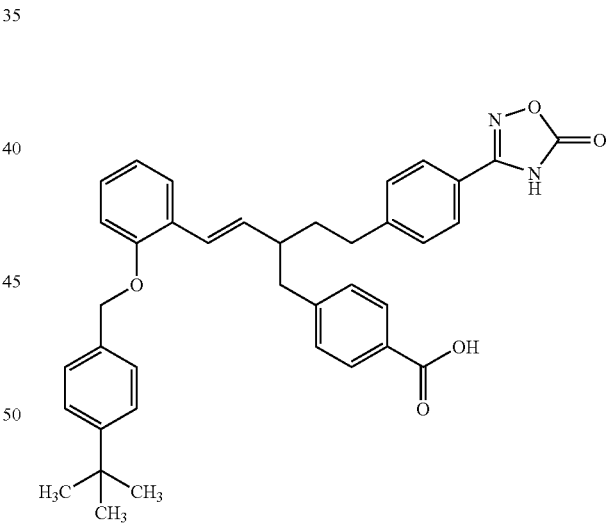

Enantiomer Separation Method:
Column: Daicel Chiralpak AD-H 250 mm×20 mm; eluent: isopropanol (with 1% water and 0.2% trifluoroacetic acid)/isohexane 50:50 (v/v); flow rate: 15 ml/min; UV detection: 220 nm; temperature: 29° C.

$R_t$ 7.5 min; purity>99.5%; >99.5% ee

Yield: 155 mg.

Example 91

4-((3E)-4-{2-[(4-tert-Butylbenzyl)oxy]phenyl}-2-{2-[4-(5-oxo-4,5-dihydro-1,2,4-oxadiazol-3-yl)phenyl]ethyl}but-3-en-1-yl)benzoic acid (enantiomer 2)

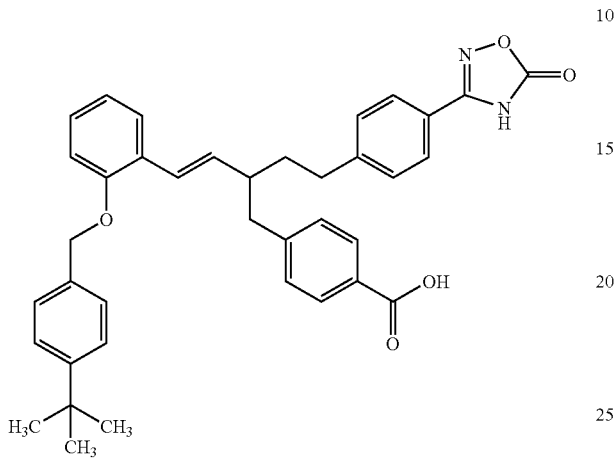

Enantiomer separation method: see Example 90.
$R_t$ 11.2 min; purity>99%; >98.5% ee
Yield: 155 mg.

The examples listed in the following table are obtained in an analogous manner:

| Example No. | Structure of example [precursors] | Analytical data |
|---|---|---|
| 92 | (Enantiomer 1) [starting from Ex. 75A and 1-bromopentane, and enantiomer separation] | $R_t$ 7.17 min; purity >99.5%; >99.5% ee. $^1$H-NMR (400 MHz, DMSO-$d_6$, δ/ppm): 12.86 (1H, br. s), 12.78 (1H, br. s), 7.85 (2H, d), 7.69 (2H, d), 7.43-7.34 (3H, m), 7.30 (2H, d), 7.17 (1H, t), 6.97-6.83 (2H, m), 6.43 (1H, d), 6.18-6.05 (1H, m), 3.98-3.84 (2H, m), 2.94-2.84 (1H, m), 2.81-2.69 (2H, m), 2.68-2.57 (1H, m), 2.56-2.41 (1H, m), 1.89-1.75 (1H, m), 1.74-1.58 (3H, m), 1.40-1.21 (4H, m), 0.83 (3H, t). LC-MS (method 1): $R_t$ = 3.09 min; m/z = 527 (M + H$^+$). |

| Example No. | Structure of example [precursors] | Analytical data |
|---|---|---|
| 93 | 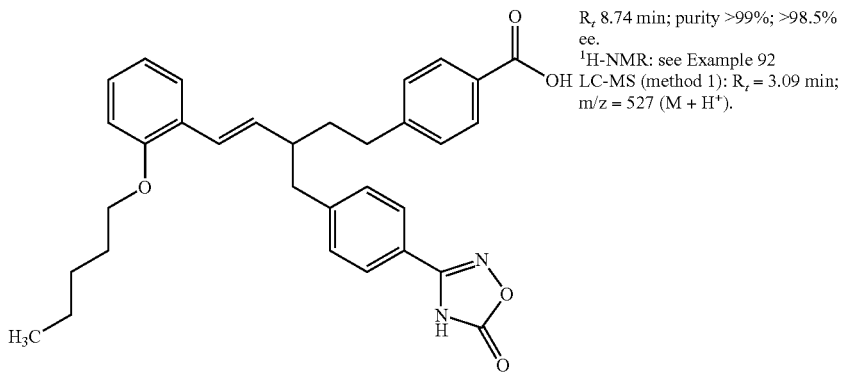<br>(Enantiomer 2)<br>[starting from Ex. 75A and 1-bromopentane, and enantiomer separation] | $R_t$ 8.74 min; purity >99%; >98.5% ee.<br>$^1$H-NMR: see Example 92<br>LC-MS (method 1): $R_t$ = 3.09 min; m/z = 527 (M + H$^+$). |
| 94 | 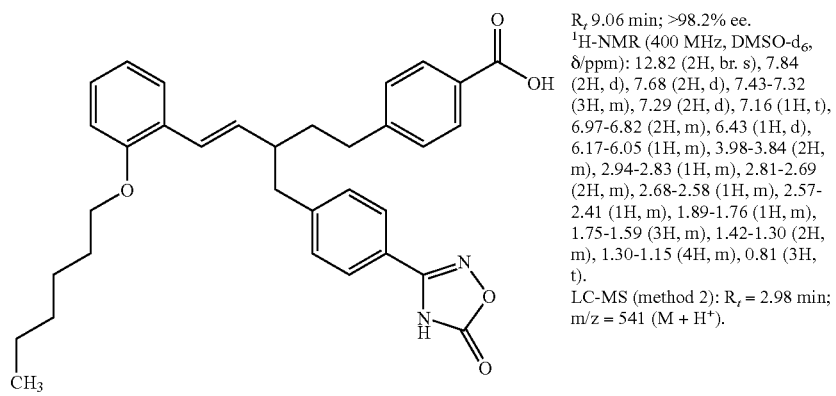<br>(Enantiomer 1)<br>[starting from Ex. 75A and 1-bromohexane, and enantiomer separation] | $R_t$ 9.06 min; >98.2% ee.<br>$^1$H-NMR (400 MHz, DMSO-d$_6$, δ/ppm): 12.82 (2H, br. s), 7.84 (2H, d), 7.68 (2H, d), 7.43-7.32 (3H, m), 7.29 (2H, d), 7.16 (1H, t), 6.97-6.82 (2H, m), 6.43 (1H, d), 6.17-6.05 (1H, m), 3.98-3.84 (2H, m), 2.94-2.83 (1H, m), 2.81-2.69 (2H, m), 2.68-2.58 (1H, m), 2.57-2.41 (1H, m), 1.89-1.76 (1H, m), 1.75-1.59 (3H, m), 1.42-1.30 (2H, m), 1.30-1.15 (4H, m), 0.81 (3H, t).<br>LC-MS (method 2): $R_t$ = 2.98 min; m/z = 541 (M + H$^+$). |
| 95 | 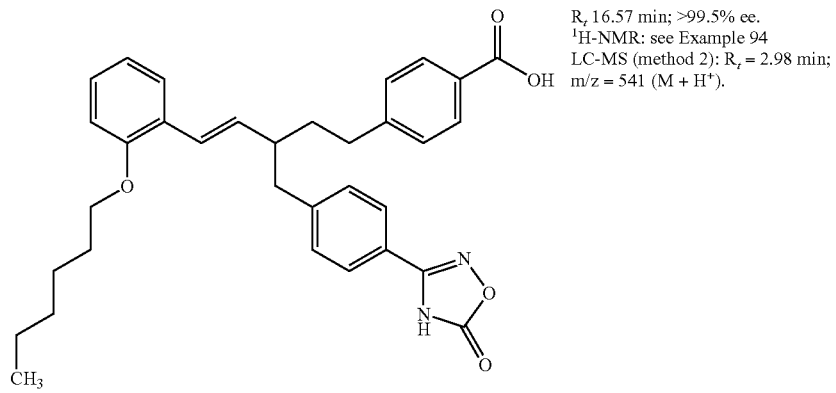<br>(Enantiomer 2)<br>[starting from Ex. 75A and 1-bromohexane, and enantiomer separation] | $R_t$ 16.57 min; >99.5% ee.<br>$^1$H-NMR: see Example 94<br>LC-MS (method 2): $R_t$ = 2.98 min; m/z = 541 (M + H$^+$). |

| Example No. | Structure of example [precursors] | Analytical data |
|---|---|---|
| 96 | (cis-Enantiomer 1) [starting from Ex. 74A and Ex. 126A, and enantiomer separation] | $R_t$ 7.69 min; >99.5% ee. $^1$H-NMR (400 MHz, DMSO-$d_6$, δ/ppm): 12.88 (2H, br. s), 7.76 (2H, d), 7.67 (2H, d), 7.37 (1H, t), 7.30 (1H, d), 7.25 (2H, d), 7.18 (1H, t), 7.13 (2H, d), 6.80 (1H, d), 6.45 (1H, d), 5.79-5.67 (1H, m), 2.90-2.79 (1H, m), 2.75-2.59 (3H, m), 2.58-2.39 (1H, m), 1.78-1.65 (1H, m), 1.65-1.52 (1H, m). LC-MS (method 4): $R_t$ = 2.77 min; m/z 525 (M + H$^+$). |
| 97 | (cis-Enantiomer 2) [starting from Ex. 74A and Ex. 126A, and enantiomer separation] | $R_t$ 13.00 min; >99.5% ee. $^1$H-NMR: see Example 96. LC-MS (method 4): $R_t$ = 2.77 min; m/z = 525 (M + H$^+$). |
| 98 | (trans-Enantiomer 1) [starting from Ex. 74A and Ex. 126A, and enantiomer separation] | $R_t$ 8.75 min; >99% ee. $^1$H-NMR (400 MHz, DMSO-$d_6$, δ/ppm): 12.85 (2H, br. s), 7.84 (2H, d), 7.68 (3H, d), 7.40-7.32 (4H, m), 7.29 (3H, d), 6.36 (1H, d), 6.31-6.21 (1H, m), 2.95-2.86 (1H, m), 2.82-2.68 (2H, m), 2.67-2.45 (1H, m), 1.91-1.78 (1H, m), 1.77-1.65 (1H, m). LC-MS (method 4): $R_t$ = 2.77 min; m/z = 525 (M + H$^+$). |

| Example No. | Structure of example [precursors] | Analytical data |
|---|---|---|
| 99 | 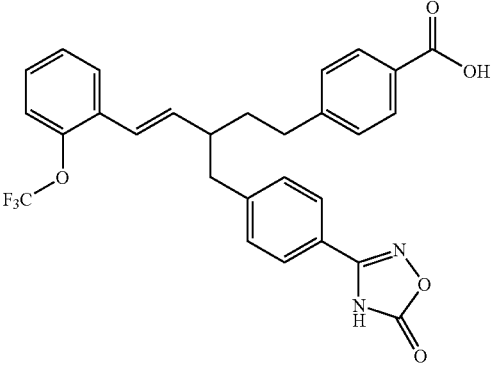<br>(trans-Enantiomer 2)<br>[starting from Ex. 74A and Ex. 126A, and enantiomer separation] | $R_t$ 10.34 min; >99% ee.<br>$^1$H-NMR: see Example 98<br>LC-MS (method 4): $R_t$ = 2.77 min; m/z = 525 (M + H$^+$). |
| 100 | 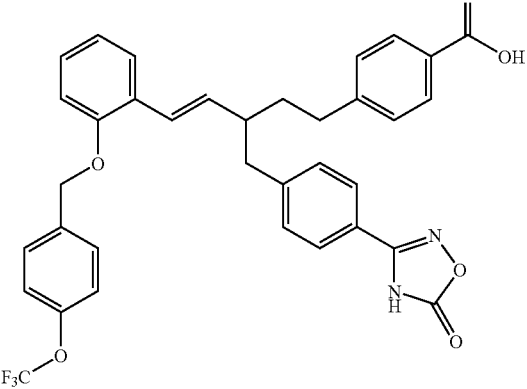<br>(Enantiomer 1)<br>[starting from Ex. 127A and 4-trifluoromethoxybenzyl bromide] | $^1$H-NMR (400 MHz, DMSO-$d_6$, δ/ppm): 12.82 (1H, br. s), 12.77 (1H, br. s), 7.81 (2H, d), 7.68 (2H, d), 7.49 (2H, d), 7.44 (1H, d), 7.39-7.29 (4H, m), 7.26 (2H, d), 7.18 (1H, t), 7.02 (1H, d), 6.92 (1H, t), 6.49 (1H, d), 6.19-6.07 (1H, m), 5.12 (2H, s), 2.93-2.82 (1H, m), 2.79-2.44 (4H, m), 1.88-1.73 (1H, m), 1.73-1.58 (1H, m).<br>LC-MS (method 2): $R_t$ = 2.86 min; m/z = 631 (M + H$^+$). |
| 101 | 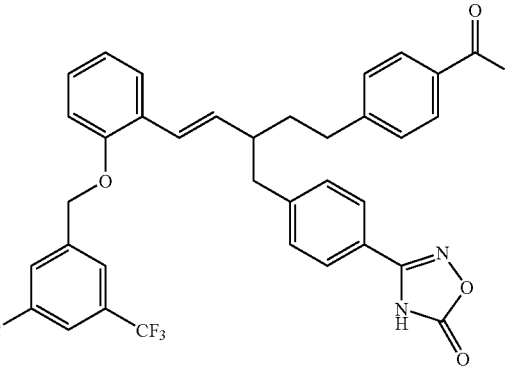<br>(Enantiomer 1)<br>[starting from Ex. 127A and 3,5-bis(trifluoromethyl)benzyl bromide] | $^1$H-NMR (400 MHz, DMSO-$d_6$, δ/ppm): 12.80 (1H, br. s), 12.76 (1H, br. s), 8.18-7.95 (3H, m), 7.76 (2H, d), 7.63 (2H, d), 7.44 (1H, d), 7.32 (2H, d), 7.21 (3H, d), 7.06 (1H, d), 6.97 (1H, t), 6.51 (1H, d), 6.21-6.08 (1H, m), 5.48-5.23 (2H, m), 2.94-2.81 (1H, m), 2.79-2.65 (2H, m), 2.65-2.41 (2H, m), 1.87-1.72 (1H, m), 1.71-1.58 (1H, m).<br>LC-MS (method 6): $R_t$ = 3.13 min; m/z = 683 (M + H$^+$). |

[Enantiomer Separation Methods:

Examples 92 and 93

Column: Daicel Chiralpak AD-H 250 mm×20 mm, 5 μm; eluent: isopropanol (with 1% water and 0.2% trifluoroacetic acid)/isohexane 30:70 (v/v); flow rate: 15 ml/min; UV detection: 220 nm; temperature: 25° C.

Examples 94 and 95

Column: Chiral silica gel phase based on the selector poly (N-methacryloyl-L-leucine tert-butyl-amide), 670 mm×40 mm; eluent: ethyl acetate; flow rate: 80 ml/min; UV detection: 270 nm; temperature: 24° C.

Examples 96-99

Column: Daicel Chiralpak AD-H 250 mm×20 mm, 5 µm; eluent: isopropanol (with 1% water and 0.2% trifluoroacetic acid)/isohexane 30:70 (v/v); flow rate: 15 ml/min; UV detection: 220 nm; temperature: 35° C.].

B. ASSESSMENT OF THE PHARMACOLOGICAL ACTIVITY

The pharmacological effect of the compounds according to the invention can be shown in the following-assays:

B-1. Vasorelaxant Effect In Vitro:

Rabbits are anesthetized and sacrificed by intravenous injection of thiopental sodium (about 50 mg/kg) and exsanguinated. The saphenous artery is removed and divided into rings 3 mm wide. The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with 95% $O_2$/5% $CO_2$ and has the following composition: NaCl 119 mM; KCl 4.8 mM; $CaCl_2 \times 2H_2O$ 1 mM; $MgSO_4 \times 7 H_2O$ 1.4 mM; $KH_2PO_4$ 1.2 mM; $NaHCO_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the height of the contraction achieved under the influence of the test substance is compared with the height of the contraction reached in the last preceding run. The concentration necessary to reduce the contraction reached in the preceding control by 50% is calculated from this ($IC_{50}$). The standard application volume is 5 µl. The proportion of DMSO in the bath solution corresponds to 0.1%.

Representative results on the compounds according to the invention are listed in Table 1:

TABLE 1

Vasorelaxant effect in vitro

| Example No. | $IC_{50}$ [nM] |
| --- | --- |
| 1 | 26 |
| 11 | 724 |
| 18 | 490 |
| 19 | 850 |
| 51 | 505 |
| 55 | 146 |
| 56 | 635 |
| 57 | 714 |
| 66 | 263 |
| 67 | 153 |
| 71 | 898 |
| 74 | 290 |
| 76 | 851 |
| 78 | 13 |
| 80 | 74 |
| 81 | 422 |
| 85 | 58 |
| 92 | 390 |
| 95 | 410 |
| 96 | 1333 |

B-2. Stimulation of Recombinant Soluble Guanylate Cyclase (sGC) In Vitro:

Investigations on the stimulation of recombinant soluble guanylate cyclase (sGC) by the compounds according to the invention with and without sodium nitroprusside, and with and without the heme-dependent sGC inhibitor 1H-1,2,4-oxadiazole-(4,3a)-quinoxalin-1-one (ODQ) are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The heme-free guanylate cyclase is obtained by adding Tween 20 to the sample buffer (0.5% in the final concentration).

The activation of sGC by a test substance is reported as n-fold stimulation of the basal activity. The result for Example 5 is shown in Table 2:

TABLE 2

Stimulation (n-fold) of recombinant soluble guanylate cyclase (sGC) in vitro by Example 55

| Concentration of Example 55 [µM] | Heme-containing sGC | | | | Heme-free sGC Basal |
| --- | --- | --- | --- | --- | --- |
| | Basal | +0.1 µM DEA/NO | +0.01 µM DEA/NO | +10 µM ODQ | |
| 0.0 | 1.0 | 52.0 | 10.7 | 3.0 | 1.0 |
| 0.001 | 1.4 | 50.3 | 10.6 | | 3.7 |
| 0.01 | 3.1 | 53.4 | 13.0 | 12.7 | 24.0 |
| 0.1 | 15.5 | 66.5 | 25.5 | 66.3 | 98.1 |
| 1 | 25.4 | 75.1 | 35.4 | 107.4 | 132.6 |
| 10 | 33.0 | 81.5 | 42.5 | 105.5 | 137.9 |

[DEA/NO = 2-(N,N-diethylamino)diazenolate 2-oxide; ODQ = 1H-1,2,4-oxadiazole-(4,3a)-quinoxalin-1-one].

It is evident from Table 2 that stimulation both of the heme-containing and of the heme-free enzyme is achieved. Furthermore, combination of Example 55 and 2-(N,N-diethylamino)diazenolate 2-oxide (DEA/NO), an NO donor, shows no synergistic effect, i.e. the effect of DEA/NO is not potentiated as would be expected with an sGC activator acting via a heme-dependent mechanism. In addition, the effect of the sGC activator according to the invention is not blocked by the heme-dependent inhibitor of soluble guanylate cyclase ODQ, but is in fact increased. The results in Table 2 thus confirm the mechanism of action of the compounds according to the invention as activators of soluble guanylate cyclase.

B-3. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitter, (2) receiver which is linked via a multiplexer to a (3) data acquisition computer. The telemetry system makes it possible to record continuously the blood pressure and heart rate on conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 in the morning and at 19.00 in the evening.

The telemetry transmitters (TAM PA-C40, DSI) as employed are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi, 50 mg/kg i.p.) and shaved and disinfected over a large area on the side of the abdomen. After the abdominal cavity has been opened along the linea alba, the liquid-filled measuring catheter of the system is inserted into the descending aorta in the cranial direction above the bifurcation and fastened with tissue glue (VetBonD™, 3M). The transmitter housing is fixed intraperitoneally to the abdominal wall muscle, and layered closure of the wound is performed. An antibiotic (Tardomyocel COMP, Bayer, 1 ml/kg s.c.) is administered postoperatively for prophylaxis of the infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring-unit is configured for 24 animals. Each experiment is recorded under an experiment number.

Each of the instrumented rats living in the system is assigned a separate receiving antenna (1010 Receiver, DSI). The implanted transmitters can be activated from outside by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file bearing the experiment number which is open for this purpose.

In the standard procedure, the following are measured for 10-second periods in each case: (1) systolic blood pressure (SBP), (2) diastolic blood pressure (DBP), (3) mean arterial pressure (MAP) and (4) heart rate (HR).

Measurement acquisition is repeated under computer control at 5-minute intervals. The source data obtained as absolute value are corrected in the diagram with the currently measured barometric pressure and stored in individual data. Further technical details are given in the documentation of the manufacturing company (DSI).

The test substances are administered at 9.00 h on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 h on the day of the experiment to 9.00 h on the following day.

The data are smoothed over a presettable time by determination of the average (15-minute average, 30-minute average) and transferred as text file to a storage medium. The measurements presorted and compressed in this way are transferred into Excel templates and tabulated.

C. EXEMPLARY EMBODIMENTS OF PHARMACEUTICAL COMPOSITIONS

The compounds according to the invention can be converted into pharmaceutical preparations in the following ways:

Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:
A mixture of compound according to the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which Can Be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:
The Rhodigel is suspended in ethanol, and the compound according to the invention is added to the suspension. The water is added while stirring. The mixture is stirred for about 6 h until the swelling of the Rhodigel is complete.

Solution which Can Be Administered Orally:
Composition:
500 mg of the compound according to the invention, 2.5 g of polysorbate and 97 g of polyethylene glycol 400.20 g of oral solution correspond to a single dose of 100 mg of the compound according to the invention.

Production:
The compound according to the invention is suspended in the mixture of polyethylene glycol and polysorbate with stirring. The stirring process is continued until the compound according to the invention has completely dissolved.

i.v.-Solution:
The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of the formula (I)

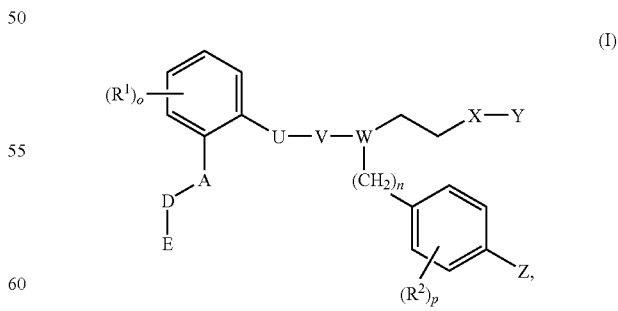

in which
U, V and W together form a group of the formula
*—CH=CH—CH<, *—CH$_2$—CH$_2$—CH< or
*—CH$_2$—CH$_2$—N<, in which * means the point of linkage to the phenyl ring, A is O or CH$_2$, D is a bond or is (C$_1$-C$_7$)-alkanediyl, (C$_2$-C$_7$)-alkenediyl or (C$_2$-C$_7$)-alkynediyl, each of which may be substituted one or more times by fluorine, E is hydrogen, trifluoromethyl or a group of the formula

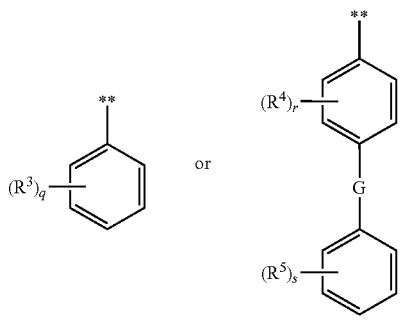

in which ** means the point of linkage to the group D and

G is a bond, CH$_2$, —CH$_2$—CH$_2$— or —CH═CH—,

X is —CH$_2$—CH$_2$— or a group of the formula

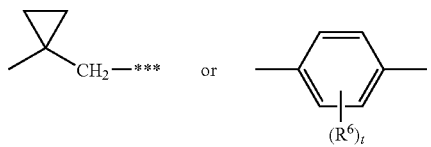

in which *** means the point of linkage to the group Y,

Y is carboxyl and

Z is a group of the formula

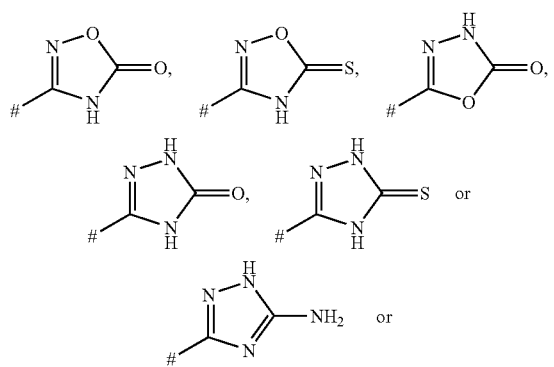

Y is a group of the formula

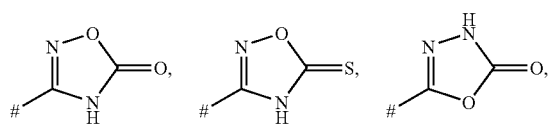

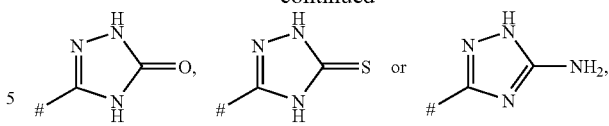

in which # means the respective point of linkage, and

Z is carboxyl, n is the number 1 or 2,

R$^1$, R$^2$, R$^3$, R$^4$, R$^5$ and R$^6$ are independently of one another substituents selected from the series halogen, (C$_1$-C$_6$)-alkyl, trifluoromethyl, (C$_1$-C$_6$)-alkoxy, trifluoromethoxy, cyano and nitro, and o, p, q, r, s and t are independently of one another each the number 0, 1, 2, 3 or 4, where in the case where R$^1$, R$^2$, R$^3$, R$^4$, R$^5$ or R$^6$ occur more than once, their meanings may in each case be identical or different, and the salts thereof.

2. The compound of the formula (I) as claimed in claim 1, in which

U, V and W together form a group of the formula *—CH═CH—CH< or *—CH$_2$—CH$_2$—N< in which * means the point of linkage to the phenyl ring, A is O, D is (C$_1$-C$_7$)-alkanediyl which may be substituted one or more times by fluorine, E is hydrogen, trifluoromethyl or is a group of the formula

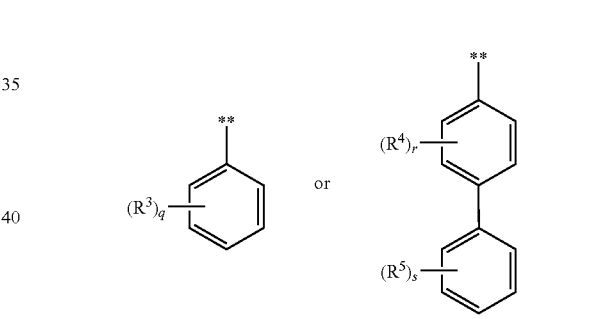

in which ** means the point of linkage to the group D,

X is —CH$_2$—CH$_2$— or a group of the formula

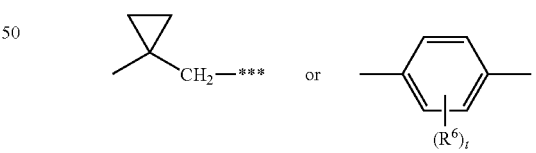

in which *** means the point of linkage to the group Y,

Y is carboxyl and

Z is a group of the formula

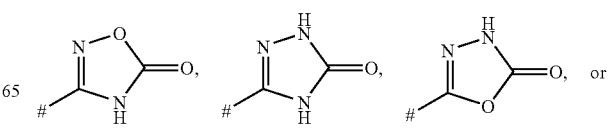

-continued

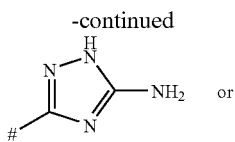

or

Y is a group of the formula

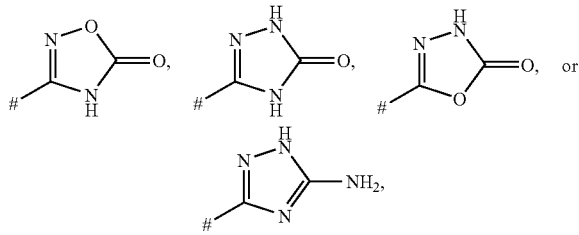

in which # means the respective point of linkage,
and
Z is carboxyl,
n is the number 1 or 2,
$R^1$, $R^3$, $R^4$ and $R^5$ are independently of one another a substituent selected from the series fluorine, chlorine, bromine, $(C_1-C_4)$-alkyl, trifluoromethyl, $(C_1-C_4)$-alkoxy and trifluoromethoxy,
o, q, r and s are independently of one another each the number 0, 1 or 2,
where in the case where $R^1$, $R^3$, $R^4$ or $R^5$ occur more than once, their meanings may in each case be identical or different,
$R^2$ and $R^6$ are each fluorine,
and
p and t are independently of one another each the number 0 or 1,
and the salts thereof.

3. A compound of the formula (I-A)

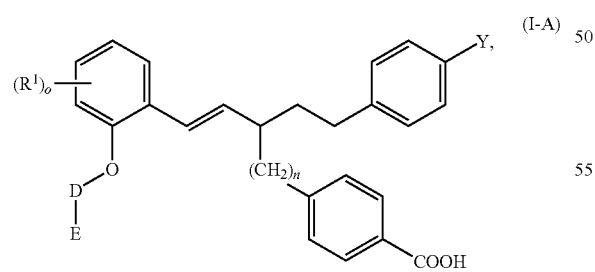

(I-A)

in which
D is $(C_1-C_7)$-alkanediyl which may be substituted one or more times by fluorine, E is hydrogen, trifluoromethyl or is a group of the formula

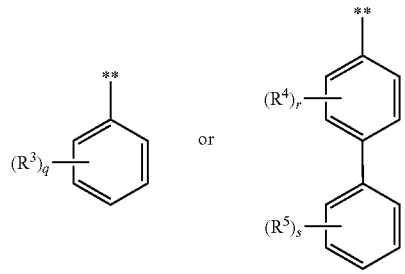

or in which ** means the point of linkage to the group D,
Y is a group of the formula

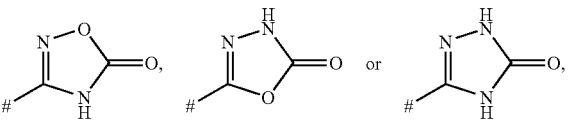

in which # means the point of linkage to the phenyl ring,
n is the number 1 or 2,
$R^1$, $R^3$, $R^4$ and $R^5$ are independently of one another a substituent selected from fluorine, chlorine, bromine, methyl, tert-butyl, trifluoromethyl, methoxy and trifluoromethoxy,
and
o, q, r and s are independently of one another each the number 0, 1 or 2,
where in the case that $R^1$, $R^3$, $R^4$ or $R^5$ occur more than once, their meanings may in each case be identical or different,
and the salts thereof.

4. A compound of the formula (I-B)

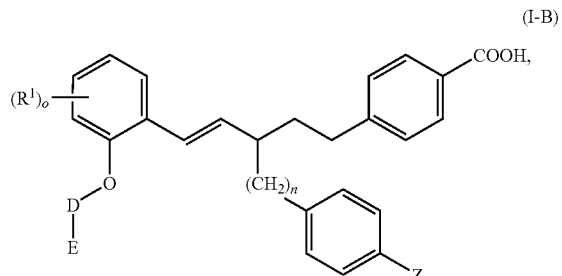

(I-B)

in which
D is $(C_1-C_7)$-alkanediyl which may be substituted one or more times by fluorine,

211

E is hydrogen, trifluoromethyl or is a group of the formula

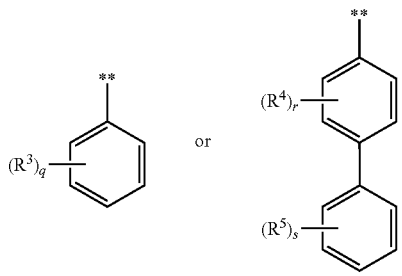

in which ** means the point of linkage to the group D,

Z is a group of the formula

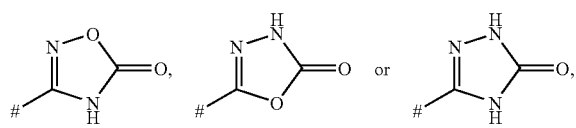

in which # means the point of linkage to the phenyl ring, n is the number 1 or 2, $R^1$, $R^3$, $R^4$ and $R^5$ are independently of one another a substituent selected from fluorine, chlorine, bromine, methyl, tert-butyl, trifluoromethyl, methoxy and trifluoromethoxy, and o, q, r and s are independently of one another each the number 0, 1 or 2, where in the case that $R^1$, $R^3$, $R^4$ or $R^5$ occur more than once, their meanings may in each case be identical or different, and the salts thereof.

5. A compound of the formula (I-C)

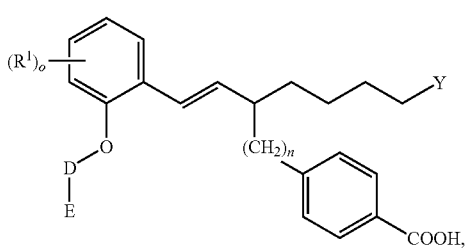

(I-C)

in which

D is ($C_1$-$C_7$)-alkanediyl which may be substituted one or more times by fluorine,

212

E is hydrogen, trifluoromethyl or is a group of the formula

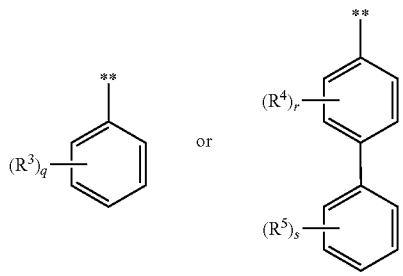

in which ** means the point of linkage to the group D,

Y is a group of the formula

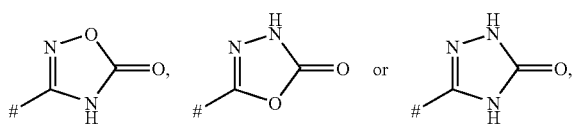

in which # means the respective point of linkage, n is the number 1 or 2, $R^1$, $R^3$, $R^4$ and $R^5$ are independently of one another a substituent selected from fluorine, chlorine, bromine, methyl, tent-butyl, trifluoromethyl, methoxy and trifluoromethoxy, and o, q, r and s are independently of one another each the number 0, 1 or 2, where in the case that $R^1$, $R^3$, $R^4$ or $R^5$ occur more than once, their meanings may in each case be identical or different, and the salts thereof.

6. A process for preparing a compound of the formula (I), (I-A), (I-B) or (I-C) as defined in claim 1, characterized in that either

[A-1] Compounds of the Formula (II-1)

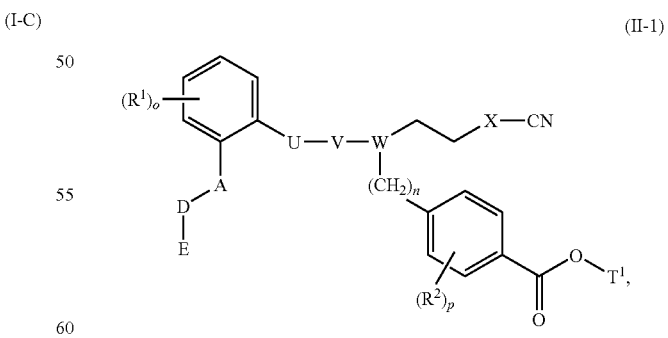

(II-1)

in which $R^1$, $R^2$, A, D, E, U, V, W, X, n, o and p each have the meanings indicated in claim 1, and $T^1$ is ($C_1$-$C_4$)-alkyl, are initially converted with hydroxylamine in an inert solvent into compounds of the formula (III-1)

(III-1)

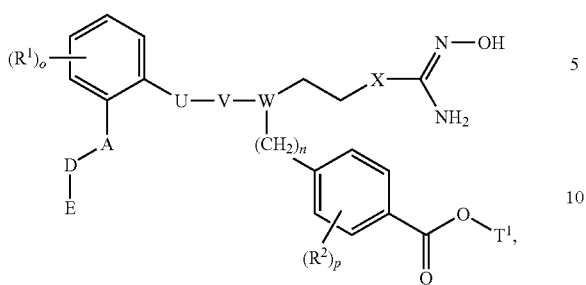

in which R¹, R², A, D, E, U, V, W, X, n, o, p and T¹ each have the meanings indicated above,
and then reacted in an inert solvent in the presence of a base with a chloroformic ester of the formula (IV)

(IV)

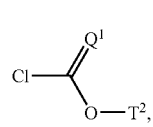

in which
$Q^1$ is O or S
and
$T^2$ is $(C_1\text{-}C_{10})$-alkyl,
and where appropriate after subsequent heating in an inert solvent to give compounds of the formula (V-1)

(V-1)

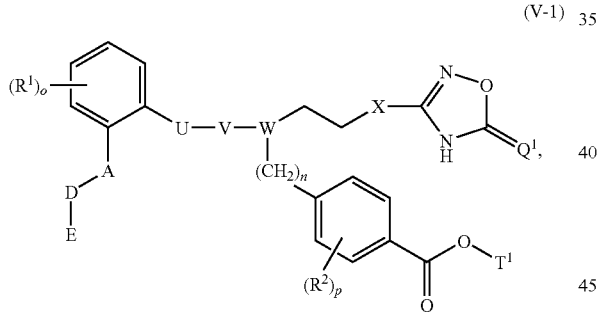

in which R¹, R², A, D, E, U, V, W, X, n, o, p, Q¹ and T¹ each have the meanings indicated above, or

[A-2] Compounds of the Formula (II-2)

(II-2)

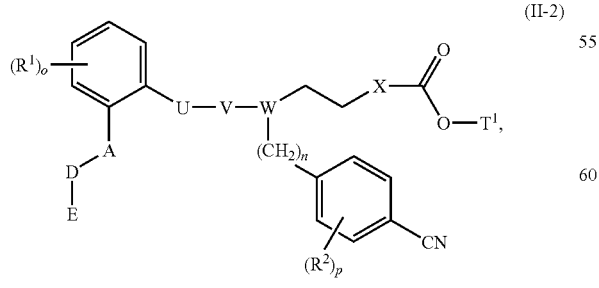

in which R¹, R², A, D, E, U, V, W, X, n, o, p and T¹ each have the meanings indicated above, are converted in a manner analogous to process [A-1] into compounds of the formula (V-2)

(V-2)

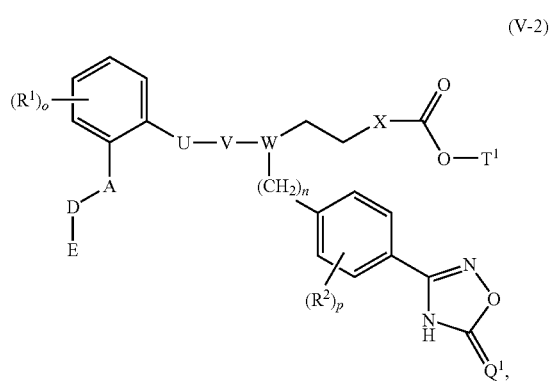

in which R¹, R², A, D, E, U, V, W, X, n, o, p, Q¹ and T¹ each have the meanings indicated above, or

[B-1] compounds of the formula (VI-1)

(VI-1)

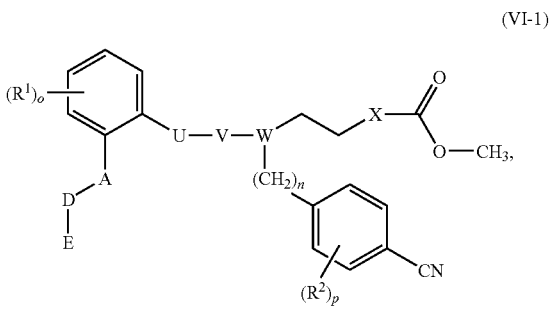

in which R¹, R², A, D, E, U, V, W, X, n, o and p each have the meanings indicated in claim 1, are initially converted with hydrazine in an inert solvent into compounds of the formula (VII-1)

(VII-1)

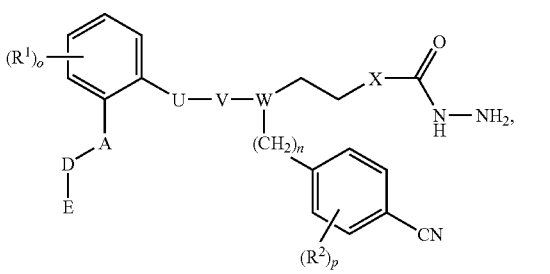

in which R¹, R², A, D, E, U, V, W, X, n, o and p each have the meanings indicated above, and then reacted in an inert solvent with phosgene or a phosgene derivative to give compounds of the formula (VIII-1)

(VIII-1)

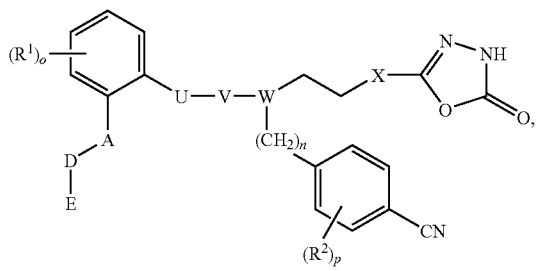

in which R¹, R², A, D, E, U, V, W, X, n, o and p each have the meanings indicated above, or

[B-2] compounds of the formula (VI-2)

(VI-2)

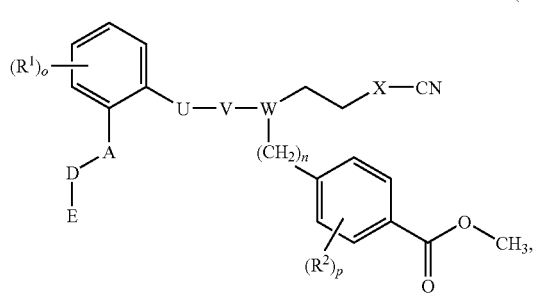

in which R¹, R², A, D, E, U, V, W, X, n, o and p each have the meanings indicated above, are converted in a manner analogous to process [B-1] into compounds of the formula (VIII-2)

(VIII-2)

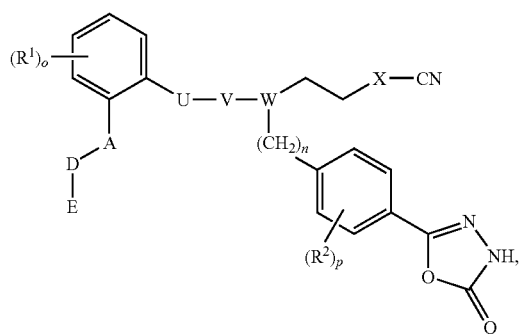

in which R¹, R², A, D, E, U, V, W, X, n, o and p each have the meanings indicated above, or

[C-1] compounds of the formula (IX-1)

(IX-1)

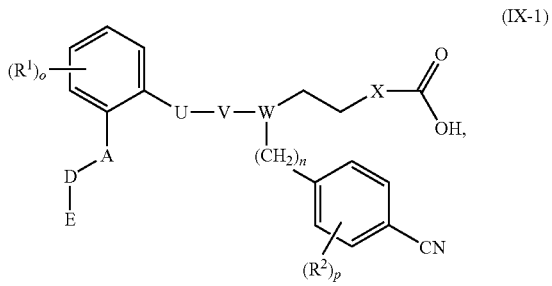

in which R¹, R², A, D, E, U, V, W, X, n, o and p each have the meanings indicated in claims 1 to 5, are initially converted in an inert solvent with oxalyl chloride, thionyl chloride or phosphoryl chloride into the corresponding carbonyl chlorides of the formula (X-1)

(X-1)

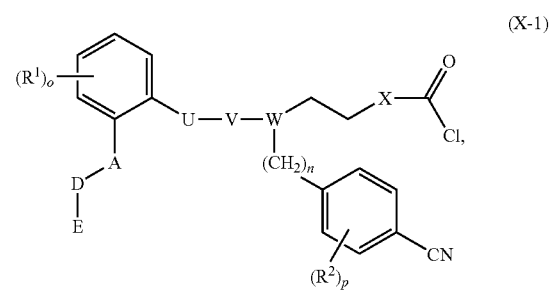

in which R¹, R², A, D, E, U, V, W, X, n, o and p each have the meanings indicated above, these are then reacted in an inert solvent with a semicarbazide of the formula (XI)

(XI)

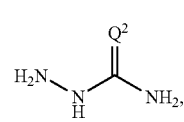

in which
Q² is O, S or NH,
to give compounds of the formula (XII-1)

(XII-1)

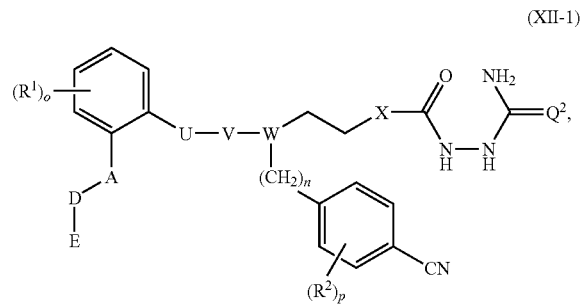

in which R¹, R², A, D, E, U, V, W, X, n, o, p and Q² each have the meanings indicated above, and subsequently cyclized in the presence of a base with simultaneous hydrolysis of the nitrile group to give compounds of the formula (XIII-1)

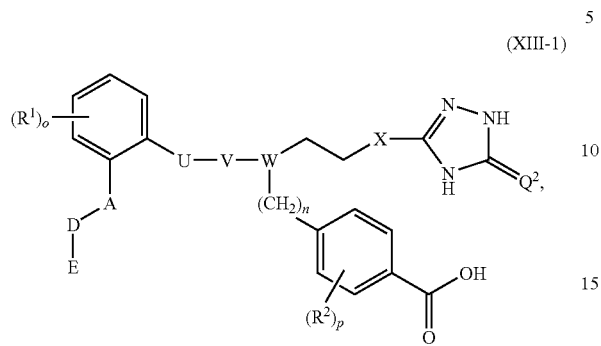

(XIII-1)

in which $R^1$, $R^2$, A, D, E, U, V, W, X, n, o, p and $Q^2$ each have the meanings indicated above, or

[C-2] compounds of the formula (IX-2)

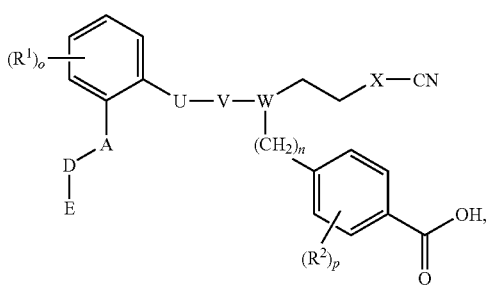

(IX-2)

in which $R^1$, $R^2$, A, D, E, U, V, W, X, n, o and p each have the meanings indicated above, are converted in a manner analogous to process [C-1] into compounds of the formula (XIII-2)

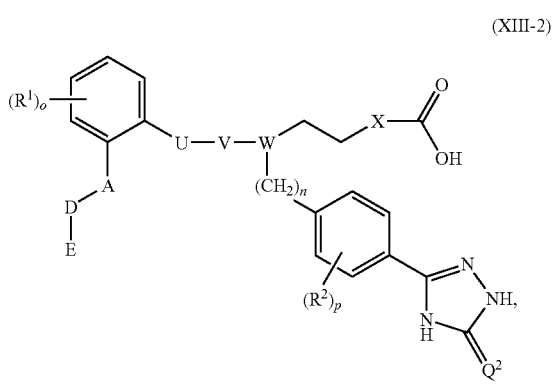

(XIII-2)

in which $R^1$, $R^2$, A, D, E, U, V, W, X, n, o, p and $Q^2$ each have the meanings indicated above, and the compounds of the formula (V-1), (V-2), (VIII-1) or (VIII-2) resulting in each case are converted by hydrolysis of the ester group —C(O)O$T^1$ or hydrolysis of the nitrile group into the corresponding carboxylic acids of the formula (I), and the compounds of the formula (I), including the compounds of the formulae (XIII-1) and (XIII-2), are reacted where appropriate with the appropriate (i) solvents and/or (ii) bases or acids to give the salts thereof.

7. A pharmaceutical composition comprising a compound as defined in claim 1 in combination with an inert, non-toxic, pharmaceutically suitable excipient.

8. The pharmaceutical composition of claim 7, further comprising an active ingredient selected from the group consisting of organic nitrates, NO donors, cGMP-PDE inhibitors, stimulators of guanylate cyclase, agents having antithrombotic activity, agents lowering blood pressure, and agents altering lipid metabolism.

\* \* \* \* \*